(12) United States Patent
Cook et al.

(10) Patent No.: US 8,304,246 B2
(45) Date of Patent: Nov. 6, 2012

(54) METHODS FOR THE DIAGNOSIS OF DEMENTIA AND OTHER NEUROLOGICAL DISORDERS

(75) Inventors: Lisa Cook, Saskatoon (CA); Dayan Burke Goodenowe, Saskatoon (CA)

(73) Assignee: Phenomenome Discoveries, Inc., Saskatoon, Saskatchewan (CA)

( * ) Notice: Subject to any disclaimer, the term of this patent is extended or adjusted under 35 U.S.C. 154(b) by 267 days.

(21) Appl. No.: 12/280,920

(22) PCT Filed: Feb. 28, 2007

(86) PCT No.: PCT/CA2007/000313
§ 371 (c)(1), (2), (4) Date: Feb. 27, 2009

(87) PCT Pub. No.: WO2007/098585
PCT Pub. Date: Sep. 7, 2007

(65) Prior Publication Data
US 2010/0003761 A1 Jan. 7, 2010

Related U.S. Application Data

(60) Provisional application No. 60/777,290, filed on Feb. 28, 2006, provisional application No. 60/804,779, filed on Jun. 14, 2006, provisional application No. 60/888,883, filed on Feb. 8, 2007.

(51) Int. Cl.
*G01N 33/92* (2006.01)
*G01N 33/49* (2006.01)

(52) U.S. Cl. .................. 436/63; 436/71; 436/104
(58) Field of Classification Search .................. None
See application file for complete search history.

(56) References Cited

U.S. PATENT DOCUMENTS

| | | | |
|---|---|---|---|
| 5,631,168 | A | 5/1997 | Growdon et al. |
| 5,731,354 | A | 3/1998 | Pruss |
| 6,177,476 | B1 | 1/2001 | Peterson et al. |
| 7,349,809 | B2 | 3/2008 | Goodenowe |

(Continued)

FOREIGN PATENT DOCUMENTS

CA 2443806 A1 10/2002

(Continued)

OTHER PUBLICATIONS

Mulder et al. "Decreased lysophosphatidylcholine/phosphatidylcholine ratio in cerebrospinal fluid in Alzheimer's disease," Journal of Neural Transmission, 2003, 110, 949-955.*

(Continued)

*Primary Examiner* — Vickie Kim
*Assistant Examiner* — Michelle Adams
(74) *Attorney, Agent, or Firm* — LeClairRyan, a Professional Corporation

(57) ABSTRACT

The present invention is directed to a method for differentially diagnosing dementia or the risk of dementia in a patient. The method comprises obtaining a sample from the patient; analyzing the sample to obtain quantifying data for one or more than one metabolite marker; comparing the quantifying data for the one or more than one metabolite marker to corresponding data obtained from one or more than one reference sample; and using the comparison to differentially diagnose dementia or the risk of dementia. The method may also assist in assessing dementia or the risk of dementia in a patient. The present invention is also directed to metabolite markers and compounds useful in the present method.

30 Claims, 38 Drawing Sheets

U.S. PATENT DOCUMENTS 8,026,099 B2 * 9/2011 Han .................................. 436/13

FOREIGN PATENT DOCUMENTS

| JP | 2007-33410 A | * | 2/2007 |
|---|---|---|---|
| WO | 01/57518 A2 | | 8/2001 |
| WO | 0221139 A2 | | 3/2002 |
| WO | 02082075 A2 | | 10/2002 |
| WO | 02090974 A2 | | 11/2002 |
| WO | 2004019043 A2 | | 3/2004 |
| WO | 2005/047484 A2 | | 5/2005 |
| WO | WO-2005/085838 A2 | * | 9/2005 |
| WO | 2005116659 A2 | | 12/2005 |

OTHER PUBLICATIONS

Lytle et al. "Utility of high performance liquid chromatography/electrospray/mass spectrometry of polar lipids in specifically Per-13C labeled Gram-negative bacteria DA001 as a tracer for acceleration of bioremediation in the subsurface," Journal of Microbiological Methods 2001, 44, 271-281.*

Murphy et al. "Analysis of Nonvolatile Lipids by Mass Spectrometry," Chem. Rev. 2001, 101, 479-526.*

Ekroos et al. "Quantitative Profiling of Phospholipids by Multiple Precursor Ion Scanning on a Hybrid QuadrupoleTime-of-Flight Mass Spectrometer," Anal. Chem. 2002, 74, 941-949.*

Marshall et al. "Fourier Transform Ion Cyclotron Resonance Mass Spectrometry: A Primer," Mass Spectrometry Reviews, 1998, 17, 1-35.*

Ujiie, M. et al. "Blood-Brain Barrier Permeability Precedes Senile Plaque Formation in an Alzheimer Disease Model," Microcirculation 2003, 10, 463-470.*

Conquer, J. A. et al. "Fatty Acid Analysis of Blood Plasma of Patients with Alzheimer's Disease, Other Types of Dementia, and Cognitive Impairment," Lipids 2000, 35, 1305-1312.*

Vreken, P. et al. "Analysis of plasmenylethanolamines using electrospray tandem mass spectrometry and its application in screening for peroxisomal disorders," J. Inherit. Metab. Dis. 23 (2000) 429-433.*

Han, X. "Lipid Alterations in the Earliest Clinically Recognizable Stage of Alzheimer's Disease: Implication of the Role of Lipids in the Pathogenesis of Alzheimer's Disease," Current Alzheimer Research, 2005, 2, 65-77.*

Maeba R. JP 2007-33410 A; Feb. 8, 2007; Derwent abstract and machine translation.*

Cummings et al., "Neuropsychiatric Aspects of Alzheimer's Disease: The Cholinergic Hypothesis Revisited," Neurology 47:876-83 (1996).

Demediuk et al., "Membrane Lipid Changes in Laminectomized and Traumatized Cat Spinal Cord," Proc. Nat'l. Acad. Sci. 82:7071-5 (1985).

Dugue et al., "Review of Dementia," Mount Sinai Journal of Medicine 70(1):45, 9p, Accession No. 8992247 (2003).

Emre et al., "Dementia Associated with Parkinson's Disease," The Lancet Neurology 2:229-37 (2003).

Kawashima et al., "Alzheimer's Disease: B-Amyloid Protein and Tau," Journal of Neuroscience Research 70:392-401 (2002).

Lee et al., "Neurodegenerative Tauopathies," Annu. Rev. Neurosci. 24:1121-59 (2001).

McKeith et al., "Consensus Guidelines for the Clinical and Pathologic Diagnosis of Dementia with Lewy Bodies (DLB): Report of the Consortium on DLB International Workshop," American Academy of Neurology 47:1113-24 (1996).

Neary et al., "Frontotemporal Lobar Degeneration: A Consensus on Clinical Diagnostic Criteria," American Academy of Neurology 51:1546-54 (1998).

Newell et al., "Application of the National Institute on Aging (NIA)-Reagan Institute Criteria for the Neuropathological Diagnosis of Alzheimer Disease," Journal of Neuropathology and Experimental Neurology 58(11):1147-55 (1999).

Polvikoski et al., "Prevalence of Alzheimer's Disease in Very Elderly People: A Prospective Neuropathological Study," Neurology 56:1690-96 (2001).

Price et al., "Neuron Number In the Entorhinal Cortex and CA1 Preclinical Alzheimer Disease," Archives of Neurology 58(9):1395-1402 (2001).

Price et al., "Tangles and Plaques in Nondemented Aging and "Preclinical" Alzheimer's Disease," Annals of Neurology 45(3):358-68 (1999).

Price et al., "The Distribution of Tangles, Plaques and Related Immunohistochemical Markers in Healthy Aging and Alzheimer's Disease," Neurology of Aging 12:295-312 (1991).

Wells et al., "Neural Membrane Phospholipids in Alzheimer Disease," Neurochemical Research 20(110):1329-33 (1995).

Zhang et al., "Free Fatty Acids, Neutral Glycerides, and Phosphoglycerides in Transient Focal Cerebral Ischemia," Journal of Neurochemistry 64(4):1688-95 (1995).

Abdi et al., "Detection of Biomarkers with a Multiplex Quantitative Proteomic Platform in Cerebrospinal Fluid of Patients with Neurodegenerative Disorders," Journal of Alzheimer's Disease 9:293-348 (2006).

Berry & Murphy, "Electrospray Ionization Tandem Mass Spectrometry of Glycerophosphoethanolamine Plasmalogen Phospholipids," J. Am. Soc. Mass. Spectrom 15:1499-1508 (2004).

Carrette et al., "A Panel of Cerebrospinal Fluid Potential Biomarkers for the Diagnosis of Alzheimer's Disease," Proteomics 3:1486-94 (2003).

Cook et al., "The Discovery of Two Sets of Serum Biomarkers: One that Identifies the Presence of AD Pathology and One that is Quantitatively Correlated with ADAS-cog," Poster on the Phenomenome Discoveries Inc. website: http//www.phenomenome.com/news.htm, Poster available at: http//www.[phenomenome.com/pdf/Posters/AD ICAD.pdf (2006).

Coon et al. "Biomarker Identification in Neurologic Diseases: Improving Diagnostic and Therapeutics," Expert Rev. Mol. Diagn. 4(3):361-5 (2004).

Davidsson et al., "Proteome Analysis of Cerebrospinal Fluid Proteins in Alzheimer Patients," NeuroReport 13(5):611-15 (2002).

Davidsson et al., "Proteome Studies of CSF and AD Patients," Mechanisms of Aging and Development 127:133-7 (2006).

Dunckley et al., "Discovery and Development of Biomarkers of Neurological Disease," Drug Discovery Today 10 (5):326-34 (2005).

Ginsberg et al., "Disease and Anatomic Specificity of Ethanolamine Plasmalogen Deficiency in Alzheimer's Disease Brain," Brain Research 698:223-6 (1995).

Ginsberg et al., "Membrane Instability, Plasmalogen Content and Alzheimer's Disease," Journal of Neurochemistry 70 (6):2533-38 (1998).

Granier et al., "Phospholipid Composition in Late Infantile Neuronal Ceroid Lipofuscinosis," European Journal of Clinical Investigation 30:1011-17 (2000).

Guan et al., "Decrease and Structural Modifications of Phosphatidylethanolamine Plasmalogen in the Brain of Alzheimer's Disease," Journal of Neuropathology and Experimental Neurology 58(7):740-7 (1999).

Han et al., "Plasmalogen Deficiency in Early Alzheimer's Disease Subjects and in Animal Models: Molecular Characterization Using Electrospray Ionization Mass Spectrometry," Journal of Neurochemistry 77:1168-80 (2001).

Jackson et al., "In Situ Structural Characterization of Glycerophospholipids and Sulfatides in Brain Tissue Using MALDI-MS/MS," J. Am. Soc. Mass Spectrom. 18:17-26 (2007).

Lin et al., "Effects of Dietary n-3 Fatty Acids on the Phospholipid Molecular Species of Monkey Brain," Journal of Neurochemistry 55(4):1200-7 (1990).

Pettegrew et al., "Brain Membrane Phospholipid Alterations in Alzheimer's Disease," Neurochemical Research 26 (7):771-82 (2001).

Rüetschi et al., "Identification of CSF Biomarkers for Frontotemporal Dementia Using SELDI-TOF," Experimental Neurology 196(2):273-81 (1999).

Schiller et al., "Combined Application of TLC and Matrix-Assisted Laser Desorption and Ionisation Time-of-Flight Mass Spectrometry (MALDI-TOF MS) to Phospholipid Analysis of Brain," Chromatographia Supplement 57:S297-S302 (2003).

Solfrizzi et al., "Circulating Biomarkers of Cognitive Decline and Dementia," Clinica Chimica Acta 364:91-112 (2006).

Wang et al., "Plasma Phospholipid Metabolic Profiling and Biomarkers of Type 2 Diabetes Mellitus Based on High-Performance Liquid Chromatography/Electrospray Mass Spectrometry and Multivariate Statistical Analysis," Anal. Chem. 77(13):4108-16 (2005).

Yamazaki et al., "Serum Biomarker Panel Specific to AD Pathology and Viability of Cholinergic Neurons," International College of Geriatric Psychoneuropharmacology Annual Meeting P-C-16 (2006).

Yang et al., "Strategy for Metabonomics Research Based on High-Performance Liquid Chromatography and Liquid Chromatography Coupled with Tandem Mass Spectrometry," Journal of Chromatography 1084:214-21 (2005).

International Search Report (Jun. 20, 2007) for PCT/CA2007/000313.

Written Opinion of the International Searching Authority for PCT/CA2007/000313.

Farooqui et al., "Membrane Phospholipid Alterations in Alzheimer's Disease: Deficiency of Ethanolamine Plasmalogens," Neurochemical Research 22(4):523-7 (1997).

Suemaru et al., "Cerebrospinal Fluid Corticotropin-Releasing Hormone and ACTH, and Peripherally Circulating Choline-Containing Phospholipid in Senile Dementia," Life Sciences 53(9):697-706 (1993).

Supplementary Partial European Search Report for European Patent Application No. EP07710657 (Apr. 17, 2009).

Farooqui et al., "Plasmalogens, Phospholipase A(2), and Docosahexaenoic Acid Turnover in Brain Tissue," J. Mol. Neuro. 16:263-272 (2001).

Ho et al., "From Proteomics to Biomarker Discovery in Alzheimer's Disease," Brain Research Reviews 48:360-369 (2005).

Lopez et al., "High-Resolution Serum Proteomic Profiling of Alzheimer Disease Samples Reveals Disease-Specific, Carrier-Protein-Bound Mass Signatures," Clin. Chem. 51(10):1946-1954 (2005).

Canadian Office Action dated, Mar. 15, 2010.

Chen et al., "Rheologic Determinant Changes of Erythrocytes in Binswanger's Disease," Chin. Med. J. (Taipei) 76:76-85 (1999).

Chen et al., "Changes of Erythrocyte and Platelet membrane Lipid Pattern in Different Subtypes of Dementia," Chin. Med. J. 78:771-773 (1998).

Conquer et al., "Fatty Acid Analysis of Blood Plasma of Patients with Alzheimer's Disease, Other Types of Dementia, and Cognitive Impairment," Lipids 35(12):1305-1312 (2000).

* cited by examiner

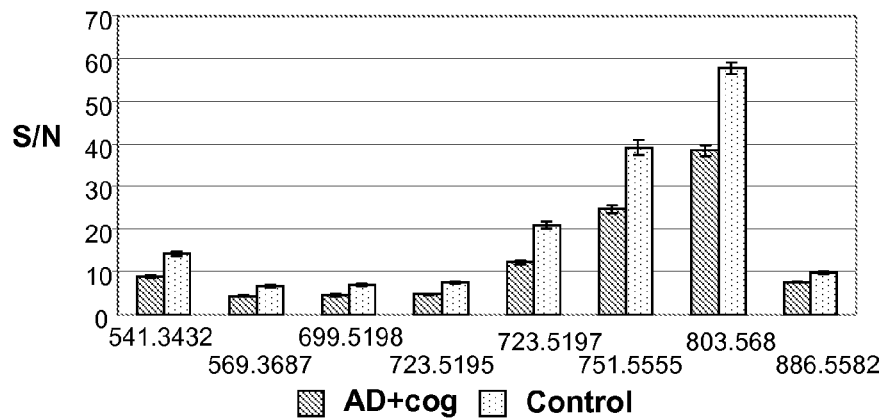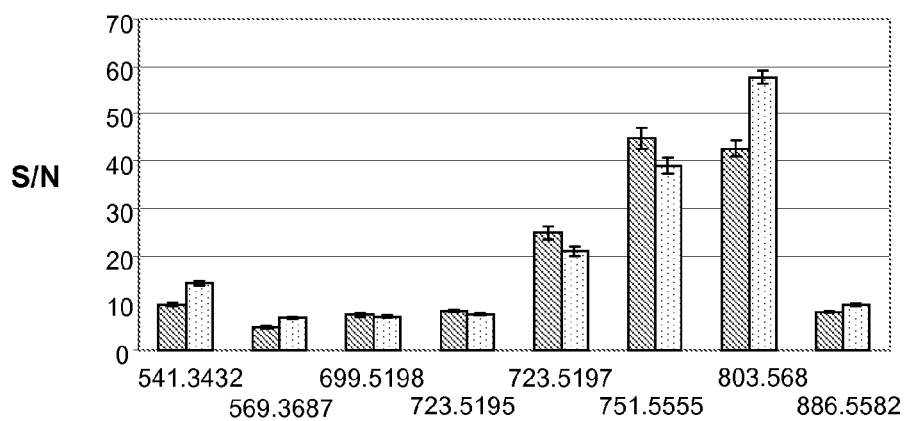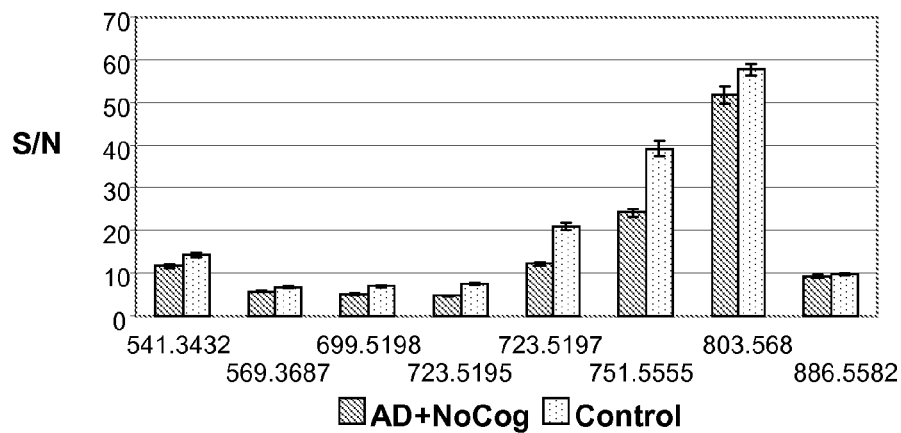
FIG. 1

E 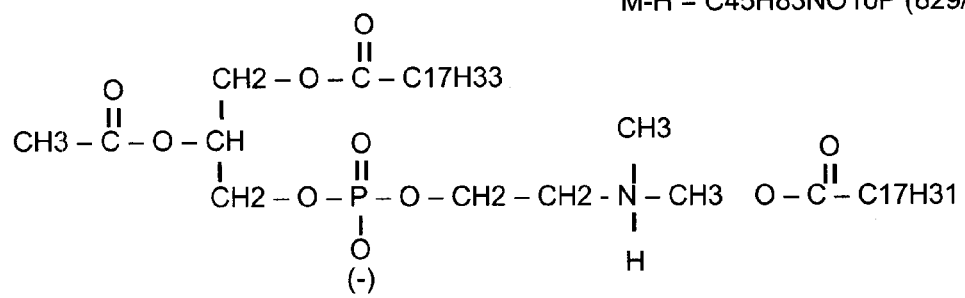
M-H = C45H83NO10P (829/828)
F 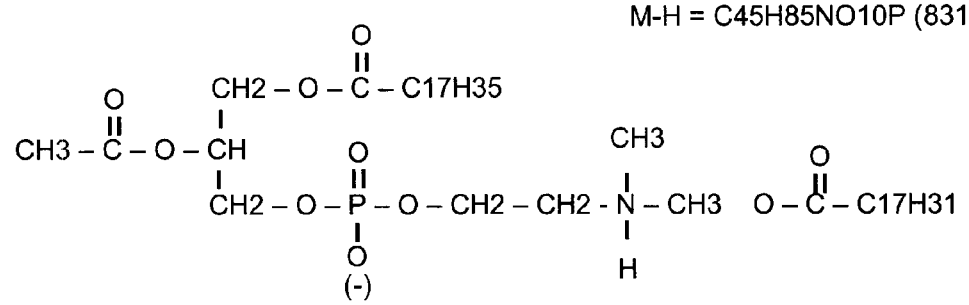
M-H = C45H85NO10P (831/830)
G 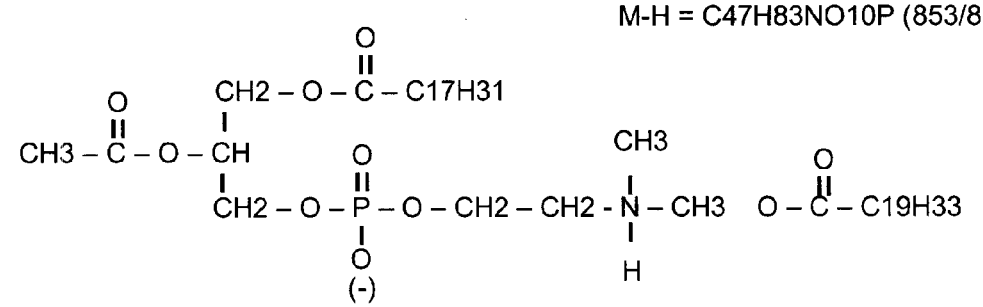
M-H = C47H83NO10P (853/852)
Fig. 15

| m/z | Formula | Molecular fragment | Fragment loss |
|---|---|---|---|
| 750 | C₄₃H₇₇NO₇P | (structure) | H⁺ |
| 482 | C₄₅H₄₁NO₆P | (structure) | HO–C₁₆H₃₃ |
| 464 | C₂₃H₄₇NO₆P | (structure) | O=C₁₉H₃₁ |
| 462 | C₂₃H₄₅NO₆P | (structure) | O=C₁₉H₃₁ |
| 444 | C₂₃H₄₃NO₅P | (structure) | 462 – H₂O |
| 436 | C₂₁H₄₃NO₆P | (structure) | 464 – C₂H₈ |
| 331 | C₂₂H₃₅O₂ | (structure) | i. (structure) ii. (structure) |
| 303 | C₂₀H₃₁O₂ | (structure) | (structure) |
| 259 | C₁₉H₃₁ | (structure) | 303 – CO₂ |
| 205 | C₇H₁₀O₅P | (structure) | 464 – H₂O, C₁₆H₃₂ & NH₃ |

Metabolite Structure:

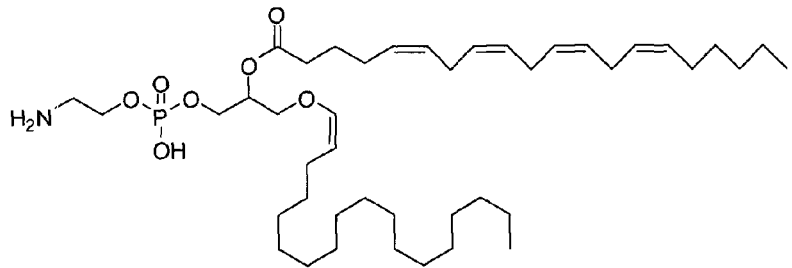

Fig. 16

| m/z | Formula | Molecular fragment | Fragment loss |
|---|---|---|---|
| 698 | $C_{39}H_{73}NO_7P$ | H₂N-CH₂-CH₂-O-P(O)(O⁻)-O-CH₂-CH(O-CO-C₁₇H₃₁)-CH₂-O-CH=CH-C₁₄H₂₉ | $H^+$ |
| 458 | $C_{23}H_{41}NO_6P$ | H₂N-CH₂-CH₂-O-P(O)(O⁻)-O-CH₂-C(O-CO-C₁₇H₃₁)=CH₂ | HO-CH=CH-C₁₄H₂₉ |
| 436 | $C_{21}H_{43}NO_6P$ | H₂N-CH₂-CH₂-O-P(O)(O⁻)-O-CH₂-CH(OH)-CH₂-O-CH=CH-C₁₄H₂₉ | O=CH-C₁₇H₃₁ |
| 418 | $C_{21}H_{41}NO_5P$ | H₂N-CH₂-CH₂-O-P(O)(O⁻)-O-CH=CH-O-CH=CH-C₁₄H₂₉ | $436 - H_2O$ |
| 279 | $C_{18}H_{31}O_2$ | $O=C(O^-)-C_{17}H_{31}$ | H₂N-CH₂-CH₂-O-P(O)(O⁻)-O-CH₂-CH₂-CH₂-O-CH=CH-C₁₄H₂₉ |
| 255 | $C_7H_{15}NO_5P^-$ | ⁻O-CH₂-CH₂-O-CH=CH-C₁₂H₂₅ | $436 - C_2H_5$ & H₂N-CH₂-CH₂-O-P(O)(O⁻)-O- |

Metabolite Structure:

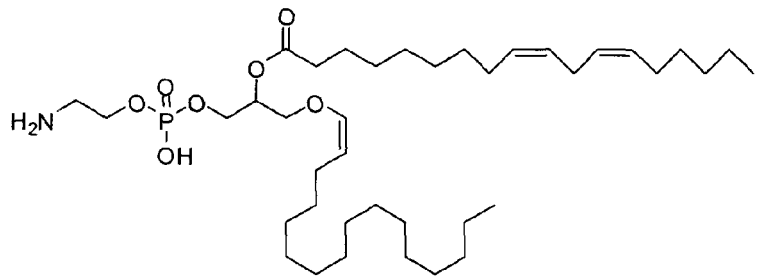

Fig. 17

| m/z | Formula | Molecular fragment | Fragment loss |
|---|---|---|---|
| 722 | $C_{41}H_{72}NO_7P$ | | $H^+$ |
| 482 | $C_{25}H_{41}NO_6P$ | | $HO\text{—}C_{14}H_{29}$ |
| 466 | $C_{24}H_{37}NO_6P$ | | $482 - CH_4$ |
| 436 | $C_{21}H_{43}NO_6P$ | | $O\text{=}C_{19}H_{31}$ |
| 418 | $C_{21}H_{41}NO_5P$ | | $O\text{=}C_{19}H_{31}$ (carboxylate) |
| 303 | $C_{20}H_{31}O_2$ | | |
| 279 | $C_{19}H_{35}O$ | | $418 - H_2N\text{-ethyl-phosphate}$ |
| 259 | $C_{19}H_{31}$ | | $303 - CO_2$ |
| 255 | $C_{15}H_{27}O_3$ | | $418 -$ & $C_4H_{10}$ |
| 205 | $C_7H_{10}O_5P$ | | $418 - C_{14}H_{30}$ & $NH_3$ |
| 140 | $C_2H_7NO_4P$ | | |

Metabolite Structure:

| Glyceryl Backbone | sn-2/R2 PtdEt/Plasmanyl/Plasmenyl |
|---|---|
| sn-1 CH$_2$-R1<br>\|<br>sn-2 CH-R2<br>\|<br>sn-3 CH$_2$-R3 | O-C(O)-C17H35 (18:0)<br>O-C(O)-C17H33 (18:1)<br>O-C(O)-C17H31 (18:2)<br>O-C(O)-C19H31 (20:4)<br>O-C(O)-C21H35 (22:4)<br>O-C(O)-C21H31 (22:6) |
| sn-1/R1<br><br>PtdEt<br>O-C(O)-C15H31 (16:0)<br>O-C(O)-C17H35 (18:0)<br>Plasmanyl<br>O-CH2-CH2-C14H29 (16:0)<br>O-CH2-CH2-C16H33 (18:0)<br>Plasmenyl<br>O-CH=CH-C14H29 (16:0)<br>O-CH=CH-C16H33 (18:0) | sn-3/R3 PtdEt/Plasmanyl/Plasmenyl<br>O-P(O)-O-C2H4-NH2<br>\|<br>OH |
| | Example<br>CH$_2$-O-CH=CH-C16H33<br>\|<br>CH-O-C(O)-C21H31<br>\|<br>CH$_2$-O-P(O)-O-C2H4-NH2<br>\|<br>OH<br>[Plasmenyl (18:0/22:6)] |

Fig. 20

METHODS FOR THE DIAGNOSIS OF DEMENTIA AND OTHER NEUROLOGICAL DISORDERS

FIELD OF INVENTION

The present invention relates to small molecules or metabolites that are found to have significantly different abundances between clinically diagnosed dementia or other neurological disorders, and normal patients. The present invention also relates to methods for diagnosing dementia and other neurological disorders.

BACKGROUND OF THE INVENTION

The most severe consequence of the aging brain is dementia, which is defined in the Diagnostic and Statistical Manual of Mental Disorders, 4th edition (DSM-IV) as "the development of multiple cognitive deficits that included memory impairment and at least one of the following cognitive disturbances: aphasia, apraxia, agnosia, or a disturbance in executive functions. The cognitive impairment must be sufficiently severe to cause impairment in occupational or social functioning and must represent a decline from a previously higher level of functioning." [1]

The number of elderly people is increasing rapidly within our society and as a consequence, dementia is growing into a major health problem. In 1991, the Canadian Study of Health and Aging had estimated 25% of the population over the age of 65 had a form of dementia. The study also estimated the number of people living with dementia will double and triple in Canada by 2011 and 2031, respectively [2].

The clinical manifestation of dementia can result from neurodegeneration (e.g. Alzheimer's Disease [AD], dementia with Lewy bodies [DLB] and frontotemporal lobe dementia [FTLD]), vascular (e.g. multi-infarct dementia) or anoxic event (e.g. cardiac arrest), trauma to the brain (e.g. dementia pugilistica [boxer's dementia]), or exposure to an infectious (e.g. Creutzfeldt-Jakob Disease) or toxic agent (e.g. alcohol-induced dementia) [3].

AD is the most common cause of dementia, followed by vascular dementia (VaD), DLB and FTLD [4]. The differential diagnosis of the types of dementia is not straightforward, and is typically based on exclusion of other disorders [5]. For example, blood chemistry values are measured to determine if Vitamin B12 deficiency, anemia, infection, venereal disease or thyroid disorder may be possible reasons for the dementia symptoms. Various neuroimaging techniques may be employed, such as magnetic resonance imaging or computerized tomography scans to determine if the symptoms may be due to the presence of a tumor, infection or vascular event [4].

If the dementia symptoms can not be explained by another disorder, a diagnosis of AD, DLB or FTLD is made exclusively based on the clinical symptoms (e.g. frequency of falls, rapid onset, presence of visual or auditory hallucinations, etc). It is not until a histopathological evaluation of the brain during autopsy is performed that a definitive diagnosis can be obtained [5-7]. A prospective study on the prevalence of AD in people over the age of 85 indicated that more than half of the individuals with neuropathological criteria for AD were either non-demented or were incorrectly diagnosed with VaD. As well, 35% of those individuals diagnosed with AD based on clinical features were incorrectly diagnosed as the neuropathological evaluation did not support that diagnosis [8]. The degree of misdiagnosis is understandable since the clinical symptoms of the various dementias often overlap and is dependent upon whether the pertinent information is made known to the clinician.

The different types of dementias are based on specific neuropathological features. A definitive diagnosis of AD relies on the deposition of two types of neuronal protein: tau in the form of intraneuronal neurofibrillary tangles (NFTs) and the accumulation of extracellular β-amyloid to form senile plaques (SPs). Tau is important for the formation of microtubules in the neuronal axon by binding and promoting polymerization of tubules. In AD, tau becomes hyperphosphorylated thereby disrupting its main function. The tau accumulates and forms tangles within the axon. The neuron can no longer function and dies. Tau protein is released into the extracellular space where it can be detected in the cerebrospinal fluid (CSF) [9]. The formation of SPs, however, is due to the accumulation of a 40 and 42 residue protein β-amyloid from amyloid precursor protein (APP) [10]. The formation and secretion of β-amyloid is closely regulated by homeostasis, but something occurs in AD that disrupts homeostasis resulting in the accumulation of the protein within the brain and disrupting the neurons within its vicinity [11-12]. The increased amount of tau and the absence of β-amyloid in CSF have been proposed as possible diagnostic markers for AD, but results have not been consistent. The problem may be due to the presence of NFTs and SPs that increase in number during normal aging [13]. In order for the NFTs and SPs to be diagnostic of AD, they must be localized together in specific areas of the brain (neocortex and limbic region) [12]. SPs without NFTs are present in the same area in individuals with mild cognitive impairment (MCI) and in 27% of non-demented individuals greater then 75 years old [13].

A diagnosis of DLB is based on the presence of protein deposits called alpha-synuclein, which is referred to as Lewy Bodies, within brainstem and cortical neurons [6]. The cognitive deficit corresponds to the amount of Lewy Bodies within the brain.

FTLD is not characterized by a specific neuropathological feature. Typically, areas of the frontal/temporal cortices have neuronal loss, spongiform changes (microvacuolation) and severe astrocytic gliosis. The clinical symptoms in FTLD are dependent upon where the pathology is found rather than the type of pathology [7].

Currently, various neuropsychological tests are used to help diagnose dementia. For example, the Alzheimer's Disease Assessment Scale (ADAS)-cognitive subset is used to test the language ability (speech and comprehension), memory, ability to copy geometric figures and orientation to current time and place. The Folstein's Mini-Mental State Exam (MMSE), which also measures cognitive impairment, is an extensively validated test of orientation, short and long-term memory, praxis, language and comprehension. While these tests may indicate the level of cognitive impairment in an individual, they give no indication of whether the dementia may be caused by AD or by non-AD dementias.

It is commonly accepted that by the time any symptom is evident in any of the dementias described, irreversible neuronal loss has occurred [14]. MCI is characterized by a prominent impairment in memory with normal cognitive functions [15]. MCI is considered a transitional stage between normal aging and several types of dementia since a large proportion of individuals with MCI are later diagnosed with AD, DLB, or FTLD and all individuals with fully developed dementia first exhibit mild dementia symptoms similar to MCI [16].

There is a need to objectively differentiate the types of dementia from one another. Preferably, such a method would be specific, accurate, and efficient. Clearly, there is a pressing need for differential diagnosis of dementia prior to autopsy.

A biomarker that could detect neuropathological changes prior to clinical symptoms would be of enormous value. A consensus was reached in 1999 [17] as to what would be expected in a biomarker in AD:
1. Detect a fundamental feature of neuropathology
2. Diagnostic sensitivity of >80% for detecting AD
3. Specificity of >80% for distinguishing other dementias
4. Reliable
5. Reproducible
6. Noninvasive
7. Simple to perform
8. Inexpensive The identification of AD-specific biomarkers in human serum would be extremely useful since it would be noninvasive and could be used to detect the presence of AD pathology prior to the manifestation of clinical symptoms and differentiate those patients who may have a different form of dementia but similar clinical symptoms.

SUMMARY OF THE INVENTION

The present invention relates to small molecules or metabolites that are found to have significantly different abundances between clinically diagnosed dementia or other neurological disorders, and normal patients. The present invention also relates to methods for diagnosing dementia and other neurological disorders.

The present invention provides a method of identifying one or more than one metabolite marker for differentially diagnosing AD dementia, non-AD dementia, cognitive impairment, or a combination thereof, comprising the steps of:
introducing one or more than one sample from one or more than one patient with clinically diagnosed AD dementia, clinically diagnosed non-AD dementia, significant cognitive impairment, or any combination thereof, said sample containing a plurality of metabolites into a high resolution mass spectrometer
obtaining quantifying data for the metabolites;
creating a database of said quantifying data;
comparing the identifying and quantifying data from the sample with corresponding data from a sample from a reference sample;
identifying one or more than one metabolite marker that differs between same sample and said reference sample,
wherein the metabolites metabolite markers are selected from the metabolites listed in Tables 1-7, 10-13, and 18, or any combination thereof. The method may further comprising selecting a minimal number of metabolite markers needed for optimal diagnosis. In a non-limiting example, the high resolution mass spectrometer is a Fourier Transform Ion Cyclotron Resonance Mass Spectrometer (FTMS).

The present invention also provides novel compounds selected from the group consisting of the metabolites listed in Tables 7-13. The 15. The metabolite may be selected from the group consisting of phosphatidylcholine-related compounds, ethanolamine plasmalogens, endogenous fatty acids, essential fatty acids, lipid oxidation byproducts, metabolite derivatives of said metabolite classes, and any metabolite that may contribute in any way to the anabolic/catabolic metabolism of said metabolite classes.

In one embodiment of the present invention, the compounds may be selected from the group consisting of metabolites with accurate masses measured in Daltons of, or substantially equivalent to, 541.3432, 569.3687, 699.5198, 723.5195, 723.5197, 751.5555, 803.568, 886.5582, 565.3394, 569.369, 801.555, and 857.6186. The metabolites with accurate masses measured in Daltons of, or substantially equivalent to, a) 541.3432, b) 569.3687, c) 699.5198, d) 723.5195, e) 751.5555, and f) 803.568 may also be characterized by
a) an extracted ion chromatogram (EIC) as shown in FIG. 4A, and an MS/MS spectrum as shown in FIG. 6;
b) an EIC as shown in FIG. 4B, and an MS/MS spectrum as shown in FIG. 7;
c) an EIC as shown in FIG. 4C, and an MS/MS spectrum as shown in FIG. 8;
d) an EIC as shown in FIG. 4D, and an MS/MS spectrum as shown in FIG. 9;
e) an EIC as shown in FIG. 4E, and an MS/MS spectrum as shown in FIG. 10; and
f) an EIC as shown in FIG. 4F, and an MS/MS spectrum as shown in FIG. 11, respectively.

The compounds as described above may also be further characterized by molecular formula a) $C_{25}H_{51}NO_9P$, b) $C_{27}H_{55}NO_9P$, c) $C_{39}H_{74}NO_7P$, d) $C_{41}H_{74}NO_7P$, e) $C_{43}H_{78}NO_7P$, and f) $C_{43}H_{81}NO_{10}P$, respectively; and/or by the structures shown in a) FIG. 12; b) FIG. 13; c) FIG. 17; d) FIG. 18; e) FIG. 19; and f) FIG. 14, respectively.

The compounds may also be selected from the group consisting of metabolites with accurate masses measured in Daltons of, or substantially equivalent to, a) 567.3547, b) 565.3394, c) 805.5832, d) 827.57, e) 829.5856, f) 831.5997, and g) 853.5854. These compounds may be further characterized by molecular formula a) $C_{27}H_{55}NO_9P$, b) $C_{27}H_{55}NO_9P$, c) $C_{43}H_{83}NO_{10}P$, d) $C_{45}H_{81}NO_{10}P$, e) $C_{45}H_{83}NO_{10}P$, f) $C_{45}H_{85}NO_{10}P$, and g) $C_{47}H_{83}NO_{10}P$, respectively; and/or by the structure shown in a) FIG. 15A; b) FIG. 15B; c) FIG. 15C; d) FIG. 15D; e) FIG. 15E; f) FIG. 15F; and g) FIG. 15G, respectively.

The compounds may further be selected from the group consisting of metabolites M05 to M24 with accurate masses of, or substantially equivalent to those listed in Table 18. Of these compounds, the metabolites with accurate masses measured in Daltons of, or substantially equivalent to, a) 701.53591, b) 699.52026, c) 723.52026, d) 747.52026, e) 729.56721, f) 727.55156, g) 779.58286, and h) 775.55156 may be further characterized by a MS/MS spectrum as shown in a) FIG. 21; b) FIG. 22; c) FIG. 23; d) FIG. 24; e) FIG. 25; f) FIG. 26; g) FIG. 27; and h) FIG. 28, respectively.

The compounds as described above may also be further characterized by molecular formula a) $C_{39}H_{76}NO_7P$, b) $C_{39}H_{74}NO_7P$, c) $C_{41}H_{74}NO_7P$, d) $C_{43}H_{74}NO_7P$, e) $C_{41}H_{80}NO_7P$, f) $C_{41}H_{78}NO_7P$, g) $C_{45}H_{82}NO_7P$, and h) $C_{45}H_{78}NO_7P$, respectively and/or by the structure

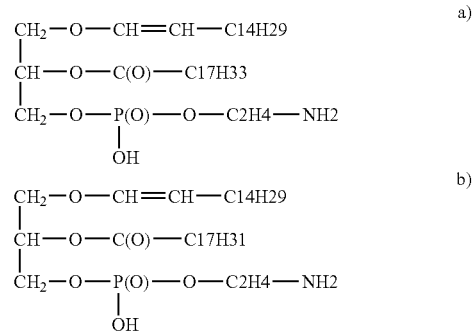

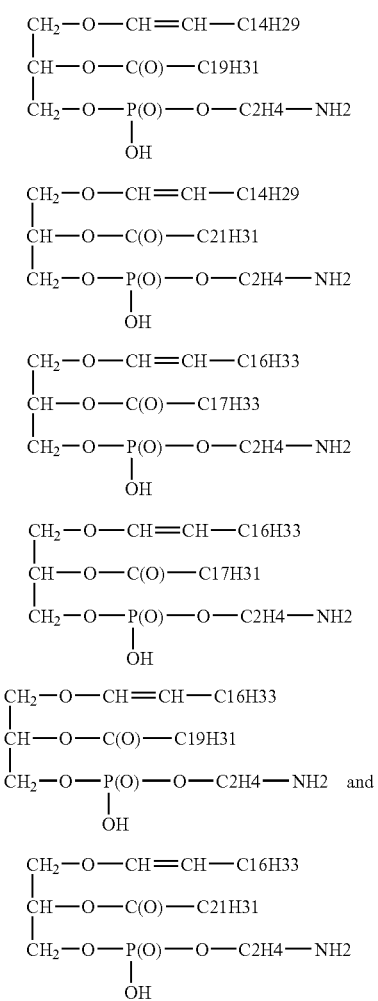

respectively.

The novel compounds may also be selected from the group consisting of the metabolites listed in Table 30. Of these compounds, the metabolites with accurate masses measured in Daltons of, or substantially equivalent to, 207.0822, 275.8712, 371.7311, 373.728, 432.1532, 485.5603, 487.6482, 562.46, 622.2539, 640.2637, 730.6493, and 742.2972 are of particular interest.

One or more than one of the compounds of the present invention may be used for the differential diagnosis of dementia.

In another embodiment, the present invention provides a method for differentially diagnosing dementia or the risk of dementia in a patient, the method comprising the steps of:
a) obtaining a sample from said patient;
b) analyzing said sample to obtain quantifying data for one or more than one metabolite marker;
c) comparing the quantifying data for said one or more than one metabolite marker to corresponding data obtained from one or more than one reference sample; and
d) using said comparison to differentially diagnose dementia or the risk of dementia.

The step of analyzing (step b) may comprise analyzing the sample by liquid chromatography mass spectrometry (LC-MS), or alternatively may comprise analyzing the sample by liquid chromatography and linear ion trap mass spectrometry when the method is a highthroughput method.

In the method as just described, the one or more than one reference sample is a first reference sample obtained from a non-demented control individual. The one or more than one reference sample may also comprise a second reference sample obtained from a patient with clinically diagnosed AD-dementia; a third reference sample obtained from a patient with clinically diagnosed non-AD dementia; and/or a fourth reference sample obtained from a patient suffering from significant cognitive impairment.

In one alternative of the method described above, the sample and the reference sample are serum samples, and the one or more than one metabolite marker is selected from the metabolites listed in Tables 1 to 7, or a combination thereof. These metabolite markers may be selected from the group consisting of phosphatidylcholine-related compounds, ethanolamine plasmalogens, endogenous fatty acids, essential fatty acids, lipid oxidation byproducts, metabolite derivatives of said metabolite classes, and any metabolite that may contribute in any way to the anabolic/catabolic metabolism of said metabolite classes.

The one or more than one metabolite marker needed for optimal diagnosis may comprise metabolites with accurate masses measured in Daltons of, or substantially equivalent to, 541.3432, 569.3687, 699.5198, 723.5195, 723.5197, 751.5555, 803.568, 886.5582, and any combination thereof. Of these, the metabolite of accurate masses 699.5198, 723.5195, 723.5197, and 751.555 are ethanolamine plasmalogens and are specifically decreased in patients with AD dementia; and the metabolite markers of accurate masses 541.3432, 569.3687, 803.568, and 886.5582 are phosphatidylcholine metabolites, are decreased in patients with cognitive impairment on ADAS-cog, and severity of cognitive impairment correlates to the degree of decrease.

The one or more than one metabolite marker may be the metabolites with accurate masses measured in Daltons of, or substantially equivalent to, a) 541.3432, b) 569.3687, c) 699.5198, d) 723.5195, e) 751.5555, and f) 803.568. These metabolites maybe further characterized by
a) an extracted ion chromatogram (EIC) as shown in FIG. 4A, and an MS/MS spectrum as shown in FIG. 6;
b) an EIC as shown in FIG. 4B, and an MS/MS spectrum as shown in FIG. 7;
c) an EIC as shown in FIG. 4C, and an MS/MS spectrum as shown in FIG. 8;
d) an EIC as shown in FIG. 4D, and an MS/MS spectrum as shown in FIG. 9;
e) an EIC as shown in FIG. 4E, and an MS/MS spectrum as shown in FIG. 10; and
f) an EIC as shown in FIG. 4F, and an MS/MS spectrum as shown in FIG. 11, respectively. The metabolite may also be further characterized by molecular formula a) $C_{25}H_{51}NO_9P$, b) $C_{27}H_{55}NO_9P$, c) $C_{39}H_{74}NO_7P$, d) $C_{41}H_{74}NO_7P$, e) $C_{43}H_{78}NO_7P$, and f) $C_{43}H_{81}NO_{10}P$, respectively; and/or by the structure shown in a) FIG. 12; b) FIG. 13; c) FIG. 17; d) FIG. 18; e) FIG. 19; and f) FIG. 14, respectively.

In another alternative of the method described above, the sample and the reference sample may be cerebrospinal fluid (CSF) samples, and the one or more than one metabolite marker is selected from the metabolites listed in Table 13, or a combination thereof. Of particular interest are metabolite markers needed for optimal diagnosis, which may comprise metabolites with accurate masses measured in Daltons of, or substantially equivalent to, 207.0822, 275.8712, 371.7311, 373.728, 432.1532, 485.5603, 487.6482, 562.46, 622.2539, 640.2637, 730.6493, 742.2972, and any combination thereof. Of these, metabolite markers 207.0822, 432.1532, 562.46, 622.2539, 640.2637, 730.6493, and 742.2972 are increased in patients with AD dementia; and metabolite markers 275.8712, 371.7311, 373.728, 485.5603, and 487.6482 are decreased inpatients with AD dementia.

In yet another alternative of the method described above, the sample and the reference sample are serum samples, and the one or more than one metabolite marker may be selected from metabolites M05 to M24 with accurate masses of, or substantially equivalent to those listed in Table 18. Of these, the one or more than one metabolite marker of particular interest may comprise metabolites with accurate masses measured in Daltons of, or substantially equivalent to, a) 701.53591, b) 699.52026, c) 723.52026, d) 747.52026, e) 729.56721, f) 727.55156, g) 779.58286, and h) 775.55156, and wherein a decrease in the level of a) to h) indicates AD dementia with a severe cognitive impairment.

The metabolites listed above may be further characterized by a MS/MS spectrum as shown in a) FIG. 21, b) FIG. 22, c) FIG. 23, d) FIG. 24, e) FIG. 25, f) FIG. 26, g) FIG. 27, and h) FIG. 28, respectively. The metabolites may also be further characterized by molecular formula a) $C_{39}H_{76}NO_7P$, b) $C_{39}H_{74}NO_7P$, c) $C_{41}H_{74}NO_7P$, d) $C_{43}H_{74}NO_7P$, e) $C_{41}H_{80}NO_7P$, f) $C_{41}H_{78}NO_7P$, g) $C_{45}H_{82}NO_7P$, and h) $C_{45}H_{78}NO_7P$, respectively; and/or by the structure

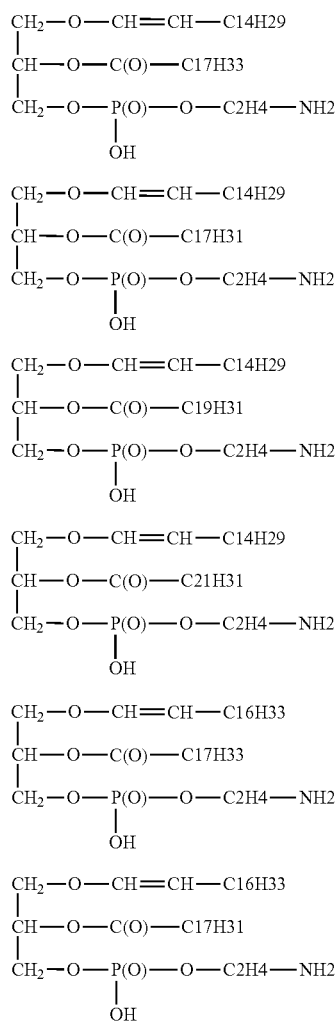
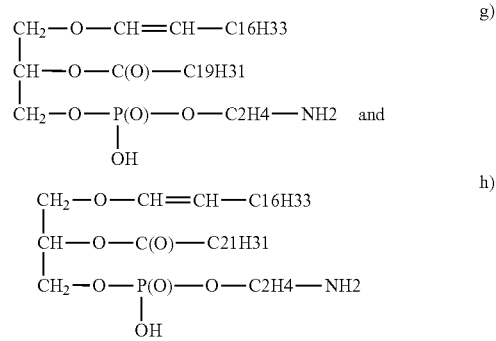

respectively.

In yet another aspect of the present invention, there is provided a method for assessing dementia or the risk of dementia in a patient, the method comprising the steps of:
  a) obtaining a serum sample from said patient;
  b) analyzing said sample to obtain quantifying data for one or more than one metabolite marker;
  c) comparing the quantifying data for said one or more than one metabolite marker to corresponding data obtained from one or more than one reference sample; and
  d) using said comparison to assess dementia or the risk of dementia.

The step of analyzing (step b) may comprise analyzing the sample by liquid chromatography mass spectrometry (LC-MS), or alternatively may comprise analyzing the sample by liquid chromatography and linear ion trap mass spectrometry when the method is a highthroughput method.

In the method as just described, the one or more than one reference sample may be a first reference sample obtained from a non-demented control individual. The one or more than one reference sample may also further comprise a second reference sample obtained from a patient with cognitive impairment as measured by ADAS-cog, and/or a third reference sample obtained from a patient with cognitive impairment as measured by MMSE.

The one or more than one metabolite marker in the method described above may be selected from the metabolites listed in Tables 10-12, or a combination thereof. Of particular interest are the one or more than one metabolite markers is selected from the group consisting of metabolites with accurate masses measured in Daltons of; or substantially equivalent to 541.3432, 569.3687, 699.5198, 723.5195, 723.5197, 751.5555, 803.568, 886.5582, 565.3394, 569.369, 801.555, 857.6186, and any combination thereof. Of these, a decrease in the patient sample in metabolite markers 699.5198, 723.5195, 723.5197, and 751.555 indicates AD pathology; a decrease in the patient sample in metabolite markers 541.3432, 569.3687, 803.568, and 886.5582 indicates cognitive impairment on ADAS-cog; and a decrease in the patient sample in metabolite markers 565.3394, 569.369, 801.555, and 857.6186 indicates cognitive impairment on MMSE.

In yet another embodiment of the present invention, a method is provided for differentially diagnosing dementia or the risk of dementia in a patient, the method comprising the steps of:
  a) obtaining a sample from said patient;
  b) analyzing said sample to obtain quantifying data for one or more than one metabolite marker;
  c) obtaining a ratio for each of the one or more than one metabolite marker to an internal control metabolite;

d) comparing each ratio of said one or more than one metabolite marker to the internal control metabolite to corresponding data obtained from one or more than one reference sample; and e) using said comparison to differentially diagnose dementia or the risk of dementia.

The step of analyzing (step b) may comprise analyzing the sample by liquid chromatography mass spectrometry (LC-MS), or alternatively may comprise analyzing the sample by liquid chromatography and linear ion trap mass spectrometry when the method is a highthroughput method.

In the method as just described, the one or more than one reference sample may be a first reference sample obtained from a non-demented control individual. The one or more than one reference sample may further comprise a second reference sample obtained from a patient with clinically diagnosed AD-dementia; a third reference sample obtained from a patient with clinically diagnosed non-AD dementia; and/or a fourth reference sample obtained from a patient suffering from significant cognitive impairment.

In one aspect of the method described above, the sample and the reference sample are serum samples, and the one or more than one metabolite marker is selected from metabolites M05 to M24 with accurate masses of, or substantially equivalent to those listed in Table 18. Of particular interest is the one or more than one metabolite marker comprising metabolites with accurate masses measured in Daltons of, or substantially equivalent to, a) 701.53591, b) 699.52026, c) 723.52026, d) 747.52026, e) 729.56721, f) 727.55156, g) 779.58286, and h) 775.55156, and the internal control metabolite comprising the metabolite with accurate mass measured in Daltons of, or substantially equivalent to, 719.54648. When these metabolites and internal control metabolite are used, a decrease in the ratio of metabolite to the internal control metabolite indicates AD dementia with a severe cognitive impairment.

The metabolites described above may be further characterized by a MS/MS spectrum as shown in a) FIG. 21, b) FIG. 22, c) FIG. 23, d) FIG. 24, e) FIG. 25, f) FIG. 26, g) FIG. 27, and h) FIG. 28, respectively. These metabolites may also be further characterized by molecular formula a) $C_{39}H_{76}NO_7P$, b) $C_{39}H_{74}NO_7P$, c) $C_{41}H_{74}NO_7P$, d) $C_{43}H_{74}NO_7P$, e) $C_{41}H_{80}NO_7P$, f) $C_{41}H_{78}NO_7P$, g) $C_{45}H_{82}NO_7P$, and h) $C_{45}H_{78}NO_7P$, respectively, and the internal control metabolite may be characterized by molecular formula $C_{39}H_{78}NO_8P$; and/or by the structure a)

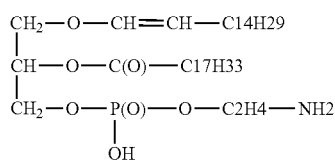

b)

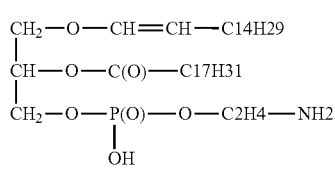

c)

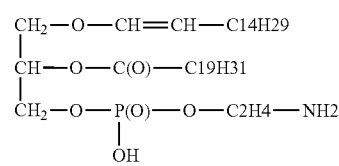

d)

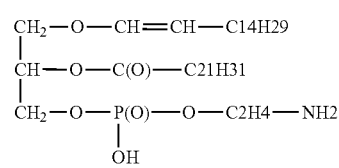

e)

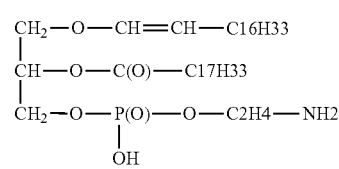

f)

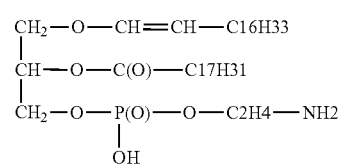

g)

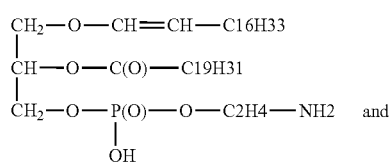

and h)

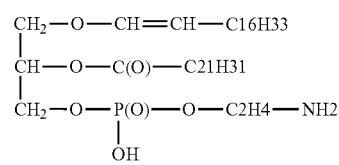

respectively, and the internal control metabolite may be further characterized by the structure

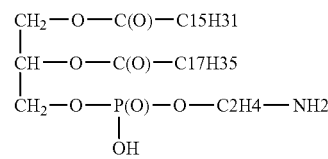

In yet another embodiment of the present invention, there is provided a method for evaluating the efficacy of a therapy for treating dementia in a patient, comprising:

a) obtaining a sample from said patient;

b) analyzing said sample to obtain quantifying data for one or more than one metabolite marker;

c) comparing said quantifying data to corresponding data obtained from one or more than one reference sample; and d) using said comparison to determine whether the therapy is improving the demented state of the patient.

The step of analyzing (step b) may comprise analyzing the sample by liquid chromatography mass spectrometry (LC-MS), or alternatively may comprise analyzing the sample by liquid chromatography and linear ion trap mass spectrometry when the method is a highthroughput method.

In the method as just described, the one or more than one reference sample may be a plurality of samples obtained from a non-demented control individuals; a plurality of samples obtained from a clinically diagnosed AD patient; one or more than one pre-therapy baseline sample obtained from the patient; or any combination thereof.

In one aspect of the above method, the sample and the reference sample are serum samples, and the one or more than one metabolite marker is selected from the metabolites listed in Tables 1 to 7, or a combination thereof. These metabolite marker markers needed for optimal diagnosis may be selected from the group consisting of phosphatidylcholine-related compounds, ethanol amine plasmalogens, endogenous fatty acids, essential fatty acids, lipid oxidation byproducts, metabolite derivatives of said metabolite classes, and any metabolite that may contribute in any way to the anabolic/catabolic metabolism of said metabolite classes. Of particular interest are the metabolites with accurate masses measured in Daltons of, or substantially equivalent to, 541.3432, 569.3687, 699.5198, 723.5195, 723.5197, 751.5555, 803.568, 886.5582.

In another aspect, the sample and the reference sample are cerebrospinal fluid (CSF) samples, and the one or more than one metabolite marker is selected from the metabolites listed in Table 13, or a combination thereof. Of particular interest are the metabolites with accurate masses measured in Daltons of, or substantially equivalent to, 207.0822, 275.8712, 371.7311, 373.728, 432.1532, 485.5603, 487.6482, 562.46, 622.2539, 640.2637, 730.6493, 742.2972.

In a third aspect, the sample and the reference sample are serum samples, and the one or more than one metabolite marker may be selected from metabolites M05 to M24 with accurate masses of, or substantially equivalent to those listed in Table 18. Of these metabolites, the metabolites with accurate masses measured in Daltons of, or substantially equivalent to, 701.53591, 699.52026, 723.52026, 747.52026, 729.56721, 727.55156, 779.58286, and 775.55156 may be of particular interest.

The present invention also provides a method for evaluating the efficacy of a therapy for treating dementia in a patient, comprising:
 a) obtaining a sample from said patient;
 b) analyzing said sample to obtain quantifying data for one or more than one metabolite marker;
 c) obtaining a ratio for each of the one or more than one metabolite marker to an internal control metabolite;
 d) comparing each ratio of said one or more than one metabolite marker to the internal control metabolite to corresponding data obtained from one or more than one reference sample; and
 e) using said comparison to determine whether the therapy is improving the demented state of the patient.

The step of analyzing (step b) may comprise analyzing the sample by liquid chromatography mass spectrometry (LC-MS), or alternatively may comprise analyzing the sample by liquid chromatography and linear ion trap mass spectrometry when the method is a highthroughput method.

In the method as just described, the one or more than one reference sample may be a plurality of samples obtained from a non-demented control individuals; a plurality of samples obtained from a clinically diagnosed AD patient; one or more than one pre-therapy baseline sample obtained from the patient; or any combination thereof.

In the method as described above, the sample and said reference sample are serum samples, and the one or more than one metabolite marker may be selected from metabolites M05 to M24 with accurate masses of, or substantially equivalent to those listed in Table 18. Of particular interest are the metabolites with accurate masses measured in Daltons of, or substantially equivalent to, 701.53591, 699.52026, 723.52026, 747.52026, 729.56721, 727.55156, 779.58286, and 775.55156, and the internal control metabolite with accurate mass measured in Daltons of, or substantially equivalent to, 719.54648.

The methods of the present invention, including HTS assays, can be used for the following, wherein the specific "health-state" in this application refers to, but is not limited to dementia:

1. identifying small-molecule metabolite biomarkers which can discriminate between multiple health-states using any biological sample taken from an individual, 2. specifically diagnosing a health-state using metabolites identified in serum, plasma, whole blood, serum, CSF, and/or other tissue biopsy as described in this application, 3. selecting the minimal number of metabolite features required for optimal diagnostic assay performance statistics using supervised statistical methods such as those mentioned in this application, 4. identifying structural characteristics of biomarker metabolites selected from non-targeted metabolomic analysis using LC-MS/MS, MSn and NMR, 5. developing a high-throughput LC-MS/MS method for assaying selected metabolite levels in serum, 6. diagnosing a given health-state, or risk for development of a health-state by determining the levels of any combination of metabolite features disclosed from the FTMS analysis patient serum, using any method including but not limited to mass spectrometry, NMR, UV detection, ELISA (enzyme-linked immunosorbant assay), chemical reaction, image analysis, or other.

The impact of the present invention on the diagnosis of dementia would be tremendous, as literally everyone could be screened longitudinally throughout their lifetime to assess risk. Given that the performance characteristics of the test of the present invention are representative for the general population, this test alone may be superior to any other currently available screening method, as it may have the potential to detect disease progression prior to the emergence of clinical symptoms.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a mean signal-to-noise +/−SEM of the AD serum 8 biomarker panel for each different clinical group (AD with significant cognitive impairment, Non-AD dementia, and AD with no significant cognitive impairment) relative to non-demented controls.

FIG. 16 shows the fragments obtained for the MS/MS analysis of the 751.5555 metabolite, along with its proposed structure.

FIG. 17 shows the fragments obtained for the MS/MS analysis of the 699.5198 metabolite, along with its proposed structure.

FIG. 20 shows the general structure of ethanolamine phospholipids, as well as the naming convention used herein.

DETAILED DESCRIPTION

Figure 2:
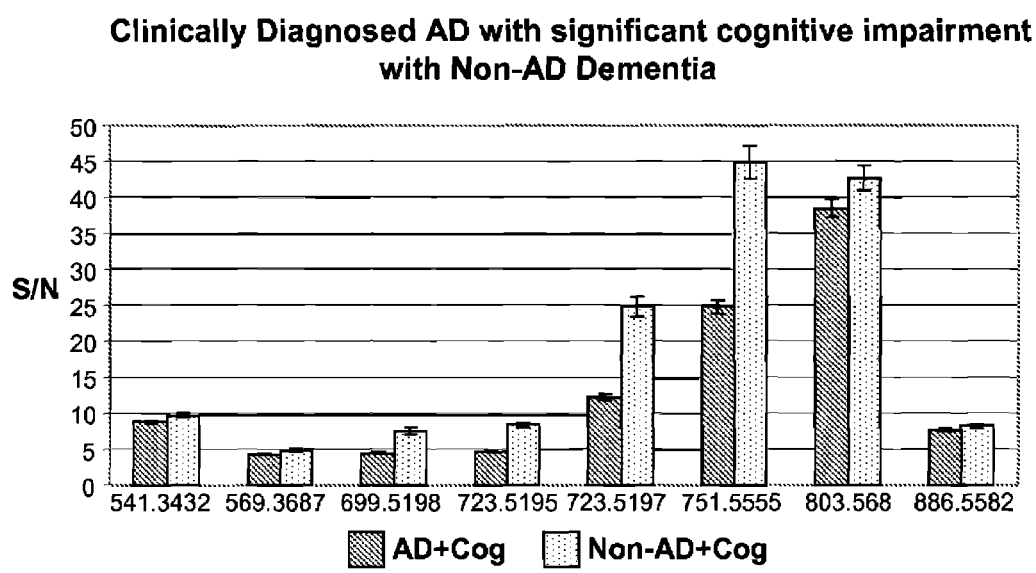
FIG. 2 shows a mean signal-to-noise +/−SEM of the AD serum 8 biomarker panel for two clinical groups with a significant cognitive impairment (AD and Non-AD dementia).

The present invention relates to small molecules or metabolites that are found to have significantly different abundances between clinically diagnosed dementia or other neurological disorders, and normal patients. The present invention also relates to methods for diagnosing dementia and other neurological disorders.

The present invention provides novel methods for discovering, validating, and implementing a metabolite markers for one or more diseases or particular health-states. In one embodiment of the present invention, there is provided a method for identifying specific biomarkers for differentially diagnosing AD dementia, non-AD dementia, cognitive impairment, or a combination thereof, comprising the steps of: introducing one or more than one sample from one or more than one patient with clinically diagnosed AD dementia, clinically diagnosed non-AD dementia, or significant cognitive impairment, said sample containing a plurality of metabolites into a high resolution mass spectrometer (for example, and without wishing to be limiting, a Fourier Transform Ion Cyclotron Resonance Mass Spectrometer (FTMS)); obtaining, identifying and quantifying data for the metabolites; creating a database of said identifying and quantifying data; comparing the identifying and quantifying data from the sample with corresponding data from a sample from a non-demented normal patient; identifying one or more than one metabolites that differ. The metabolite markers identified using the method of the present invention may include the metabolites listed in Tables 1-7, 10-13, and 18. The method may further comprise selecting the minimal number of metabolite markers needed for optimal diagnosis.

In order to determine the biochemical markers of a given health-state in a particular population, a group of patients representative of the health state (i.e. a particular disease) and/or a group of "normal" counterparts are required. Biological samples taken from the patients in the particular health-state category can then be compared to the same samples taken from the normal population as well as to patients in similar health-state category in the hopes of identifying biochemical differences between the two groups, by analyzing the biochemicals present in the samples using FTMS and/or LC-MS.

The method for the discovery of metabolite markers as described above may be done using non-targeted metabolomic strategies or methods. Multiple non-targeted metabolomics strategies have been described in the scientific literature including NMR [18], GC-MS [19-21], LC-MS, and FTMS strategies [18, 22-24]. The metabolic profiling strategy employed for the discovery of differentially expressed metabolites in the present invention was the non-targeted FTMS strategy by Phenomenome Discoveries [21, 24-27; see also US Published Application No. 2004-0029120 A1, Canadian Application No. 2,298,181, and WO 0157518]. Non-targeted analysis involves the measurement of as many molecules in a sample as possible, without any prior knowledge or selection of components prior to the analysis. Therefore, the potential for non-targeted analysis to discover novel metabolite biomarkers is high versus targeted methods, which detect a predefined list of molecules. The present invention uses a non-targeted method to identify metabolite components in serum samples that differ between clinically diagnosed AD individuals and non AD individuals. The same technology was used to identify metabolite components that differ between clinically diagnosed AD individuals with dementia from clinically diagnosed non-AD individuals with dementia in CSF samples.

However, a person skilled in the art would recognize that other metabolite profiling strategies could be used to discover some or all of the differentially regulated metabolites disclosed in the present invention and that the metabolites described herein, however discovered or measured, represent unique chemical entities that are independent of the analytical technology that may be used to detect and measure them.

The present invention also provides a method for differentially diagnosing dementia or the risk of dementia in a patient, the method comprising the steps of:
a) obtaining a sample from said patient;
b) analyzing said sample to obtain quantifying data for one or more than one metabolite marker;
c) comparing the quantifying data for said one or more than one metabolite marker to corresponding data obtained from one or more than one reference sample; and
d) using said comparison to differentially diagnose dementia or the risk of dementia.

The step of analyzing the sample (steb b) may comprise analyzing the sample using a mass spectrometer (MS). For example, and without wishing to be limiting, such mass spectrometer could be of the FTMS, orbitrap, time of flight (TOF) or quadrupole types. Alternatively, the mass spectrometer could be equipped with an additional pre-detector mass filter. For example, and without wishing to be limiting such instruments are commonly referred to as quadrupole-FTMS (Q-FTMS), quadrupole-TOF (Q-TOF) or triple quadrupole (TQ or QQQ). In addition, the mass spectrometer could be operated in either the parent ion detection mode (MS) or in MSn mode, where $n \geq 2$. MSn refers to the situation where the parent ion is fragmented by collision induced dissociation (CID) or other fragmentation procedures to create fragment ions, and then one or more than one of said fragments are detected by the mass spectrometer. Such fragments can then be further fragmented to create further fragments. Alternatively, the sample could be introduced into the mass spectrometer using a liquid or gas chromatographic system or by direct injection.

By the term "differential diagnosis" or "differentially diagnosing", it is meant that various aspects of a disease state may be distinguished from one another. In particular, the present invention allows for differential diagnosis a various states of dementia; for example and without wishing to be limiting, the present invention may provide differential diagnosis of AD dementia, non-AD dementia, cognitive impairment, or a combination thereof.

The diagnosis of or the exclusion of any types of neurological disorders is contemplated by the present invention, using all or a subset of the metabolites disclosed herein. The term "dementia" is used herein as a broad term indicating both cognitive impairment as well as pathologies causing cognitive impairment. Dementia may be caused by a number of neurological disorders. "AD dementia" as used herein refers to dementia caused by Alzheimer's disease (AD, which may also be referred to herein as "SDAT"); types of "non-AD dementia" include, but are not limited to, dementia with Lewy bodies (DLB), frontotemporal lobe dementia (FTD), vascular induced dementia (e.g. multi-infarct dementia), anoxic event induced dementia (e.g. cardiac arrest), trauma to the brain induced dementia (e.g. dementia pugilistica [boxer's dementia]), dementia resulting from exposure to an infectious (e.g. Creutzfeldt-Jakob Disease) or toxic agent (e.g. alcohol-induced dementia), Autism, Multiple Sclerosis, Parkinson's Disease, Bipolar Disorder, Ischemia, Huntington's Chorea, Major Depressive Disorder, Closed Head Injury, Hydrocephalus, Amnesia, Anxiety Disorder, Traumatic Brain Injury, Obsessive Compulsive Disorder, Schizophrenia, Mental Retardation, and/or Epilepsy. Of particular interest are AD dementia, and FTD and DLB non-AD dementias.

Cognitive impairment can be assessed by any method known in the art. For example, and without wishing to be limiting, the Alzheimer's Disease Assessment Scale (ADAS)-cognitive subset may be used. This neuropsychological test is used to test the language ability (speech and comprehension), memory, ability to copy geometric figures and orientation to current time and place. Errors on the test are recorded resulting in a reverse score impairment (i.e., the higher the score on ADAS, the greater the cognitive impairment). A score of 0-15 is considered normal, 16-47 is considered mild-moderate impairment and a score of 48-70 is considered moderate-severe impairment [28]. Another neuropsychological test, Folstein's Mini-Mental State Exam (MMSE), which measures cognitive impairment, may be used. The MMSE is widely used and is an extensively validated test of orientation, short and long-term memory, praxis, language and comprehension. A person skilled in the art would recognize that additional neuropsychological assessment that measure aspects of the same cognitive deficit, such as, but not exclusive to, the Blessed Roth Dementia Rating Scale, the 7-Minute Screen, Wechsler Memory Scale (WMS), Halstead-Reitan Battery, Rey Auditory Verbal Learning Test, California Verbal Learning Test, Buschke Selective Reminding Test, Boston Naming Test, Clinical Evaluation of Language Functioning, Peabody Picture Vocabulary Tests, Mattis Dementia Rating Scale, Memory Assessment Scale, Tests of Memory and Learning, Wide Range Assessment of Memory and Learning, can also be used.

In addition, a person skilled in the art would recognize that any imaging technique that has the potential to show a cognitive impairment or structural change, such as, but not exclusive to, structural magnetic resonance imaging (MRI), positron emission tomography (PET), computerized tomography (CT), functional magnetic resonance imaging (fMRI), electroencephalography (EEG), single positron emission tomography (SPECT), event related potentials, magnetoencephalography, multi-modal imaging, would be measuring the structural/regional brain areas that are responsible for that cognitive deficit and AD pathology, and therefore, would be related to the metabolites disclosed in this invention.

In accordance with the present invention, any type of biological sample that originates from anywhere within the body, for example but not limited to, blood (serum/plasma), CSF, urine, stool, breath, saliva, or biopsy of any solid tissue including tumor, adjacent normal, smooth and skeletal muscle, adipose tissue, liver, skin, hair, brain, kidney, pancreas, lung, colon, stomach, or other may be used. Of particular interest are samples that are serum or CSF. While the term "serum" is used herein, those skilled in the art will recognize that plasma or whole blood or a sub-fraction of whole blood may also be used. CSF may be obtained by a lumbar puncture requiring a local anesthetic.

In a non-limiting example, when a blood sample is drawn from a patient there are several ways in which the sample can be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are also contemplated by the present invention.

In another non-limiting example, CSF samples may be collected using a lumbar puncture procedure; a local anesthetic is applied to the lower back. A needle is then inserted into the numbed skin between the L4 and L5 vertebrae until it pierces the subdural space. The CSF may be collected into sterile tubes.

For example, but not considered to be limiting in any manner, while obtaining a CSF sample may result in more discomfort for the patient than taking a blood sample, a CSF assay used after a positive result on a AD-specific serum test, a differential diagnosis between AD and non-AD has a higher degree of confirmation.

Without wishing to be limiting in any manner, the processed blood, serum or CSF sample described above may then be further processed to make it compatible with the methodical analysis technique to be employed in the detection and measurement of the metabolites contained within the processed serum or CSF sample. The types of processing can range from as little as no further processing to as complex as differential extraction and chemical derivatization. Extraction methods could include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. A method of particular interest for extracting metabolites for FTMS non-targeted analysis is to perform a liquid/liquid extraction whereby non-polar metabolites dissolve in an organic solvent and polar metabolites dissolve in an aqueous solvent.

The extracted samples may be analyzed using any suitable method know in the art. For example, and without wishing to be limiting in any manner, extracts of biological samples are amenable to analysis on essentially any mass spectrometry platform, either by direct injection or following chromatographic separation. Typical mass spectrometers are comprised of a source which ionizes molecules within the sample, and a detector for detecting the ionized molecules or fragments of molecules. Non-limiting examples of common sources include electron impact, electrospray ionization (ESI), atmospheric pressure chemical ionization (APCI), atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), Orbitrap, and derivations and combinations thereof. The advantage of FTMS over other MS-based platforms is its high resolving capability that allows for the separation of metabolites differing by only hundredths of a Dalton, many of which would be missed by lower resolution instruments.

By the term "metabolite", it is meant specific small molecules, the levels or intensities of which are measured in a sample, and that may be used as markers to diagnose a disease state. These small molecules may also be referred to herein as "metabolite marker", "metabolite component", "biomarker", or "biochemical marker".

The metabolites are generally characterized by their accurate mass, as measured by mass spectrometry technique used in the above method. The accurate mass may also be referred to as "accurate neutral mass" or "neutral mass". The accurate mass of a metabolite is given herein in Daltons (Da), or a mass substantially equivalent thereto. By "substantially equivalent thereto", it is meant that a +/−5 ppm difference in the accurate mass would indicate the same metabolite, as would be recognized by a person of skill in the art. The accurate mass is given as the mass of the neutral metabolite. As would be recognized by a person of skill in the art, the ionization of the metabolites, which occurs during analysis of the sample, the metabolite will cause either a loss or gain of one or more hydrogen atoms and a loss or gain of an electron. This changes the accurate mass to the "ionized mass", which differs from the accurate mass by the mass of hydrogens and electrons lost or gained during ionization. Unless otherwise specified, the accurate neutral mass will be referred to herein.

Similarly, when a metabolite is described by its molecular formula or structure, the molecular formula or structure of the neutral metabolite will be given. Naturally, the molecular formula or structure of the ionized metabolite will differ from the neutral molecular formula or structure by the number of hydrogens lost or gained during ionization.

Data is collected during analysis and quantifying data for one or more than one metabolite is obtained. "Quantifying data" is obtained by measuring the levels or intensities of specific metabolites present in a sample.

The quantifying data is compared to corresponding data from one or more than one reference sample. The "reference sample" is any suitable reference sample for the particular disease state. For example, and without wishing to be limiting in any manner, in the present invention the reference sample may be a sample from a non-demented control individual, i.e., a person not suffering from AD dementia, non-AD dementia or cognitive impairment (also referred to herein as a "'normal' counterpart"); the reference sample may also be a sample obtained from a patient with clinically diagnosed with AD, a patient with clinically diagnosed non-AD dementia, or a patient diagnosed with significant cognitive impairment. As would be understood by a person of skill in the art, more than one reference sample may be used for comparison to the quantifying data. For example and without wishing to be limiting, the one or more than one reference sample may be a first reference sample obtained from a non-demented control individual. The one or more than one reference sample may further include a second reference sample obtained from a patient with clinically diagnosed AD-dementia, a third reference sample obtained from a patient with clinically diagnosed non-AD dementia, a fourth reference sample obtained from a patient suffering from significant cognitive impairment, or any combination thereof.

The present invention also provides novel compounds, identified using the methods of the present invention. The novel compounds may be used as metabolite markers in the differential diagnosis of dementia, as described above.

In one embodiment, the compounds may be selected from the metabolites listed in Tables 1 to 7, or a combination thereof. These metabolites were identified in serum samples, and may be phosphatidylcholine-related compounds, ethanolamine plasmalogens, endogenous fatty acids, essential fatty acids, lipid oxidation byproducts, metabolite derivatives of said metabolite classes, and any metabolite that may contribute in any way to the anabolic/catabolic metabolism of said metabolite classes.

An optimal panel of compounds may be identified from those metabolites listed in Tables 1 to 7. For example and without wishing to be limiting, the metabolite markers may be metabolites with accurate masses measured in Daltons of, or substantially equivalent to, 541.3432, 569.3687, 699.5198, 723.5195, 723.5197, 751.5555, 803.568, 886.5582. The metabolites of accurate masses 699.5198, 723.5195, 723.5197, and 751.555 have presently been identified as ethanolamine plasmalogens, and are specifically decreased in patients with AD dementia. The metabolite markers of accurate masses 541.3432, 569.3687, 803.568, and 886.5582 have presently been identified as phosphatidylcholine related metabolites, and are decreased in patients with cognitive impairment on ADAS-cog, and severity of cognitive impairment correlates to the degree of decrease.

Figure 6:
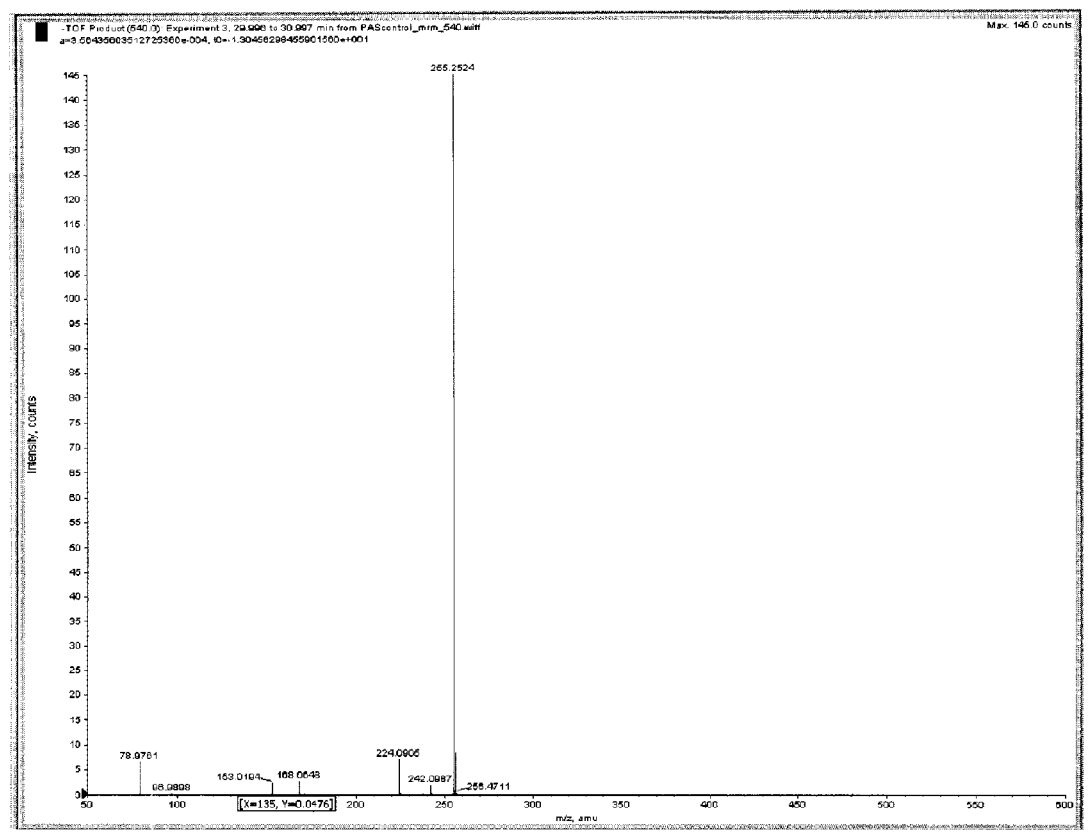
FIG. 6 shows MS/MS spectra for metabolite 541.3432 with CE voltage −50V.
Figure 7:
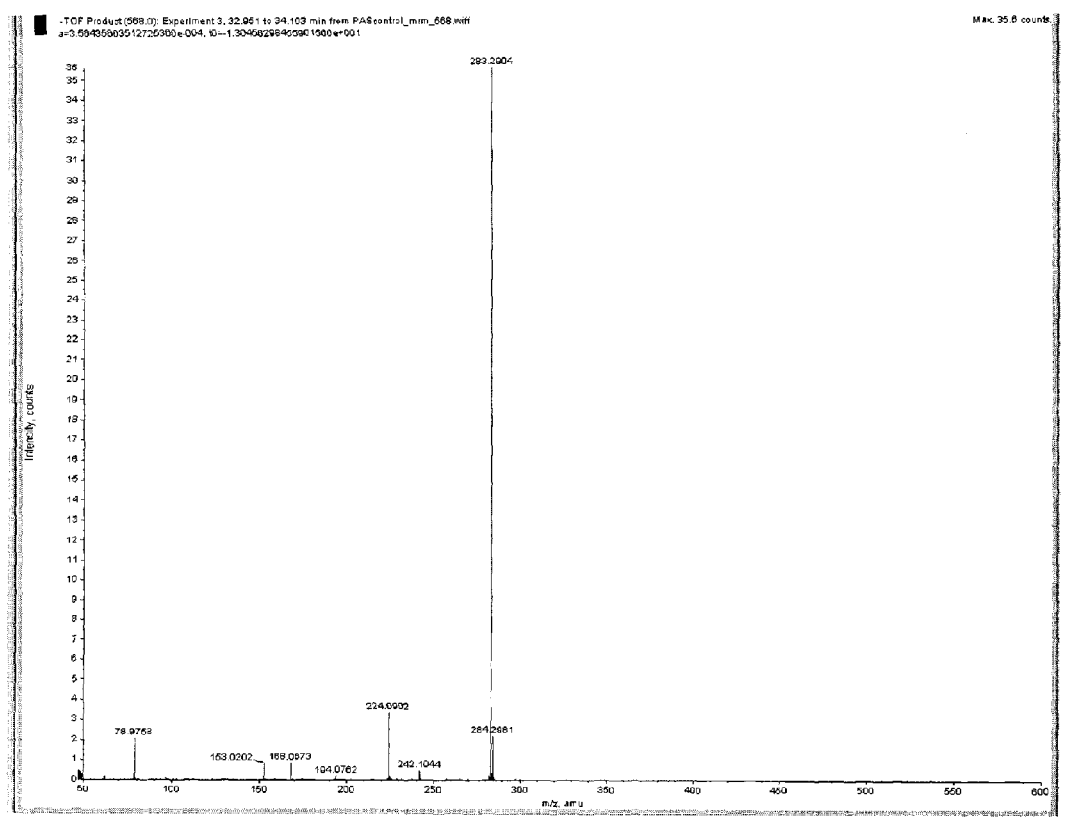
FIG. 7 shows MS/MS spectra for metabolite 569.3687 with CE voltage −50V.
Figure 8:
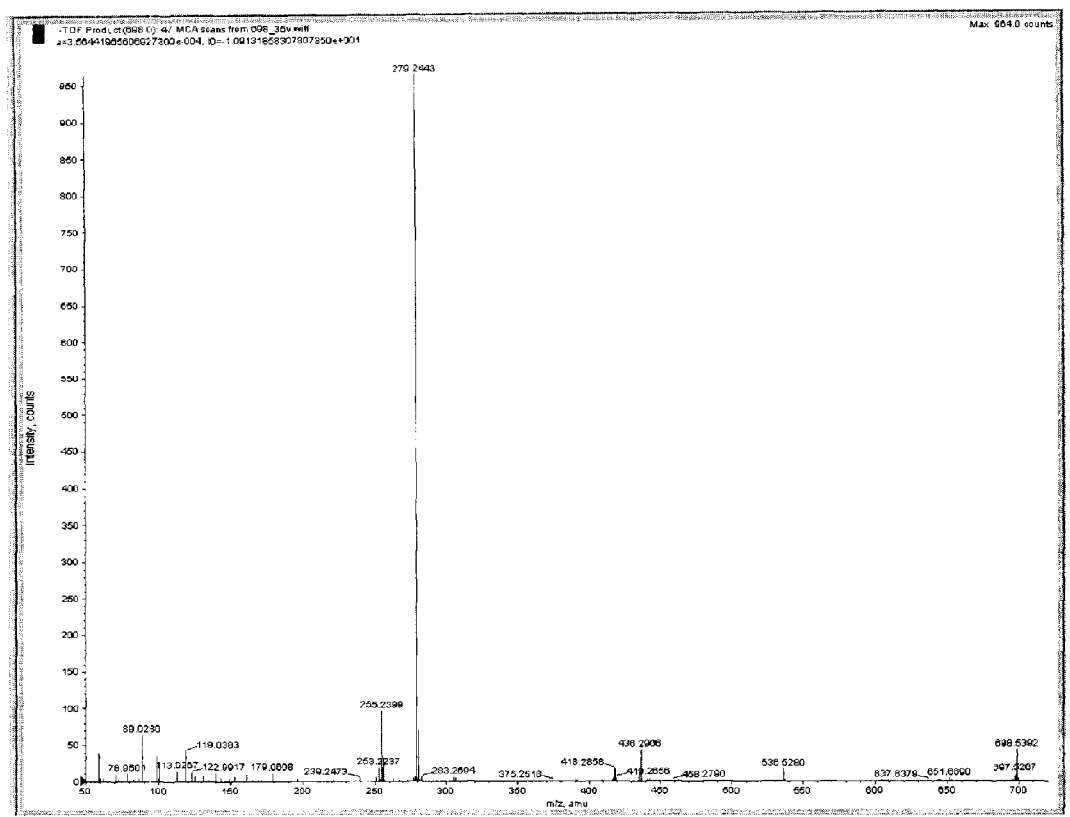
FIG. 8 shows MS/MS spectra for metabolite 699.5198 with CE voltage −50V.
Figure 9:
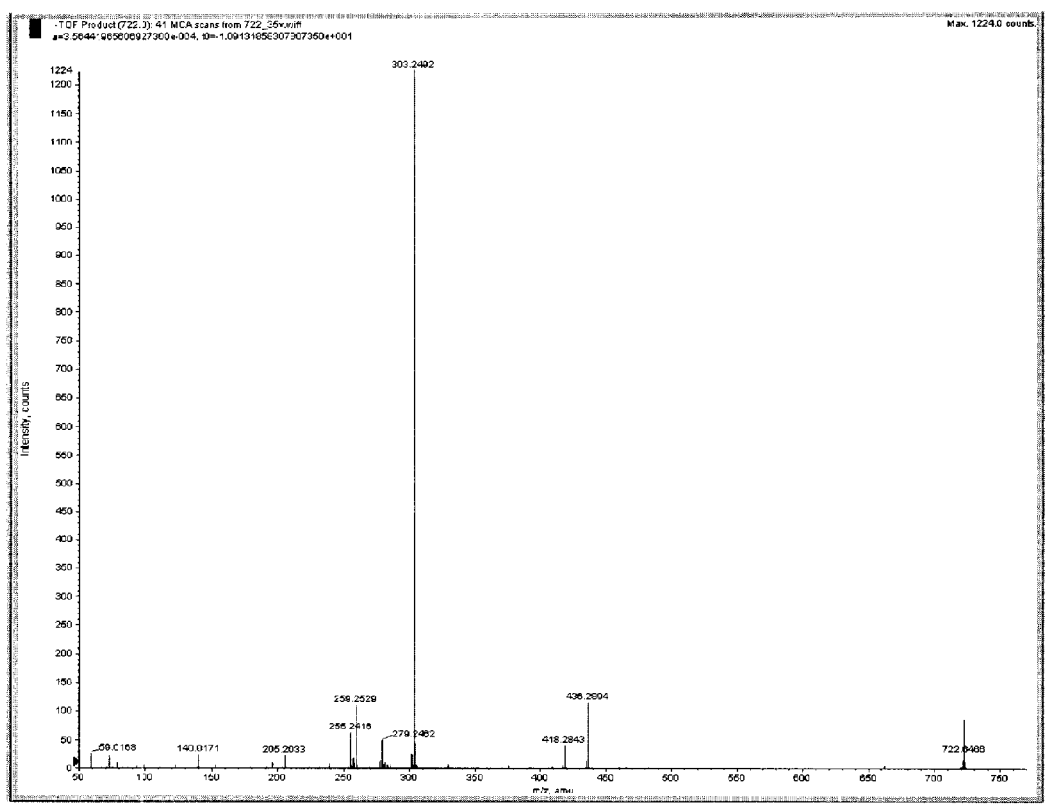
FIG. 9 shows MS/MS spectra for metabolite 723.5195 with CE voltage −50V.
Figure 10:
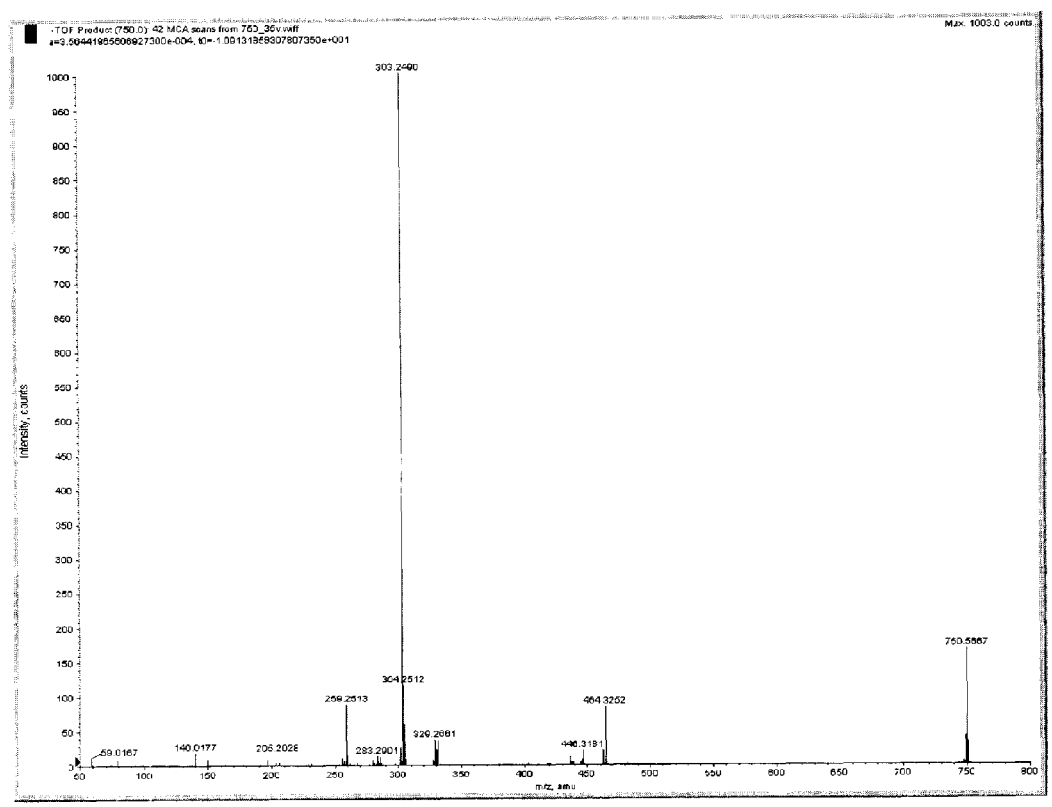
FIG. 10 shows MS/MS spectra for metabolite 751.5555 with CE voltage −50V.
Figure 11:
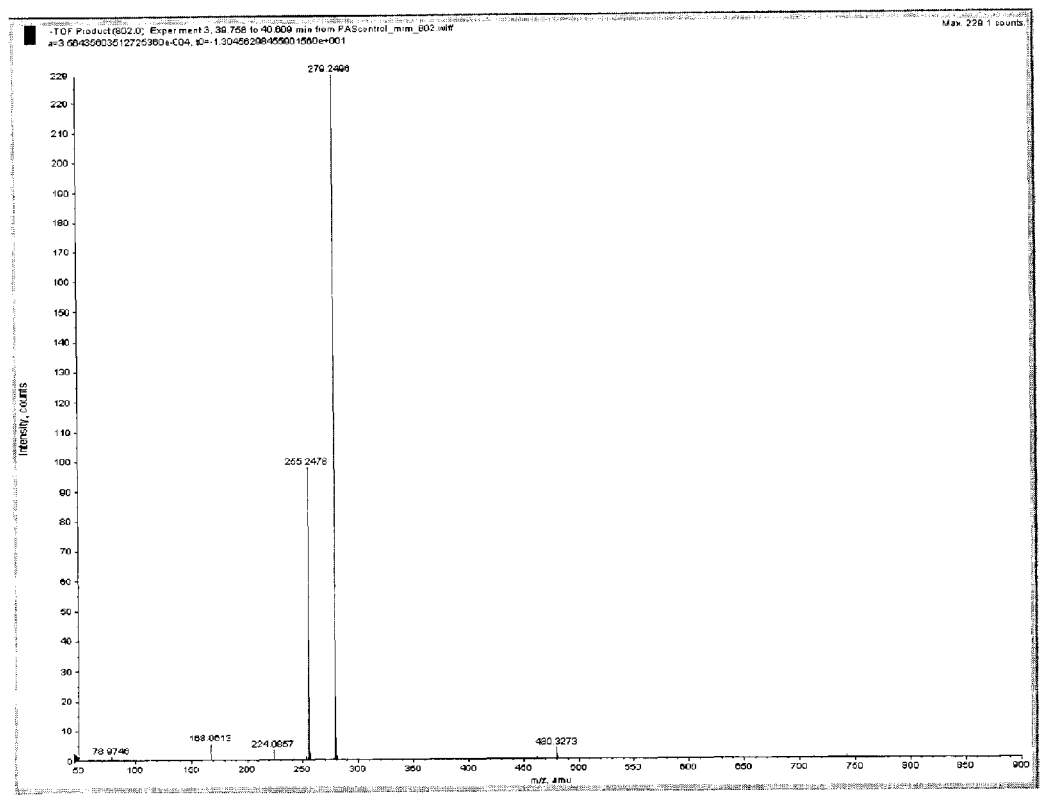
FIG. 11 shows MS/MS spectra for metabolite 803.568 with CE voltage −50V.
Figure 12:
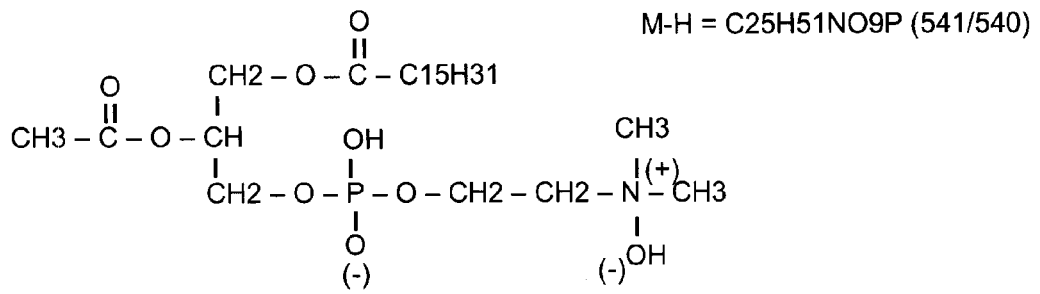
FIG. 12 shows structural determination of ADAS-cog serum biomarker 541.3432.
Figure 13:
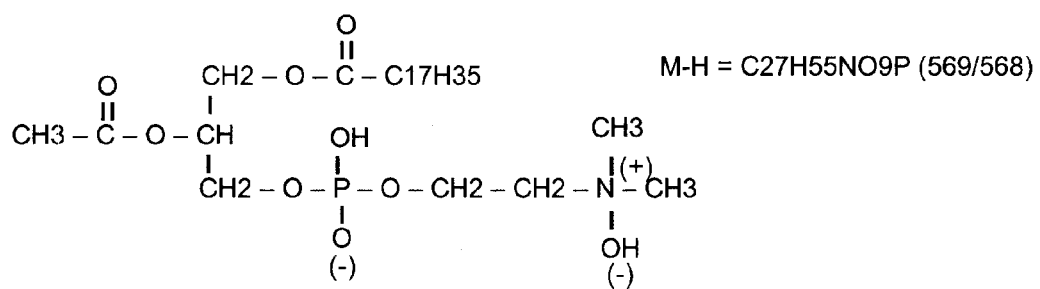
FIG. 13 shows structural determination of ADAS-cog serum biomarker 569.3687.
Figure 14:
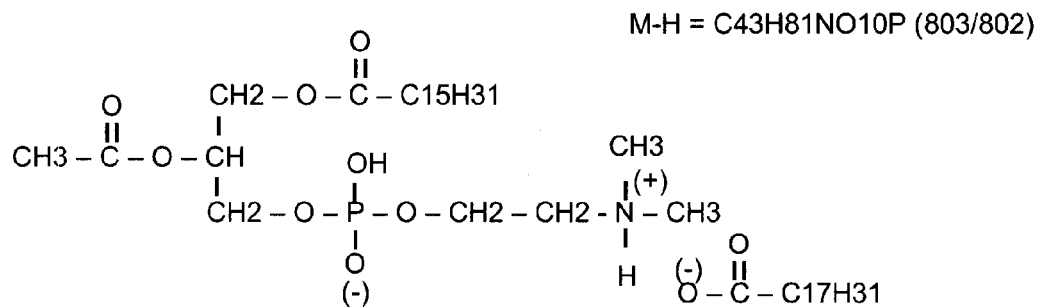
FIG. 14 shows structural determination of ADAS-cog serum biomarker 803.568.
Figure 18:
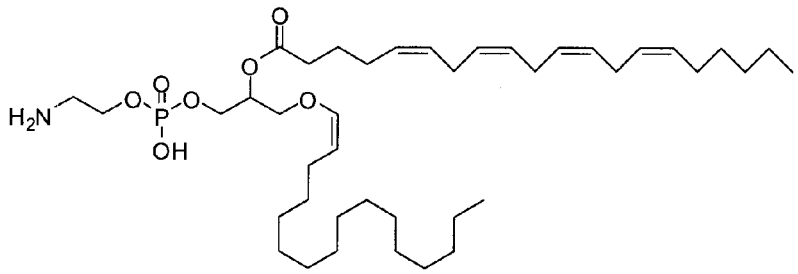
FIG. 18 shows the fragments obtained for the MS/MS analysis of the 723.5195 metabolite, along with its proposed structure.
Figure 19:
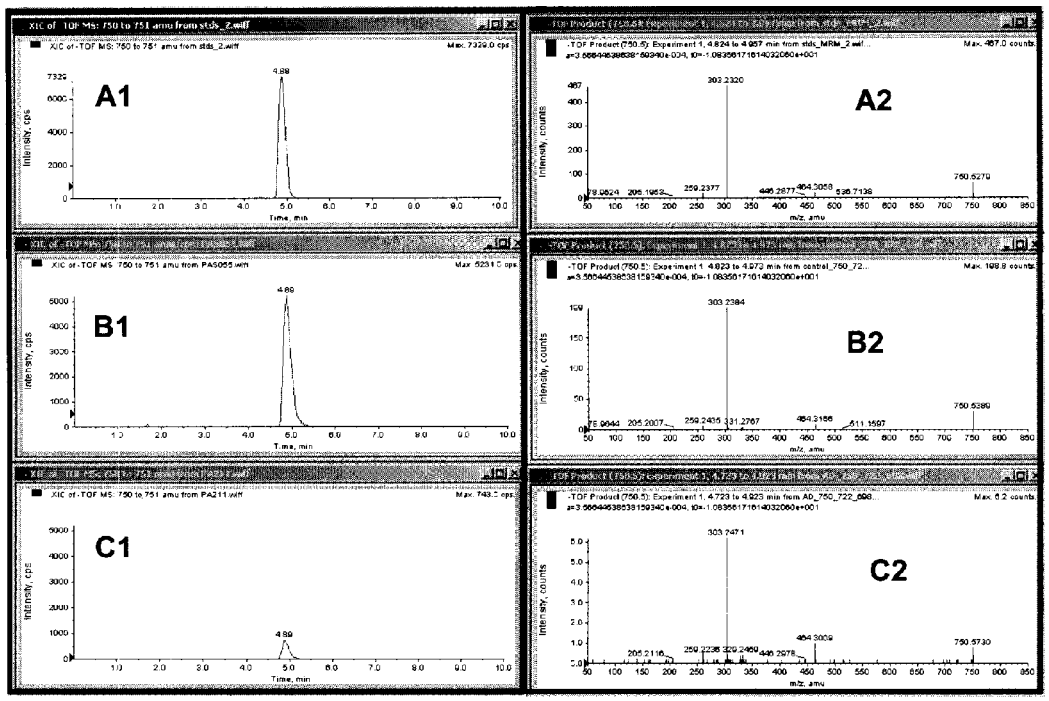
FIG. 19 shows the LC-MS and MS/MS analysis of the 751.5555 metabolite (18:0/20:4 EtnPls). Panel A1 is an extracted ion chromatogram (EIC) of parent ion 750 (M-H—) of a pure standard; panel A2 is MS/MS spectra of parent ion M/Z750 @ retention time 4.8-5.0 minutes. Panel B1 is the EIC of parent ion 750 from a cognitively normal subject; panel B2 is the MS/MS spectra of parent ion M/Z 750@4.8-5.0 min. Panel C1 is the EIC of parent ion 750 from an AD subject; and panel C2 is the MS/MS spectra of parent ion M/Z 750 @4.8-5.0 min.

The metabolites with accurate masses measured in Daltons of, or substantially equivalent to, a) 541.3432, b) 569.3687, c) 699.5198, d) 723.5195, e) 751.5555, f) 803.568, can be further characterized by a) an extracted ion chromatogram (EIC) as shown in FIG. 4A, and an MS/MS spectrum as shown in FIG. 6; a molecular formula of $C_{25}H_{51}NO_9P$; and/or the structure shown in FIG. 12;

b) an EIC as shown in FIG. 4B, and an MS/MS spectrum as shown in FIG. 7; a molecular formula of $C_{27}H_{55}NO_9P$; and/or the structure shown in FIG. 13;

c) an EIC as shown in FIG. 4C, and an MS/MS spectrum as shown in FIG. 8; a molecular formula of $C_{39}H_{74}NO_7P$; and/or the structure shown in FIG. 17;

d) an EIC as shown in FIG. 4D, and an MS/MS spectrum as shown in FIG. 9; a molecular formula of $C_{41}H_{74}NO_7P$; and/or the structure shown in FIG. 18;

e) an EIC as shown in FIG. 4E, and an MS/MS spectrum as shown in FIG. 10; a molecular formula of $C_{43}H_{78}NO_7P$; and/or the structure shown in FIG. 19;

f) an EIC as shown in FIG. 4F, and an MS/MS spectrum as shown in FIG. 11; a molecular formula of $C_{43}H_{81}NO_{10}P$; and/or the structure shown in FIG. 14, respectively.

It is presently shown that the ethanolamine plasmalogen metabolites (neutral masses 699.5198, 723.5195, 751.5555) and the phosphatidylcholine metabolites (neutral masses 699.5198, 723.5195, 751.5555) are decreased in the serum of AD subjects exhibiting significant cognitive impairment. This is the first report of serum-based changes in these metabolites associated with AD and dementia. It is further shown that the decrease in the disclosed serum phospatidylcholine related metabolites occurs in all patients exhibiting a significant cognitive impairment as measured by the ADAS-cog regardless of AD status, and that the degree of decrease correlates with the severity of the cognitive impairment. However, the observed decrease in disclosed ethanolamine plasmalogens is independent of cognitive impairment, occurs specifically in subjects with AD and is therefore a true diagnostic of AD.

Ethanolamine plasmalogens are a type of ethanolamine phospholipid. Ethanolamine phospholipids can be further differentiated based on their sn-I configurations (either acyl, ether, or vinyl ether). The sn-2 position is typically acyl and the sn-3 position contains the phosphoethanolamine moiety. Therefore, the three classes are described as either diacyl (also referred to herein as PtdEt), alkyl-acyl (also referred to herein as plasmanyl) or alkenyl-acyl (also referred to herein as EtnPl or plasmenyl). Various basic structures of ethanolamine phospholipids are shown in FIG. 20, along with the standard naming convention used herein.

A decrease in the disclosed ethanolamine plasmalogens may represent the initial or early stages AD, and can be detected non-invasively in living subjects by measuring serum levels of specific ethanolamine plasmalogens. Similarly, cognitive impairment can be quantitated non-invasively by measuring the serum levels of specific phosphatidylcholine metabolites.

Other metabolites have also been identified. For example, the metabolites with accurate masses measured in Daltons of, or substantially equivalent to, a) 541.3432, b) 569.3687, c) 699.5198, d) 723.5195, e) 751.5555, f) 803.568, which may be further characterized by a) the molecular formula $C_{27}H_{55}NO_9P$; and/or the structure shown in FIG. 15A b) the molecular formula $C_{27}H_{55}NO_9P$; and/or the structure shown in FIG. 15B c) the molecular formula $C_{43}H_{83}NO_{10}P$; and/or the structure shown in FIG. 15C;

d) the molecular formula $C_{45}H_{81}NO_{10}P$; and/or the structure shown in FIG. 15D;

e) the molecular formula $C_{45}H_{83}NO_{10}P$; and/or the structure shown in FIG. 15E;

f) the molecular formula $C_{45}H_{85}NO_{10}P$; and/or the structure shown in FIG. 15F;

g) the molecular formula $C_{47}H_{83}NO_{10}P$; and/or the structure shown in FIG. 15G, respectively.

Based on the identification of metabolites specific to AD dementia (accurate masses 699.5198, 723.5195, 723.5197, 751.555) as ethanolamine plasmalogens, other ethanolamine phospholipid metabolite markers were identified. These are metabolites M05 to M24 as listed and characterized (accurate mass, name/composition, molecular formula) in Table 18. The structure of the metabolite can be deduced based on the metabolite name as indicated in Table 18 and the nomenclature, as indicated in FIG. 20.

Figure 21:
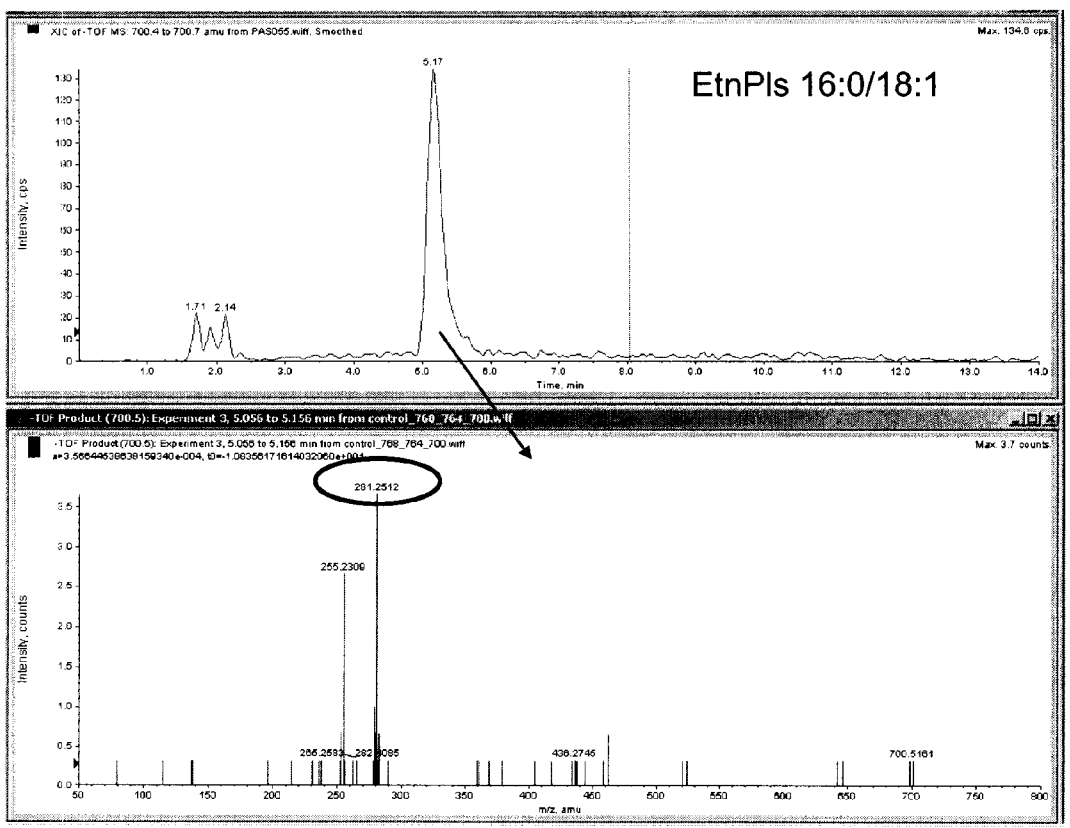
FIG. 21 is an extracted ion chromatogram (upper panel) and MS/MS spectrum (lower panel) of EtnPls 16:0/18:1 (M15) in human serum.

Of the compounds listed in Table 18, those of particular interest include metabolites with accurate masses measured in Daltons of, or substantially equivalent to, a) 701.53591, b) 699.52026, c) 723.52026, d) 747.52026, e) 729.56721, f) 727.55156, g) 779.58286, and h) 775.55156, which can be further characterized by a) a MS/MS spectrum as shown in FIG. 21; molecular formula $C_{27}H_{55}NO_9P$; and/or the structure

Figure 22:
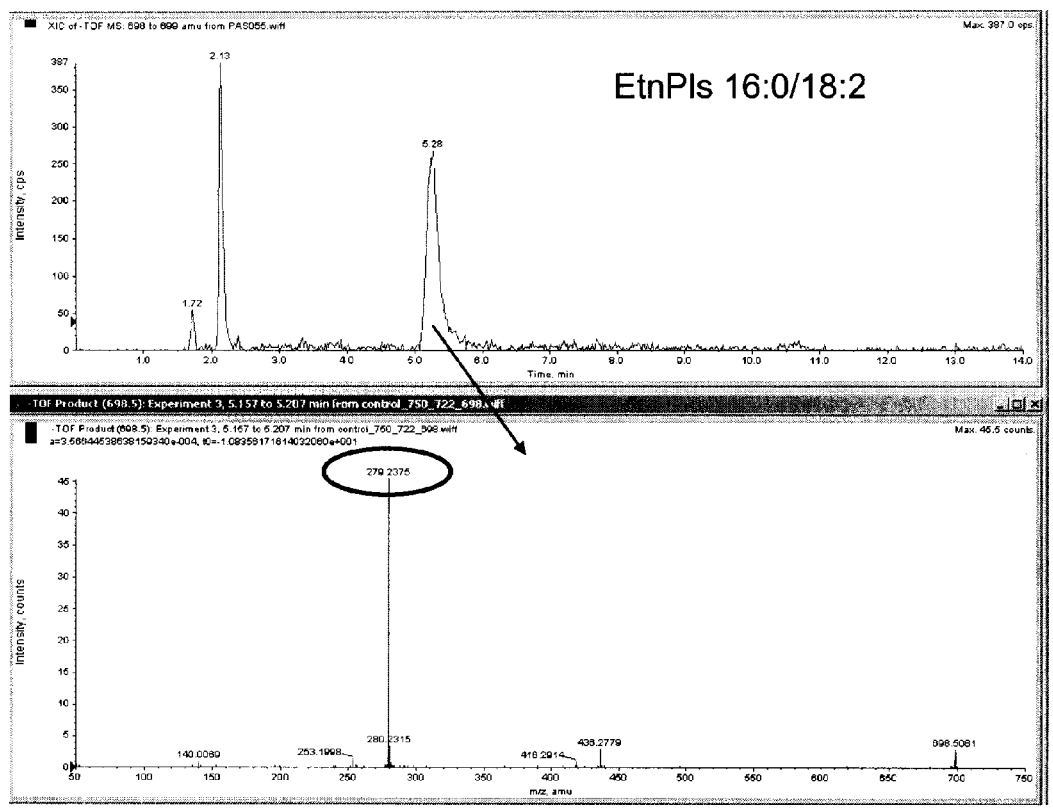
FIG. 22 is an extracted ion chromatogram (upper panel) and MS/MS spectrum (lower panel) of EtnPls 16:0/18:2 (M16) in human serum.

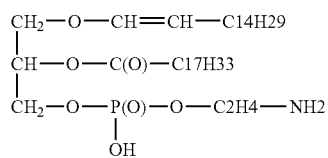

b) a MS/MS spectrum as shown in FIG. 22; molecular formula $C_{39}H_{74}NO_7P$; and/or the structure

Figure 23:
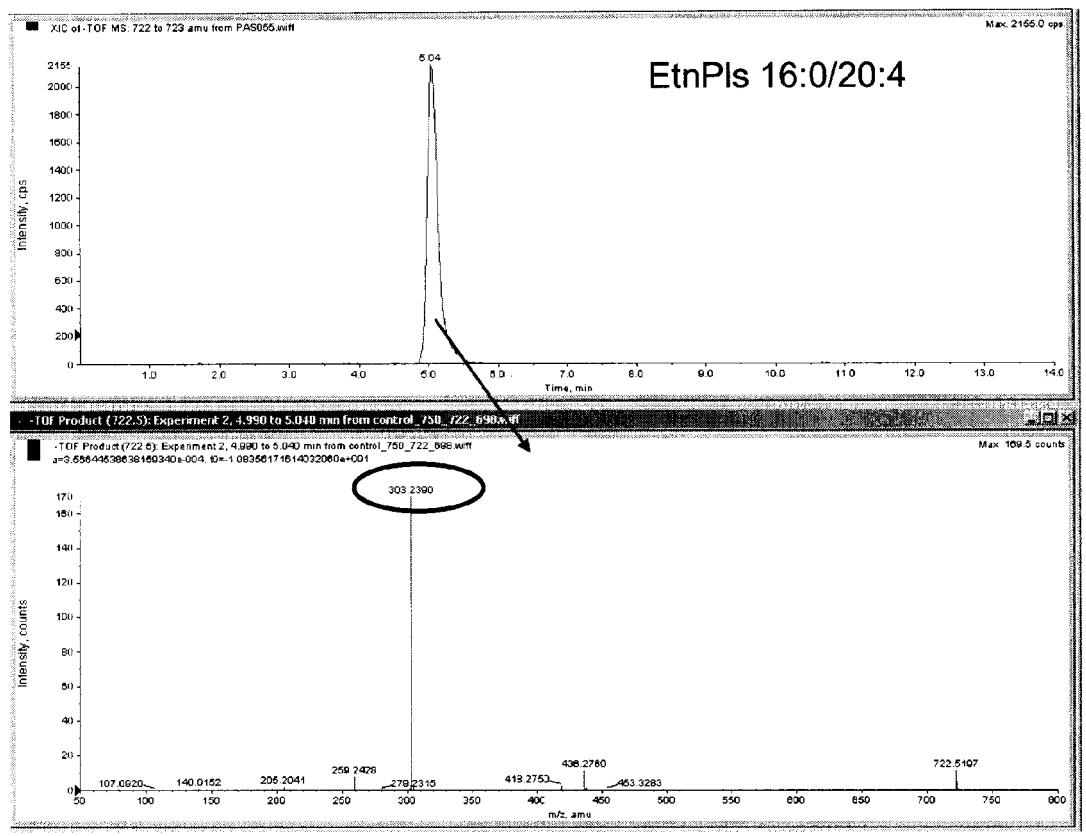
FIG. 23 is an extracted ion chromatogram (upper panel) and MS/MS spectrum (lower panel) of EtnPls 16:0/20:4 (M17) in human serum.

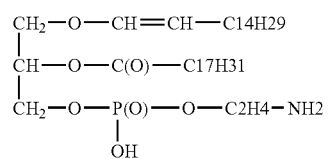

c) a MS/MS spectrum as shown in FIG. 23; molecular formula $C_{41}H_{74}NO_7P$; and/or the structure

Figure 24:
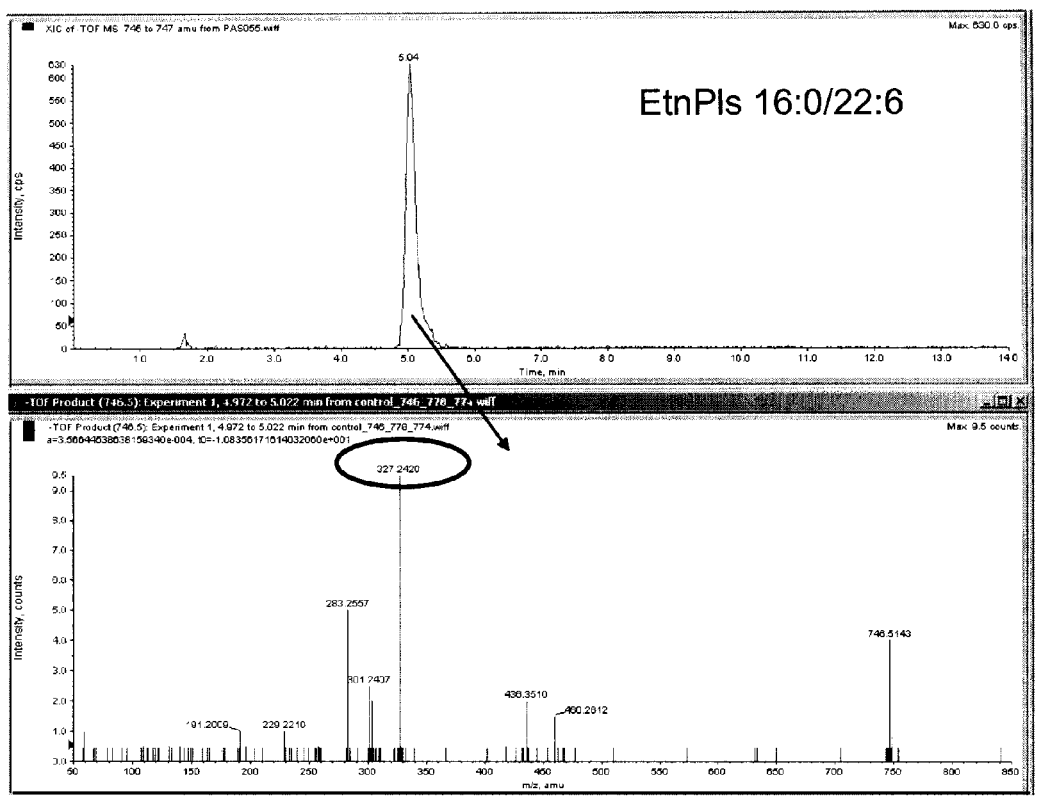
FIG. 24 is an extracted ion chromatogram (upper panel) and MS/MS spectrum (lower panel) of EtnPls 16:0/22:6 (M19) in human serum.

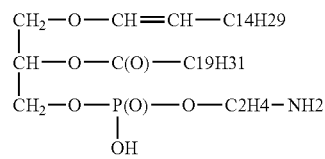

d) a MS/MS spectrum as shown in FIG. 24; molecular formula $C_{43}H_{74}NO_7P$; and/or the structure

Figure 25:
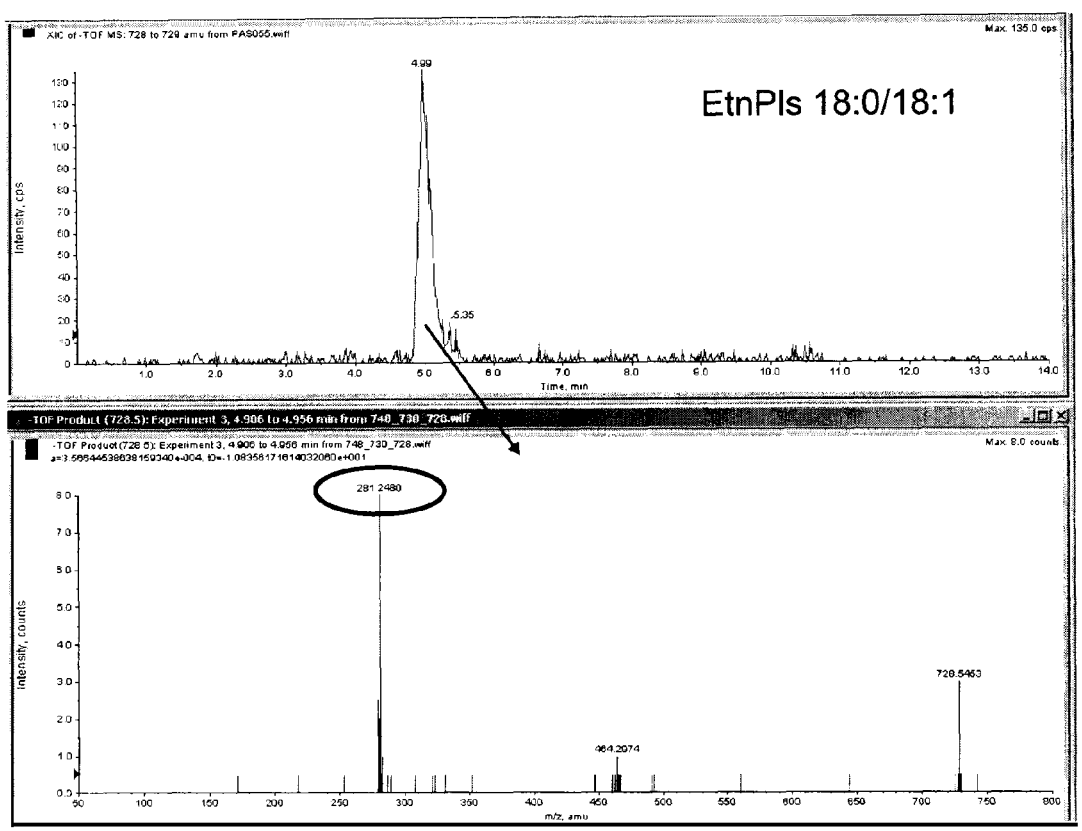
FIG. 25 is an extracted ion chromatogram (upper panel) and MS/MS spectrum (lower panel) of EtnPls 18:0/18:1 (M20) in human serum.

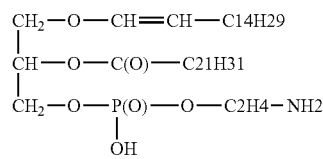

e) a MS/MS spectrum as shown in FIG. 25; molecular formula $C_{41}H_{80}NO_7P$; and/or the structure

Figure 26:
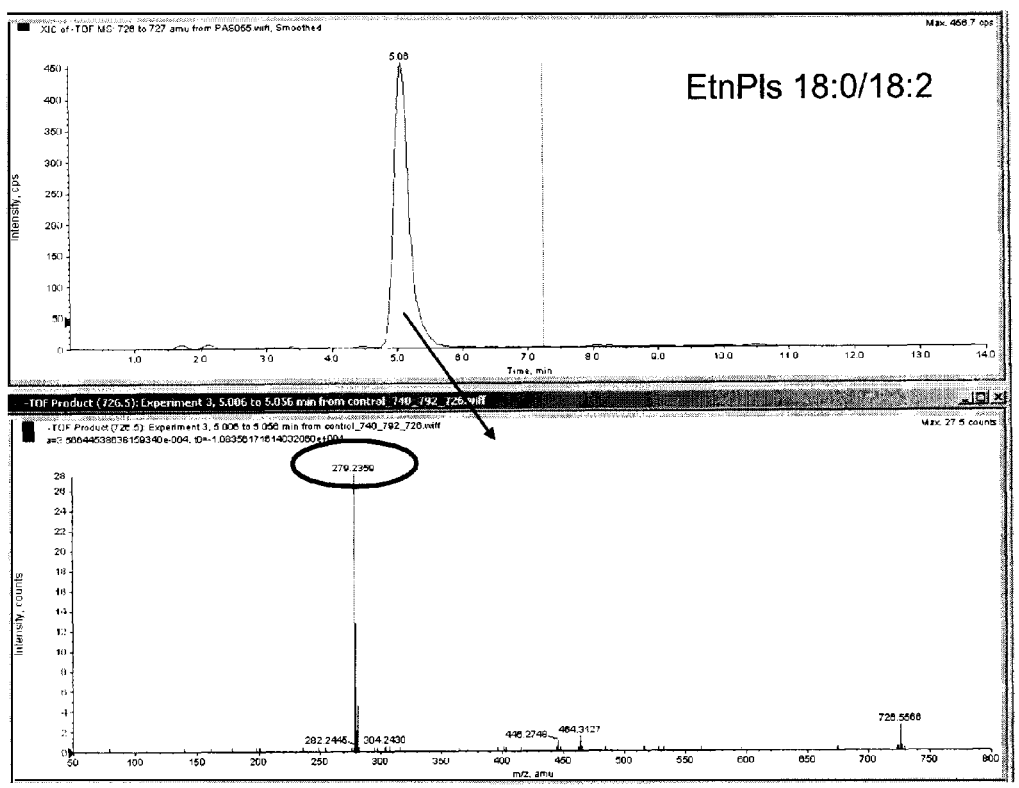
FIG. 26 is an extracted ion chromatogram (upper panel) and MS/MS spectrum (lower panel) of EtnPls 18:0/18:2 (M21) in human serum.

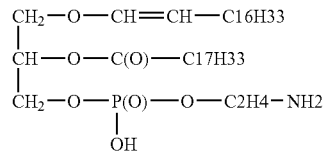

f) a MS/MS spectrum as shown in FIG. 26; molecular formula $C_{41}H_{78}NO_7P$; and/or the structure

Figure 27:
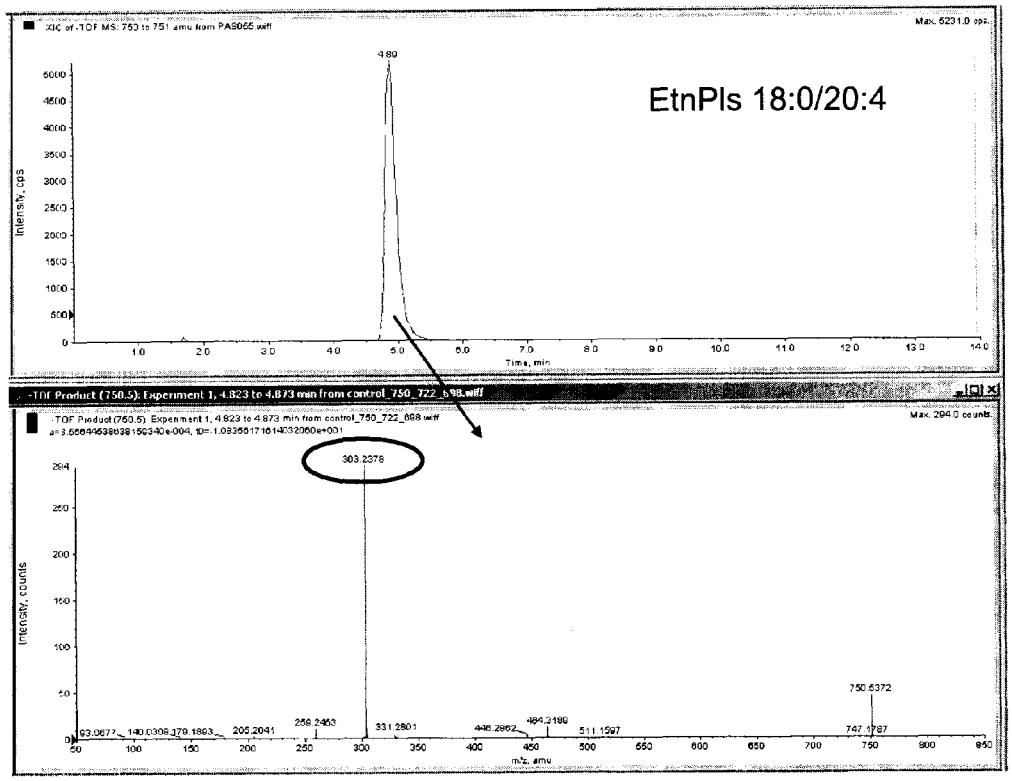
FIG. 27 is an extracted ion chromatogram (upper panel) and MS/MS spectrum (lower panel) of EtnPls 18:0/20:4 (M23) in human serum.

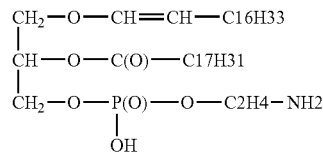

g) a MS/MS spectrum as shown in FIG. 27; molecular formula $C_{45}H_{82}NO_7P$; and/or the structure

Figure 28:
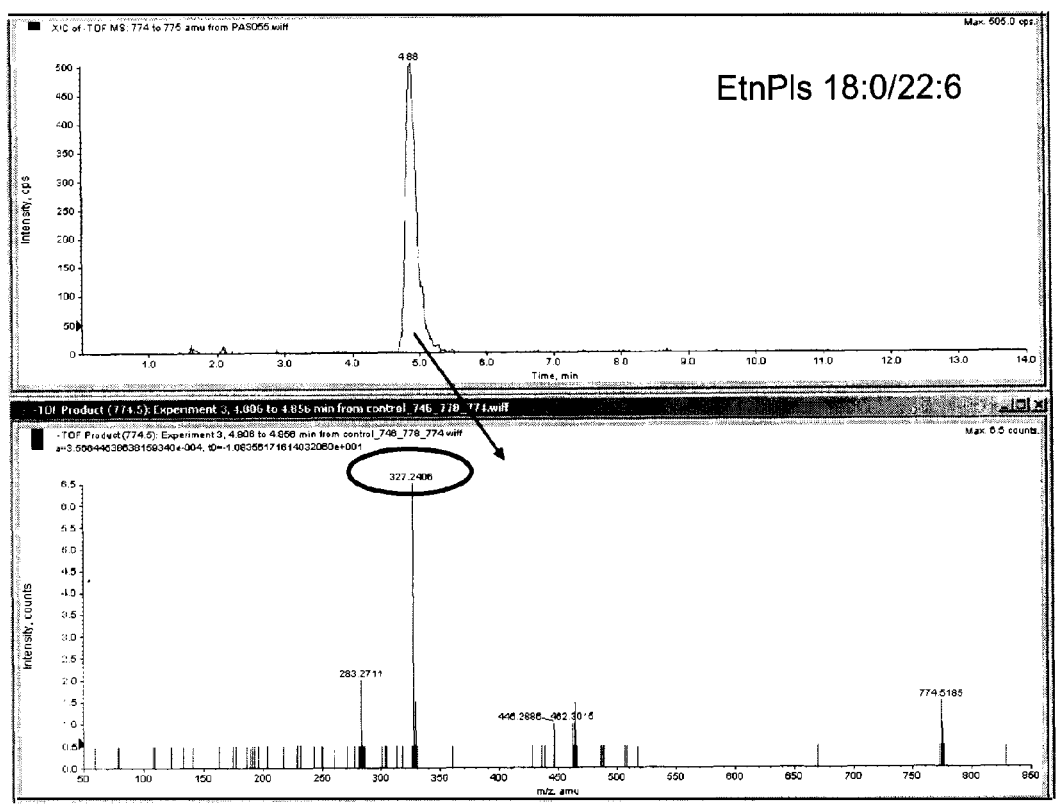
FIG. 28 is an extracted ion chromatogram (upper panel) and MS/MS spectrum (lower panel) of EtnPls 18:0/22:6 (M24) in human serum.
Figure 29:
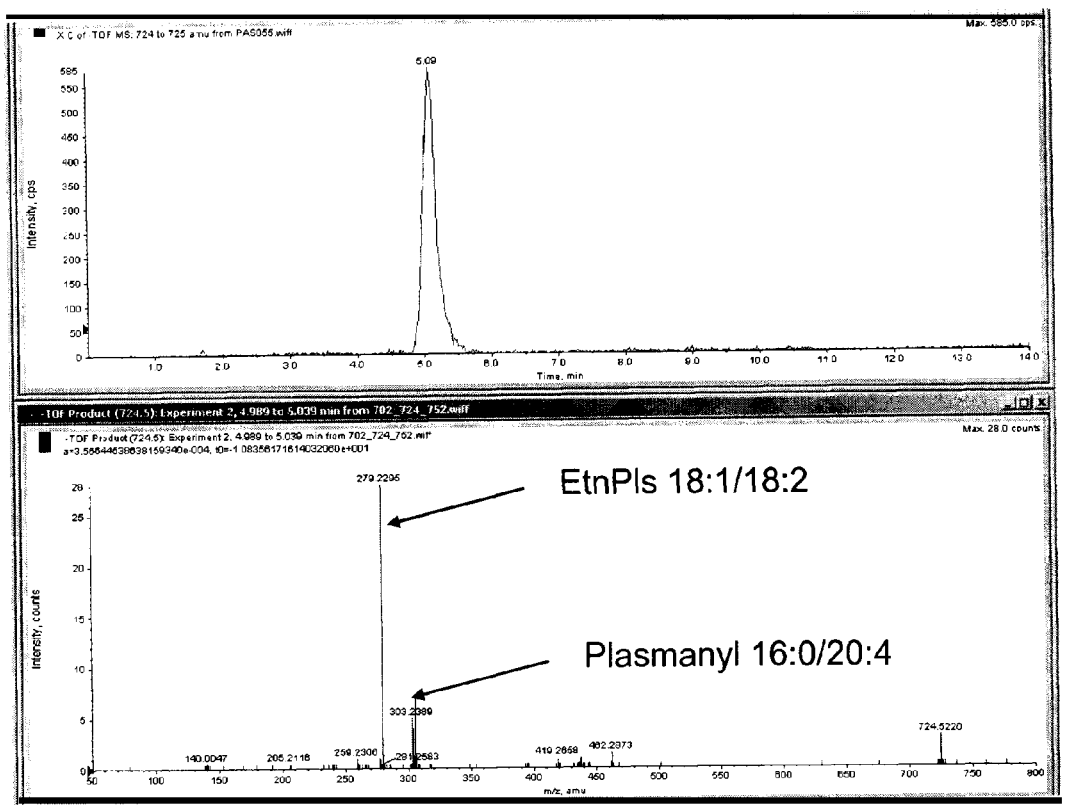
FIG. 29 is an extracted ion chromatogram (upper panel) and MS/MS spectrum (lower panel) of EtnPls 18:1/18:2 and Plasmanyl 16:0/20:4 (M07) in human serum.
Figure 30:
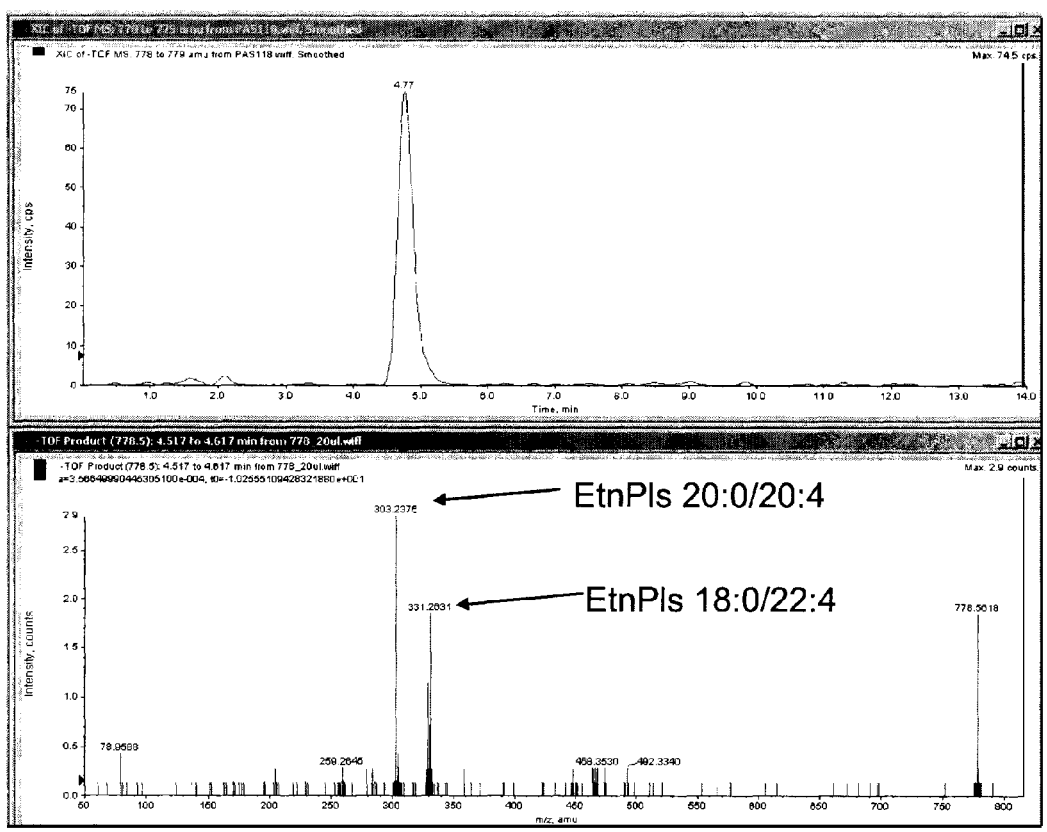
FIG. 30 is an extracted ion chromatogram (upper panel) and MS/MS spectrum (lower panel) of EtnPls 20:0/20:4 and EtnPls 18:0/22:4 (M23) in human serum.
Figure 31:
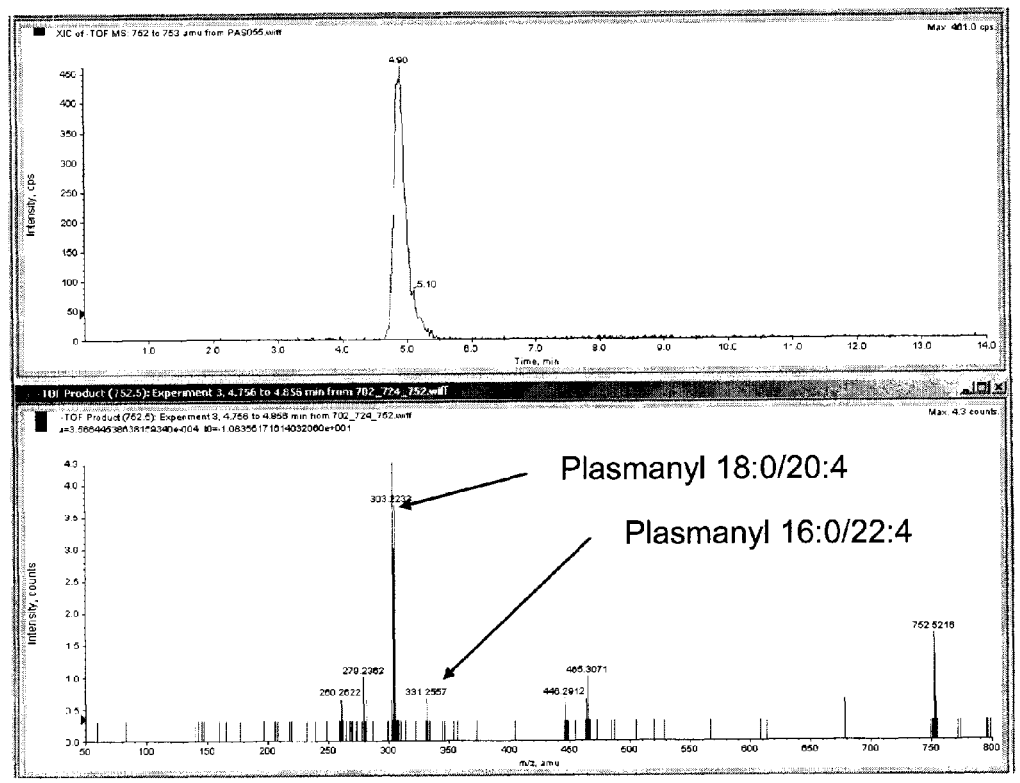
FIG. 31 is an extracted ion chromatogram (upper panel) and MS/MS spectrum (lower panel) of Plasmanyl 18:0/20:4 (M12) and Plasmanyl 16:0/22:4 (M08) in human serum.
Figure 32:
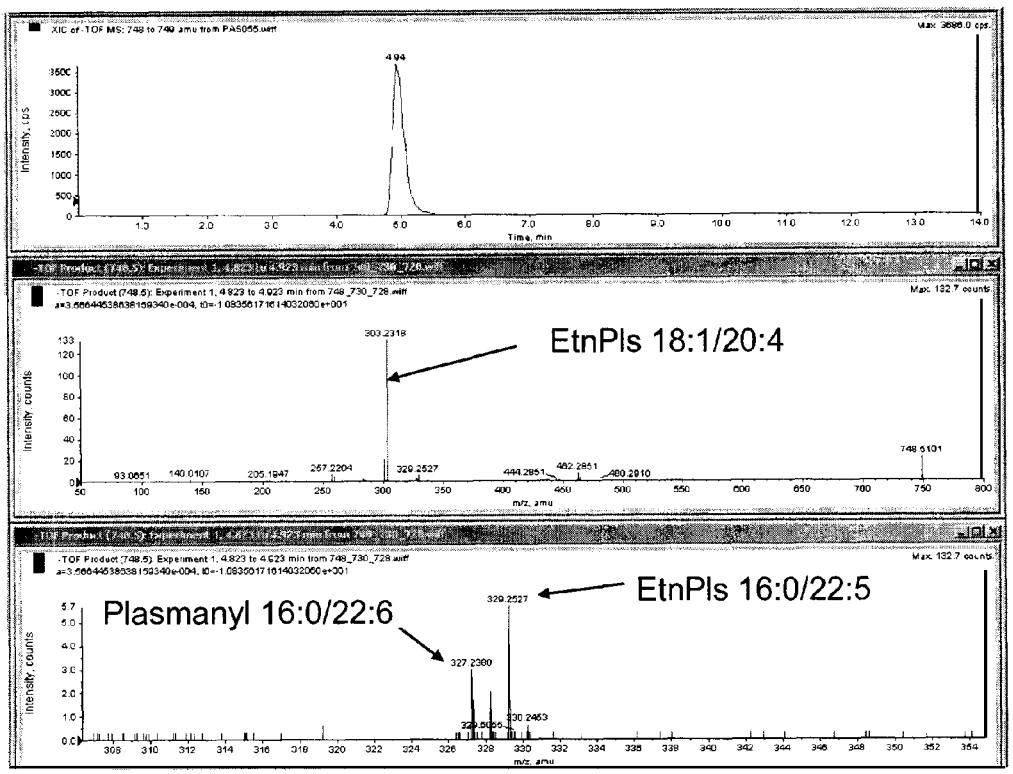
FIG. 32 is an extracted ion chromatogram (upper panel) and MS/MS spectrum (lower panels) of EtnPls 18:1/20:4, EtnPls 16:0/22:5, Plasmanyl 16:0/22:6 (M09) in human serum.

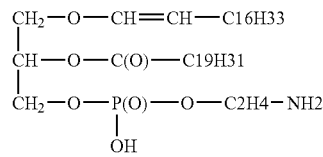

h) a MS/MS spectrum as shown in FIG. 28; molecular formula $C_{45}H_{78}NO_7P$; and/or the structure

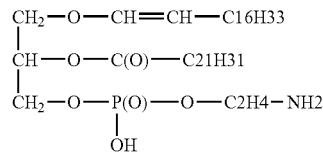

respectively.

In another embodiment of the present invention, the compounds may be selected from the metabolites listed in Table 13, or a combination thereof. These metabolites were identified in CSF samples. Of particular interest are the metabolites with accurate masses measured in Daltons of, or substantially equivalent to, 207.0822, 275.8712, 371.7311, 373.728, 432.1532, 485.5603, 487.6482, 562.46, 622.2539, 640.2637, 730.6493, 742.2972. When used to diagnose dementia, the metabolite markers 207.0822, 432.1532, 562.46, 622.2539, 640.2637, 730.6493, and 742.2972 are increased in patients with AD dementia; and metabolite markers 275.8712, 371.7311, 373.728, 485.5603, and 487.6482 are decreased in patients with AD dementia.

In a further method of the present invention, a method for assessing dementia or the risk of dementia in a patient is described. The method comprises the steps of:
a) obtaining a serum sample from said patient;
b) analyzing said sample to obtain quantifying data for one or more than one metabolite marker;
c) comparing the quantifying data for said one or more than one metabolite marker to corresponding data obtained from one or more than one reference sample; and
d) using said comparison to assess dementia or the risk of dementia.

The step of analyzing the sample (steb b)) may comprise analyzing the sample by liquid chromatography mass spectrometry (LC-MS). Alternatively, the step of analyzing the sample (step b)) may comprise analyzing the sample by linear ion trap mass spectrometry followed by liquid chromatograph, when the method is a highthroughput method.

The one or more than one reference sample may include a first reference sample obtained from a non-demented control individual, a second reference sample obtained from a patient with cognitive impairment as measured by ADAS-cog, a third reference sample obtained from a patient with cognitive impairment as measured by MMSE, or a combination of one or more of these.

Without wishing to be limiting in any manner, the one or more than one metabolite marker used to assess dementia or the risk of dementia may be selected from the metabolites listed in Tables 10-12, or a combination thereof. Of particular interest are metabolites with accurate masses measured in Daltons of, or substantially equivalent to 541.3432, 569.3687, 699.5198, 723.5195, 723.5197, 751.5555, 803.568, 886.5582, 565.3394, 569.369, 801.555, 857.6186. A decrease in the patient sample in metabolite markers 699.5198, 723.5195, 723.5197, and 751.555 indicates AD pathology; a decrease in the patient sample in metabolite markers 541.3432, 569.3687, 803.568, and 886.5582 indicates cognitive impairment on ADAS-cog; and 565.3394, 569.369, 801.555, and 857.6186 indicates cognitive impairment on MMSE.

In yet another embodiment of the present invention, there is provided a method for differentially diagnosing dementia or the risk of dementia in a patient. The method comprising the steps of:
a) obtaining a sample from said patient;
b) analyzing said sample to obtain quantifying data for one or more than one metabolite marker;
c) obtaining a ratio for each of the one or more than one metabolite marker to an internal control metabolite;
d) comparing each ratio of said one or more than one metabolite marker to the internal control metabolite to corresponding data obtained from one or more than one reference sample; and
e) using said comparison to differentially diagnose dementia or the risk of dementia.

The step of analyzing the sample (steb b) may comprise analyzing the sample using a mass spectrometer (MS). For example, and without wishing to be limiting, such mass spectrometer could be of the FTMS, orbitrap, time of flight (TOF) or quadrupole types. Alternatively, the mass spectrometer could be equipped with an additional pre-detector mass filter. For example, and without wishing to be limiting such instruments are commonly referred to as quadrupole-FTMS (Q-FTMS), quadrupole-TOF (Q-TOF) or triple quadrupole (TQ or QQQ). In addition, the mass spectrometer could be operated in either the parent ion detection mode (MS) or in MSn mode, where n>=2. MSn refers to the situation where the parent ion is fragmented by collision induced dissociation (CID) or other fragmentation procedures to create fragment ions, and then one or more than one of said fragments are detected by the mass spectrometer. Such fragments can then be further fragmented to create further fragments. Alternatively, the sample could be introduced into the mass spectrometer using a liquid or gas chromatographic system or by direct injection.

In the method as just described above, the one or more than one reference sample may be a first reference sample obtained from a non-demented control individual. The one or more than one reference sample may further include a second reference sample obtained from a patient with clinically diagnosed AD-dementia, a third reference sample obtained from a patient with clinically diagnosed non-AD dementia, a fourth reference sample obtained from a patient suffering from significant cognitive impairment, or any combination thereof.

In the method as described above, the sample and reference sample may be serum samples. The one or more than one metabolite marker may be selected from the metabolites as listed and characterized (accurate mass, name/composition, molecular formula) in Table 18. The "internal control metabolite" refers to an endogenous metabolite naturally present in the patient. Any suitable endogenous metabolite that does not vary over the disease states can be used as the internal control metabolite. For example, and without wishing to be limiting, the internal control metabolite may be phosphatidylethanolamine 16:0/18:0 (PtdEt 16:0/18:0, M01), as shown in Table 18; this internal control metabolite has a molecular formula of $C_{39}H_{78}NO_8P$, and a structure characterized as

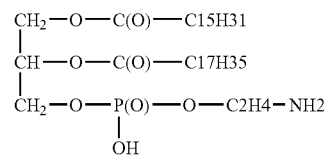

Use of the ratio of the metabolite marker to the internal control metabolite offers measurement that are more stable and reproducible than measurement of absolute levels of the metabolite marker. As the internal control metabolite is naturally present in all samples and does not appear to vary significantly over disease states, the sample-to-sample variability (due to handling, extraction, etc) is minimized.

Of the compounds listed in Table 18, those of particular interest in the above method include metabolites with accurate masses measured in Daltons of, or substantially equivalent to, a) 701.53591, b) 699.52026, c) 723.52026, d) 747.52026, e) 729.56721, f) 727.55156, g) 779.58286, and h) 775.55156. A decrease in the ratio of a) to h) to the internal control metabolite indicates AD dementia with a severe cognitive impairment. These metabolites can be further characterized by
a) a MS/MS spectrum as shown in FIG. 21; molecular formula $C_{27}H_{55}NO_9P$; and/or the structure

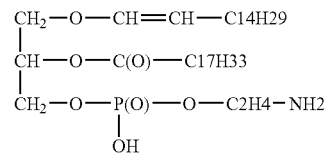

b) a MS/MS spectrum as shown in FIG. 22; molecular formula $C_{39}H_{74}NO_7P$; and/or the structure

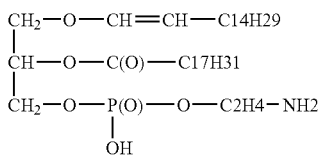

c) a MS/MS spectrum as shown in FIG. 23; molecular formula $C_{41}H_{74}NO_7P$; and/or the structure

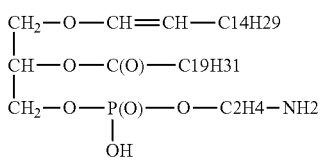

d) a MS/MS spectrum as shown in FIG. 24, molecular formula $C_{43}H_{74}NO_7P$; and/or the structure

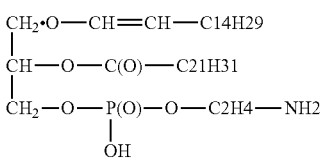

e) a MS/MS spectrum as shown in FIG. 25; molecular formula $C_{41}H_{80}NO_7P$; and/or the structure

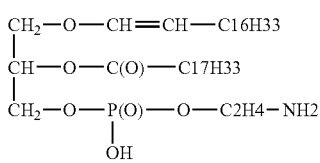

f) a MS/MS spectrum as shown in FIG. 26; molecular formula $C_{41}H_{78}NO_7P$; and/or the structure

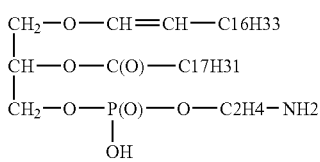

g) a MS/MS spectrum as shown in FIG. 27; molecular formula $C_{45}H_{82}NO_7P$; and/or the structure

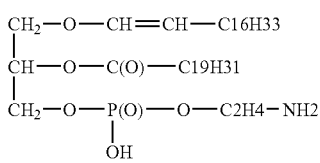

h) a MS/MS spectrum as shown in FIG. 28; molecular formula $C_{45}H_{78}NO_7P$; and/or the structure

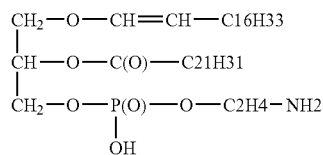

respectively.

In yet another embodiment of the present invention, there is provided a method for evaluating the efficacy of a therapy for treating dementia in a patient, comprising:
a) obtaining a sample from said patient;
b) analyzing said sample to obtain quantifying data for one or more than one metabolite marker;
c) comparing said quantifying data to corresponding data obtained from one or more than one reference sample; and
d) using said comparison to determine whether the therapy is improving the demented state of the patient.

Optionally, after the step of analyzing (step b), a ratio for each of the one or more than one metabolite marker to an internal control metabolite may be obtained. In this case, each ratio of said one or more than one metabolite marker to the internal control metabolite to corresponding data obtained from one or more than one reference sample is compared to evaluate the efficacy of the therapy.

The step of analyzing (step b) may comprise analyzing the sample by liquid chromatography mass spectrometry (LC-MS), or alternatively may comprise analyzing the sample by liquid chromatography and linear ion trap mass spectrometry when the method is a highthroughput method.

By the term "therapy", it is meant any suitable course of therapy that may improve the health state or demented state of the patient being evaluated. When evaluating the efficacy of the therapy, the effect of the particular therapy in improving or degrading the health state of the patient will be measured. In doing so, a person of skill in the art would be capable of determining whether the therapy is effective for treating the demented state.

In the methods as described, the one or more than one reference sample may be any suitable reference sample. For example, and without wishing to be limiting in any manner, the reference sample may be a plurality of samples obtained from non-demented control individuals; a plurality of samples obtained from clinically diagnosed AD patients; one or more than one pre-therapy baseline sample obtained from the patient; or any combination thereof. A pre-therapy baseline sample from the patient is particularly useful, as the variation in metabolites will then be specific to the patient.

The sample and the reference sample may be serum samples. In this case, the one or more than one metabolite marker could be selected from the metabolites listed in Tables 1 to 7, or a combination thereof, for example, metabolite markers with accurate masses measured in Daltons of, or substantially equivalent to, 541.3432, 569.3687, 699.5198, 723.5195, 723.5197, 751.5555, 803.568, 886.5582. Alternatively, the metabolite markers may be selected from metabolites M05 to M24 with accurate masses of, or substantially equivalent to those listed in Table 18, for example, metabolites with accurate masses measured in Daltons of, or substantially equivalent to, 701.53591, 699.52026, 723.52026, 747.52026, 729.56721, 727.55156, 779.58286, and 775.55156. Metabolites M05-M24 could also be used when a ratio is obtained between the metabolites and the internal control metabolite; the internal metabolite could be, for example, metabolite M01, as described in Table 18.

The sample and the reference sample may also be cerebrospinal fluid (CSF) samples. In this case, the one or more than one metabolite marker could be selected from the metabolites listed in Table 13, or a combination thereof; for example, metabolites with accurate masses measured in Daltons of, or substantially equivalent to, 207.0822, 275.8712, 371.7311, 373.728, 432.1532, 485.5603, 487.6482, 562.46, 622.2539, 640.2637, 730.6493, 742.2972.

The identified metabolites can be readily measured systemically. This point is of fundamental importance, since the majority of research pertaining to AD and other neurological disorders has ignored the peripheral systems. The ability to measure neurodegenerative processes within a blood sample is of substantial value in the diagnosis of dementia. With respect to the specific ethanolamine plasmalogen metabolites of the present invention, these are a valid biochemical marker of AD pathology since this molecular species' content does not change in Parkinson's disease, a disease which is often accompanied by dementia [29]. Furthermore, the specificity of the plasmalogen metabolites to AD indicates that its levels in serum could be readily measured longitudinally throughout the lifetime of an individual to assess the risk or for early detection of the disease prior to the emergence of clinical symptoms.

The present invention also provides high throughput methods for differential diagnosis of AD dementia and non-AD dementia states. The method may involve fragmentation of the parent molecule; in a non-limiting example, this may be accomplished by a Q-Trap™ system. Detection of the metabolites may be performed using one of various assay platforms, including calorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems.

A high-throughput method for determining the levels of the metabolites in a person's blood and comparing the levels to levels in a normal "reference" population can lead to a prediction of whether the person has AD or not. This can be carried out in several ways. One way is to use a prediction algorithm to classify the test sample, as previously described, which would output a percentage probability for having AD. A predictive approach would work independently of the assay method, as long as the intensities of the metabolites could be measured. Another method could simply be based on setting a threshold intensity level from the mass spectrometer, and determining whether a person's profile is above or below the threshold which would indicate their AD status. Alternatively, and without wishing to be limiting in any manner, a preferred method is a truly quantitative assay could be performed to determine the molar concentration of the six metabolites in the non-demented normal and AD population. An absolute threshold concentration could then be determined for AD-positivity. In a clinical setting, this would mean that if the measured levels of the metabolites, or combinations of the metabolites, were below a certain concentration, there would be an associated probability that the individual is positive for AD. Therefore, the optimal diagnostic test could comprise a method of measuring the intensities of the metabolites in serum, and an algorithm for taking the intensity values and outputting a predicted probability for having AD as well as for being healthy (i.e., AD-negative).

The methods and identified biomarkers of the present invention, based on small molecules or metabolites in a sample, fulfills the criteria identified in 1999 for an ideal screening test [82], as development of assays capable of detecting specific metabolites is relatively simple and cost effective per assay. The test is minimally invasive and is indicative of cognitive impairment and of AD pathology. Translation of the method into a clinical assay compatible with current clinical chemistry laboratory hardware is commercially acceptable and effective. Furthermore, the method of the present invention does not require highly trained personnel to perform and interpret the test.

The present invention will be further illustrated in the following examples.

EXAMPLE 1

Identification of Differentially Expressed Metabolites

Differentially expressed metabolites were identified in clinically diagnosed AD with and without significant cognitive impairment, clinically diagnosed non-AD and non-demented controls.

Clinical Samples. For the AD serum diagnostic assay described, samples were obtained from representative populations of non-demented healthy individuals and of clinically diagnosed AD and non-AD dementia patients. The biochemical markers of AD described in the invention were derived from the analysis of 75 serum samples from patients clinically diagnosed with probable AD (43 patients with significant cognitive impairment, 32 with no cognitive impairment), serum samples from 30 patients with clinically diagnosed non-AD dementia, and 31 serum samples from non-demented controls. Samples in the three groups were from a diverse population of individuals, ranging in age, ethnicity, weight, occupation, and displaying varying non-dementia-related health-states. All samples were single time-point collections. Cognitive impairment of the patients was also assessed using the Alzheimer's Disease Assessment Scale (ADAS)-cognitive subset.

For the AD CSF diagnostic assay described, samples were obtained from a group of patients that represented clinically diagnosed AD with dementia and non-AD patients with dementia. The biochemical markers of AD described in this invention were derived from the analysis of 6 CSF samples from clinically diagnosed AD patients with dementia and 5 CSF samples from clinically diagnosed non-AD patients with dementia.

Samples in both groups were from a diverse population of individuals, ranging in age, ethnicity, weight, occupation, and displaying varying non-dementia-related health-states. All samples were single time-point collections. The metabolites contained within the 136 serum samples and 11 CSF samples used in this application were separated into polar and non-polar extracts through sonication and vigorous mixing (vortex mixing).

Mass Spectrometry Analysis. Analysis of serum extracts collected from 136 individuals (75 clinically diagnosed AD, 30 clinically diagnosed non-AD, and 31 non-demented healthy controls) and 11 CSF extracts (6 clinically-diagnosed AD and 5 clinically diagnosed non-AD patients) was performed by direct injection into a FTMS and ionization by either ESI or atmospheric pressure chemical ionization (APCI) in both positive and negative modes. Sample extracts were diluted either three or six-fold in methanol:0.1% (v/v) ammonium hydroxide (50:50, v/v) for negative ionization modes, or in methanol:0.1% (v/v) formic acid (50:50, v/v) for positive ionization modes. For APCI, sample extracts were directly injected without diluting. All analyses were performed on a Bruker Daltonics APEX III Fourier transform ion cyclotron resonance mass spectrometer equipped with a 7.0 T actively shielded superconducting magnet (Bruker Daltonics, Billerica, Mass.). Samples were directly injected using electrospray ionization (ESI) and/or APCI at a flow rate of 1200 µL per hour. Ion transfer/detection parameters were optimized using a standard mix of serine, tetra-alanine, reserpine, Hewlett-Packard tuning mix and the adrenocorticotrophic hormone fragment 4-10. In addition, the instrument conditions were tuned to optimize ion intensity and broad-band accumulation over the mass range of 100-1000 amu according to the instrument manufacturer's recommendations. A mixture of the abovementioned standards was used to internally calibrate each sample spectrum for mass accuracy over the acquisition range of 100-1000 amu.

In total, six separate analyses comprising combinations of extracts and ionization modes were obtained for each sample:
Aqueous Extract
1. Positive ESI (analysis mode 1101)
2. Negative ESI (analysis mode 1102)
Organic Extract
3. Positive ESI (analysis mode 1201)
4. Negative ESI (analysis mode 1202)
5. Positive APCI (analysis mode 1203)
6. Negative APCI (analysis mode 1204)

Mass Spectrometry Data Processing. Using a linear least-squares regression line, mass axis values were calibrated such that each internal standard mass peak had a mass error of <1 p.p.m. compared with its theoretical mass. Using XMASS software from Bruker Daltonics Inc., data file sizes of 1 megaword were acquired and zero-filled to 2 megawords. A sin m data transformation was performed prior to Fourier transform and magnitude calculations. The mass spectra from each analysis were integrated, creating a peak list that contained the accurate mass and absolute intensity of each peak. Compounds in the range of 100-2000 m/z were analyzed. In order to compare and summarize data across different ionization modes and polarities, all detected mass peaks were converted to their corresponding neutral masses assuming hydrogen adduct formation. A self-generated two-dimensional (mass vs. sample intensity) array was then created using DISCOVAmetricS™ software (Phenomenome Discoveries Inc., Saskatoon, SK, Canada). The data from multiple files were integrated and this combined file was then processed to determine the unique masses. The average of each unique mass was determined, representing the y axis. This value represents the average of all of the detected accurate masses that were statistically determined to be equivalent. Considering that the mass accuracy of the instrument for the calibration standards is approximately 1 ppm, a person skilled in the art will recognize that these average masses may include individual masses that fall within +/−5 ppm of this average mass. A column was created for each file that was originally selected to be analyzed, representing the x axis. The intensity for each mass found in each of the files selected was then filled into its representative x,y coordinate. Coordinates that did not contain an intensity value were left blank. Once in the array, the data were further processed, visualized and interpreted, and putative chemical identities were assigned. Each of the spectra were then peak picked to obtain the mass and intensity of all metabolites detected. These data from all of the modes were then merged to create one data file per sample. The data from all 136 samples was then merged and aligned to create a two-dimensional metabolite array in which each sample is represented by a column and each unique metabolite is represented by a single row. In the cell corresponding to a given metabolite sample combination, the intensity of the metabolite in that sample is displayed. When the data is represented in this format, metabolites showing differences between groups of samples were determined. The same procedure was utilized to combine the 11 CSF samples in a two-dimensional metabolite array.

A. Serum Biomarkers

A student's T-test was used to select for metabolites which differed significantly between the following different clinical groups in serum. Metabolites that were less than $p<0.05$ were considered significant.

A1—Clinically diagnosed AD patients (n=75) vs. non-demented controls (n=31). This comparison yielded 262 metabolites (see Table 1).

A2—Clinically diagnosed AD patients with a significant cognitive impairment (n=32) vs. non-demented controls (n=31). This comparison yielded 292 metabolites (see Table 2).

A3—Clinically diagnosed AD patients with a significant cognitive impairment (n=32) vs. clinically diagnosed non-AD patients with a significant cognitive impairment (n=30); this comparison yielded 118 metabolites markers (see Table 3).

A4—Clinically diagnosed AD patients with significant cognitive impairment (n=32) vs. clinically diagnosed AD patients without significant cognitive impairment (n=43). This comparison yielded 97 metabolites markers (see Table 4).

A5—Clinically diagnosed non-AD patients (n=30) vs. non-demented controls (n=31); this comparison yielded 199 metabolites markers (see Table 5).

A6—Clinically diagnosed AD patients with mild cognitive impairment (n=43) vs. non-demented controls (n=31). This comparison yielded 136 metabolites (see Table 6).

A7—Patients with significant cognitive impairment (n=42) and patients with a mild cognitive impairment (n=43). This comparison yielded 81 metabolites (Table 7).

Tables 1-7 show biochemical markers whose concentrations or amounts in serum are significantly different ($p<0.05$) between the tested populations and therefore have potential diagnostic utility for identifying each of the aforesaid populations. The features are described by their accurate mass and analysis mode, which together are sufficient to provide the putative molecular formulas and chemical characteristics (such as polarity and putative functional groups) for each metabolite.

From the initial lists of several hundred possible metabolites, it was determined that a combination of 8 metabolites fulfills the criteria for a serum dementia test: the combination can differentiate AD dementia from non-AD dementia, the early stages of AD and healthy controls. The best combination of 8 metabolites included the metabolites with neutral masses (measured in Daltons) 541.3432, 569.3687, 699.5198, 723.5195, 723.5197, 751.5555, 803.568, 886.5582. Although these are the actual masses, a person skilled in the art of this technology would recognize that +/−5 ppm difference would indicate the same metabolite.

In analyzing the present results, a person of skill in the art would understand that the following clinical groups are of interest: non-AD with significant cognitive impairment, AD with significant cognitive impairment, AD without significant cognitive impairment and non-demented controls. Bar graphs representing the mean+/−SEM of the 8 biomarkers for the four different clinical groups are shown in FIG. 1. Relative to control, non-demented individuals, the three non-control states can be described as follows:

1. Non-AD with significant cognitive impairment vs. control:
   a. Biomarker 541.3432—decreased
   b. Biomarker 569.3687—decreased
   c. Biomarker 699.5198—no difference
   d. Biomarker 723.5195—no difference
   e. Biomarker 723.5197—no difference
   f. Biomarker 751.5555—no difference
   g. Biomarker 803.568—decreased
   h. Biomarker 886.5582—decreased 2. Clinically diagnosed AD with significant cognitive impairment vs. control
   a. Biomarker 541.3432—decreased
   b. Biomarker 569.3687—decreased
   c. Biomarker 699.5198—decreased
   d. Biomarker 723.5195—decreased
   e. Biomarker 723.5197—decreased
   f. Biomarker 751.5555—decreased
   g. Biomarker 803.568—decreased
   h. Biomarker 886.5582—decreased 3. Clinically diagnosed AD without significant cognitive impairment vs. control
   a. Biomarker 541.3432—decreased
   b. Biomarker 569.3687—no difference
   c. Biomarker 699.5198—decreased
   d. Biomarker 723.5195—decreased
   e. Biomarker 723.5197—decreased
   f. Biomarker 751.5555—decreased
   g. Biomarker 803.568—no difference
   h. Biomarker 886.5582—no difference In each of the three non-control cases described above, a unique subset of markers was decreased.

Bar graphs representing the mean+/−SEM of the 8 biomarkers for the two different clinical groups with a significant cognitive impairment are shown in FIG. 2. Relative to non-AD dementia with significant cognitive impairment, AD patients with significant cognitive impairment can be described as:
   a. Biomarker 541.3432—no difference
   b. Biomarker 569.3687—no difference
   c. Biomarker 699.5198—decreased
   d. Biomarker 723.5195—decreased
   e. Biomarker 723.5197—decreased
   f. Biomarker 751.5555—decreased
   g. Biomarker 803.568—no difference
   h. Biomarker 886.5582—no difference The results of this invention show a clear distinction between the serum of individuals with clinically diagnosed AD WITH a significant cognitive impairment, individuals with clinically diagnosed AD WITHOUT a significant cognitive impairment (this could be early stage AD), individuals with non-AD dementia WITH a significant cognitive impairment, and non-demented controls. These findings are capable of identifying and distinguishing the different types of dementia from one another and from the early stages of cognitive impairment as described in this application. From the above results, it can be further concluded that the metabolite markers with masses 699.5198, 723.5195, 723.5997, 751.5555 are specific for AD pathology; while markers with masses of 541.3432, 569.3687, 803.568, 886.5582 are specific for cognitive impaired based on ADAS-cog testing.

A second neuropsychological test, Folstein's Mini-Mental State Exam (MMSE), which measures cognitive impairment, was applied to all 136 patients. The MMSE is widely used and is an extensively validated test of orientation, short and long-term memory, praxis, language and comprehension. In the clinically diagnosed AD patients that had no significant cognitive impairment (n—43), 15 of those patients had a score on MMSE that would indicate normal cognition (MMSE≧28), whereas the remaining 28 patients had MMSE scores that indicated a mild impairment (score 18-23, n=11) or severe cognitive impairment (score 9-17, n=17). A F-test was used to select for metabolites which differed significantly between the MMSE scores (normal, mild or severe cognitive impairment) for 43 clinically diagnosed AD patients with no significant cognitive impairment on the ADAS-cog test ($p<0.05$). 23 metabolites met this criterion (shown in Table 8). These are all features which differ statistically between the two populations and therefore have potential diagnostic utility. The features are described by their accurate mass and analysis mode, which together are sufficient to provide the putative molecular formulas and chemical characteristics (such as polarity and putative functional groups) of each metabolite.

An optimal subset of 4 metabolites, all of which were observed to decrease, from the 23 metabolites was selected using Principal Components Analysis (PCA). The 4 metabolites able to produce the greatest separation between the groups were 565.3394, 569.369, 801.555, 857.6186. The metabolites are indicated by asterisks on Table 8 and represent a 4-metabolite biomarker panel associated with cognitive impairment on MMSE. The fact that a second set of metabolites were associated cognitive impairment suggests that the MMSE must be specific to one or several other cognitive states that the ADAS-cog is not specifically measuring.

Therefore, a total of three 4-biomarker panels can be applied to the 136 patients to classify them into one of 8 categories which will simultaneously indicate the presence of AD pathology (biomarkers 699.5198, 723.5195, 723.5997, 751.5555), cognitive impaired on ADAS-cog (541.3432, 569.3687, 803.568, 886.5582) and cognitive impaired on MMSE (565.3394, 569.369, 801.555, 857.6186). Using a 0/1 binary model, each patient can be labeled using a 3 digit code from "000" indicating no cognitive impairment and no AD pathology to "111" indicating both MMSE and ADAS-cog impairment and AD pathology. Table 9 indicates the separation of the patient samples into the 8 categories.

The three 4-biomaker panels were applied individually to the metabolite array and the patients that showed the best separation on the PCA plot were selected. These patients were selected because they represented the best discriminator between the 3 different groups [AD (n=20) vs. non-AD pathology (n=20), high ADAS score (n=20) vs. low ADAS score (n=12), impaired cognition on the MMSE score (n=20) vs. normal cognition on the MMSE score (n=20)]. A student's t-test was performed between the different clinical groups ($p<0.05$). The 116 metabolites that met the p-value criteria for AD vs. non-AD pathology are listed in Table 10. Table 11 lists the 124 metabolites that met the p-value criteria for high ADAS score vs. low ADAS score, and Table 12 contains the list of 344 metabolites that met the p-value criteria for impaired score on MMSE and normal cognition on MMSE.

Both the ADAS-cog and MMSE neuropsychological tests measure cognitive errors related to praxis, orientation, memory and language ability. Therefore, it would be reasonable to suggest biomarkers associated with ADAS-cog score and/or MMSE are related to the ability to conceive of, organize and initiate unfamiliar sequences, the awareness of one's self and environment, as well as memory and language ability. As such, these biomarkers are not exclusive to cognitive impairment associated with dementia; rather any condition that results in any type of praxis, orientation, memory and/or language deficit would show a similar reduction within a biological sample.

The sample set (136 individuals) used for this discovery was not trivial, and was comprised of individuals of various ethnic and geographical backgrounds, and of varying age and health status. Therefore, there is sound reason to expect that the findings are representative of the general dementia population.

B. CSF Biomarkers.

A student's T-test was used to select for metabolites which differ between the clinically diagnosed AD patients and clinically diagnosed non-AD patients in CSF samples (p<0.05). 42 metabolites met this criterion (shown in Table 13). These metabolites differed statistically between the two populations and therefore have potential diagnostic utility. The metabolites are described by their accurate mass and analysis mode, which together are sufficient to provide the putative molecular formulas and chemical characteristics (such as polarity and putative functional groups) of each metabolite.

An optimal subset of 12 metabolites from the 42 metabolites described above was selected. These metabolites had the greatest statistical difference between the two groups (p<0.01). Metabolites were excluded if they were not detected in at least 60% of the samples in each group (4/6 clinically diagnosed AD and 3/5 clinically diagnosed non-AD). The panel comprises masses 207.0822, 275.8712, 371.7311, 373.728, 432.1532, 485.5603, 487.6482, 562.46, 622.2539, 640.2637, 730.6493, 742.2972. Although these are the actual masses, a person skilled in the art of this technology would recognize that an +/−5 ppm difference would indicate the same metabolite.

The 12 biomarker panel was tested using 5 CSF samples from undiagnosed patients. The only information available on the samples was the subject's age, gender, and whether an individual had a cognitive deficit. If the 12 biomarker panel was correct, the subject could be diagnosed as having AD dementia, non-AD dementia, or normal. From the 5 CSF samples provided by undiagnosed patients, 1 was diagnosed with non-AD dementia, 2 with AD dementia, and 2 as normal. The two normal subjects did not have a cognitive impairment as indicated by the Mini Mental State Examination (MMSE) score. Therefore, using a 12 metabolite feature set it was possible to both diagnose AD and non-AD dementia.

Figure 3:
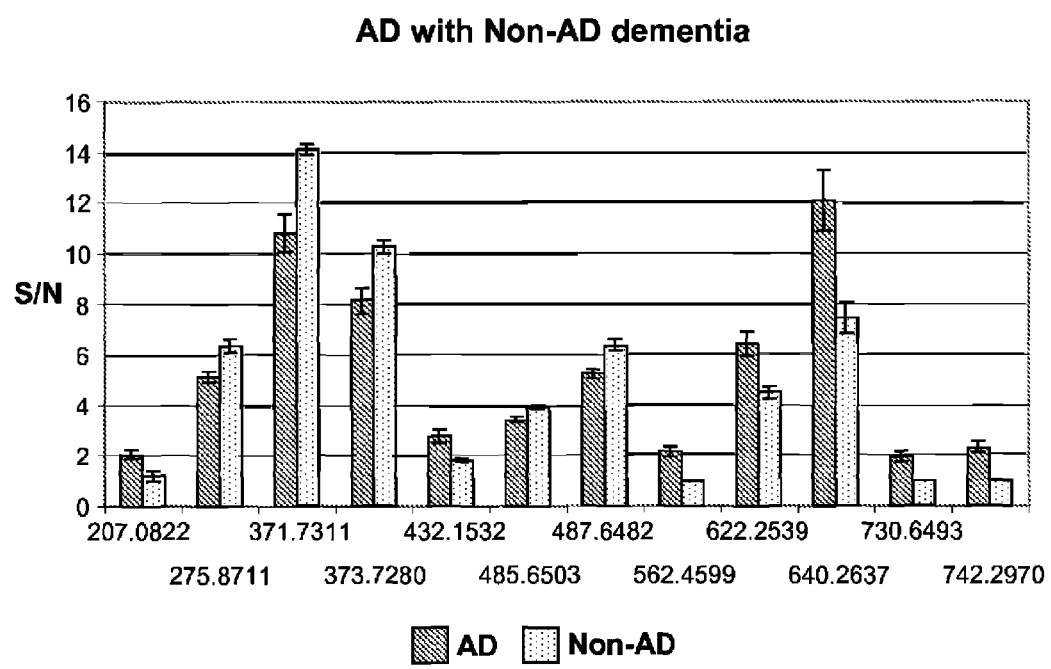
FIG. 3 shows a mean signal-to-noise +/−SEM of the AD CSF 12 biomarker panel for two clinical groups with a significant cognitive impairment (AD and Non-AD dementia).

Bar graphs representing the mean+/−SEM of the 12 biomarkers for the two different clinical groups are shown in FIG. 3. Relative to non-AD dementia with significant cognitive impairment, AD patients with a significant cognitive impairment can be described as:

a. Biomarker 207.0822—increased
b. Biomarker 275.8712—decreased
c. Biomarker 371.7311—decreased
d. Biomarker 373.728—decreased
e. Biomarker 432.1532—increased
f. Biomarker 485.5603—decreased
g. Biomarker 487.6482—decreased
h. Biomarker 562.46—increased
i. Biomarker 622.2539—increased
j. Biomarker 640.2637—increased
k. Biomarker 730.6493—increased
l. Biomarker 742.2972—increased Based on these results, a clear distinction was made between the CSF of clinically diagnosed non-AD and AD patients. Therefore, such findings are capable of identifying and distinguishing AD dementia from non-AD dementia and can form the basis of a dementia diagnostic test in CSF as described in this application. It is expected that the finding are representative of the general dementia population.

Although a non-targeted FTMS-based platform was used in the identification and selection of the optimal metabolites in serum and CSF, other methods of subsequently detecting the molecules, including other MS-based platforms, ELISAs, calorimetric assays, etc can used to detect the molecules.

EXAMPLE 2

Independent Method Confirmation of Discovered Metabolites

A. Serum Biomarkers

An independent mass spectrometry method was used to verify the intensity differences between non-demented normal and clinically-diagnosed AD serums of the eight diagnostic metabolites discovered using the FTMS method. Eight representative clinically-diagnosed AD sample extracts and eight representative non-demented control sample extracts were analyzed by LC-MS using an HP 1100 high-performance liquid chromatography interfaced to an ABI Q-Star mass spectrometer.

Aqueous fractions from five clinically-diagnosed AD and five non-demented control sample extracts were evaporated under nitrogen gas and reconstituted in 100 uL of methanol: water:formic acid (5:94.9:0.1). Five µL of the reconstituted sample was subjected to HPLC (Agilent Technologies) (HP 1100 with Metasil AQ 3u, 100×2 mm column) for full scan and 10 µL for MS/MS at a flow rate of 0.2 ml/min.

Eluate from the HPLC was analyzed using an ABI Q-Star XL mass spectrometer fitted with a Turboion spray ion (ESI) source in negative mode. The scan type in full scan mode was time-of-flight (TOF) with an accumulation time of 1.0000 seconds, mass range between 50 and 1500 Da, and duration time of 70 min. Source parameters were as follows: Ion source gas 1 (GS1) 55; Ion source gas 2 (GS2) 90; Curtain gas (CUR) 40; Nebulizer Current (NC) 0; Temperature 450° C.; Declustering Potential (DP)-55; Focusing Potential (FP)-265; Declustering Potential 2 (DP2)-15. In MS/MS mode, scan type was product ion, accumulation time was 1.0000 seconds, scan range between 50 and 1000 Da and duration time 70 min. All source parameters are the same as above, with a collision energy of (CE) of −50 V and collision gas (CAD, nitrogen) of 5 psi.

Six of the eight metabolite masses previously discovered on the FTMS were verified on the ABI Q-Star mass spectrometer. The metabolites with the accurate masses of 723.5195 and 723.5197 were determined to be the same metabolite, and the metabolite with accurate mass of 886.5582 was not detected. Therefore, only six metabolites (699.5198, 723.5195, 751.5555, 541.3432, 569.3687, 803.568) were used for the remaining analyses.

Figure 4:
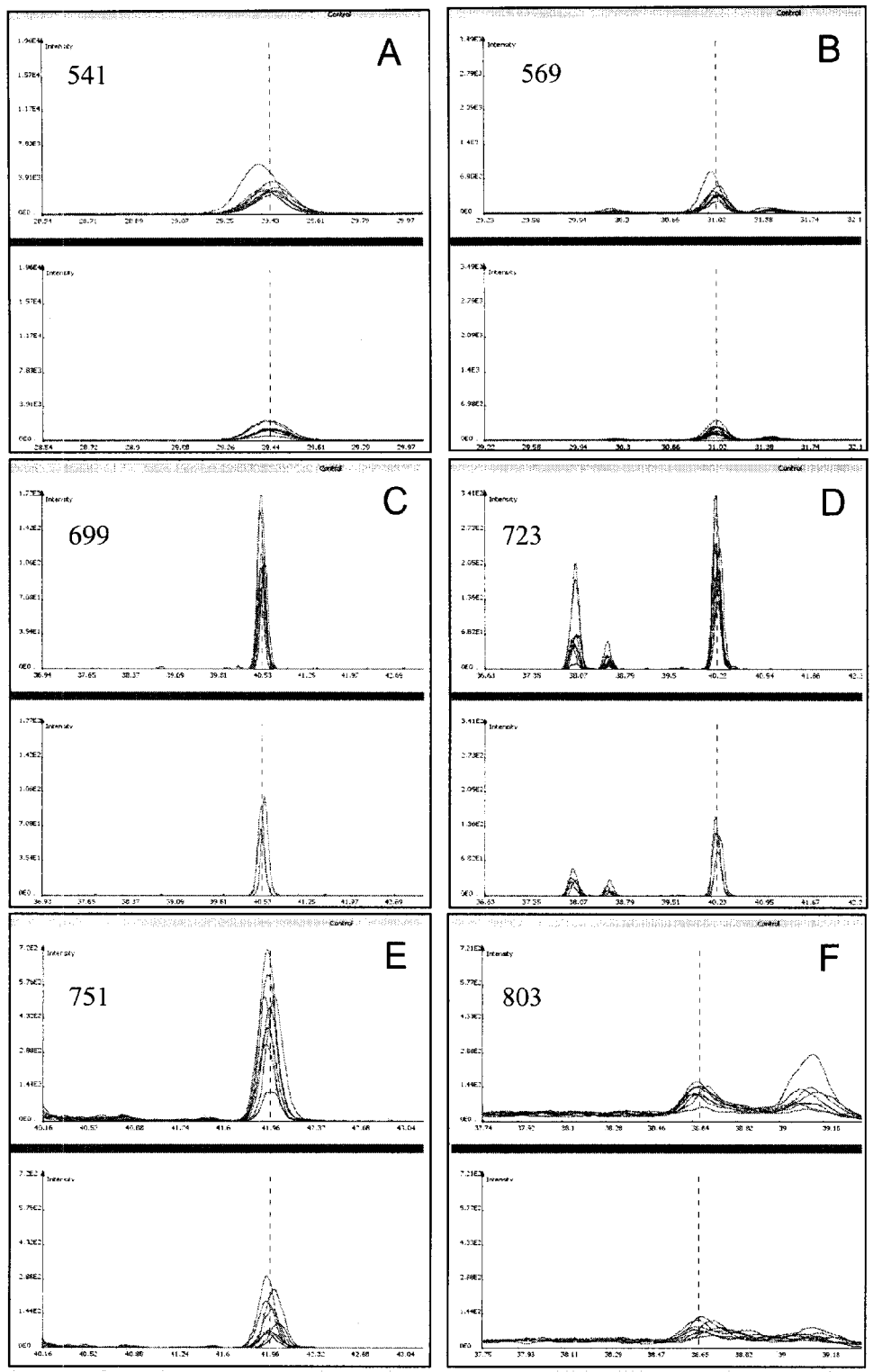
FIG. 4 shows Q-Star extracted ion chromatograms (EIC) for the metabolites 541.3432 (A), 569.3687 (B), 699.5198 (C), 723.5195 (D), 751.5555 (E), and 803.568 (F). Top panel, 8 samples from non-demented subjects, bottom panel, 8 samples from clinically-diagnosed AD subjects.
Figure 5:
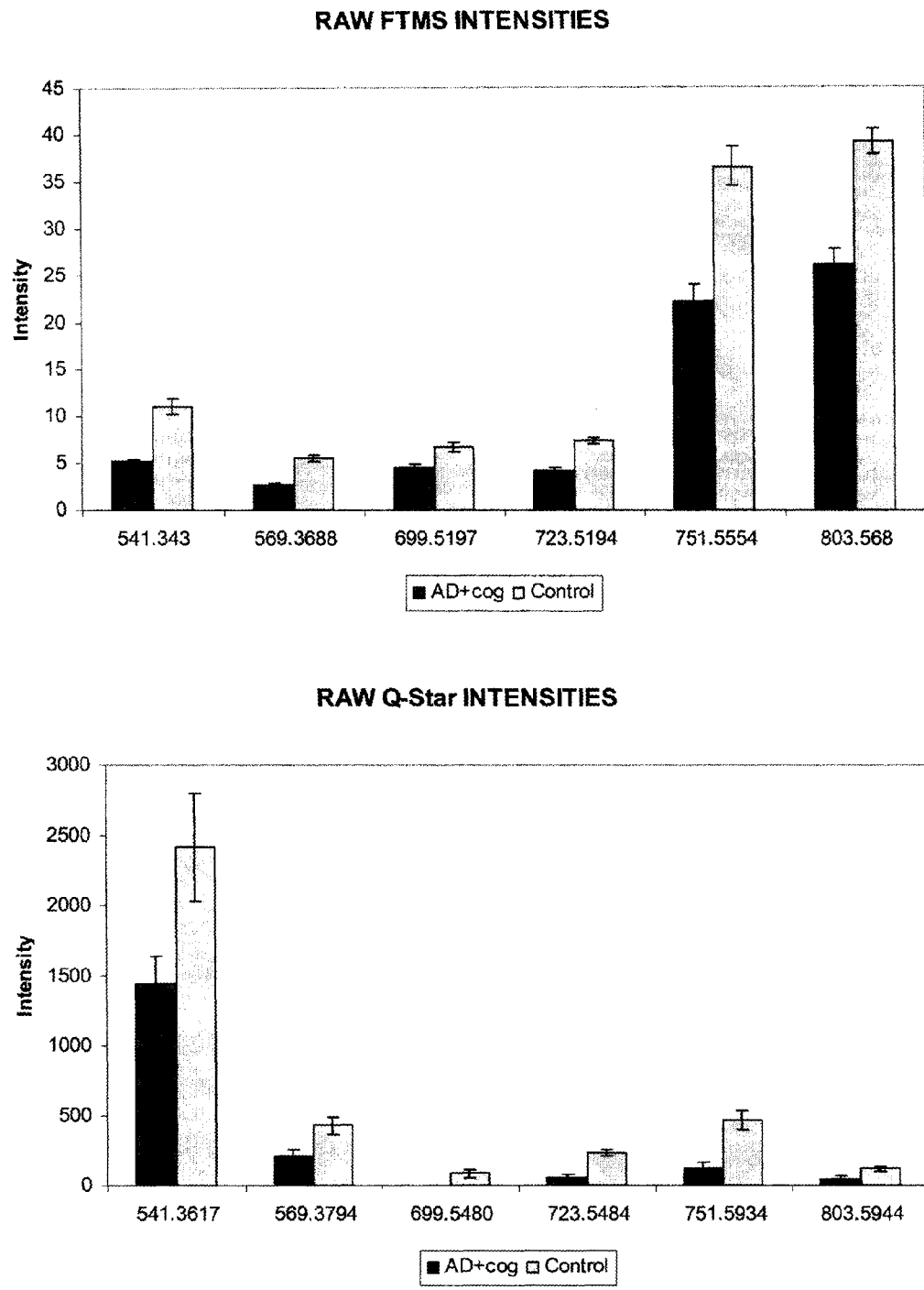
FIG. 5 shows averaged AD biomarker intensities of the 8 AD and 8 non-demented controls samples from FTMS and Q-Star Analysis.

The extracted ion chromatograms (EICs) for the six biomarkers are shown in FIG. 4 The top panel shows the eight non-demented control EICs, and the bottom panel of each shows the eight clinically-diagnosed AD EICs. The sensitivity of the Q-star is superior to the FTMS, resulting in a greater magnitude in intensity difference between the non-demented control subjects and clinically diagnosed AD population for the selected biomarkers. FIG. 5 shows the average raw intensity of the six biomarkers of the eight non-demented control and eight clinically-diagnosed AD samples as detected on the FTMS and Q-Star.

B. CSF Biomarkers

The metabolites and their associations with the clinical variables described in this invention are further confirmed using an independent mass spectrometry system. Representative sample extracts from each variable group are re-analyzed by LC-MS using an HP 1050 high-performance liquid chromatography, or equivalent interfaced to an ABI Q-Star, or equivalent mass spectrometer to obtain mass and intensity information for the purpose of identifying metabolites that differ in intensity between the clinical variables under investigation.

EXAMPLE 3

Structure Elucidation of the Primary Metabolite Biomarkers

Characteristics that can be used for structure elucidation of metabolites include accurate mass and molecular formula determination, polarity, acid/base properties, NMR spectra, and MS/MS or MSn spectra. These data, and in particular the MS/MS spectrum, can be used as fingerprints of a particular metabolite and are unique identifiers of a particular metabolite regardless of whether the complete structure has been determined.

A. Serum Biomarkers—Structural Elucidation

1. LC retention time. The extracts containing the metabolites of interest were subjected to reverse phase LC-MS using a C18 column and analysis by MS as described in Example 2 above. Table 14 lists the resulting retention times and detected masses for each of the six serum metabolite markers. The retention time for all six of the biomarkers is approximately 29-42 minutes under these HPLC conditions.

2. Extraction conditions. The conditions of extraction also provide insights about the chemical properties of the biomarkers. All eight metabolites in the serum (from Example 1) were ionized in negative mode (3 in APCI and 5 in ESI), which is indicative of a molecule containing an acidic moiety such as a carboxylic acid or phosphate. Any moiety capable of losing a hydrogen atom can be detected in negative ionization mode. Three of the metabolite markers were extracted into an organic ethyl acetate fraction (plasmalogen metabolites), indicating that these metabolites are non-polar tinder acidic condition; one was extracted into an organic ethyl acetate fraction dried down and resuspended in butanol, indicating that this metabolite (plasmalogen metabolite) is non-polar under acidic conditions. Four of the metabolites (phosphatidyl choline related metabolites) did not extract into the organic fraction, but rather remained in the aqueous methanol/ammonium hydroxide fraction, indicating that these metabolites are very polar.

3. MS/MS spectra. The six serum metabolites identified as having the best diagnostic ability were subject to MS/MS fragmentation using collision induced dissociation (CID). The structure of a given molecule will dictate a specific fragmentation pattern under defined conditions that is specific for that molecule (equivalent to a person's fingerprint). Even slight changes to the molecule's structure can result in a different fragmentation pattern. In addition to providing a fingerprint of the molecule's identity, the fragments generated by CID can be used to gain insights about the structure of a molecule, and for generating a very specific high-throughput quantitative detection method (see [30-33] for examples). FIGS. 6 through 11 show the MS/MS spectra for each of the six markers at −50V collision energy (CE) voltages.

The masses resulting from CID MS/MS of each parent mass were then used to calculate putative formulas for each of the fragment ions for the metabolites specific to the ADAS-cog scores, as shown in the tables for each marker (Tables 15 to 17). The information inherent in the fragmentation data is highly specific and descriptive for each metabolite, which can be used to gain structural insights about each molecule. MS/MS was carried out on the ABI-Q Star XL with all parameters as previously mentioned using Nitrogen as the collision gas at 5 psi and collision energy (CE) settings of −50 volts.

Figure 15:
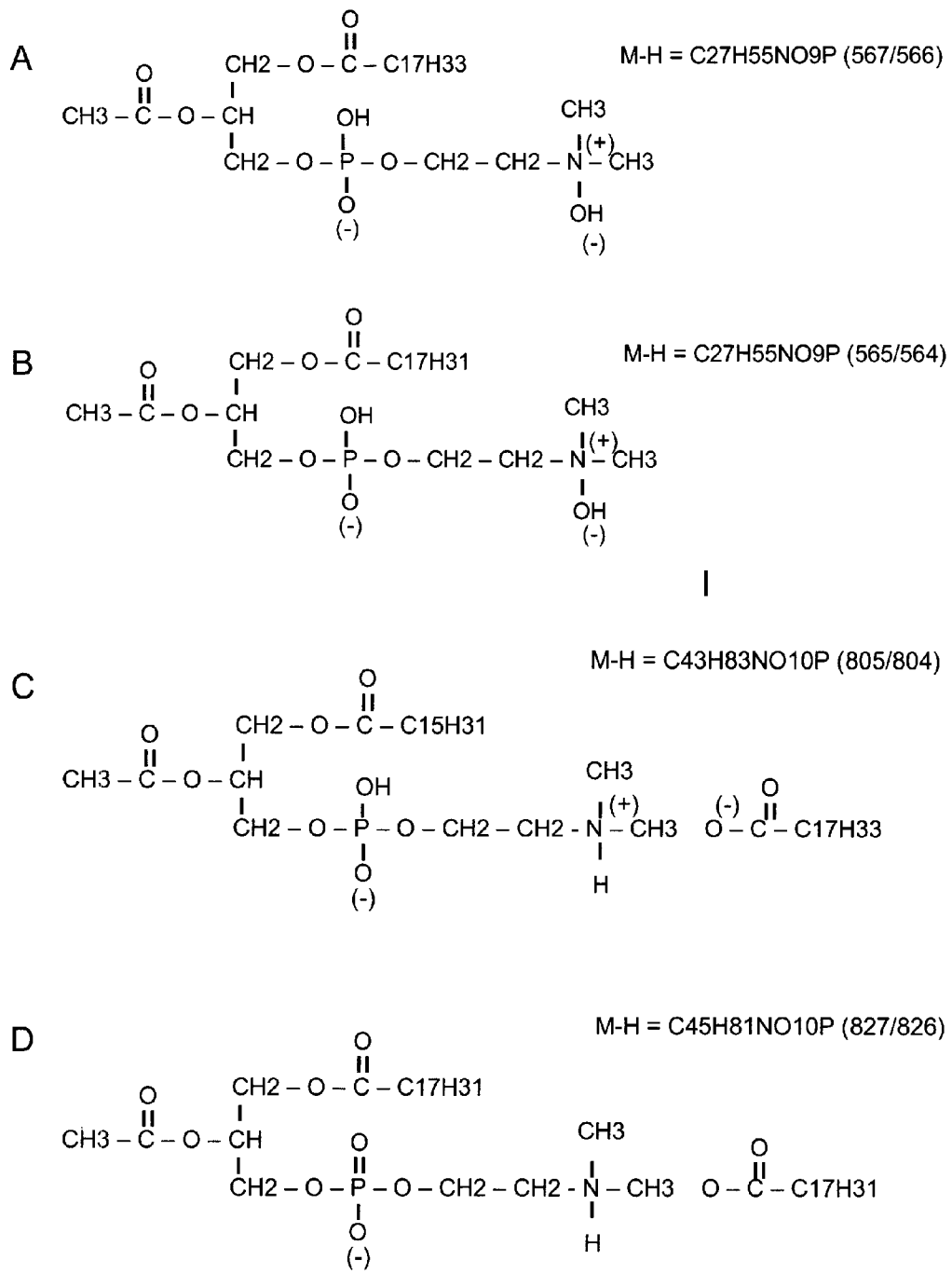
FIG. 15 shows putative structures of additional serum biomarkers. A—metabolite with mass of 567.3547; B—metabolite with mass of 565.3394; C—metabolite with mass of 805.5832; D—metabolite with mass of 827.57; E—metabolite with mass of 829.5856; F—metabolite with mass of 531.5997; and G—metabolite with mass of 853.5854.

Based on the fragmentation pattern and masses, the metabolite markers specific to the ADAS-cog scores have been assigned structures having a phosphatidylcholine-related backbone. From the CID MS/MS, the molecular formulae of 3 metabolites specific to the ADAS-cog scores (accurate neutral masses of 541.3432, 569.3687, 803.568) were determined to be $C_{25}H_{51}NO_9P$, $C_{27}H_{55}NO_9P$, and $C_{43}H_{81}NO_{10}P$, respectively. Their structures are shown in FIGS. 12-14. The putative structures of additional markers are shown in FIG. 15.

The 3 metabolites specific to AD pathology, with accurate neutral masses of 751.5555, 699.5198, and 723.5195, were analyzed using FT-ICRMS and LC/MS techniques, and by HRAPCI-MS, and MS/MS spectral analysis. Daughter ions determined from the fragmentation pattern for each metabolite marker are shown in FIGS. 16-18. The molecular formulae were determined to be $C_{43}H_{78}NO_7P$, $C_{39}H_{74}NO_7P$, and $C_{41}H_{74}NO_7P$, respectively. Based on the fragmentation pattern and masses, the metabolite markers specific to AD patehology have been assigned structures having an ethanolamine plasmalogen backbone.

For the 751.5555 metabolite ($C_{43}H_{78}NO_7P$), and due to negative ionization conditions, the HRAPCI-MS m/z measured was 750.5482 ([M-H]—, calcd. 750.5477 for $C_{43}H_{77}NO_7P$). The relative intensity of the MS/MS fragment masses (MS/MS m/z) were measured as follows: 750 ([M-H]—, 25%), 482 (1%), 464 (12%), 446 (5%), 329 (8%), 303 (100%), 259 (12%), 205 (8%), 140 (8%). The MS/MS fragments are shown in FIG. 16. The strong MS/MS fragment ion at m/z 303 and other fragment ions due to loss of sn-2 acyl group (m/z 464) as a ketone, loss of the sn-1 vinyl ether side chain (m/z 482) though small, and the fragment ion due to phosphoethanolamine (m/z 140) indicated the metabolite to be a plasmenyl phosphatidylethanolamine-type molecule with arachidonic acid at the sn-2 position. Based on these results, the structure of the 751.5555 metabolite was elucidated as 1-O-1'-(Z)-octadecenyl-2-arachidoyl-sn-glycero-3-phosphoethanolamine. This was confirmed by comparison of their LC/MS and MS/MS spectral data (FIG. 19)

The two remaining metabolites with molecular formulae $C_{39}H_{74}NO_7P$ (neutral mass 699.5198) and $C_{41}H_{74}NO_7P$ (neutral mass 723.5195) were found to co-elute with the 751.5555 metabolite in LC/MS. The metabolites' MS/MS fragment ions and fragmentation patterns were similar to those of the 751.5555 metabolite.

For the 699.5198 metabolite, the HRAPCI-MS m/z measured was 698.5125 ([M-H]—, calcd. 698.5130 for $C_{39}H_{73}NO_7P$). The relative intensity of the MS/MS m/z were measured as follows: 698 ([M-H]$^-$, 8%), 536 (4%), 279 (100%), 255 (15%), 119 (10%). The MS/MS fragments are shown in FIG. 17. Based on these results and on its structural similarity to the 751.5555 metabolite, the structure of the 699.5198 metabolite was determined to be 1-O-1'-(Z)-hexadecenyl-2-linoleyl-sn-glycero-3-phosphoethanolamine.

For the 723.5195 metabolite, the HRAPCI-MS m/z measured was 722.5124 ([M-H]$^-$, calcd. 722.5130 for $C_{41}H_{73}NO_7P$). The relative intensity of the MS/MS m/z were measured as follows: 722 ([M-H]$^-$, 12%), 482 (1%), 436 (15%), 418 (6%), 303 (100%), 279 (6%), 259 (15%), 255 (10%), 205 (4%), 140 (5%). The MS/MS fragments are shown in FIG. 18. Based on these results and on its structural similarity to the 751.5555 metabolite, the structure of the 723.5195 metabolite was proposed as 1-O-1'-(Z)-hexadecenyl-2-arachidoyl-sn-glycero-3-phosphoethanolamine.

4. NMR spectra. The MS/MS fragmentation provides highly specific descriptive information about a metabolite. However, nuclear magnetic resonance (NMR) can assist in solving and confirming the structures of the metabolites. As NMR analysis techniques are typically less sensitive than mass spectrometry techniques, multiple injections are performed on the HPLC and the retention time window corresponding to the metabolites of interest collected and combined. The combined extract is then evaporated to dryness and reconstituted in the appropriate solvent for NMR analysis.

Multiple NMR techniques and instruments are available, for example, NMR spectral data are recorded on Bruker Avance 600 MHz spectrometer with cryogenic probe after the chromatographic separation and purification of the metabolites of interest. 1H NMR, 13C NMR, noe-difference spec, as well as 2-D NMR techniques like heteronuclear multiple quantum correlation (HMQC), and heteronuclear multiple bond correlation (HMBC) are used for structure elucidation work on the biomarkers.

B. CSF Biomarkers

The structural characteristics (LC retention time, extraction conditions, MS/MS fragments) for the 12 CSF metabolite markers are determined in the same manner as detailed above.

EXAMPLE 4

Characterization of Ethanolamine Phospholipids in Serum

Based on the fact that the metabolite markers specific to AD pathology have an ethanolamine plasmalogen backbone, it was further investigated whether other serum plasmalogens could be indicative of AD. This characterization of ethanolamine phospholipids in serum was made using a chromatographic method combined with a mass spectrometric detector.

For MS/MS applications and experiments involving chromatography, an Agilent 1100 HPLC system was used in combination with an Applied Biosystems QSTAR XL mass spectrometer. An Agilent Zorbax RX-SIL (4.6×150 mm, 5 μm) column was used for normal phase chromatography. Conditions included an isocratic mobile phase (55:40:5 isopropanol:hexane:H2O) at a flow rate of 1.0 mL/min for a total run time of 15 min. The column was heated to 35° C. The sample injection volume was 10 μL. Organic solvent extracts (ethyl acetate) of samples were evaporated to dryness under nitrogen gas and the residue was reconstituted in 100 μL of 55:40:5 isopropanol:hexane:H2O solution prior to injection.

The QSTAR XL instrument was equipped with an APCI (Heated Nebulizer) source operating in negative mode. Values of major instrument parameters were DP, −60; FP, −265; DP2, −15; GS1, 75; GS2, 15; CUR, 30; NC, −3; TEM, 400° C.; Scan range, 50-1500 amu; Accumulation time, 1 sec.

The three classes of ethanolamine phospholipids are described as diacyl (also referred to herein as PtdEt), alkyl-acyl (also referred to herein as plasmanyl) or alkenyl-acyl (also referred to herein as EtnPl or plasmenyl). Various basic structures of ethanolamine phospholipids are shown in FIG. 20, along with the standard naming convention used herein. Table 18 shows a list of plasmanyl and plasmenyl ethanolamine phospholipids (M5-M24) that are presently identified and are of particular interest.

FIGS. 21-32 show structural information pertaining to selected metabolites detected in serum. These figures illustrate the retention time, MS/MS fragmentation patterns, and putative structures for selected molecules. Due to the conserved MS/MS fragmentation mechanism between these molecules, the theoretical MS/MS transition can be determined for any ethanolamine phospholipid by using a combination of the parent ion mass and the fragment mass of the moiety at either the sn-1 or sn-2 position.

EXAMPLE 5

High Throughput Commercial Method Development

A high throughput method for differential diagnosis of AD dementia and non-AD dementia states was established.

Figure 33:
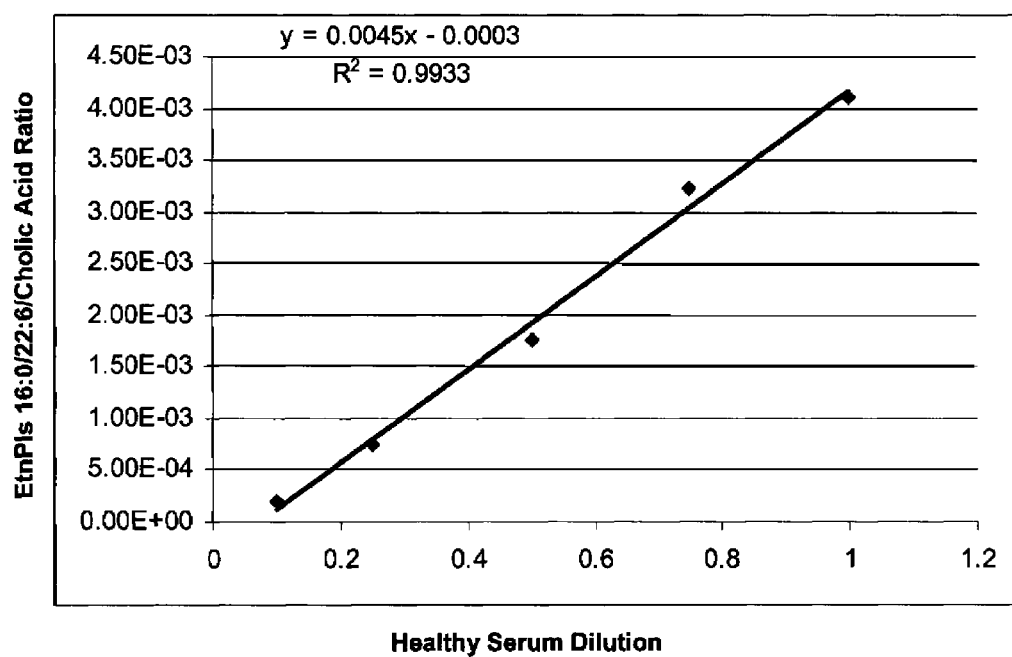
FIG. 33 shows a Q-Trap flow injection analysis standard curve of EtnPls 16:0/22:6 (M19) in healthy human serum.

High throughput screening (HTS) was performed with a linear ion trap mass spectrometer (Q-trap 4000, Applied Biosystem) coupled with Agilent 100 LC system. Sample was prepared by adding 15 uL of internal standard (5 μg/mL of (24-13C)-Cholic Acid in methanol) to 120 uL ethyl acetate fraction of each sample. 100 ul sample was injected by flow injection analysis (FIA), and monitored under negative APCI mode. The method was based on multiple reaction monitoring (MRM) scan mode of one parent/daughter transition for each metabolite and one internal standard. Each transition was scanned for 70 ms for a total cycle time of 2.475 sec. The isocratic 10% EtOAc in MeOH elution was performed with a flow rate at 360 μl/min for 1 min. The source parameters were set as follows: CUR: 10.0, CAD: 8, NC: −4.0, TEM: 400, GS1: 30, GS2: 50, interface heater on. The compound parameters were set as follows: DP: −120.0, EP: −10, NC: −4.0, CE: −40, CXP: −15. FIG. 33 illustrates a representative standard curve for this method for EtnPls 16:0/22:6 generated by diluting a normal serum sample while maintaining a constant concentration of internal standard (24-13C)-Cholic Acid).

EXAMPLE 6

Effect of Aging and Severity of Dementia on Serum Levels of Ethanolamine Phospholipids The effect of aging and severity of dementia on serum levels of e thanolamine phospholipids in 752 subjects aged 40-95 with various levels of dementia was investigated. The clinical data on the subject cohorts is shown in Table 19.

The effect of age was evaluated using a set of aged 30 to 95 subjects of untested cognitive status who did not suffer from dementia. Subjects were divided into one of five subgroups based upon their decade of life (30's, 40's, 50's, 60's, and ≧70). The 40-49 cohort was used as the pre-dementia reference group due to the low incidence of dementia at this age. The metabolites of interest (see Table 18) were measured using the high throughput method described in Example 5.

The effect of dementia severity was determined in subjects aged 56 to 95, comprised of 68 cognitively confirmed non-demented subjects (MMSE≧28); 256 subjects currently diagnosed with SDAT (ADAS-cog 6-70, MMSE 0-26); 20 post-mortem confirmed SDAT and 20 post-mortem confirmed controls. Subjects were grouped into one of four dementia subgroups based upon either their MMSE score [≧28═Cognitively Normal] or their ADAS-cog score [5-19═low cognitive impairment); 20-39═moderate; 40-70═severe].

6A. Absolute levels of Ethanolamine Phospholipids

A significant gender bias was observed in that only females exhibited an age-related decrease in EtnPls. Free docosohexanoic acid (DHA, Free 22:6, M25) in both males and females was significantly increased in the 50-59, 60-69, and 70+ cohorts relative to the 40-49 cohorts. However, only males exhibited a concomitant increase in both 16:0/22:6-EtnPl (M19) and 18:0/22:6-EtnPl (M24) (see Tables 20-21 for males; Tables 22-23 for females). These data indicate that, in females, there may be an age-related dysfunction in the packaging of DHA into EtnPls. This gender difference may explain the increased incidence of dementia in very old females (19).

In both males and females, the majority of EtnPls in all dementia subgroups were significantly reduced relative to cognitive controls. In both males and females, free DHA (M25) was significantly decreased only in severely demented subjects. In females, a dementia effect was observed for three EtnPls (16:0/18:2 (M16), 18:0/18:2 (M21), and 16:0/20:4 (M17)) in that both 18:2-containing EtnPls were significantly lower in severely demented subjects versus either low or moderately demented females, and 16:0/20:4 (M17) was lower in the severe group versus the low group (see Tables 24-26). In males, a dementia effect was observed for DHA (M25) and 16:0/22:6 (M19) in that free DHA (M25) was reduced in the moderate group versus the low group and in the severe group versus the moderate group and 16:0/22:6 (M19) was reduced in the severe group versus the low group (see Tables 27-29). These results indicate that the progressive cognitive deterioration in AD manifests slightly differently in the two sexes.

Brain white matter contains primarily 18:1- and 18:2-containing EtnPls with low levels of 20:4-containing and 22:6-containing EtnPls, whereas gray matter contains significantly higher levels of 20:4-containing and 22:6-containing EtnPls [34]. In females, increasing dementia appears to affect both white (18:2) and gray (20:4) matter EtnPls equally, whereas in males predominantly gray (22:6) matter EtnPls appear to be affected to a greater extent.

Post-mortem collected serum samples from 20 pathologically confirmed AD subjects and 20 subjects containing minimal amyloid deposition were also analyzed. Both gray and white matter EtnPls were significantly decreased in post-mortem confirmed AD relative to age matched controls (see Tables 30 and 31).

6B. Relative levels of Ethanolamine Phospholipids

The data collected above was re-analyzed to obtain a ratio between the levels of each ethanolamine phospholipids with 16:0/18:0 PtdEt (M01). Measurement of the ethanolamine phospholipid levels in this manner is more stable and reproducible than measurement of the absolute levels. Furthermore, because the 16:0/18:0 PtdEt (M01) is naturally present in all samples and does not appear to vary significantly over disease states, this approach minimizes the sample-to-sample variability (due to handling, extraction, etc).

The results obtained further support the observations and conclusions made in 6A. The gender bias was with respect to an age-related decrease in EtnPls was evident in data where ratios to M01 were measured (see Tables 32-33 for males; Tables 34-35 for females). The same trends with respect to the severity of cognitive impairment were also observed (see Tables 36-38 for males; Tables 39-41 for females). In addition, pathology results on post-mortem serum samples show similar trends (Tables 42 and 43).

Both the absolute EtnPls levels and the EtnPls to M01 ratio exhibited a significant dementia effect. The EtnPls to M01 ratios of all eight EtnPls (16:0/18:1 (M15), 16:0/18:2 (M16), 16:0/20:4 (M17), 16:0/22:6 (M19), 18:0/18:1 (M20), 18:0/18:2 (M21), 18:0/20:4 (M22), 18:0/22:6 (M24)) were significantly lower in the severely demented group relative to the low group while six of the eight were significantly lower in the severe group relative to the moderate group

EXAMPLE 7

The Grey and White Matter Score Distribution

A white and gray matter specific EtnPl scoring system was developed whereby each EtnPl in each subject was normalized to their respective gender-specific cognitively normal mean, log 2 transformed and mean centered. Each subject's white matter score was taken as the lowest such value of plasmenyl 16:0/18:1 (M15), 16:0/18:2 (M16), 18:0/18:1 (M20), and 18:0/18:2 (M21) EtnPls, and their gray matter score as the lowest of plasmenyl 16:0/20:4 (M17), 16:0/22:6 (M19), 18:0/20:4 (M22), and 18:0/22:6 (M24) EtnPls.

Figure 39:
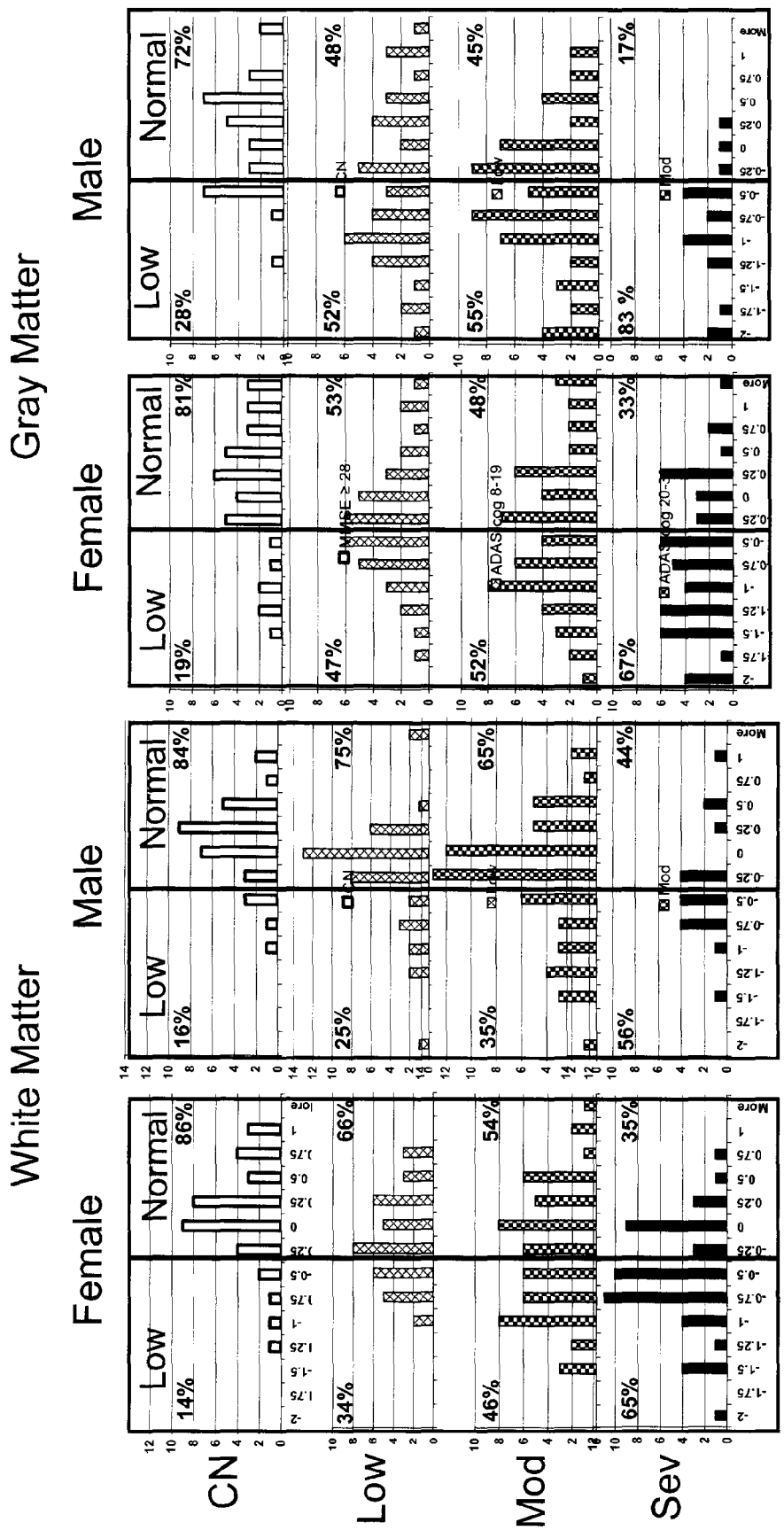
FIG. 39 shows the distribution of serum white and gray matter EtnPl scores in males and females.

These simplified scores revealed that both gray and white matter EtnPls were decreased at all stages of AD (FIG. 39) and that the levels in post-mortem confirmed AD closely matched levels in severely demented subjects of both sexes (Tables 44-45). The cross-sectional white and gray matter score distributions in subjects of various levels of dementia clearly showed a dementia dependent shift in the population means (Tables 46-47). The effect of age on the white and gray matter scores was also determined (Tables 48-49). This also indicated that changes in serum levels of gray matter EtnPls may precede white matter changes and potentially be an early risk factor for AD. Such cross-sectional data does not account for baseline variability among subjects. Individual longitudinal trajectories of these scores may be more accurate at detecting early risk of AD in otherwise healthy, non-demented subjects.

Based on these scores, risk prediction can be performed on both male and female subjects (Tables 49-50) where a cut-off value that results in approximately 20-30% of cognitively normal subjects being classified as either intermediate or high risk is used. Using this cut-off value, a subject's white and gray matter score is evaluated. If the subject tests normal on both scores, the subject is deemed to be at low risk. If the subject tests positive on one of the scores, the subjects is deemed to be at intermediate risk and if the subject tests positive on both scores, the subject is deemed to be at high risk.

EXAMPLE 8

Effect of Dementia Severity and AD Pathology on Serum EtnPls Levels in Combined Male and Female Subjects The effect of dementia severity was determined using 324 subjects (176 female, 148 male) aged 56 to 95, comprised of 68 cognitively confirmed non-demented subjects (MMSE≧28) and 256 subjects currently diagnosed with AD (ADAS-cog 6-70, MMSE 0-26). The effect of AD pathology was determined using serum samples collected from 20 post-mortem confirmed AD and 19 control subjects (Table 19). Subjects were grouped into one of four dementia severity cohorts based upon either their MMSE score [≧28=Cognitively Normal] or their ADAS-cog score [5-19=low cognitive impairment; 20-39=moderate; 40-70=severe].

Figure 34:
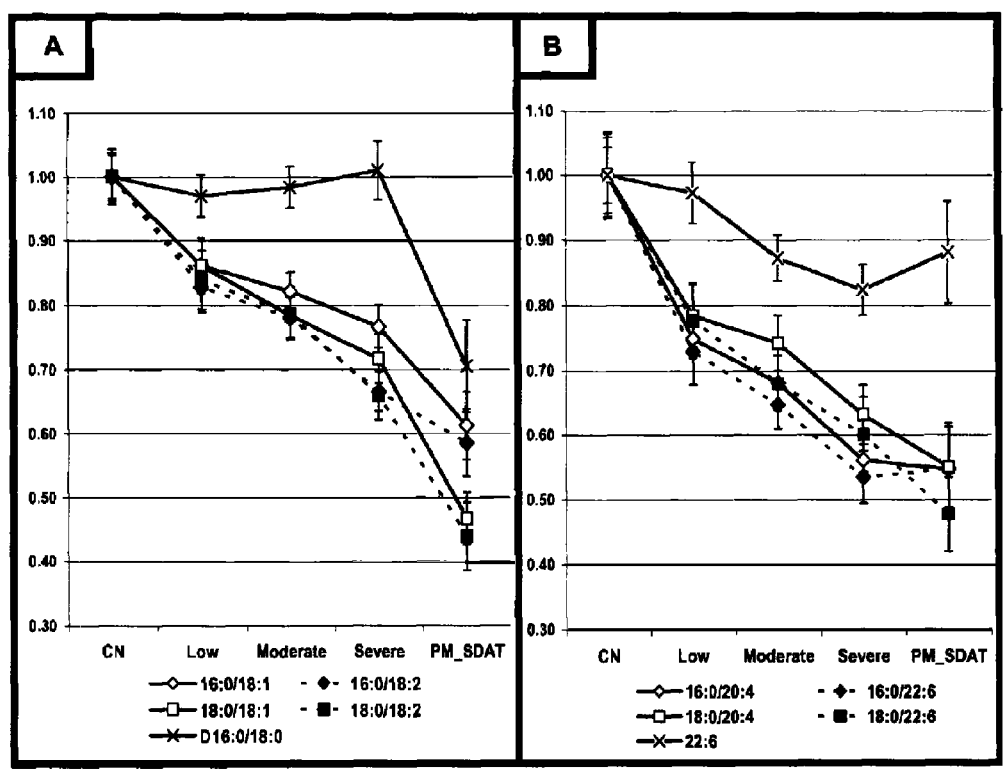
FIG. 34 shows the effect of dementia severity and SDAT pathology on serum EtnPl levels (male and female subjects combined). (A) Mono and di-unsaturated EtnPls and saturated PtdEt internal control. (B) Polyunsaturated EtnPls and free DHA (22:6). EtnPls abbreviations: (fatty acid carbons: double bonds, not including the vinyl ether double bond) and position on glycerol backbone (sn-1/sn-2). D16:0/18:0 represents diacylglycerophosphatidylethanolamine with palmitic acid (16:0) at sn-1 and stearic acid (18:0) at sn-2; 22:6 represents free DHA. Values are expressed as mean±SEM (n=19-112).

Mean serum levels of 16:0/18:1 (M15), 16:0/18:2 (M16), 16:0/20:4 (M17), 16:0/22:6 (M19), 18:0/18:1 (M20), 18:0/18:2 (M21), 18:0/20:4 (M22), 18:0/22:6 (M24) EtnPls; free docosahexaenoic acid (DHA, Free 22:6, M25); and phosphatidylethanolamine (PtdEt) 16:0/18:0 (D16:0/18:0; M01) were determined for each group (FIG. 34). All eight EtnPls in all dementia subgroups were observed to be significantly reduced relative to cognitive controls (24 pair-wise comparisons, t-test p-values 2.6e-2 to 2.0e-10, median=3.9e-5). Free DHA (M25) was significantly decreased in both moderately and severely demented subjects (p<0.05). All eight EtnPls were also significantly decreased in post-mortem confirmed SDAT relative to age matched controls. D16:0/18:0 (M01) levels, a non-plasmalogen phoshopholipid remained unchanged across the different dementia cohorts.

EXAMPLE 9

Population Distributions as a Function of Dementia Severity

Figure 35:
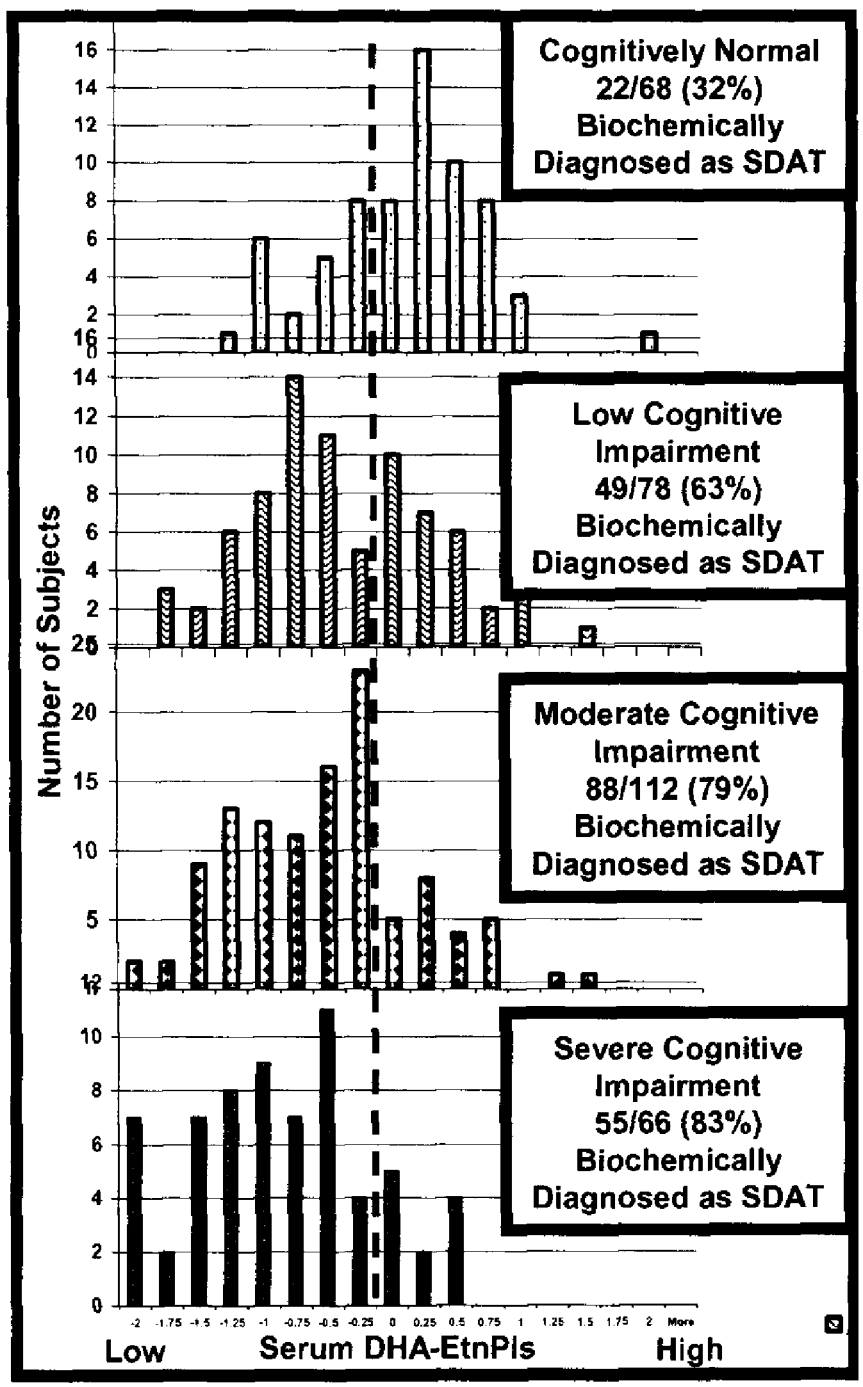
FIG. 35 shows serum DHA-EtnPls (Log(2) EtnPls 16:0/22:6 (M19) to PtdEt 16:0/18:0 (M01) ratio) distributions in subjects with different levels of dementia severity (male and female subjects combined).

The EtnPls 16:0/22:6 (M 19) to PtdEt 16:0/18:0 ratio (M01) (DHA-EtnPls) showed the strongest overall sex-independent dementia effect (Tables 38, 41) and was used for all subsequent population distributions and comparisons. A summary of the key comparisons using this ratio are listed in Table 52. This ratio was then log(2) transformed and used to create a population histogram for each cohort of increasing cognitive impairment (FIG. 35). A cut-off value was selected based upon the findings of Bennett et al [35], (i.e. ~30% of the CN group being detected as AD) (FIG. 35, dotted line). Using this cut-off, 63%, 79% and 83% of low, moderate and severely demented subjects, respectively, were subsequently classified as AD.

Figure 36:
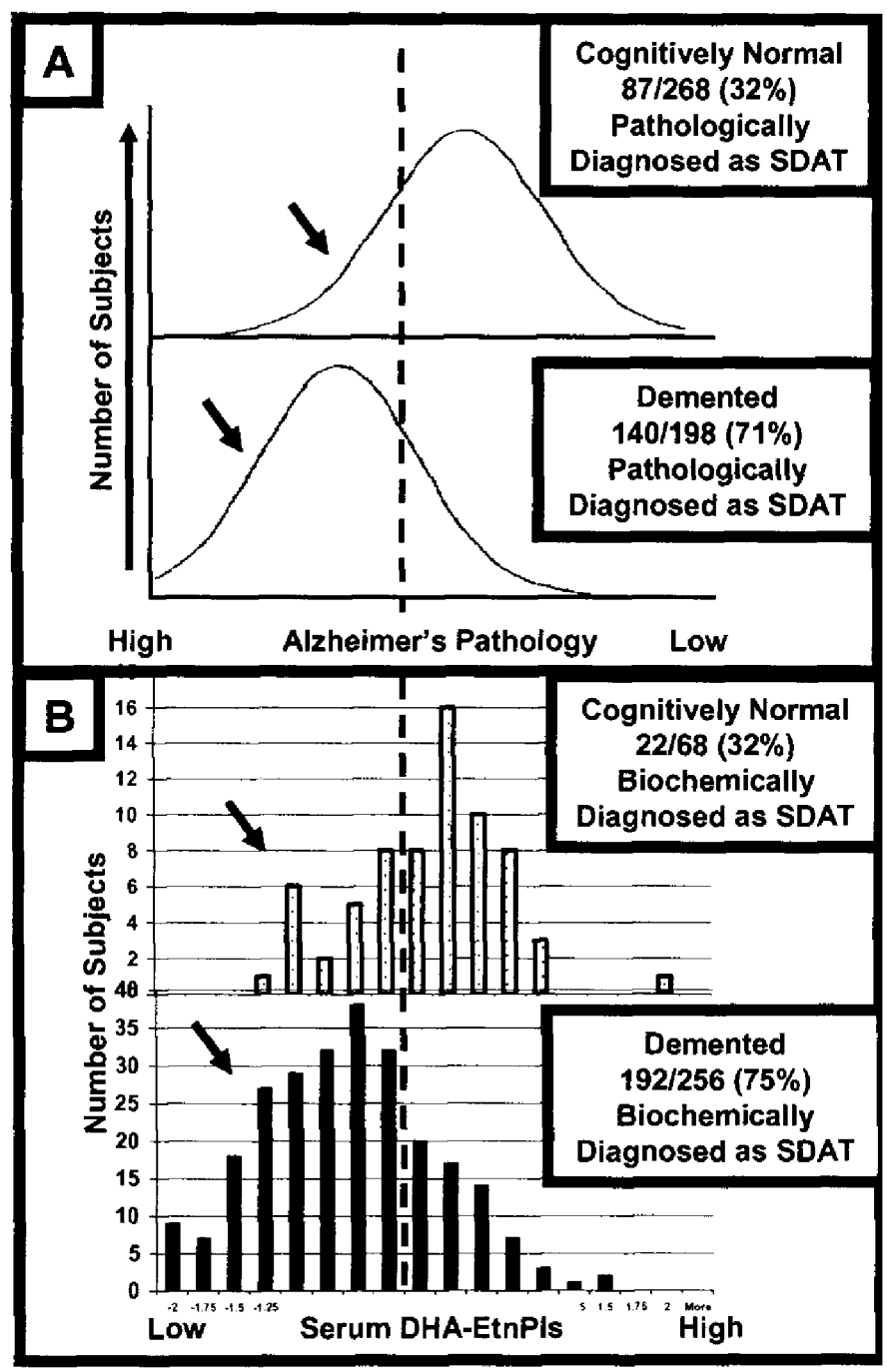
FIG. 36 is a comparison of theoretical distributions of AD pathology (A) compiled from references 5-8 and experimentally determined distributions of serum 22:6-containing EtnPls (Log(2) EtnPls 16:0/22:6 (M19) to PtdEt 16:0/18:0 (M01) ratio) (B) in cognitively normal and demented subjects. Arrow indicates positive diagnosis of AD.

To compare these distributions with the known distributions of Aβ pathology in AD, the results of four prospective pathology studies [8, 35-37] were combined to generate the theoretical population distributions of Aβ pathology in demented and non-demented populations, assuming that Aβ is normally distributed in each population (FIG. 36A). These studies reported that only 71% (140/198) of clinically diagnosed AD subjects have AD pathology at death and that 32% (87/268) of cognitively normal subjects meet neuropathological criteria for AD at death. When the data from all of our cognitively tested subjects were combined, 32% (22/68) of our non-demented population and 75% (192/256) of our demented population were classified as AD positive based upon their serum EtnPls level (FIG. 36B). This comparison revealed that the observed distribution of depleted 22:6-containing EtnPls perfectly matched the theoretical distribution of AD pathology in demented and non-demented subjects.

EXAMPLE 10

Linear Extrapolation of Disease Progression and Serum EtnPls Depletion

Figure 37:
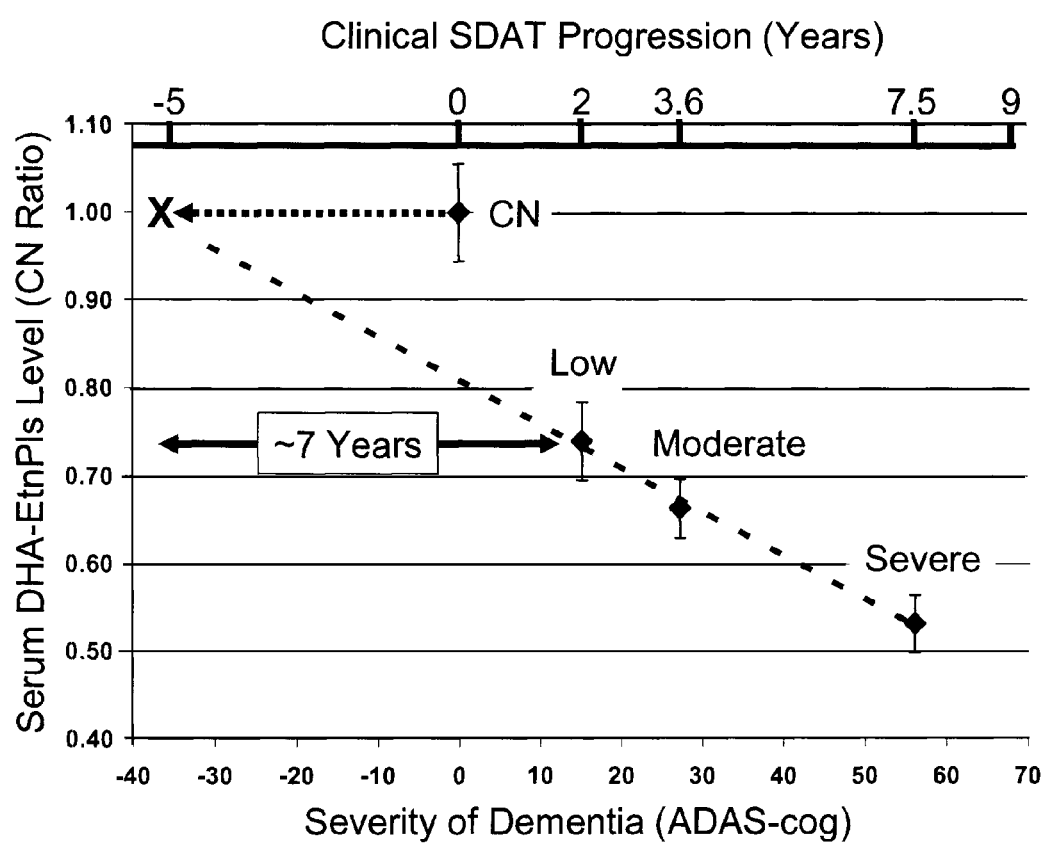
FIG. 37 is a linear regression analysis of disease severity (ADAS-cog) and serum 22:6-containing EtnPls (EtnPls 16:0/22:6 (M19) to PtdEt 16:0/18:0 (M01) ratio) levels in 256 AD subjects. X=predicted initiation of EtnPls depletion. Values are expressed as mean±SEM (n=66-112). Clinical progression assumes 7.5 ADAS-cog points/year.

To investigate whether a correlation between the decrease in EtnPls and increasing dementia in the clinically diagnosed AD population exists, a linear regression analysis was performed using the mean 22:6-containing EtnPls level (normalized to CN) of each of the dementia cohorts and the average ADAS-cog score for each of these three cohorts (FIG. 37). A very high correlation was observed between the mean 22:6-containing EtnPls level and the mean ADAS-cog scores of the three dementia cohorts (r2=0.99). However, this linear decrease did not extrapolate back to the CN group (X vs. CN). Assuming a clinical AD progression of 7.5 ADAS-cog units per year, this extrapolation predicts that that 22:6-containing EtnPls levels begin to decline approximately seven years before clinical cognitive impairment (ADAS-cog=15) is evident.

EXAMPLE 11

The Effect of Chronological Age on Serum DHA-EtnPls Levels

Figure 38:
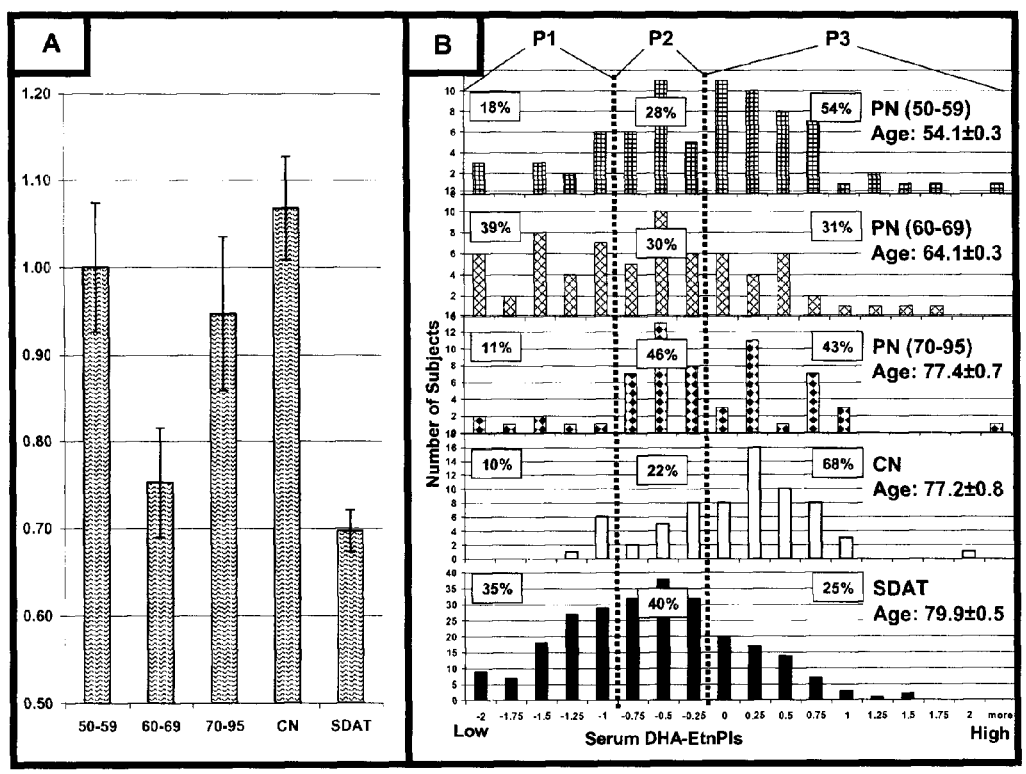
FIG. 38 shows serum 22:6-containing EtnPls (EtnPls 16:0/22:6 (M19) to PtdEt 16:0/18:0 (M01) ratio) levels in AD, Cognitive Normal, and general population subjects. (A) Mean±SEM (n=68-256). (B) Log(2) distributions.

To investigate whether the above prediction could be verified experimentally, the serum 22:6-containing EtnPls levels in 209 subjects (110 male, 99 female, Table 19) of unknown cognitive status but currently not diagnosed with dementia was determined and compared to the clinical AD and CN cohorts (FIG. 38). The results of this analysis revealed a significant drop in serum 22:6-containing EtnPls in the aged 60-69 cohort versus the aged 50-59 cohort (FIG. 38A). This cohort also had significantly lower levels versus the CN group even though the CN group was, on average, 13 years older. Interestingly, the aged 70-95 cohort was not significantly different from either the aged 50-59 cohort or the CN cohort, but had significantly higher levels than the SDAT cohort.

EXAMPLE 12

Sub-Populations Identified by Serum DHA-EtnPls Levels

The distribution of serum DHA-EtnPls within each age group, as shown in FIG. 38B, was also examined. The population distributions of the five groups (three age groups, CN and AD) differentiated by age and dementia status reveal the presence of three distinct populations (P1-P3, FIG. 38B). The populations were assigned as: P1-subjects with AD pathology and no remaining reserve capacity; P3—subjects with little or no AD pathology; P2—subjects that are transitioning from P3 to P1. These P2 subjects are hypothesized to have AD pathology and some level of reserve remaining.

Since AD subjects have a life expectancy of less than 10 years from diagnosis [38, 39] and low 22:6-containing EtnPls are highly associated with AD severity, the decreased number of P1 subjects observed in the aged 70-95 cohort is most likely due to differences in life expectancy between P1 and P2 or P3. The transitory nature of P2 is best illustrated by examining the different ratios between the percentages of subjects present in P3 compared to P2, as observed in the lower three panels of FIG. 7B. These three cohorts differ only in dementia status. The P3 to P2 ratio changes from 3:1 (68% versus 22%) in the confirmed cognitive normal group to an intermediate ratio of 1:1 (43% versus 46%) in the normal healthy elderly group of unknown cognitive status, to 0.6:1 (25% versus 40%) in the confirmed demented AD cohort.

All citations are hereby incorporated by reference.

The present invention has been described with regard to one or more embodiments. However, it will be apparent to persons skilled in the art that a number of variations and modifications can be made without departing from the scope of the invention as defined in the claims.

TABLE 1

Accurate mass features differing between clinically diagnosed
AD patients and non-demented controls (p < 0.05, log2 transformed).

| Detected Mass | Analysis Mode | AVG (log2) AD | SEM AD | AVG (log2) Normal | SEM Normal | log(2) Ratio | P Value |
|---|---|---|---|---|---|---|---|
| 723.5197 | 1204 | 3.576 | 0.039 | 4.350 | 0.056 | 0.822 | 5.09E−19 |
| 723.5195 | 1202 | 2.186 | 0.040 | 2.892 | 0.052 | 0.756 | 4.86E−17 |
| 724.5257 | 1204 | 2.866 | 0.032 | 3.463 | 0.055 | 0.828 | 4.15E−16 |
| 749.5367 | 1202 | 3.176 | 0.034 | 3.714 | 0.041 | 0.855 | 3.82E−15 |
| 751.5555 | 1204 | 4.575 | 0.041 | 5.248 | 0.060 | 0.872 | 1.07E−14 |
| 751.5529 | 1202 | 3.335 | 0.036 | 3.920 | 0.050 | 0.851 | 1.14E−14 |
| 752.5564 | 1202 | 2.251 | 0.038 | 2.836 | 0.050 | 0.794 | 3.13E−14 |
| 752.5583 | 1204 | 3.472 | 0.042 | 4.094 | 0.061 | 0.848 | 6.47E−13 |
| 699.5198 | 1204 | 2.216 | 0.038 | 2.775 | 0.054 | 0.799 | 6.76E−13 |
| 750.544 | 1204 | 3.279 | 0.038 | 3.858 | 0.063 | 0.850 | 1.07E−12 |
| 749.5407 | 1204 | 4.426 | 0.039 | 5.012 | 0.064 | 0.883 | 1.33E−12 |
| 541.3432 | 1102 | 3.315 | 0.033 | 3.798 | 0.048 | 0.873 | 1.42E−12 |
| 750.5402 | 1202 | 2.192 | 0.038 | 2.704 | 0.044 | 0.811 | 2.76E−12 |
| 725.5385 | 1204 | 2.884 | 0.043 | 3.417 | 0.054 | 0.844 | 1.28E−10 |
| 569.3687 | 1102 | 2.262 | 0.039 | 2.724 | 0.048 | 0.830 | 6.22E−10 |
| 727.5568 | 1204 | 3.518 | 0.038 | 3.986 | 0.060 | 0.882 | 1.70E−09 |
| 804.5713 | 1102 | 4.207 | 0.042 | 4.610 | 0.033 | 0.913 | 3.88E−08 |
| 803.568 | 1102 | 5.432 | 0.043 | 5.838 | 0.035 | 0.930 | 7.10E−08 |
| 726.5461 | 1204 | 2.808 | 0.032 | 3.150 | 0.050 | 0.892 | 7.50E−08 |
| 827.57 | 1102 | 4.151 | 0.048 | 4.630 | 0.062 | 0.897 | 9.42E−08 |
| 803.5445 | 1101 | 5.123 | 0.055 | 5.655 | 0.059 | 0.906 | 1.01E−07 |
| 555.3102 | 1102 | 1.818 | 0.045 | 2.240 | 0.046 | 0.812 | 1.27E−07 |
| 565.3394 | 1102 | 3.480 | 0.050 | 3.958 | 0.055 | 0.879 | 1.28E−07 |
| 804.5476 | 1101 | 4.169 | 0.056 | 4.703 | 0.060 | 0.887 | 1.33E−07 |
| 828.5737 | 1102 | 3.138 | 0.046 | 3.590 | 0.061 | 0.874 | 1.89E−07 |
| 567.3547 | 1102 | 2.822 | 0.041 | 3.218 | 0.054 | 0.877 | 2.89E−07 |
| 728.5627 | 1204 | 2.935 | 0.033 | 3.281 | 0.060 | 0.895 | 5.16E−07 |
| 817.5377 | 1102 | 2.282 | 0.048 | 2.712 | 0.057 | 0.842 | 8.85E−07 |
| 779.5444 | 1101 | 6.433 | 0.053 | 6.874 | 0.043 | 0.936 | 1.06E−06 |
| 780.5474 | 1101 | 5.437 | 0.053 | 5.875 | 0.043 | 0.925 | 1.28E−06 |
| 812.5762 | 1202 | 1.659 | 0.050 | 2.084 | 0.058 | 0.796 | 2.24E−06 |
| 832.6026 | 1102 | 3.455 | 0.041 | 3.795 | 0.040 | 0.910 | 2.48E−06 |
| 811.5732 | 1202 | 2.705 | 0.036 | 3.027 | 0.055 | 0.893 | 3.40E−06 |
| 871.5528 | 1102 | 3.068 | 0.042 | 3.408 | 0.040 | 0.900 | 3.47E−06 |
| 831.5997 | 1102 | 4.564 | 0.042 | 4.903 | 0.040 | 0.931 | 3.48E−06 |
| 793.5386 | 1102 | 3.604 | 0.043 | 3.950 | 0.039 | 0.912 | 3.50E−06 |
| 782.5085 | 1204 | 3.401 | 0.045 | 3.780 | 0.055 | 0.900 | 3.81E−06 |
| 805.5832 | 1102 | 4.075 | 0.047 | 4.485 | 0.068 | 0.909 | 3.87E−06 |
| 781.5617 | 1101 | 6.109 | 0.061 | 6.610 | 0.072 | 0.924 | 5.14E−06 |
| 813.5885 | 1202 | 3.012 | 0.030 | 3.276 | 0.048 | 0.919 | 6.23E−06 |
| 794.5421 | 1102 | 2.523 | 0.042 | 2.853 | 0.040 | 0.885 | 6.30E−06 |
| 814.5917 | 1202 | 2.041 | 0.026 | 2.289 | 0.051 | 0.892 | 7.46E−06 |
| 747.5245 | 1204 | 3.473 | 0.043 | 3.886 | 0.090 | 0.894 | 9.55E−06 |
| 837.5027 | 1101 | 3.578 | 0.045 | 3.933 | 0.050 | 0.910 | 1.02E−05 |
| 782.565 | 1101 | 5.083 | 0.063 | 5.589 | 0.078 | 0.909 | 1.09E−05 |
| 746.5717 | 1204 | 3.085 | 0.031 | 3.362 | 0.061 | 0.918 | 1.82E−05 |
| 829.5856 | 1102 | 4.043 | 0.048 | 4.398 | 0.046 | 0.919 | 1.85E−05 |
| 784.5237 | 1204 | 3.310 | 0.040 | 3.603 | 0.037 | 0.919 | 1.91E−05 |
| 786.5416 | 1204 | 3.815 | 0.035 | 4.087 | 0.043 | 0.933 | 1.91E−05 |
| 760.5216 | 1204 | 4.075 | 0.036 | 4.347 | 0.039 | 0.938 | 2.11E−05 |
| 745.5658 | 1204 | 3.937 | 0.034 | 4.242 | 0.068 | 0.928 | 2.12E−05 |
| 744.5536 | 1204 | 4.322 | 0.034 | 4.605 | 0.058 | 0.939 | 2.46E−05 |
| 783.5672 | 1101 | 3.755 | 0.068 | 4.259 | 0.079 | 0.882 | 3.48E−05 |
| 807.5758 | 1101 | 5.736 | 0.052 | 6.102 | 0.047 | 0.940 | 3.69E−05 |
| 808.5792 | 1101 | 4.697 | 0.052 | 5.063 | 0.047 | 0.928 | 4.20E−05 |
| 743.5471 | 1204 | 5.286 | 0.036 | 5.579 | 0.063 | 0.947 | 4.94E−05 |
| 482.3215 | 1202 | 1.971 | 0.038 | 2.251 | 0.062 | 0.875 | 0.0001 |
| 755.486 | 1204 | 3.221 | 0.047 | 3.561 | 0.057 | 0.905 | 0.0001 |
| 758.5092 | 1204 | 4.574 | 0.033 | 4.808 | 0.042 | 0.951 | 0.0001 |
| 775.5533 | 1202 | 2.120 | 0.044 | 2.449 | 0.068 | 0.866 | 0.0001 |
| 787.5729 | 1202 | 1.847 | 0.040 | 2.145 | 0.057 | 0.861 | 0.0001 |
| 795.5181 | 1101 | 2.630 | 0.059 | 3.044 | 0.064 | 0.864 | 0.0001 |
| 795.555 | 1102 | 2.665 | 0.043 | 2.986 | 0.065 | 0.892 | 0.0001 |
| 805.5605 | 1101 | 5.414 | 0.057 | 5.785 | 0.048 | 0.936 | 0.0001 |
| 831.5759 | 1101 | 4.297 | 0.056 | 4.677 | 0.060 | 0.919 | 0.0001 |
| 855.6016 | 1102 | 3.538 | 0.045 | 3.873 | 0.065 | 0.914 | 0.0001 |
| 517.314 | 1101 | 5.470 | 0.038 | 5.755 | 0.069 | 0.951 | 0.0002 |
| 541.3139 | 1101 | 4.091 | 0.053 | 4.494 | 0.096 | 0.910 | 0.0002 |
| 542.3173 | 1101 | 2.284 | 0.055 | 2.687 | 0.089 | 0.850 | 0.0002 |
| 747.5201 | 1202 | 1.937 | 0.051 | 2.313 | 0.088 | 0.838 | 0.0002 |
| 757.4991 | 1101 | 3.644 | 0.065 | 4.073 | 0.070 | 0.895 | 0.0002 |
| 775.5528 | 1204 | 3.197 | 0.045 | 3.537 | 0.085 | 0.904 | 0.0002 |
| 806.5639 | 1101 | 4.423 | 0.057 | 4.779 | 0.049 | 0.926 | 0.0002 |
| 832.5791 | 1101 | 3.357 | 0.055 | 3.723 | 0.061 | 0.902 | 0.0002 |

TABLE 1-continued

Accurate mass features differing between clinically diagnosed
AD patients and non-demented controls (p < 0.05, log2 transformed).

| Detected Mass | Analysis Mode | AVG (log2) AD | SEM AD | AVG (log2) Normal | SEM Normal | log(2) Ratio | P Value |
|---|---|---|---|---|---|---|---|
| 915.5191 | 1101 | 2.376 | 0.051 | 2.717 | 0.063 | 0.874 | 0.0002 |
| 755.5468 | 1101 | 2.326 | 0.064 | 2.753 | 0.085 | 0.845 | 0.0003 |
| 777.553 | 1202 | 1.859 | 0.072 | 2.384 | 0.130 | 0.780 | 0.0003 |
| 829.5604 | 1101 | 3.535 | 0.053 | 3.875 | 0.058 | 0.912 | 0.0003 |
| 518.3174 | 1101 | 3.438 | 0.038 | 3.717 | 0.073 | 0.925 | 0.0004 |
| 731.5464 | 1101 | 1.945 | 0.096 | 2.600 | 0.157 | 0.748 | 0.0004 |
| 757.5626 | 1101 | 6.655 | 0.074 | 7.108 | 0.079 | 0.936 | 0.0004 |
| 758.5656 | 1101 | 5.702 | 0.075 | 6.160 | 0.078 | 0.926 | 0.0004 |
| 759.5779 | 1101 | 5.547 | 0.069 | 5.997 | 0.099 | 0.925 | 0.0004 |
| 760.5811 | 1101 | 4.419 | 0.071 | 4.886 | 0.103 | 0.904 | 0.0004 |
| 768.5539 | 1204 | 3.964 | 0.046 | 4.279 | 0.077 | 0.927 | 0.0004 |
| 748.5287 | 1204 | 2.277 | 0.091 | 2.820 | 0.088 | 0.807 | 0.0005 |
| 783.5148 | 1204 | 3.284 | 0.047 | 3.574 | 0.056 | 0.919 | 0.0005 |
| 821.5712 | 1102 | 3.064 | 0.040 | 3.304 | 0.044 | 0.927 | 0.0005 |
| 523.4679 | 1203 | 3.252 | 0.121 | 4.011 | 0.165 | 0.811 | 0.0006 |
| 781.562 | 1201 | 7.364 | 0.040 | 7.638 | 0.071 | 0.964 | 0.0006 |
| 810.5399 | 1204 | 2.835 | 0.050 | 3.145 | 0.066 | 0.901 | 0.0006 |
| 732.4938 | 1204 | 4.249 | 0.042 | 4.511 | 0.057 | 0.942 | 0.0007 |
| 522.4635 | 1203 | 4.713 | 0.126 | 5.485 | 0.176 | 0.859 | 0.0008 |
| 810.5969 | 1101 | 3.957 | 0.072 | 4.370 | 0.080 | 0.905 | 0.0009 |
| 853.5854 | 1102 | 2.626 | 0.043 | 2.880 | 0.052 | 0.912 | 0.0009 |
| 819.5551 | 1102 | 2.394 | 0.046 | 2.654 | 0.046 | 0.902 | 0.001 |
| 828.5743 | 1202 | 5.243 | 0.058 | 5.598 | 0.085 | 0.936 | 0.001 |
| 478.254 | 1201 | 1.584 | 0.083 | 1.051 | 0.148 | 1.507 | 0.0011 |
| 579.5325 | 1203 | 4.102 | 0.089 | 4.636 | 0.127 | 0.885 | 0.0011 |
| 744.4956 | 1204 | 3.881 | 0.039 | 4.117 | 0.058 | 0.943 | 0.0011 |
| 761.5843 | 1101 | 2.422 | 0.065 | 2.829 | 0.106 | 0.856 | 0.0011 |
| 809.5936 | 1101 | 4.964 | 0.070 | 5.362 | 0.079 | 0.926 | 0.0011 |
| 886.5582 | 1102 | 3.041 | 0.037 | 3.250 | 0.041 | 0.936 | 0.0011 |
| 481.3172 | 1202 | 3.923 | 0.039 | 4.159 | 0.060 | 0.943 | 0.0012 |
| 767.5495 | 1204 | 5.063 | 0.049 | 5.369 | 0.082 | 0.943 | 0.0012 |
| 782.5653 | 1201 | 6.339 | 0.043 | 6.614 | 0.076 | 0.959 | 0.0012 |
| 827.5701 | 1202 | 6.306 | 0.063 | 6.684 | 0.092 | 0.943 | 0.0012 |
| 847.5316 | 1101 | 2.742 | 0.059 | 3.091 | 0.083 | 0.887 | 0.0012 |
| 789.5892 | 1202 | 1.723 | 0.036 | 1.952 | 0.065 | 0.883 | 0.0013 |
| 543.3296 | 1101 | 3.733 | 0.044 | 4.023 | 0.087 | 0.928 | 0.0014 |
| 575.2728 | 1101 | 2.470 | 0.043 | 2.739 | 0.074 | 0.902 | 0.0014 |
| 580.5351 | 1203 | 1.456 | 0.127 | 2.192 | 0.174 | 0.664 | 0.0014 |
| 521.4522 | 1203 | 2.302 | 0.131 | 3.028 | 0.158 | 0.760 | 0.0016 |
| 731.4916 | 1204 | 5.482 | 0.046 | 5.746 | 0.063 | 0.954 | 0.0016 |
| 759.5163 | 1204 | 4.724 | 0.042 | 4.954 | 0.048 | 0.954 | 0.0016 |
| 306.2569 | 1204 | 2.998 | 0.046 | 3.266 | 0.067 | 0.918 | 0.0017 |
| 771.5814 | 1204 | 4.164 | 0.036 | 4.367 | 0.046 | 0.954 | 0.0017 |
| 786.5967 | 1101 | 4.808 | 0.074 | 5.203 | 0.078 | 0.924 | 0.0019 |
| 458.2405 | 1101 | 1.736 | 0.040 | 1.986 | 0.077 | 0.874 | 0.0021 |
| 520.4499 | 1203 | 3.956 | 0.112 | 4.577 | 0.148 | 0.864 | 0.0021 |
| 748.5735 | 1202 | 3.918 | 0.035 | 3.722 | 0.050 | 1.053 | 0.0021 |
| 490.3641 | 1203 | 1.944 | 0.092 | 1.397 | 0.159 | 1.391 | 0.0023 |
| 545.3453 | 1101 | 3.606 | 0.051 | 3.898 | 0.078 | 0.925 | 0.0023 |
| 605.5457 | 1203 | 5.135 | 0.068 | 5.509 | 0.089 | 0.932 | 0.0023 |
| 769.5656 | 1204 | 3.963 | 0.038 | 4.174 | 0.054 | 0.950 | 0.0023 |
| 570.3725 | 1202 | 2.976 | 0.032 | 3.155 | 0.045 | 0.943 | 0.0024 |
| 785.5933 | 1101 | 5.884 | 0.074 | 6.271 | 0.080 | 0.938 | 0.0024 |
| 582.2473 | 1201 | 3.325 | 0.096 | 2.793 | 0.141 | 1.191 | 0.0026 |
| 569.369 | 1202 | 4.908 | 0.033 | 5.089 | 0.047 | 0.964 | 0.0027 |
| 784.5811 | 1101 | 4.405 | 0.079 | 4.817 | 0.089 | 0.915 | 0.0027 |
| 811.6096 | 1101 | 3.078 | 0.083 | 3.511 | 0.096 | 0.877 | 0.0027 |
| 590.343 | 1202 | 4.025 | 0.050 | 4.304 | 0.076 | 0.935 | 0.0028 |
| 856.672 | 1202 | 2.764 | 0.038 | 2.553 | 0.057 | 1.082 | 0.0028 |
| 833.5932 | 1101 | 3.276 | 0.068 | 3.608 | 0.056 | 0.908 | 0.003 |
| 506.2851 | 1201 | 3.142 | 0.077 | 2.656 | 0.165 | 1.183 | 0.0031 |
| 793.5681 | 1204 | 3.155 | 0.040 | 3.372 | 0.055 | 0.936 | 0.0031 |
| 546.3485 | 1101 | 1.999 | 0.050 | 2.287 | 0.089 | 0.874 | 0.0036 |
| 591.3542 | 1202 | 4.045 | 0.061 | 4.345 | 0.058 | 0.931 | 0.0037 |
| 741.5305 | 1204 | 2.931 | 0.056 | 3.250 | 0.102 | 0.902 | 0.0042 |
| 796.5876 | 1204 | 2.634 | 0.043 | 2.860 | 0.062 | 0.921 | 0.0042 |
| 804.7227 | 1203 | 1.842 | 0.145 | 2.611 | 0.220 | 0.705 | 0.0044 |
| 807.59 | 1202 | 2.463 | 0.045 | 2.718 | 0.082 | 0.906 | 0.0045 |
| 506.3213 | 1202 | 2.538 | 0.040 | 2.748 | 0.061 | 0.923 | 0.0046 |
| 552.5022 | 1203 | 3.164 | 0.088 | 3.643 | 0.147 | 0.869 | 0.0047 |
| 589.3403 | 1202 | 5.876 | 0.056 | 6.171 | 0.085 | 0.952 | 0.0048 |
| 806.5873 | 1202 | 4.366 | 0.047 | 4.635 | 0.092 | 0.942 | 0.0048 |
| 550.4957 | 1203 | 6.898 | 0.096 | 7.415 | 0.160 | 0.930 | 0.0049 |
| 604.5433 | 1203 | 6.554 | 0.069 | 6.901 | 0.089 | 0.950 | 0.005 |

TABLE 1-continued

Accurate mass features differing between clinically diagnosed
AD patients and non-demented controls (p < 0.05, log2 transformed).

| Detected Mass | Analysis Mode | AVG (log2) AD | SEM AD | AVG (log2) Normal | SEM Normal | log(2) Ratio | P Value |
|---|---|---|---|---|---|---|---|
| 805.5839 | 1202 | 5.562 | 0.048 | 5.841 | 0.097 | 0.952 | 0.0052 |
| 551.4986 | 1203 | 5.480 | 0.095 | 5.988 | 0.158 | 0.915 | 0.0053 |
| 743.5469 | 1202 | 3.061 | 0.055 | 3.348 | 0.086 | 0.914 | 0.0056 |
| 541.3435 | 1202 | 5.669 | 0.059 | 5.974 | 0.094 | 0.949 | 0.0058 |
| 183.0661 | 1101 | 2.590 | 0.091 | 3.015 | 0.094 | 0.859 | 0.006 |
| 858.6212 | 1202 | 2.707 | 0.059 | 2.994 | 0.074 | 0.904 | 0.0061 |
| 614.4914 | 1203 | 2.779 | 0.060 | 2.448 | 0.114 | 1.135 | 0.0062 |
| 787.5465 | 1204 | 2.675 | 0.077 | 3.017 | 0.054 | 0.887 | 0.0062 |
| 772.5862 | 1204 | 3.287 | 0.031 | 3.437 | 0.042 | 0.956 | 0.007 |
| 837.5881 | 1202 | 2.429 | 0.027 | 2.577 | 0.053 | 0.942 | 0.007 |
| 509.3493 | 1202 | 2.403 | 0.035 | 2.579 | 0.055 | 0.931 | 0.0071 |
| 529.3167 | 1202 | 3.032 | 0.048 | 3.265 | 0.069 | 0.928 | 0.0075 |
| 564.5134 | 1203 | 2.706 | 0.075 | 3.075 | 0.111 | 0.880 | 0.0075 |
| 566.3434 | 1202 | 5.203 | 0.049 | 5.436 | 0.062 | 0.957 | 0.0075 |
| 833.7571 | 1203 | 2.962 | 0.109 | 3.507 | 0.170 | 0.845 | 0.0077 |
| 631.628 | 1203 | 1.795 | 0.127 | 2.391 | 0.161 | 0.751 | 0.008 |
| 857.6186 | 1202 | 3.773 | 0.058 | 4.049 | 0.076 | 0.932 | 0.008 |
| 858.6861 | 1202 | 2.943 | 0.040 | 2.756 | 0.052 | 1.068 | 0.0081 |
| 519.3321 | 1101 | 3.964 | 0.084 | 4.382 | 0.133 | 0.905 | 0.0083 |
| 685.26 | 1202 | 1.771 | 0.048 | 1.998 | 0.063 | 0.886 | 0.0083 |
| 757.5014 | 1204 | 3.755 | 0.048 | 3.971 | 0.052 | 0.946 | 0.0085 |
| 744.55 | 1202 | 1.968 | 0.051 | 2.222 | 0.083 | 0.886 | 0.0086 |
| 671.5723 | 1204 | 2.231 | 0.084 | 2.604 | 0.087 | 0.857 | 0.0087 |
| 304.241 | 1204 | 4.887 | 0.041 | 5.088 | 0.066 | 0.961 | 0.0092 |
| 536.4794 | 1203 | 2.320 | 0.101 | 2.799 | 0.143 | 0.829 | 0.0093 |
| 542.3461 | 1202 | 3.873 | 0.049 | 4.106 | 0.074 | 0.943 | 0.0095 |
| 675.6377 | 1204 | 3.953 | 0.043 | 4.160 | 0.066 | 0.950 | 0.0098 |
| 520.3354 | 1101 | 2.240 | 0.085 | 2.646 | 0.130 | 0.846 | 0.01 |
| 832.7523 | 1203 | 3.859 | 0.107 | 4.374 | 0.169 | 0.882 | 0.0103 |
| 409.0208 | 1202 | 2.806 | 0.035 | 2.980 | 0.063 | 0.942 | 0.0106 |
| 768.5503 | 1202 | 1.942 | 0.076 | 2.277 | 0.090 | 0.853 | 0.0111 |
| 303.1079 | 1202 | 5.648 | 0.034 | 5.802 | 0.047 | 0.973 | 0.0113 |
| 592.3571 | 1202 | 2.291 | 0.063 | 2.560 | 0.062 | 0.895 | 0.0115 |
| 837.718 | 1204 | 2.888 | 0.176 | 3.662 | 0.217 | 0.788 | 0.0121 |
| 832.7492 | 1204 | 3.286 | 0.119 | 3.848 | 0.190 | 0.854 | 0.0125 |
| 832.6037 | 1202 | 5.066 | 0.047 | 5.274 | 0.062 | 0.961 | 0.013 |
| 411.3212 | 1202 | 2.868 | 0.038 | 3.033 | 0.048 | 0.946 | 0.0134 |
| 838.7226 | 1204 | 2.313 | 0.148 | 2.973 | 0.206 | 0.778 | 0.0136 |
| 670.569 | 1204 | 3.239 | 0.061 | 3.515 | 0.093 | 0.921 | 0.0141 |
| 795.5838 | 1204 | 3.566 | 0.046 | 3.769 | 0.063 | 0.946 | 0.0141 |
| 767.547 | 1202 | 3.073 | 0.064 | 3.358 | 0.092 | 0.915 | 0.0143 |
| 305.2438 | 1204 | 2.519 | 0.044 | 2.719 | 0.067 | 0.926 | 0.0146 |
| 505.3229 | 1202 | 3.994 | 0.051 | 4.222 | 0.076 | 0.946 | 0.0156 |
| 803.5677 | 1202 | 7.196 | 0.070 | 7.502 | 0.098 | 0.959 | 0.0157 |
| 711.2577 | 1202 | 2.250 | 0.049 | 2.454 | 0.056 | 0.917 | 0.0159 |
| 827.5448 | 1101 | 3.549 | 0.077 | 3.873 | 0.095 | 0.916 | 0.016 |
| 548.4815 | 1203 | 7.094 | 0.072 | 7.405 | 0.103 | 0.958 | 0.0174 |
| 568.3573 | 1202 | 4.008 | 0.035 | 4.167 | 0.060 | 0.962 | 0.0175 |
| 578.5277 | 1203 | 4.301 | 0.303 | 5.548 | 0.355 | 0.775 | 0.0175 |
| 601.5164 | 1203 | 7.640 | 0.038 | 7.463 | 0.069 | 1.024 | 0.0185 |
| 549.4845 | 1203 | 5.666 | 0.077 | 5.994 | 0.110 | 0.945 | 0.0187 |
| 743.5466 | 1203 | 1.987 | 0.064 | 2.266 | 0.099 | 0.877 | 0.0189 |
| 772.5278 | 1204 | 3.324 | 0.039 | 3.488 | 0.055 | 0.953 | 0.019 |
| 765.5334 | 1204 | 3.269 | 0.060 | 3.540 | 0.104 | 0.923 | 0.0193 |
| 440.3532 | 1204 | 1.417 | 0.096 | 0.975 | 0.180 | 1.453 | 0.0205 |
| 495.332 | 1101 | 5.251 | 0.073 | 5.565 | 0.112 | 0.944 | 0.0205 |
| 804.5718 | 1202 | 5.877 | 0.057 | 6.117 | 0.080 | 0.961 | 0.0206 |
| 340.2976 | 1203 | 1.597 | 0.082 | 1.937 | 0.112 | 0.825 | 0.0208 |
| 856.6061 | 1202 | 4.565 | 0.056 | 4.805 | 0.086 | 0.950 | 0.0212 |
| 584.2646 | 1204 | 3.136 | 0.115 | 2.649 | 0.172 | 1.184 | 0.0218 |
| 733.6426 | 1204 | 2.978 | 0.049 | 2.718 | 0.126 | 1.096 | 0.0219 |
| 588.4731 | 1203 | 2.387 | 0.064 | 2.031 | 0.179 | 1.175 | 0.0223 |
| 765.5313 | 1202 | 1.802 | 0.073 | 2.098 | 0.095 | 0.859 | 0.0226 |
| 523.3634 | 1101 | 3.466 | 0.082 | 3.791 | 0.103 | 0.914 | 0.0235 |
| 830.5894 | 1202 | 4.847 | 0.051 | 5.051 | 0.064 | 0.960 | 0.0236 |
| 887.7352 | 1204 | 6.295 | 0.082 | 5.963 | 0.113 | 1.056 | 0.0244 |
| 598.5124 | 1204 | 2.094 | 0.134 | 1.513 | 0.233 | 1.385 | 0.0249 |
| 616.5052 | 1203 | 4.205 | 0.062 | 3.957 | 0.084 | 1.062 | 0.025 |
| 916.7743 | 1204 | 5.894 | 0.081 | 5.571 | 0.107 | 1.058 | 0.025 |
| 430.3818 | 1204 | 4.938 | 0.075 | 5.253 | 0.122 | 0.940 | 0.0262 |
| 855.6023 | 1202 | 5.552 | 0.056 | 5.784 | 0.087 | 0.960 | 0.0266 |
| 684.5489 | 1204 | 2.523 | 0.055 | 2.745 | 0.080 | 0.919 | 0.0269 |
| 831.6001 | 1202 | 6.192 | 0.053 | 6.404 | 0.074 | 0.967 | 0.0269 |
| 826.7069 | 1204 | 2.482 | 0.089 | 2.819 | 0.099 | 0.880 | 0.0275 |

TABLE 1-continued

Accurate mass features differing between clinically diagnosed
AD patients and non-demented controls (p < 0.05, log2 transformed).

| Detected Mass | Analysis Mode | AVG (log2) AD | SEM AD | AVG (log2) Normal | SEM Normal | log(2) Ratio | P Value |
|---|---|---|---|---|---|---|---|
| 915.7681 | 1204 | 6.304 | 0.085 | 5.972 | 0.116 | 1.056 | 0.0293 |
| 615.3539 | 1202 | 2.463 | 0.043 | 2.629 | 0.058 | 0.937 | 0.0296 |
| 431.386 | 1204 | 3.491 | 0.075 | 3.795 | 0.118 | 0.920 | 0.0298 |
| 942.7879 | 1204 | 3.487 | 0.078 | 3.195 | 0.092 | 1.091 | 0.0302 |
| 665.501 | 1204 | 3.388 | 0.071 | 3.074 | 0.142 | 1.102 | 0.0305 |
| 861.7806 | 1203 | 2.531 | 0.099 | 2.902 | 0.119 | 0.872 | 0.0306 |
| 618.4829 | 1201 | 1.791 | 0.120 | 1.310 | 0.185 | 1.367 | 0.0309 |
| 830.7352 | 1204 | 4.252 | 0.096 | 4.638 | 0.150 | 0.917 | 0.031 |
| 801.555 | 1202 | 2.660 | 0.056 | 2.881 | 0.082 | 0.923 | 0.0311 |
| 739.5143 | 1204 | 2.754 | 0.087 | 3.121 | 0.158 | 0.883 | 0.0317 |
| 492.3816 | 1203 | 3.513 | 0.055 | 3.302 | 0.077 | 1.064 | 0.0339 |
| 741.5319 | 1202 | 1.106 | 0.080 | 1.424 | 0.125 | 0.777 | 0.0339 |
| 914.7583 | 1204 | 5.082 | 0.083 | 4.763 | 0.118 | 1.067 | 0.0339 |
| 507.3316 | 1202 | 2.940 | 0.035 | 3.094 | 0.071 | 0.950 | 0.034 |
| 504.3814 | 1203 | 1.701 | 0.070 | 1.413 | 0.124 | 1.204 | 0.0341 |
| 496.3355 | 1101 | 3.442 | 0.074 | 3.736 | 0.119 | 0.921 | 0.0347 |
| 521.3477 | 1101 | 3.717 | 0.075 | 4.021 | 0.127 | 0.925 | 0.0351 |
| 829.5859 | 1202 | 5.976 | 0.056 | 6.181 | 0.070 | 0.967 | 0.0353 |
| 686.4877 | 1204 | 2.700 | 0.051 | 2.881 | 0.052 | 0.937 | 0.0358 |
| 888.7394 | 1204 | 5.702 | 0.080 | 5.400 | 0.110 | 1.056 | 0.0358 |
| 825.6926 | 1203 | 1.840 | 0.110 | 2.235 | 0.124 | 0.823 | 0.0369 |
| 746.557 | 1202 | 2.166 | 0.030 | 2.057 | 0.037 | 1.053 | 0.0378 |
| 757.5625 | 1201 | 7.728 | 0.046 | 7.909 | 0.077 | 0.977 | 0.0391 |
| 615.4798 | 1204 | 2.647 | 0.049 | 2.827 | 0.067 | 0.936 | 0.0396 |
| 831.7408 | 1203 | 4.104 | 0.085 | 4.425 | 0.130 | 0.928 | 0.0405 |
| 761.5846 | 1201 | 3.155 | 0.051 | 3.357 | 0.091 | 0.940 | 0.0414 |
| 581.3344 | 1202 | 1.927 | 0.076 | 2.207 | 0.110 | 0.873 | 0.0423 |
| 1098.9739 | 1204 | 2.955 | 0.090 | 2.606 | 0.152 | 1.134 | 0.0427 |
| 380.3096 | 1204 | 1.650 | 0.070 | 1.899 | 0.090 | 0.869 | 0.0434 |
| 565.3394 | 1202 | 7.001 | 0.052 | 7.186 | 0.068 | 0.974 | 0.0439 |
| 478.3664 | 1203 | 1.493 | 0.068 | 1.212 | 0.143 | 1.232 | 0.0475 |
| 835.7006 | 1204 | 2.799 | 0.115 | 3.214 | 0.167 | 0.871 | 0.0485 |
| 320.2356 | 1204 | 1.447 | 0.070 | 1.686 | 0.085 | 0.858 | 0.0486 |
| 493.385 | 1203 | 1.979 | 0.066 | 1.722 | 0.124 | 1.149 | 0.049 |
| 512.4082 | 1204 | 2.415 | 0.121 | 1.954 | 0.215 | 1.236 | 0.0493 |
| 610.3686 | 1201 | 5.156 | 0.083 | 4.771 | 0.223 | 1.081 | 0.0495 |
| 760.5811 | 1201 | 5.225 | 0.052 | 5.422 | 0.091 | 0.964 | 0.0495 |
| 600.5127 | 1203 | 8.858 | 0.044 | 8.692 | 0.074 | 1.019 | 0.0496 |
| 715.5167 | 1204 | 2.592 | 0.082 | 2.902 | 0.141 | 0.893 | 0.0498 |
| 759.5779 | 1201 | 6.347 | 0.051 | 6.541 | 0.090 | 0.970 | 0.0499 |

TABLE 2

Accurate mass features differing between clinically diagnosed
AD patients with a significant cognitive impairment and
non-demented controls (p < 0.05, log2 transformed).

| Detected Mass | Analysis Mode | AVG (log2) AD + Cog | SEM AD + Cog | AVG (log2) Normal | SEM Normal | log(2) Ratio | P Value |
|---|---|---|---|---|---|---|---|
| 541.3432 | 1102 | 3.138 | 0.034 | 3.798 | 0.048 | 1.210 | 3.45E−17 |
| 569.3687 | 1102 | 2.063 | 0.042 | 2.724 | 0.048 | 1.320 | 1.67E−15 |
| 723.5197 | 1204 | 3.581 | 0.053 | 4.350 | 0.056 | 1.215 | 1.04E−14 |
| 803.568 | 1102 | 5.238 | 0.048 | 5.838 | 0.035 | 1.115 | 2.00E−14 |
| 804.5713 | 1102 | 4.017 | 0.048 | 4.610 | 0.033 | 1.148 | 2.02E−14 |
| 723.5195 | 1202 | 2.193 | 0.056 | 2.892 | 0.052 | 1.319 | 4.37E−13 |
| 749.5367 | 1202 | 3.187 | 0.044 | 3.714 | 0.041 | 1.165 | 2.12E−12 |
| 555.3102 | 1102 | 1.634 | 0.053 | 2.240 | 0.046 | 1.371 | 3.10E−12 |
| 565.3394 | 1102 | 3.265 | 0.058 | 3.958 | 0.055 | 1.212 | 3.23E−12 |
| 724.5257 | 1204 | 2.850 | 0.048 | 3.463 | 0.055 | 1.215 | 4.54E−12 |
| 699.5198 | 1204 | 2.129 | 0.055 | 2.775 | 0.054 | 1.303 | 9.18E−12 |
| 871.5528 | 1102 | 2.885 | 0.049 | 3.408 | 0.040 | 1.181 | 2.08E−11 |
| 567.3547 | 1102 | 2.629 | 0.050 | 3.218 | 0.054 | 1.224 | 2.92E−11 |
| 751.5555 | 1204 | 4.591 | 0.056 | 5.248 | 0.060 | 1.143 | 3.18E−11 |
| 780.5474 | 1101 | 5.241 | 0.064 | 5.875 | 0.043 | 1.121 | 3.70E−11 |
| 752.5564 | 1202 | 2.281 | 0.049 | 2.836 | 0.050 | 1.244 | 4.78E−11 |
| 779.5444 | 1101 | 6.239 | 0.065 | 6.874 | 0.043 | 1.102 | 5.01E−11 |
| 829.5856 | 1102 | 3.806 | 0.059 | 4.398 | 0.046 | 1.156 | 9.29E−11 |
| 794.5421 | 1102 | 2.364 | 0.048 | 2.853 | 0.040 | 1.206 | 1.01E−10 |
| 793.5386 | 1102 | 3.435 | 0.052 | 3.950 | 0.039 | 1.150 | 1.05E−10 |
| 831.5997 | 1102 | 4.372 | 0.055 | 4.903 | 0.040 | 1.121 | 1.61E−10 |

TABLE 2-continued

Accurate mass features differing between clinically diagnosed AD patients with a significant cognitive impairment and non-demented controls ($p < 0.05$, log2 transformed).

| Detected Mass | Analysis Mode | AVG (log2) AD + Cog | SEM AD + Cog | AVG (log2) Normal | SEM Normal | log(2) Ratio | P Value |
|---|---|---|---|---|---|---|---|
| 832.6026 | 1102 | 3.268 | 0.055 | 3.795 | 0.040 | 1.161 | 1.67E-10 |
| 751.5529 | 1202 | 3.369 | 0.052 | 3.920 | 0.050 | 1.163 | 1.89E-10 |
| 749.5407 | 1204 | 4.423 | 0.047 | 5.012 | 0.064 | 1.133 | 1.93E-10 |
| 827.57 | 1102 | 3.984 | 0.059 | 4.630 | 0.062 | 1.162 | 1.95E-10 |
| 725.5385 | 1204 | 2.815 | 0.058 | 3.417 | 0.054 | 1.214 | 2.58E-10 |
| 804.5476 | 1101 | 3.987 | 0.073 | 4.703 | 0.060 | 1.180 | 2.67E-10 |
| 837.5027 | 1101 | 3.402 | 0.050 | 3.933 | 0.050 | 1.156 | 2.76E-10 |
| 803.5445 | 1101 | 4.941 | 0.074 | 5.655 | 0.059 | 1.144 | 3.46E-10 |
| 752.5583 | 1204 | 3.484 | 0.056 | 4.094 | 0.061 | 1.175 | 3.59E-10 |
| 828.5737 | 1102 | 2.982 | 0.056 | 3.590 | 0.061 | 1.204 | 3.85E-10 |
| 750.544 | 1204 | 3.258 | 0.054 | 3.858 | 0.063 | 1.184 | 6.22E-10 |
| 750.5402 | 1202 | 2.210 | 0.052 | 2.704 | 0.044 | 1.224 | 1.19E-09 |
| 805.5832 | 1102 | 3.874 | 0.056 | 4.485 | 0.068 | 1.158 | 1.95E-09 |
| 727.5568 | 1204 | 3.445 | 0.055 | 3.986 | 0.060 | 1.157 | 7.95E-09 |
| 807.5758 | 1101 | 5.531 | 0.069 | 6.102 | 0.047 | 1.103 | 8.66E-09 |
| 805.5605 | 1101 | 5.184 | 0.074 | 5.785 | 0.048 | 1.116 | 9.26E-09 |
| 808.5792 | 1101 | 4.488 | 0.071 | 5.063 | 0.047 | 1.128 | 1.11E-08 |
| 806.5639 | 1101 | 4.199 | 0.075 | 4.779 | 0.049 | 1.138 | 3.65E-08 |
| 915.5191 | 1101 | 2.189 | 0.058 | 2.717 | 0.063 | 1.241 | 5.21E-08 |
| 817.5377 | 1102 | 2.175 | 0.064 | 2.712 | 0.057 | 1.247 | 5.29E-08 |
| 781.5617 | 1101 | 5.928 | 0.084 | 6.610 | 0.072 | 1.115 | 8.47E-08 |
| 819.5551 | 1102 | 2.198 | 0.058 | 2.654 | 0.046 | 1.208 | 9.28E-08 |
| 726.5461 | 1204 | 2.759 | 0.044 | 3.150 | 0.050 | 1.141 | 1.31E-07 |
| 783.5672 | 1101 | 3.535 | 0.092 | 4.259 | 0.079 | 1.205 | 1.69E-07 |
| 886.5582 | 1102 | 2.911 | 0.041 | 3.250 | 0.041 | 1.117 | 2.03E-07 |
| 782.565 | 1101 | 4.901 | 0.088 | 5.589 | 0.078 | 1.140 | 2.35E-07 |
| 784.5237 | 1204 | 3.211 | 0.056 | 3.603 | 0.037 | 1.122 | 4.12E-07 |
| 853.5854 | 1102 | 2.449 | 0.056 | 2.880 | 0.052 | 1.176 | 4.56E-07 |
| 795.555 | 1102 | 2.520 | 0.054 | 2.986 | 0.065 | 1.185 | 5.49E-07 |
| 855.6016 | 1102 | 3.386 | 0.060 | 3.873 | 0.065 | 1.144 | 6.32E-07 |
| 821.5712 | 1102 | 2.919 | 0.053 | 3.304 | 0.044 | 1.132 | 6.68E-07 |
| 795.5181 | 1101 | 2.458 | 0.082 | 3.044 | 0.064 | 1.238 | 7.57E-07 |
| 832.5791 | 1101 | 3.184 | 0.076 | 3.723 | 0.061 | 1.169 | 9.68E-07 |
| 786.5416 | 1204 | 3.729 | 0.049 | 4.087 | 0.043 | 1.096 | 1.02E-06 |
| 831.5759 | 1101 | 4.123 | 0.080 | 4.677 | 0.060 | 1.134 | 1.03E-06 |
| 728.5627 | 1204 | 2.875 | 0.047 | 3.281 | 0.060 | 1.141 | 1.07E-06 |
| 757.4991 | 1101 | 3.450 | 0.089 | 4.073 | 0.070 | 1.181 | 1.08E-06 |
| 760.5216 | 1204 | 4.008 | 0.048 | 4.347 | 0.039 | 1.084 | 1.13E-06 |
| 829.5604 | 1101 | 3.360 | 0.075 | 3.875 | 0.058 | 1.153 | 1.41E-06 |
| 847.5316 | 1101 | 2.564 | 0.060 | 3.091 | 0.083 | 1.205 | 1.84E-06 |
| 755.5468 | 1101 | 2.115 | 0.086 | 2.753 | 0.085 | 1.302 | 1.88E-06 |
| 782.5085 | 1204 | 3.369 | 0.056 | 3.780 | 0.055 | 1.122 | 2.13E-06 |
| 755.486 | 1204 | 3.146 | 0.061 | 3.561 | 0.057 | 1.132 | 5.93E-06 |
| 833.5932 | 1101 | 3.045 | 0.095 | 3.608 | 0.056 | 1.185 | 7.05E-06 |
| 758.5656 | 1101 | 5.511 | 0.107 | 6.160 | 0.078 | 1.118 | 1.11E-05 |
| 758.5092 | 1204 | 4.504 | 0.047 | 4.808 | 0.042 | 1.068 | 1.24E-05 |
| 757.5626 | 1101 | 6.470 | 0.106 | 7.108 | 0.079 | 1.099 | 1.48E-05 |
| 760.5811 | 1101 | 4.216 | 0.099 | 4.886 | 0.103 | 1.159 | 1.48E-05 |
| 744.5536 | 1204 | 4.260 | 0.047 | 4.605 | 0.058 | 1.081 | 1.55E-05 |
| 759.5779 | 1101 | 5.352 | 0.096 | 5.997 | 0.099 | 1.121 | 1.60E-05 |
| 811.6096 | 1101 | 2.801 | 0.116 | 3.511 | 0.096 | 1.253 | 1.84E-05 |
| 731.5464 | 1101 | 1.634 | 0.139 | 2.600 | 0.157 | 1.591 | 1.89E-05 |
| 812.5762 | 1202 | 1.752 | 0.045 | 2.084 | 0.058 | 1.190 | 1.95E-05 |
| 743.5471 | 1204 | 5.227 | 0.047 | 5.579 | 0.063 | 1.067 | 2.40E-05 |
| 784.5811 | 1101 | 4.161 | 0.112 | 4.817 | 0.089 | 1.158 | 3.03E-05 |
| 632.5762 | 1203 | 0.925 | 0.149 | 1.830 | 0.132 | 1.979 | 3.07E-05 |
| 761.5843 | 1101 | 2.241 | 0.084 | 2.829 | 0.106 | 1.262 | 4.28E-05 |
| 517.314 | 1101 | 5.399 | 0.050 | 5.755 | 0.069 | 1.066 | 0.0001 |
| 518.3174 | 1101 | 3.358 | 0.051 | 3.717 | 0.073 | 1.107 | 0.0001 |
| 591.3542 | 1202 | 3.870 | 0.092 | 4.345 | 0.058 | 1.123 | 0.0001 |
| 732.4938 | 1204 | 4.186 | 0.056 | 4.511 | 0.057 | 1.078 | 0.0001 |
| 745.5658 | 1204 | 3.881 | 0.052 | 4.242 | 0.068 | 1.093 | 0.0001 |
| 746.5717 | 1204 | 3.047 | 0.043 | 3.362 | 0.061 | 1.103 | 0.0001 |
| 747.5245 | 1204 | 3.433 | 0.058 | 3.886 | 0.090 | 1.132 | 0.0001 |
| 777.553 | 1202 | 1.720 | 0.100 | 2.384 | 0.130 | 1.386 | 0.0001 |
| 783.5148 | 1204 | 3.217 | 0.063 | 3.574 | 0.056 | 1.111 | 0.0001 |
| 785.5933 | 1101 | 5.687 | 0.112 | 6.271 | 0.080 | 1.103 | 0.0001 |
| 786.5967 | 1101 | 4.611 | 0.112 | 5.203 | 0.078 | 1.128 | 0.0001 |
| 809.5936 | 1101 | 4.786 | 0.104 | 5.362 | 0.079 | 1.120 | 0.0001 |
| 810.5969 | 1101 | 3.779 | 0.108 | 4.370 | 0.080 | 1.157 | 0.0001 |
| 811.5732 | 1202 | 2.729 | 0.047 | 3.027 | 0.055 | 1.109 | 0.0001 |
| 858.6212 | 1202 | 2.533 | 0.080 | 2.994 | 0.074 | 1.182 | 0.0001 |
| 306.2569 | 1204 | 2.878 | 0.070 | 3.266 | 0.067 | 1.135 | 0.0002 |

TABLE 2-continued

Accurate mass features differing between clinically diagnosed
AD patients with a significant cognitive impairment and
non-demented controls (p < 0.05, log2 transformed).

| Detected Mass | Analysis Mode | AVG (log2) AD + Cog | SEM AD + Cog | AVG (log2) Normal | SEM Normal | log(2) Ratio | P Value |
|---|---|---|---|---|---|---|---|
| 482.3215 | 1202 | 1.940 | 0.050 | 2.251 | 0.062 | 1.160 | 0.0002 |
| 522.4635 | 1203 | 4.489 | 0.181 | 5.485 | 0.176 | 1.222 | 0.0002 |
| 523.4679 | 1203 | 3.035 | 0.180 | 4.011 | 0.165 | 1.322 | 0.0002 |
| 579.5325 | 1203 | 3.962 | 0.112 | 4.636 | 0.127 | 1.170 | 0.0002 |
| 759.5163 | 1204 | 4.645 | 0.061 | 4.954 | 0.048 | 1.066 | 0.0002 |
| 787.5729 | 1202 | 1.834 | 0.054 | 2.145 | 0.057 | 1.170 | 0.0002 |
| 810.5399 | 1204 | 2.760 | 0.071 | 3.145 | 0.066 | 1.140 | 0.0002 |
| 814.5917 | 1202 | 2.054 | 0.035 | 2.289 | 0.051 | 1.114 | 0.0002 |
| 857.6186 | 1202 | 3.614 | 0.081 | 4.049 | 0.076 | 1.121 | 0.0002 |
| 458.2405 | 1101 | 1.632 | 0.054 | 1.986 | 0.077 | 1.217 | 0.0003 |
| 481.3172 | 1202 | 3.866 | 0.050 | 4.159 | 0.060 | 1.076 | 0.0003 |
| 541.3139 | 1101 | 4.022 | 0.081 | 4.494 | 0.096 | 1.117 | 0.0003 |
| 545.3453 | 1101 | 3.500 | 0.071 | 3.898 | 0.078 | 1.114 | 0.0003 |
| 592.3571 | 1202 | 2.113 | 0.095 | 2.560 | 0.062 | 1.212 | 0.0003 |
| 757.5014 | 1204 | 3.642 | 0.067 | 3.971 | 0.052 | 1.091 | 0.0003 |
| 833.7551 | 1204 | 2.061 | 0.223 | 3.140 | 0.161 | 1.524 | 0.0003 |
| 543.3296 | 1101 | 3.652 | 0.055 | 4.023 | 0.087 | 1.102 | 0.0004 |
| 605.5457 | 1203 | 5.025 | 0.091 | 5.509 | 0.089 | 1.096 | 0.0004 |
| 731.4916 | 1204 | 5.419 | 0.060 | 5.746 | 0.063 | 1.060 | 0.0004 |
| 775.5533 | 1202 | 2.106 | 0.063 | 2.449 | 0.068 | 1.163 | 0.0004 |
| 813.5885 | 1202 | 3.034 | 0.043 | 3.276 | 0.048 | 1.080 | 0.0004 |
| 542.3173 | 1101 | 2.234 | 0.087 | 2.687 | 0.089 | 1.203 | 0.0005 |
| 722.5335 | 1101 | 2.406 | 0.062 | 2.717 | 0.056 | 1.129 | 0.0005 |
| 744.55 | 1202 | 1.842 | 0.064 | 2.222 | 0.083 | 1.206 | 0.0005 |
| 769.5656 | 1204 | 3.889 | 0.055 | 4.174 | 0.054 | 1.073 | 0.0005 |
| 807.59 | 1202 | 2.348 | 0.061 | 2.718 | 0.082 | 1.158 | 0.0005 |
| 828.5743 | 1202 | 5.181 | 0.076 | 5.598 | 0.085 | 1.081 | 0.0005 |
| 521.4522 | 1203 | 2.124 | 0.191 | 3.028 | 0.158 | 1.425 | 0.0007 |
| 604.5433 | 1203 | 6.440 | 0.091 | 6.901 | 0.089 | 1.072 | 0.0007 |
| 744.4956 | 1204 | 3.851 | 0.049 | 4.117 | 0.058 | 1.069 | 0.0007 |
| 748.5287 | 1204 | 2.249 | 0.127 | 2.820 | 0.088 | 1.254 | 0.0007 |
| 771.5814 | 1204 | 4.118 | 0.051 | 4.367 | 0.046 | 1.061 | 0.0007 |
| 827.5701 | 1202 | 6.245 | 0.082 | 6.684 | 0.092 | 1.070 | 0.0007 |
| 747.5201 | 1202 | 1.886 | 0.083 | 2.313 | 0.088 | 1.226 | 0.0008 |
| 775.5528 | 1204 | 3.176 | 0.061 | 3.537 | 0.085 | 1.114 | 0.0008 |
| 787.5465 | 1204 | 2.543 | 0.116 | 3.017 | 0.054 | 1.187 | 0.0008 |
| 827.5448 | 1101 | 3.373 | 0.104 | 3.873 | 0.095 | 1.148 | 0.0008 |
| 546.3485 | 1101 | 1.890 | 0.073 | 2.287 | 0.089 | 1.210 | 0.0009 |
| 520.4499 | 1203 | 3.775 | 0.176 | 4.577 | 0.148 | 1.212 | 0.001 |
| 570.3725 | 1202 | 2.926 | 0.047 | 3.155 | 0.045 | 1.078 | 0.001 |
| 781.562 | 1201 | 7.334 | 0.054 | 7.638 | 0.071 | 1.041 | 0.001 |
| 632.5032 | 1203 | 1.435 | 0.112 | 0.795 | 0.154 | 0.554 | 0.0011 |
| 743.5469 | 1202 | 2.976 | 0.070 | 3.348 | 0.086 | 1.125 | 0.0012 |
| 768.5539 | 1204 | 3.928 | 0.069 | 4.279 | 0.077 | 1.089 | 0.0012 |
| 806.5873 | 1202 | 4.280 | 0.057 | 4.635 | 0.092 | 1.083 | 0.0012 |
| 575.2728 | 1101 | 2.419 | 0.061 | 2.739 | 0.074 | 1.132 | 0.0013 |
| 550.4957 | 1203 | 6.766 | 0.117 | 7.415 | 0.160 | 1.096 | 0.0014 |
| 805.5839 | 1202 | 5.470 | 0.060 | 5.841 | 0.097 | 1.068 | 0.0014 |
| 183.0661 | 1101 | 2.412 | 0.147 | 3.015 | 0.094 | 1.250 | 0.0015 |
| 551.4986 | 1203 | 5.350 | 0.117 | 5.988 | 0.158 | 1.119 | 0.0015 |
| 741.5305 | 1204 | 2.825 | 0.080 | 3.250 | 0.102 | 1.150 | 0.0015 |
| 541.3435 | 1202 | 5.595 | 0.072 | 5.974 | 0.094 | 1.068 | 0.0018 |
| 552.5022 | 1203 | 3.055 | 0.110 | 3.643 | 0.147 | 1.193 | 0.0018 |
| 506.3213 | 1202 | 2.487 | 0.054 | 2.748 | 0.061 | 1.105 | 0.0019 |
| 569.369 | 1202 | 4.867 | 0.049 | 5.089 | 0.047 | 1.046 | 0.0019 |
| 782.5653 | 1201 | 6.310 | 0.058 | 6.614 | 0.076 | 1.048 | 0.002 |
| 490.3641 | 1203 | 2.028 | 0.121 | 1.397 | 0.159 | 0.689 | 0.0021 |
| 542.3461 | 1202 | 3.803 | 0.061 | 4.106 | 0.074 | 1.080 | 0.0021 |
| 566.3434 | 1202 | 5.130 | 0.071 | 5.436 | 0.062 | 1.060 | 0.0022 |
| 833.7571 | 1203 | 2.853 | 0.122 | 3.507 | 0.170 | 1.229 | 0.0022 |
| 837.718 | 1204 | 2.593 | 0.250 | 3.662 | 0.217 | 1.412 | 0.0023 |
| 549.4845 | 1203 | 5.510 | 0.107 | 5.994 | 0.110 | 1.088 | 0.0025 |
| 793.5681 | 1204 | 3.116 | 0.058 | 3.372 | 0.055 | 1.082 | 0.0025 |
| 478.254 | 1201 | 1.629 | 0.116 | 1.051 | 0.148 | 0.645 | 0.0027 |
| 536.4794 | 1203 | 2.188 | 0.134 | 2.799 | 0.143 | 1.279 | 0.0027 |
| 548.4815 | 1203 | 6.949 | 0.103 | 7.405 | 0.103 | 1.066 | 0.0027 |
| 832.6037 | 1202 | 4.981 | 0.069 | 5.274 | 0.062 | 1.059 | 0.0028 |
| 830.5894 | 1202 | 4.738 | 0.076 | 5.051 | 0.064 | 1.066 | 0.0029 |
| 1098.9739 | 1204 | 3.097 | 0.070 | 2.606 | 0.152 | 0.842 | 0.0031 |
| 767.5495 | 1204 | 5.033 | 0.074 | 5.369 | 0.082 | 1.067 | 0.0034 |
| 675.6377 | 1204 | 3.875 | 0.066 | 4.160 | 0.066 | 1.074 | 0.0035 |
| 564.5134 | 1203 | 2.641 | 0.093 | 3.075 | 0.111 | 1.164 | 0.0036 |
| 789.5892 | 1202 | 1.703 | 0.053 | 1.952 | 0.065 | 1.147 | 0.0036 |

TABLE 2-continued

Accurate mass features differing between clinically diagnosed
AD patients with a significant cognitive impairment and
non-demented controls (p < 0.05, log2 transformed).

| Detected Mass | Analysis Mode | AVG (log2) AD + Cog | SEM AD + Cog | AVG (log2) Normal | SEM Normal | log(2) Ratio | P Value |
|---|---|---|---|---|---|---|---|
| 832.7523 | 1203 | 3.734 | 0.131 | 4.374 | 0.169 | 1.171 | 0.0036 |
| 748.5735 | 1202 | 3.940 | 0.052 | 3.722 | 0.050 | 0.945 | 0.0037 |
| 801.555 | 1202 | 2.543 | 0.077 | 2.881 | 0.082 | 1.133 | 0.0037 |
| 856.672 | 1202 | 2.777 | 0.048 | 2.553 | 0.057 | 0.919 | 0.0037 |
| 858.6861 | 1202 | 2.982 | 0.055 | 2.756 | 0.052 | 0.924 | 0.0043 |
| 803.5677 | 1202 | 7.101 | 0.095 | 7.502 | 0.098 | 1.057 | 0.0045 |
| 838.7226 | 1204 | 2.127 | 0.200 | 2.973 | 0.206 | 1.398 | 0.0046 |
| 685.26 | 1202 | 1.708 | 0.074 | 1.998 | 0.063 | 1.169 | 0.0047 |
| 826.7069 | 1204 | 2.279 | 0.148 | 2.819 | 0.099 | 1.237 | 0.0047 |
| 582.2473 | 1201 | 3.332 | 0.122 | 2.793 | 0.141 | 0.838 | 0.0049 |
| 590.343 | 1202 | 4.005 | 0.069 | 4.304 | 0.076 | 1.075 | 0.005 |
| 832.7492 | 1204 | 3.163 | 0.146 | 3.848 | 0.190 | 1.217 | 0.0051 |
| 829.5859 | 1202 | 5.864 | 0.082 | 6.181 | 0.070 | 1.054 | 0.0053 |
| 772.5862 | 1204 | 3.263 | 0.043 | 3.437 | 0.042 | 1.053 | 0.0054 |
| 409.0208 | 1202 | 2.753 | 0.050 | 2.980 | 0.063 | 1.082 | 0.0055 |
| 509.3493 | 1202 | 2.358 | 0.054 | 2.579 | 0.055 | 1.094 | 0.0056 |
| 589.3403 | 1202 | 5.847 | 0.076 | 6.171 | 0.085 | 1.056 | 0.0057 |
| 430.3818 | 1204 | 4.790 | 0.109 | 5.253 | 0.122 | 1.097 | 0.0061 |
| 804.5718 | 1202 | 5.801 | 0.078 | 6.117 | 0.080 | 1.054 | 0.0066 |
| 505.3229 | 1202 | 3.931 | 0.071 | 4.222 | 0.076 | 1.074 | 0.0068 |
| 523.3634 | 1101 | 3.365 | 0.111 | 3.791 | 0.103 | 1.127 | 0.0072 |
| 671.5723 | 1204 | 2.131 | 0.140 | 2.604 | 0.087 | 1.222 | 0.0073 |
| 830.7352 | 1204 | 4.091 | 0.130 | 4.638 | 0.150 | 1.134 | 0.0073 |
| 431.386 | 1204 | 3.354 | 0.108 | 3.795 | 0.118 | 1.132 | 0.0074 |
| 631.628 | 1203 | 1.746 | 0.166 | 2.391 | 0.161 | 1.369 | 0.0075 |
| 825.6926 | 1203 | 1.644 | 0.169 | 2.235 | 0.124 | 1.359 | 0.0079 |
| 614.4914 | 1203 | 2.821 | 0.080 | 2.448 | 0.114 | 0.868 | 0.008 |
| 831.6001 | 1202 | 6.109 | 0.077 | 6.404 | 0.074 | 1.048 | 0.0081 |
| 615.3539 | 1202 | 2.394 | 0.063 | 2.629 | 0.058 | 1.098 | 0.0083 |
| 568.3573 | 1202 | 3.959 | 0.049 | 4.167 | 0.060 | 1.053 | 0.0088 |
| 767.547 | 1202 | 2.992 | 0.097 | 3.358 | 0.092 | 1.122 | 0.0088 |
| 768.5503 | 1202 | 1.849 | 0.125 | 2.277 | 0.090 | 1.231 | 0.0089 |
| 831.7408 | 1203 | 3.971 | 0.109 | 4.425 | 0.130 | 1.114 | 0.0089 |
| 411.3212 | 1202 | 2.838 | 0.054 | 3.033 | 0.048 | 1.069 | 0.0099 |
| 796.5876 | 1204 | 2.633 | 0.059 | 2.860 | 0.062 | 1.087 | 0.0099 |
| 863.6876 | 1204 | 4.853 | 0.087 | 5.188 | 0.092 | 1.069 | 0.0104 |
| 492.3816 | 1203 | 3.588 | 0.076 | 3.302 | 0.077 | 0.920 | 0.0105 |
| 772.5278 | 1204 | 3.282 | 0.056 | 3.488 | 0.055 | 1.063 | 0.0107 |
| 825.5544 | 1202 | 2.644 | 0.112 | 3.084 | 0.126 | 1.167 | 0.0108 |
| 320.2356 | 1204 | 1.302 | 0.114 | 1.686 | 0.085 | 1.295 | 0.011 |
| 380.3096 | 1204 | 1.580 | 0.083 | 1.899 | 0.090 | 1.202 | 0.0112 |
| 519.3321 | 1101 | 3.914 | 0.122 | 4.382 | 0.133 | 1.119 | 0.0116 |
| 711.2577 | 1202 | 2.205 | 0.075 | 2.454 | 0.056 | 1.113 | 0.0118 |
| 493.385 | 1203 | 2.083 | 0.073 | 1.722 | 0.124 | 0.827 | 0.0119 |
| 565.3394 | 1202 | 6.924 | 0.073 | 7.186 | 0.068 | 1.038 | 0.0119 |
| 670.569 | 1204 | 3.179 | 0.090 | 3.515 | 0.093 | 1.106 | 0.012 |
| 856.6061 | 1202 | 4.500 | 0.081 | 4.805 | 0.086 | 1.068 | 0.0121 |
| 340.2976 | 1203 | 1.502 | 0.124 | 1.937 | 0.112 | 1.290 | 0.0124 |
| 287.2824 | 1101 | 1.958 | 0.180 | 1.265 | 0.202 | 0.646 | 0.0126 |
| 495.332 | 1101 | 5.196 | 0.094 | 5.565 | 0.112 | 1.071 | 0.0137 |
| 304.241 | 1204 | 4.876 | 0.053 | 5.088 | 0.066 | 1.044 | 0.0138 |
| 305.2438 | 1204 | 2.492 | 0.061 | 2.719 | 0.067 | 1.091 | 0.0145 |
| 616.5052 | 1203 | 4.260 | 0.086 | 3.957 | 0.084 | 0.929 | 0.0145 |
| 746.5119 | 1204 | 2.615 | 0.165 | 3.137 | 0.119 | 1.200 | 0.0152 |
| 861.7806 | 1203 | 2.533 | 0.092 | 2.902 | 0.119 | 1.146 | 0.0152 |
| 686.4877 | 1204 | 2.617 | 0.088 | 2.881 | 0.052 | 1.101 | 0.0155 |
| 830.7363 | 1203 | 4.834 | 0.111 | 5.263 | 0.135 | 1.089 | 0.0162 |
| 835.7006 | 1204 | 2.651 | 0.155 | 3.214 | 0.167 | 1.212 | 0.0165 |
| 867.7579 | 1204 | 2.654 | 0.185 | 3.308 | 0.189 | 1.246 | 0.0167 |
| 870.7307 | 1203 | 3.361 | 0.074 | 2.985 | 0.142 | 0.888 | 0.0169 |
| 246.1465 | 1202 | 3.761 | 0.084 | 4.072 | 0.096 | 1.083 | 0.017 |
| 507.3316 | 1202 | 2.891 | 0.047 | 3.094 | 0.071 | 1.070 | 0.0173 |
| 855.6023 | 1202 | 5.497 | 0.079 | 5.784 | 0.087 | 1.052 | 0.0173 |
| 578.5277 | 1203 | 4.183 | 0.420 | 5.548 | 0.355 | 1.326 | 0.0176 |
| 615.4938 | 1203 | 1.386 | 0.133 | 0.902 | 0.148 | 0.651 | 0.0177 |
| 808.5803 | 1201 | 5.667 | 0.029 | 5.784 | 0.039 | 1.021 | 0.0177 |
| 860.7752 | 1204 | 3.643 | 0.124 | 4.070 | 0.125 | 1.117 | 0.0185 |
| 518.4345 | 1203 | 1.584 | 0.180 | 2.199 | 0.178 | 1.388 | 0.0186 |
| 520.3354 | 1101 | 2.215 | 0.123 | 2.646 | 0.130 | 1.195 | 0.0188 |
| 765.5313 | 1202 | 1.717 | 0.123 | 2.098 | 0.095 | 1.222 | 0.0195 |
| 777.5287 | 1201 | 2.793 | 0.063 | 3.020 | 0.072 | 1.082 | 0.0198 |
| 887.8005 | 1203 | 2.948 | 0.118 | 3.306 | 0.086 | 1.122 | 0.0198 |
| 739.5143 | 1204 | 2.602 | 0.149 | 3.121 | 0.158 | 1.200 | 0.0199 |

TABLE 2-continued

Accurate mass features differing between clinically diagnosed AD patients with a significant cognitive impairment and non-demented controls (p < 0.05, log2 transformed).

| Detected Mass | Analysis Mode | AVG (log2) AD + Cog | SEM AD + Cog | AVG (log2) Normal | SEM Normal | log(2) Ratio | P Value |
|---|---|---|---|---|---|---|---|
| 831.7387 | 1204 | 3.193 | 0.121 | 3.648 | 0.150 | 1.142 | 0.02 |
| 521.3477 | 1101 | 3.643 | 0.099 | 4.021 | 0.127 | 1.104 | 0.0203 |
| 584.2646 | 1204 | 3.154 | 0.130 | 2.649 | 0.172 | 0.840 | 0.0207 |
| 661.6233 | 1204 | 2.430 | 0.088 | 2.715 | 0.079 | 1.117 | 0.0209 |
| 715.5167 | 1204 | 2.449 | 0.131 | 2.902 | 0.141 | 1.185 | 0.0218 |
| 529.3167 | 1202 | 3.031 | 0.071 | 3.265 | 0.069 | 1.077 | 0.0221 |
| 544.4481 | 1203 | 2.105 | 0.067 | 2.333 | 0.071 | 1.108 | 0.0234 |
| 866.7532 | 1204 | 4.149 | 0.145 | 4.693 | 0.189 | 1.131 | 0.0235 |
| 581.3344 | 1202 | 1.844 | 0.111 | 2.207 | 0.110 | 1.197 | 0.0245 |
| 795.5838 | 1204 | 3.569 | 0.060 | 3.769 | 0.063 | 1.056 | 0.0246 |
| 807.5768 | 1201 | 6.720 | 0.030 | 6.829 | 0.037 | 1.016 | 0.0256 |
| 854.5902 | 1202 | 3.801 | 0.070 | 4.031 | 0.073 | 1.060 | 0.0266 |
| 865.7487 | 1204 | 4.895 | 0.152 | 5.445 | 0.193 | 1.112 | 0.0268 |
| 496.3355 | 1101 | 3.396 | 0.095 | 3.736 | 0.119 | 1.100 | 0.027 |
| 755.5467 | 1201 | 3.507 | 0.072 | 3.755 | 0.084 | 1.071 | 0.0274 |
| 1019.3838 | 1102 | 3.035 | 0.036 | 2.919 | 0.037 | 0.962 | 0.0291 |
| 684.5489 | 1204 | 2.508 | 0.071 | 2.745 | 0.080 | 1.094 | 0.0294 |
| 774.0316 | 1204 | 1.789 | 0.192 | 1.167 | 0.203 | 0.652 | 0.0294 |
| 765.5334 | 1204 | 3.218 | 0.101 | 3.540 | 0.104 | 1.100 | 0.0299 |
| 630.5587 | 1203 | 3.126 | 0.072 | 3.344 | 0.064 | 1.070 | 0.0301 |
| 488.3873 | 1203 | 2.241 | 0.069 | 1.986 | 0.096 | 0.886 | 0.0321 |
| 302.2255 | 1204 | 3.506 | 0.085 | 3.765 | 0.081 | 1.074 | 0.0322 |
| 757.5625 | 1201 | 7.689 | 0.066 | 7.909 | 0.077 | 1.029 | 0.0325 |
| 617.5089 | 1203 | 2.978 | 0.089 | 2.698 | 0.092 | 0.906 | 0.0328 |
| 829.7239 | 1204 | 2.802 | 0.120 | 3.185 | 0.131 | 1.137 | 0.0344 |
| 303.1079 | 1202 | 5.656 | 0.048 | 5.802 | 0.047 | 1.026 | 0.0348 |
| 826.5581 | 1202 | 1.648 | 0.107 | 2.032 | 0.149 | 1.233 | 0.0362 |
| 506.2851 | 1201 | 3.080 | 0.117 | 2.656 | 0.165 | 0.862 | 0.0363 |
| 504.3814 | 1203 | 1.746 | 0.098 | 1.413 | 0.124 | 0.809 | 0.0366 |
| 691.1957 | 1102 | 2.130 | 0.060 | 1.938 | 0.068 | 0.910 | 0.0373 |
| 626.5278 | 1203 | 3.820 | 0.064 | 4.009 | 0.060 | 1.049 | 0.0375 |
| 522.3511 | 1101 | 1.753 | 0.091 | 2.069 | 0.121 | 1.180 | 0.0385 |
| 759.5779 | 1201 | 6.294 | 0.076 | 6.541 | 0.090 | 1.039 | 0.0386 |
| 625.5161 | 1203 | 2.856 | 0.057 | 3.045 | 0.070 | 1.066 | 0.0387 |
| 760.5811 | 1201 | 5.173 | 0.077 | 5.422 | 0.091 | 1.048 | 0.0395 |
| 484.3794 | 1204 | 2.181 | 0.092 | 1.776 | 0.178 | 0.815 | 0.0396 |
| 819.5642 | 1202 | 2.811 | 0.080 | 3.104 | 0.120 | 1.104 | 0.0404 |
| 853.5862 | 1202 | 4.775 | 0.069 | 4.985 | 0.075 | 1.044 | 0.0423 |
| 700.552 | 1101 | 2.278 | 0.124 | 2.617 | 0.102 | 1.149 | 0.0426 |
| 709.2594 | 1202 | 2.152 | 0.092 | 2.382 | 0.053 | 1.107 | 0.0426 |
| 662.5175 | 1204 | 3.806 | 0.120 | 3.420 | 0.145 | 0.899 | 0.0432 |
| 761.5846 | 1201 | 3.118 | 0.074 | 3.357 | 0.091 | 1.077 | 0.0436 |
| 743.5466 | 1203 | 2.011 | 0.077 | 2.266 | 0.099 | 1.127 | 0.0442 |
| 478.3664 | 1203 | 1.545 | 0.088 | 1.212 | 0.143 | 0.785 | 0.0447 |
| 784.5811 | 1201 | 5.585 | 0.073 | 5.809 | 0.082 | 1.040 | 0.0448 |
| 860.7756 | 1203 | 4.383 | 0.087 | 4.653 | 0.100 | 1.061 | 0.0448 |
| 601.5164 | 1203 | 7.642 | 0.056 | 7.463 | 0.069 | 0.976 | 0.0453 |
| 758.5655 | 1201 | 6.637 | 0.074 | 6.860 | 0.084 | 1.034 | 0.0488 |
| 371.3542 | 1203 | 3.253 | 0.055 | 3.435 | 0.074 | 1.056 | 0.0489 |
| 783.5778 | 1201 | 6.661 | 0.074 | 6.883 | 0.083 | 1.033 | 0.049 |
| 921.8145 | 1204 | 2.716 | 0.211 | 3.255 | 0.155 | 1.198 | 0.0494 |
| 824.6892 | 1203 | 2.657 | 0.108 | 2.964 | 0.108 | 1.116 | 0.0497 |

TABLE 3

Accurate mass features differing between clinically diagnosed AD patients with a significant cognitive impairment and clinically diagnosed non-AD patients with a significant cognitive impairment (p < 0.05, log2 transformed).

| Detected Mass | Analysis Mode | AVG (log2) AD + Cog | SEM AD + Cog | AVG (log2) Non-AD + Cog | SEM Non-AD + Cog | log(2) Ratio | P Value |
|---|---|---|---|---|---|---|---|
| 723.5197 | 1204 | 3.581 | 0.053 | 4.571 | 0.070 | 0.783 | 1.07E−17 |
| 723.5195 | 1202 | 2.193 | 0.056 | 3.033 | 0.049 | 0.723 | 2.70E−17 |
| 749.5367 | 1202 | 3.187 | 0.044 | 3.812 | 0.045 | 0.836 | 5.25E−15 |
| 724.5257 | 1204 | 2.850 | 0.048 | 3.630 | 0.066 | 0.785 | 1.68E−14 |
| 752.5564 | 1202 | 2.281 | 0.049 | 2.975 | 0.056 | 0.767 | 5.71E−14 |
| 751.5555 | 1204 | 4.591 | 0.056 | 5.427 | 0.071 | 0.846 | 6.78E−14 |

TABLE 3-continued

Accurate mass features differing between clinically diagnosed
AD patients with a significant cognitive impairment and clinically
diagnosed non-AD patients with a significant cognitive
impairment (p < 0.05, log2 transformed).

| Detected Mass | Analysis Mode | AVG (log2) AD + Cog | SEM AD + Cog | AVG (log2) Non-AD + Cog | SEM Non-AD + Cog | log(2) Ratio | P Value |
|---|---|---|---|---|---|---|---|
| 751.5529 | 1202 | 3.369 | 0.052 | 4.055 | 0.054 | 0.831 | 1.46E−13 |
| 752.5583 | 1204 | 3.484 | 0.056 | 4.284 | 0.070 | 0.813 | 2.38E−13 |
| 749.5407 | 1204 | 4.423 | 0.047 | 5.185 | 0.073 | 0.853 | 5.02E−13 |
| 750.5402 | 1202 | 2.210 | 0.052 | 2.804 | 0.044 | 0.788 | 9.50E−13 |
| 750.544 | 1204 | 3.258 | 0.054 | 4.004 | 0.074 | 0.814 | 7.49E−12 |
| 725.5385 | 1204 | 2.815 | 0.058 | 3.543 | 0.078 | 0.794 | 1.10E−10 |
| 699.5198 | 1204 | 2.129 | 0.055 | 2.825 | 0.079 | 0.754 | 3.41E−10 |
| 727.5568 | 1204 | 3.445 | 0.055 | 4.039 | 0.076 | 0.853 | 1.48E−08 |
| 728.5627 | 1204 | 2.875 | 0.047 | 3.301 | 0.056 | 0.871 | 1.21E−07 |
| 726.5461 | 1204 | 2.759 | 0.044 | 3.175 | 0.057 | 0.869 | 1.35E−07 |
| 775.5528 | 1204 | 3.176 | 0.061 | 3.712 | 0.075 | 0.856 | 3.75E−07 |
| 813.5885 | 1202 | 3.034 | 0.043 | 3.369 | 0.049 | 0.901 | 2.08E−06 |
| 775.5533 | 1202 | 2.106 | 0.063 | 2.524 | 0.056 | 0.834 | 4.26E−06 |
| 747.5245 | 1204 | 3.433 | 0.058 | 3.933 | 0.088 | 0.873 | 8.18E−06 |
| 814.5917 | 1202 | 2.054 | 0.035 | 2.355 | 0.055 | 0.872 | 1.16E−05 |
| 747.5201 | 1202 | 1.886 | 0.083 | 2.357 | 0.062 | 0.800 | 2.25E−05 |
| 811.5732 | 1202 | 2.729 | 0.047 | 3.041 | 0.055 | 0.897 | 4.54E−05 |
| 789.5892 | 1202 | 1.703 | 0.053 | 2.013 | 0.061 | 0.846 | 0.0002 |
| 810.5399 | 1204 | 2.760 | 0.071 | 3.111 | 0.064 | 0.887 | 0.0004 |
| 795.5838 | 1204 | 3.569 | 0.060 | 3.845 | 0.050 | 0.928 | 0.0007 |
| 856.6061 | 1202 | 4.500 | 0.081 | 4.894 | 0.078 | 0.919 | 0.0008 |
| 783.5148 | 1204 | 3.217 | 0.063 | 3.512 | 0.061 | 0.916 | 0.0011 |
| 855.6023 | 1202 | 5.497 | 0.079 | 5.876 | 0.079 | 0.935 | 0.0011 |
| 858.6212 | 1202 | 2.533 | 0.080 | 2.917 | 0.080 | 0.868 | 0.0011 |
| 787.5465 | 1204 | 2.543 | 0.116 | 2.964 | 0.045 | 0.858 | 0.0013 |
| 857.6186 | 1202 | 3.614 | 0.081 | 3.989 | 0.081 | 0.906 | 0.0015 |
| 773.537 | 1202 | 1.581 | 0.066 | 1.875 | 0.065 | 0.843 | 0.002 |
| 784.5237 | 1204 | 3.211 | 0.056 | 3.464 | 0.056 | 0.927 | 0.002 |
| 748.5287 | 1204 | 2.249 | 0.127 | 2.811 | 0.123 | 0.800 | 0.0021 |
| 828.5743 | 1202 | 5.181 | 0.076 | 5.517 | 0.075 | 0.939 | 0.0023 |
| 827.5701 | 1202 | 6.245 | 0.082 | 6.608 | 0.083 | 0.945 | 0.0026 |
| 786.5416 | 1204 | 3.729 | 0.049 | 3.961 | 0.058 | 0.941 | 0.0029 |
| 871.5934 | 1202 | 1.841 | 0.085 | 2.189 | 0.076 | 0.841 | 0.0031 |
| 744.5536 | 1204 | 4.260 | 0.047 | 4.473 | 0.054 | 0.952 | 0.0037 |
| 787.5729 | 1202 | 1.834 | 0.054 | 2.081 | 0.065 | 0.881 | 0.0042 |
| 755.486 | 1204 | 3.146 | 0.061 | 3.395 | 0.059 | 0.927 | 0.0044 |
| 796.5876 | 1204 | 2.633 | 0.059 | 2.868 | 0.056 | 0.918 | 0.0048 |
| 812.5762 | 1202 | 1.752 | 0.045 | 2.034 | 0.088 | 0.861 | 0.0049 |
| 817.5377 | 1102 | 2.175 | 0.064 | 2.427 | 0.060 | 0.896 | 0.0053 |
| 383.3284 | 1204 | 1.263 | 0.120 | 1.722 | 0.107 | 0.733 | 0.0055 |
| 840.6063 | 1202 | 2.746 | 0.042 | 2.927 | 0.050 | 0.938 | 0.0065 |
| 544.397 | 1204 | 2.998 | 0.111 | 2.235 | 0.255 | 1.342 | 0.0066 |
| 570.3725 | 1202 | 2.926 | 0.047 | 3.115 | 0.049 | 0.939 | 0.0071 |
| 782.5085 | 1204 | 3.369 | 0.056 | 3.596 | 0.062 | 0.937 | 0.0077 |
| 847.5954 | 1202 | 2.317 | 0.089 | 2.662 | 0.090 | 0.870 | 0.0079 |
| 855.6016 | 1102 | 3.386 | 0.060 | 3.619 | 0.062 | 0.936 | 0.0082 |
| 769.5656 | 1204 | 3.889 | 0.055 | 4.103 | 0.057 | 0.948 | 0.0084 |
| 819.5642 | 1202 | 2.811 | 0.080 | 3.149 | 0.099 | 0.893 | 0.0089 |
| 828.5737 | 1102 | 2.982 | 0.056 | 3.197 | 0.058 | 0.933 | 0.009 |
| 590.343 | 1202 | 4.005 | 0.069 | 4.261 | 0.066 | 0.940 | 0.0091 |
| 719.6231 | 1204 | 4.528 | 0.074 | 4.158 | 0.119 | 1.089 | 0.0092 |
| 589.3403 | 1202 | 5.847 | 0.076 | 6.129 | 0.075 | 0.954 | 0.0098 |
| 768.5539 | 1204 | 3.928 | 0.069 | 4.189 | 0.071 | 0.938 | 0.0102 |
| 839.6031 | 1202 | 3.723 | 0.041 | 3.895 | 0.051 | 0.956 | 0.0102 |
| 821.5712 | 1102 | 2.919 | 0.053 | 3.120 | 0.056 | 0.936 | 0.0106 |
| 1226.097 | 1203 | 3.278 | 0.092 | 2.921 | 0.105 | 1.122 | 0.0122 |
| 664.5323 | 1204 | 4.909 | 0.126 | 4.391 | 0.161 | 1.118 | 0.0126 |
| 733.6426 | 1204 | 2.981 | 0.074 | 2.625 | 0.120 | 1.135 | 0.0126 |
| 771.5814 | 1204 | 4.118 | 0.051 | 4.313 | 0.057 | 0.955 | 0.0126 |
| 809.5937 | 1201 | 6.453 | 0.060 | 6.677 | 0.065 | 0.966 | 0.0126 |
| 720.6258 | 1204 | 3.565 | 0.076 | 3.215 | 0.117 | 1.109 | 0.0127 |
| 667.5475 | 1204 | 3.516 | 0.124 | 3.013 | 0.157 | 1.167 | 0.0132 |
| 665.5354 | 1204 | 3.705 | 0.121 | 3.182 | 0.170 | 1.164 | 0.0133 |
| 666.5456 | 1204 | 4.713 | 0.126 | 4.232 | 0.146 | 1.114 | 0.0142 |
| 793.5386 | 1102 | 3.435 | 0.052 | 3.632 | 0.061 | 0.946 | 0.015 |
| 810.5971 | 1201 | 5.436 | 0.063 | 5.665 | 0.068 | 0.959 | 0.015 |
| 832.6037 | 1202 | 4.981 | 0.069 | 5.231 | 0.074 | 0.952 | 0.0151 |
| 663.5216 | 1204 | 2.566 | 0.145 | 1.946 | 0.210 | 1.319 | 0.0159 |
| 743.5471 | 1204 | 5.227 | 0.047 | 5.417 | 0.062 | 0.965 | 0.0162 |
| 767.5495 | 1204 | 5.033 | 0.074 | 5.287 | 0.074 | 0.952 | 0.017 |
| 796.5292 | 1204 | 2.928 | 0.063 | 3.142 | 0.062 | 0.932 | 0.017 |

TABLE 3-continued

Accurate mass features differing between clinically diagnosed
AD patients with a significant cognitive impairment and clinically
diagnosed non-AD patients with a significant cognitive
impairment (p < 0.05, log2 transformed).

| Detected Mass | Analysis Mode | AVG (log2) AD + Cog | SEM AD + Cog | AVG (log2) Non-AD + Cog | SEM Non-AD + Cog | log(2) Ratio | P Value |
|---|---|---|---|---|---|---|---|
| 671.5723 | 1204 | 2.131 | 0.140 | 2.568 | 0.113 | 0.830 | 0.0173 |
| 758.5092 | 1204 | 4.504 | 0.047 | 4.670 | 0.051 | 0.964 | 0.0188 |
| 509.3493 | 1202 | 2.358 | 0.054 | 2.542 | 0.056 | 0.927 | 0.0192 |
| 827.57 | 1102 | 3.984 | 0.059 | 4.191 | 0.064 | 0.951 | 0.0194 |
| 569.369 | 1202 | 4.867 | 0.049 | 5.033 | 0.049 | 0.967 | 0.02 |
| 831.6001 | 1202 | 6.109 | 0.077 | 6.380 | 0.085 | 0.958 | 0.02 |
| 638.5149 | 1204 | 3.530 | 0.120 | 3.086 | 0.150 | 1.144 | 0.0224 |
| 768.5503 | 1202 | 1.849 | 0.125 | 2.190 | 0.080 | 0.845 | 0.0249 |
| 313.1153 | 1204 | 3.859 | 0.102 | 3.338 | 0.209 | 1.156 | 0.025 |
| 592.3571 | 1202 | 2.113 | 0.095 | 2.375 | 0.065 | 0.890 | 0.0262 |
| 794.5421 | 1102 | 2.364 | 0.048 | 2.536 | 0.061 | 0.932 | 0.0276 |
| 662.5175 | 1204 | 3.806 | 0.120 | 3.377 | 0.153 | 1.127 | 0.0292 |
| 670.569 | 1204 | 3.179 | 0.090 | 3.474 | 0.101 | 0.915 | 0.0312 |
| 870.7307 | 1203 | 3.361 | 0.074 | 3.012 | 0.144 | 1.116 | 0.0312 |
| 1098.974 | 1204 | 3.097 | 0.070 | 2.739 | 0.151 | 1.131 | 0.0313 |
| 694.6161 | 1204 | 2.845 | 0.080 | 2.437 | 0.173 | 1.168 | 0.0324 |
| 541.3432 | 1102 | 3.138 | 0.034 | 3.255 | 0.043 | 0.964 | 0.0335 |
| 581.3344 | 1202 | 1.844 | 0.111 | 2.147 | 0.087 | 0.859 | 0.0351 |
| 691.596 | 1204 | 2.394 | 0.098 | 1.999 | 0.159 | 1.198 | 0.0351 |
| 803.5677 | 1202 | 7.101 | 0.095 | 7.405 | 0.108 | 0.959 | 0.0364 |
| 591.3542 | 1202 | 3.870 | 0.092 | 4.110 | 0.064 | 0.942 | 0.0367 |
| 705.6093 | 1204 | 3.137 | 0.072 | 2.823 | 0.132 | 1.111 | 0.0367 |
| 847.5316 | 1101 | 2.564 | 0.060 | 2.815 | 0.104 | 0.911 | 0.0367 |
| 854.5902 | 1202 | 3.801 | 0.070 | 4.027 | 0.082 | 0.944 | 0.0376 |
| 215.9153 | 1101 | 4.405 | 0.297 | 5.221 | 0.247 | 0.844 | 0.0379 |
| 569.3687 | 1102 | 2.063 | 0.042 | 2.217 | 0.062 | 0.931 | 0.0404 |
| 640.5294 | 1204 | 3.725 | 0.127 | 3.313 | 0.154 | 1.124 | 0.0407 |
| 853.5862 | 1202 | 4.775 | 0.069 | 4.993 | 0.081 | 0.956 | 0.0413 |
| 830.5894 | 1202 | 4.738 | 0.076 | 4.968 | 0.082 | 0.954 | 0.0415 |
| 760.5216 | 1204 | 4.008 | 0.048 | 4.156 | 0.053 | 0.964 | 0.0417 |
| 530.3821 | 1204 | 2.614 | 0.172 | 2.016 | 0.240 | 1.296 | 0.0441 |
| 1225.092 | 1203 | 3.451 | 0.135 | 3.011 | 0.170 | 1.146 | 0.0445 |
| 819.5551 | 1102 | 2.198 | 0.058 | 2.369 | 0.062 | 0.928 | 0.0456 |
| 743.5469 | 1202 | 2.976 | 0.070 | 3.200 | 0.087 | 0.930 | 0.0464 |
| 444.2717 | 1202 | 1.304 | 0.083 | 1.577 | 0.109 | 0.827 | 0.0471 |
| 678.5477 | 1204 | 3.874 | 0.101 | 3.523 | 0.145 | 1.099 | 0.0485 |
| 741.5305 | 1204 | 2.825 | 0.080 | 3.086 | 0.104 | 0.916 | 0.0489 |
| 759.5163 | 1204 | 4.645 | 0.061 | 4.811 | 0.057 | 0.966 | 0.0493 |
| 820.568 | 1202 | 1.757 | 0.128 | 2.102 | 0.117 | 0.836 | 0.0497 |

TABLE 4

Accurate mass features differing between clinically diagnosed
AD patients with a significant cognitive impairment and clinically
diagnosed AD patients without a significant cognitive
impairment (p < 0.05, log2 transformed).

| Detected Mass | Analysis Mode | AVG (log2) AD | SEM AD | AVG (log2) AD noCog | SEM AD noCog | log(2) Ratio | P Value |
|---|---|---|---|---|---|---|---|
| 541.3432 | 1102 | 3.138 | 0.034 | 3.518 | 0.039 | 0.892 | 3.47E−10 |
| 569.3687 | 1102 | 2.063 | 0.042 | 2.479 | 0.045 | 0.832 | 3.90E−09 |
| 829.5856 | 1102 | 3.806 | 0.059 | 4.301 | 0.048 | 0.885 | 1.30E−08 |
| 567.3547 | 1102 | 2.629 | 0.050 | 3.031 | 0.045 | 0.868 | 1.02E−07 |
| 831.5997 | 1102 | 4.372 | 0.055 | 4.774 | 0.042 | 0.916 | 1.93E−07 |
| 832.6026 | 1102 | 3.268 | 0.055 | 3.662 | 0.042 | 0.892 | 2.67E−07 |
| 804.5713 | 1102 | 4.017 | 0.048 | 4.426 | 0.054 | 0.908 | 3.40E−07 |
| 803.568 | 1102 | 5.238 | 0.048 | 5.656 | 0.057 | 0.926 | 3.97E−07 |
| 871.5528 | 1102 | 2.885 | 0.049 | 3.279 | 0.054 | 0.880 | 8.30E−07 |
| 565.3394 | 1102 | 3.265 | 0.058 | 3.728 | 0.064 | 0.876 | 1.14E−06 |
| 805.5832 | 1102 | 3.874 | 0.056 | 4.292 | 0.055 | 0.903 | 1.41E−06 |
| 819.5551 | 1102 | 2.198 | 0.058 | 2.604 | 0.053 | 0.844 | 2.52E−06 |
| 555.3102 | 1102 | 1.634 | 0.053 | 2.033 | 0.059 | 0.803 | 3.32E−06 |
| 853.5854 | 1102 | 2.449 | 0.056 | 2.824 | 0.051 | 0.867 | 5.09E−06 |
| 805.5605 | 1101 | 5.184 | 0.074 | 5.665 | 0.065 | 0.915 | 6.42E−06 |
| 808.5792 | 1101 | 4.488 | 0.071 | 4.925 | 0.057 | 0.911 | 9.48E−06 |
| 793.5386 | 1102 | 3.435 | 0.052 | 3.799 | 0.057 | 0.904 | 1.17E−05 |
| 807.5758 | 1101 | 5.531 | 0.069 | 5.961 | 0.059 | 0.928 | 1.20E−05 |

TABLE 4-continued

Accurate mass features differing between clinically diagnosed AD patients with a significant cognitive impairment and clinically diagnosed AD patients without a significant cognitive impairment ($p < 0.05$, log2 transformed).

| Detected Mass | Analysis Mode | AVG (log2) AD | SEM AD | AVG (log2) AD noCog | SEM AD noCog | log(2) Ratio | P Value |
|---|---|---|---|---|---|---|---|
| 806.5639 | 1101 | 4.199 | 0.075 | 4.669 | 0.066 | 0.899 | 1.28E−05 |
| 837.5027 | 1101 | 3.402 | 0.050 | 3.781 | 0.064 | 0.900 | 1.45E−05 |
| 794.5421 | 1102 | 2.364 | 0.048 | 2.703 | 0.059 | 0.875 | 2.79E−05 |
| 780.5474 | 1101 | 5.241 | 0.064 | 5.661 | 0.070 | 0.926 | 3.62E−05 |
| 779.5444 | 1101 | 6.239 | 0.065 | 6.654 | 0.070 | 0.938 | 4.37E−05 |
| 821.5712 | 1102 | 2.919 | 0.053 | 3.221 | 0.048 | 0.906 | 0.0001 |
| 827.57 | 1102 | 3.984 | 0.059 | 4.337 | 0.063 | 0.919 | 0.0001 |
| 886.5582 | 1102 | 2.911 | 0.041 | 3.189 | 0.053 | 0.913 | 0.0001 |
| 915.5191 | 1101 | 2.189 | 0.058 | 2.592 | 0.073 | 0.845 | 0.0001 |
| 722.5335 | 1101 | 2.406 | 0.062 | 2.735 | 0.057 | 0.880 | 0.0002 |
| 828.5737 | 1102 | 2.982 | 0.056 | 3.313 | 0.063 | 0.900 | 0.0002 |
| 833.5932 | 1101 | 3.045 | 0.095 | 3.522 | 0.077 | 0.865 | 0.0002 |
| 855.6016 | 1102 | 3.386 | 0.060 | 3.704 | 0.055 | 0.914 | 0.0002 |
| 755.5468 | 1101 | 2.115 | 0.086 | 2.563 | 0.082 | 0.825 | 0.0003 |
| 795.555 | 1102 | 2.520 | 0.054 | 2.818 | 0.057 | 0.894 | 0.0003 |
| 803.5445 | 1101 | 4.941 | 0.074 | 5.324 | 0.070 | 0.928 | 0.0003 |
| 811.6096 | 1101 | 2.801 | 0.116 | 3.370 | 0.096 | 0.831 | 0.0003 |
| 804.5476 | 1101 | 3.987 | 0.073 | 4.370 | 0.073 | 0.912 | 0.0004 |
| 829.5604 | 1101 | 3.360 | 0.075 | 3.728 | 0.063 | 0.901 | 0.0004 |
| 783.5672 | 1101 | 3.535 | 0.092 | 3.993 | 0.085 | 0.885 | 0.0005 |
| 832.5791 | 1101 | 3.184 | 0.076 | 3.541 | 0.067 | 0.899 | 0.0008 |
| 847.5316 | 1101 | 2.564 | 0.060 | 2.955 | 0.095 | 0.868 | 0.0008 |
| 784.5811 | 1101 | 4.161 | 0.112 | 4.668 | 0.093 | 0.891 | 0.0009 |
| 831.5759 | 1101 | 4.123 | 0.080 | 4.485 | 0.066 | 0.919 | 0.0009 |
| 757.4991 | 1101 | 3.450 | 0.089 | 3.866 | 0.083 | 0.892 | 0.0011 |
| 781.5617 | 1101 | 5.928 | 0.084 | 6.305 | 0.075 | 0.940 | 0.0014 |
| 795.5181 | 1101 | 2.458 | 0.082 | 2.823 | 0.073 | 0.871 | 0.0015 |
| 782.565 | 1101 | 4.901 | 0.088 | 5.279 | 0.080 | 0.928 | 0.0022 |
| 760.5811 | 1101 | 4.216 | 0.099 | 4.632 | 0.089 | 0.910 | 0.0027 |
| 759.5779 | 1101 | 5.352 | 0.096 | 5.752 | 0.085 | 0.930 | 0.0028 |
| 591.3542 | 1202 | 3.870 | 0.092 | 4.224 | 0.068 | 0.916 | 0.0031 |
| 592.3571 | 1202 | 2.113 | 0.095 | 2.472 | 0.070 | 0.855 | 0.0035 |
| 761.5843 | 1101 | 2.241 | 0.084 | 2.609 | 0.088 | 0.859 | 0.0035 |
| 858.6212 | 1202 | 2.533 | 0.080 | 2.870 | 0.078 | 0.883 | 0.0037 |
| 458.2405 | 1101 | 1.632 | 0.054 | 1.858 | 0.054 | 0.878 | 0.0042 |
| 785.5933 | 1101 | 5.687 | 0.112 | 6.096 | 0.083 | 0.933 | 0.0047 |
| 786.5967 | 1101 | 4.611 | 0.112 | 5.018 | 0.084 | 0.919 | 0.005 |
| 758.5656 | 1101 | 5.511 | 0.107 | 5.915 | 0.094 | 0.932 | 0.0061 |
| 306.2569 | 1204 | 2.878 | 0.070 | 3.125 | 0.053 | 0.921 | 0.0066 |
| 857.6186 | 1202 | 3.614 | 0.081 | 3.925 | 0.076 | 0.921 | 0.0066 |
| 757.5626 | 1101 | 6.470 | 0.106 | 6.861 | 0.094 | 0.943 | 0.0075 |
| 809.5936 | 1101 | 4.786 | 0.104 | 5.150 | 0.081 | 0.929 | 0.0077 |
| 810.5969 | 1101 | 3.779 | 0.108 | 4.144 | 0.083 | 0.912 | 0.0095 |
| 807.59 | 1202 | 2.348 | 0.061 | 2.574 | 0.062 | 0.912 | 0.0113 |
| 383.3284 | 1204 | 1.263 | 0.120 | 1.659 | 0.095 | 0.761 | 0.012 |
| 786.5416 | 1204 | 3.729 | 0.049 | 3.903 | 0.046 | 0.955 | 0.012 |
| 744.55 | 1202 | 1.842 | 0.064 | 2.093 | 0.074 | 0.880 | 0.0124 |
| 827.5448 | 1101 | 3.373 | 0.104 | 3.751 | 0.105 | 0.899 | 0.0128 |
| 784.5237 | 1204 | 3.211 | 0.056 | 3.405 | 0.052 | 0.943 | 0.0133 |
| 746.5119 | 1204 | 2.615 | 0.165 | 3.058 | 0.057 | 0.855 | 0.0145 |
| 817.5377 | 1102 | 2.175 | 0.064 | 2.405 | 0.066 | 0.905 | 0.0155 |
| 699.5198 | 1204 | 2.129 | 0.055 | 2.309 | 0.047 | 0.922 | 0.0161 |
| 757.5014 | 1204 | 3.642 | 0.067 | 3.869 | 0.063 | 0.941 | 0.0161 |
| 826.7069 | 1204 | 2.279 | 0.148 | 2.684 | 0.086 | 0.849 | 0.0215 |
| 758.5092 | 1204 | 4.504 | 0.047 | 4.652 | 0.043 | 0.968 | 0.0235 |
| 546.3485 | 1101 | 1.890 | 0.073 | 2.115 | 0.064 | 0.894 | 0.0236 |
| 801.555 | 1202 | 2.543 | 0.077 | 2.788 | 0.077 | 0.912 | 0.0272 |
| 829.7239 | 1204 | 2.802 | 0.120 | 3.161 | 0.105 | 0.886 | 0.0272 |
| 748.5721 | 1102 | 3.795 | 0.067 | 3.996 | 0.060 | 0.950 | 0.0288 |
| 518.3174 | 1101 | 3.358 | 0.051 | 3.523 | 0.054 | 0.953 | 0.0296 |
| 826.5581 | 1202 | 1.648 | 0.107 | 1.983 | 0.108 | 0.831 | 0.0309 |
| 830.5894 | 1202 | 4.738 | 0.076 | 4.956 | 0.064 | 0.956 | 0.0317 |
| 430.3818 | 1204 | 4.790 | 0.109 | 5.108 | 0.096 | 0.938 | 0.0322 |
| 313.1153 | 1204 | 3.859 | 0.102 | 3.311 | 0.233 | 1.166 | 0.0327 |
| 755.5467 | 1201 | 3.507 | 0.072 | 3.728 | 0.072 | 0.941 | 0.0327 |
| 545.3453 | 1101 | 3.500 | 0.071 | 3.713 | 0.069 | 0.943 | 0.0353 |
| 320.2356 | 1204 | 1.302 | 0.114 | 1.590 | 0.070 | 0.819 | 0.0363 |
| 183.0661 | 1101 | 2.412 | 0.147 | 2.779 | 0.096 | 0.868 | 0.0416 |
| 825.5544 | 1202 | 2.644 | 0.112 | 2.968 | 0.109 | 0.891 | 0.0418 |
| 549.4845 | 1203 | 5.510 | 0.107 | 5.818 | 0.103 | 0.947 | 0.0424 |
| 829.5859 | 1202 | 5.864 | 0.082 | 6.087 | 0.070 | 0.963 | 0.0433 |
| 431.386 | 1204 | 3.354 | 0.108 | 3.651 | 0.099 | 0.919 | 0.0463 |

TABLE 4-continued

Accurate mass features differing between clinically diagnosed AD patients with a significant cognitive impairment and clinically diagnosed AD patients without a significant cognitive impairment ($p < 0.05$, log2 transformed).

| Detected Mass | Analysis Mode | AVG (log2) AD | SEM AD | AVG (log2) AD noCog | SEM AD noCog | log(2) Ratio | P Value |
|---|---|---|---|---|---|---|---|
| 784.5811 | 1201 | 5.585 | 0.073 | 5.782 | 0.064 | 0.966 | 0.0463 |
| 777.5287 | 1201 | 2.793 | 0.063 | 2.986 | 0.072 | 0.935 | 0.0466 |
| 278.2254 | 1204 | 4.828 | 0.056 | 4.996 | 0.062 | 0.966 | 0.0467 |
| 548.4815 | 1203 | 6.949 | 0.103 | 7.233 | 0.096 | 0.961 | 0.0472 |
| 777.553 | 1202 | 1.720 | 0.100 | 2.002 | 0.098 | 0.859 | 0.0483 |
| 517.314 | 1101 | 5.399 | 0.050 | 5.547 | 0.055 | 0.973 | 0.0488 |
| 661.6233 | 1204 | 2.430 | 0.088 | 2.638 | 0.054 | 0.921 | 0.0489 |

TABLE 5

Accurate mass features differing between clinically diagnosed non-AD patients and non-demented controls ($p < 0.05$, log2 transformed).

| Detected Mass | Analysis Mode | AVG (log2) NON-AD | SEM NON-AD | AVG (log2) Normal | SEM Normal | log(2) Ratio | P Value |
|---|---|---|---|---|---|---|---|
| 541.3432 | 1102 | 3.255 | 0.043 | 3.679 | 0.048 | 0.885 | 3.43E-12 |
| 567.3547 | 1102 | 2.621 | 0.052 | 3.117 | 0.054 | 0.841 | 2.78E-11 |
| 805.5605 | 1101 | 5.159 | 0.072 | 5.604 | 0.048 | 0.921 | 1.08E-09 |
| 806.5639 | 1101 | 4.150 | 0.073 | 4.630 | 0.049 | 0.896 | 1.51E-09 |
| 804.5713 | 1102 | 4.159 | 0.056 | 4.466 | 0.033 | 0.931 | 3.79E-09 |
| 783.5672 | 1101 | 3.515 | 0.077 | 4.126 | 0.079 | 0.852 | 4.13E-09 |
| 781.5617 | 1101 | 5.919 | 0.072 | 6.403 | 0.072 | 0.924 | 4.19E-09 |
| 780.5474 | 1101 | 5.276 | 0.075 | 5.691 | 0.043 | 0.927 | 4.35E-09 |
| 803.568 | 1102 | 5.379 | 0.056 | 5.656 | 0.035 | 0.951 | 4.43E-09 |
| 779.5444 | 1101 | 6.291 | 0.073 | 6.659 | 0.043 | 0.945 | 5.24E-09 |
| 760.5811 | 1101 | 4.034 | 0.079 | 4.733 | 0.103 | 0.852 | 6.28E-09 |
| 805.5832 | 1102 | 3.897 | 0.057 | 4.344 | 0.068 | 0.897 | 6.49E-09 |
| 759.5779 | 1101 | 5.166 | 0.082 | 5.810 | 0.099 | 0.889 | 1.04E-08 |
| 782.565 | 1101 | 4.878 | 0.077 | 5.415 | 0.078 | 0.901 | 1.14E-08 |
| 829.5856 | 1102 | 3.952 | 0.051 | 4.261 | 0.046 | 0.927 | 1.44E-08 |
| 569.3687 | 1102 | 2.217 | 0.062 | 2.639 | 0.048 | 0.840 | 1.99E-08 |
| 755.5468 | 1101 | 1.974 | 0.089 | 2.667 | 0.085 | 0.740 | 2.63E-08 |
| 757.4991 | 1101 | 3.368 | 0.086 | 3.945 | 0.070 | 0.854 | 2.69E-08 |
| 871.5528 | 1102 | 2.960 | 0.059 | 3.301 | 0.040 | 0.897 | 4.58E-08 |
| 804.5476 | 1101 | 4.125 | 0.073 | 4.556 | 0.060 | 0.906 | 6.76E-08 |
| 803.5445 | 1101 | 5.084 | 0.072 | 5.478 | 0.059 | 0.928 | 7.46E-08 |
| 758.5656 | 1101 | 5.440 | 0.089 | 5.968 | 0.078 | 0.912 | 8.14E-08 |
| 565.3394 | 1102 | 3.359 | 0.081 | 3.834 | 0.055 | 0.876 | 8.59E-08 |
| 757.5626 | 1101 | 6.417 | 0.087 | 6.886 | 0.079 | 0.932 | 1.74E-07 |
| 808.5792 | 1101 | 4.527 | 0.078 | 4.904 | 0.047 | 0.923 | 2.30E-07 |
| 795.5181 | 1101 | 2.491 | 0.071 | 2.948 | 0.064 | 0.845 | 2.65E-07 |
| 807.5758 | 1101 | 5.569 | 0.080 | 5.911 | 0.047 | 0.942 | 3.99E-07 |
| 731.5464 | 1101 | 1.460 | 0.132 | 2.519 | 0.157 | 0.580 | 4.14E-07 |
| 837.5027 | 1101 | 3.437 | 0.071 | 3.810 | 0.050 | 0.902 | 4.34E-07 |
| 761.5843 | 1101 | 2.053 | 0.092 | 2.740 | 0.106 | 0.749 | 5.01E-07 |
| 784.5811 | 1101 | 4.092 | 0.095 | 4.666 | 0.089 | 0.877 | 5.41E-07 |
| 831.5997 | 1102 | 4.512 | 0.057 | 4.749 | 0.040 | 0.950 | 6.07E-07 |
| 832.6026 | 1102 | 3.409 | 0.056 | 3.677 | 0.040 | 0.927 | 6.72E-07 |
| 555.3102 | 1102 | 1.792 | 0.066 | 2.170 | 0.046 | 0.826 | 8.11E-07 |
| 833.5932 | 1101 | 3.038 | 0.087 | 3.495 | 0.056 | 0.869 | 1.09E-06 |
| 829.5604 | 1101 | 3.381 | 0.077 | 3.754 | 0.058 | 0.901 | 3.91E-06 |
| 811.6096 | 1101 | 2.826 | 0.097 | 3.401 | 0.096 | 0.831 | 4.19E-06 |
| 785.5933 | 1101 | 5.629 | 0.100 | 6.075 | 0.080 | 0.927 | 5.08E-06 |
| 786.5967 | 1101 | 4.566 | 0.101 | 5.041 | 0.078 | 0.906 | 5.43E-06 |
| 827.57 | 1102 | 4.191 | 0.064 | 4.486 | 0.062 | 0.934 | 6.39E-06 |
| 828.5737 | 1102 | 3.197 | 0.058 | 3.478 | 0.061 | 0.919 | 1.44E-05 |
| 810.5969 | 1101 | 3.785 | 0.100 | 4.234 | 0.080 | 0.894 | 2.51E-05 |
| 809.5936 | 1101 | 4.804 | 0.094 | 5.194 | 0.079 | 0.925 | 2.81E-05 |
| 517.314 | 1010 | 5.339 | 0.065 | 5.575 | 0.069 | 0.958 | 3.58E-05 |
| 495.332 | 1101 | 5.003 | 0.083 | 5.391 | 0.112 | 0.928 | 0.0001 |
| 518.3174 | 1101 | 3.325 | 0.062 | 3.601 | 0.073 | 0.923 | 0.0001 |
| 793.5386 | 1102 | 3.632 | 0.061 | 3.827 | 0.039 | 0.949 | 0.0001 |
| 794.5421 | 1102 | 2.536 | 0.061 | 2.763 | 0.040 | 0.918 | 0.0001 |
| 832.5791 | 1101 | 3.305 | 0.080 | 3.607 | 0.061 | 0.916 | 0.0001 |
| 853.5854 | 1102 | 2.527 | 0.065 | 2.790 | 0.052 | 0.906 | 0.0001 |
| 915.5191 | 1101 | 2.278 | 0.083 | 2.632 | 0.063 | 0.866 | 0.0001 |
| 183.0661 | 1101 | 2.324 | 0.143 | 2.920 | 0.094 | 0.796 | 0.0002 |

TABLE 5-continued

Accurate mass features differing between clinically diagnosed non-AD patients and non-demented controls ($p < 0.05$, log2 transformed).

| Detected Mass | Analysis Mode | AVG (log2) NON-AD | SEM NON-AD | AVG (log2) Normal | SEM Normal | log(2) Ratio | P Value |
|---|---|---|---|---|---|---|---|
| 521.3477 | 1101 | 3.406 | 0.099 | 3.895 | 0.127 | 0.875 | 0.0002 |
| 523.3634 | 1101 | 3.221 | 0.102 | 3.673 | 0.103 | 0.877 | 0.0002 |
| 543.3296 | 1101 | 3.579 | 0.072 | 3.898 | 0.087 | 0.918 | 0.0002 |
| 795.555 | 1102 | 2.608 | 0.069 | 2.893 | 0.065 | 0.902 | 0.0002 |
| 831.5759 | 1101 | 4.272 | 0.080 | 4.531 | 0.060 | 0.943 | 0.0002 |
| 886.5582 | 1102 | 2.998 | 0.049 | 3.149 | 0.041 | 0.952 | 0.0002 |
| 496.3355 | 1101 | 3.200 | 0.086 | 3.620 | 0.119 | 0.884 | 0.0004 |
| 827.5448 | 1101 | 3.340 | 0.105 | 3.752 | 0.095 | 0.890 | 0.0004 |
| 819.5551 | 1102 | 2.369 | 0.062 | 2.571 | 0.046 | 0.922 | 0.0005 |
| 522.3511 | 1101 | 1.480 | 0.111 | 2.005 | 0.121 | 0.738 | 0.0006 |
| 817.5377 | 1102 | 2.427 | 0.060 | 2.627 | 0.057 | 0.924 | 0.001 |
| 545.3453 | 1101 | 3.512 | 0.082 | 3.776 | 0.078 | 0.930 | 0.0011 |
| 575.2728 | 1101 | 2.381 | 0.076 | 2.653 | 0.074 | 0.897 | 0.0012 |
| 700.552 | 1101 | 2.150 | 0.094 | 2.535 | 0.102 | 0.848 | 0.0012 |
| 722.5335 | 1101 | 2.437 | 0.062 | 2.632 | 0.056 | 0.926 | 0.0014 |
| 520.3354 | 1101 | 2.075 | 0.117 | 2.564 | 0.130 | 0.809 | 0.0016 |
| 458.2405 | 1101 | 1.664 | 0.064 | 1.924 | 0.077 | 0.865 | 0.0017 |
| 542.3173 | 1101 | 2.268 | 0.092 | 2.603 | 0.089 | 0.871 | 0.0017 |
| 519.3321 | 1101 | 3.807 | 0.121 | 4.245 | 0.133 | 0.897 | 0.0019 |
| 546.3485 | 1101 | 1.931 | 0.069 | 2.216 | 0.089 | 0.872 | 0.0021 |
| 541.3139 | 1101 | 4.077 | 0.092 | 4.353 | 0.096 | 0.937 | 0.0025 |
| 1019.384 | 1102 | 3.095 | 0.042 | 2.828 | 0.037 | 1.094 | 0.0026 |
| 804.7227 | 1203 | 1.612 | 0.233 | 2.530 | 0.220 | 0.637 | 0.0027 |
| 831.7408 | 1203 | 3.839 | 0.137 | 4.286 | 0.130 | 0.896 | 0.0028 |
| 303.1079 | 1202 | 5.575 | 0.057 | 5.621 | 0.047 | 0.992 | 0.0032 |
| 549.4845 | 1203 | 5.480 | 0.127 | 5.807 | 0.110 | 0.944 | 0.0033 |
| 548.4815 | 1203 | 6.917 | 0.122 | 7.174 | 0.103 | 0.964 | 0.0034 |
| 746.5717 | 1204 | 3.115 | 0.058 | 3.257 | 0.061 | 0.957 | 0.0046 |
| 830.7363 | 1203 | 4.694 | 0.139 | 5.098 | 0.135 | 0.921 | 0.0046 |
| 306.2569 | 1204 | 3.015 | 0.059 | 3.164 | 0.067 | 0.953 | 0.0058 |
| 760.5216 | 1204 | 4.156 | 0.053 | 4.211 | 0.039 | 0.987 | 0.0058 |
| 732.4938 | 1204 | 4.274 | 0.060 | 4.370 | 0.057 | 0.978 | 0.0059 |
| 855.6016 | 1102 | 3.619 | 0.062 | 3.752 | 0.065 | 0.965 | 0.0059 |
| 523.4679 | 1203 | 3.249 | 0.212 | 3.886 | 0.165 | 0.836 | 0.0065 |
| 522.4635 | 1203 | 4.717 | 0.208 | 5.313 | 0.176 | 0.888 | 0.0066 |
| 1227.107 | 1203 | 3.235 | 0.116 | 3.547 | 0.100 | 0.912 | 0.0074 |
| 833.7551 | 1204 | 2.396 | 0.213 | 3.042 | 0.161 | 0.788 | 0.0075 |
| 520.4499 | 1203 | 3.898 | 0.194 | 4.434 | 0.148 | 0.879 | 0.0076 |
| 1228.111 | 1203 | 2.587 | 0.203 | 3.131 | 0.105 | 0.826 | 0.0077 |
| 521.4522 | 1203 | 2.319 | 0.204 | 2.933 | 0.158 | 0.790 | 0.0083 |
| 591.3542 | 1202 | 4.110 | 0.064 | 4.209 | 0.058 | 0.976 | 0.0085 |
| 856.672 | 1202 | 2.741 | 0.042 | 2.473 | 0.057 | 1.108 | 0.0086 |
| 777.553 | 1202 | 1.958 | 0.096 | 2.309 | 0.130 | 0.848 | 0.009 |
| 552.5022 | 1203 | 3.097 | 0.142 | 3.529 | 0.147 | 0.878 | 0.0092 |
| 777.5287 | 1201 | 2.781 | 0.055 | 2.926 | 0.072 | 0.951 | 0.0092 |
| 675.6377 | 1204 | 3.806 | 0.112 | 4.030 | 0.066 | 0.945 | 0.0098 |
| 748.5735 | 1202 | 3.883 | 0.036 | 3.606 | 0.050 | 1.077 | 0.0101 |
| 467.807 | 1101 | 1.408 | 0.134 | 0.863 | 0.144 | 1.631 | 0.0104 |
| 832.7523 | 1203 | 3.763 | 0.160 | 4.237 | 0.169 | 0.888 | 0.0104 |
| 837.718 | 1204 | 2.737 | 0.273 | 3.548 | 0.217 | 0.771 | 0.0107 |
| 745.5658 | 1204 | 4.005 | 0.060 | 4.109 | 0.068 | 0.975 | 0.0109 |
| 568.3573 | 1202 | 3.960 | 0.053 | 4.037 | 0.060 | 0.981 | 0.0113 |
| 550.4957 | 1203 | 6.848 | 0.150 | 7.184 | 0.160 | 0.953 | 0.0114 |
| 833.7571 | 1203 | 2.911 | 0.156 | 3.397 | 0.170 | 0.857 | 0.0115 |
| 838.7226 | 1204 | 2.158 | 0.237 | 2.880 | 0.206 | 0.749 | 0.0119 |
| 551.4986 | 1203 | 5.429 | 0.150 | 5.801 | 0.158 | 0.936 | 0.0121 |
| 585.2673 | 1202 | 1.612 | 0.153 | 1.034 | 0.148 | 1.558 | 0.0125 |
| 821.5712 | 1102 | 3.120 | 0.056 | 3.200 | 0.044 | 0.975 | 0.0133 |
| 835.7006 | 1204 | 2.553 | 0.198 | 3.113 | 0.167 | 0.820 | 0.0136 |
| 731.4916 | 1204 | 5.523 | 0.062 | 5.567 | 0.063 | 0.992 | 0.0138 |
| 867.7579 | 1204 | 2.503 | 0.252 | 3.205 | 0.189 | 0.781 | 0.0139 |
| 482.3215 | 1202 | 2.040 | 0.058 | 2.181 | 0.062 | 0.935 | 0.0145 |
| 858.6861 | 1202 | 2.935 | 0.050 | 2.670 | 0.052 | 1.099 | 0.0145 |
| 584.2646 | 1204 | 3.282 | 0.185 | 2.567 | 0.172 | 1.279 | 0.0148 |
| 829.7246 | 1203 | 4.743 | 0.119 | 4.973 | 0.101 | 0.954 | 0.015 |
| 828.7207 | 1203 | 5.497 | 0.121 | 5.716 | 0.107 | 0.962 | 0.0154 |
| 723.5197 | 1204 | 4.571 | 0.070 | 4.214 | 0.056 | 1.085 | 0.0167 |
| 864.738 | 1204 | 4.725 | 0.142 | 5.051 | 0.141 | 0.936 | 0.0171 |
| 691.1957 | 1102 | 2.168 | 0.067 | 1.878 | 0.068 | 1.155 | 0.0181 |
| 585.2664 | 1204 | 1.716 | 0.183 | 1.077 | 0.170 | 1.593 | 0.0187 |
| 749.5777 | 1202 | 2.879 | 0.034 | 2.659 | 0.046 | 1.083 | 0.0189 |
| 757.5014 | 1204 | 3.770 | 0.066 | 3.847 | 0.052 | 0.980 | 0.0197 |
| 863.7336 | 1204 | 5.458 | 0.146 | 5.763 | 0.147 | 0.947 | 0.02 |

TABLE 5-continued

Accurate mass features differing between clinically diagnosed non-AD patients and non-demented controls ($p < 0.05$, log2 transformed).

| Detected Mass | Analysis Mode | AVG (log2) NON-AD | SEM NON-AD | AVG (log2) Normal | SEM Normal | log(2) Ratio | P Value |
|---|---|---|---|---|---|---|---|
| 830.7352 | 1204 | 4.133 | 0.151 | 4.493 | 0.150 | 0.920 | 0.0202 |
| 252.2095 | 1204 | 1.665 | 0.076 | 1.852 | 0.070 | 0.899 | 0.0206 |
| 860.7756 | 1203 | 4.306 | 0.109 | 4.507 | 0.100 | 0.955 | 0.0222 |
| 863.6876 | 1204 | 4.889 | 0.090 | 5.026 | 0.092 | 0.973 | 0.0227 |
| 861.7806 | 1203 | 2.435 | 0.158 | 2.811 | 0.119 | 0.866 | 0.0228 |
| 840.6063 | 1202 | 2.927 | 0.050 | 2.664 | 0.059 | 1.099 | 0.0229 |
| 632.5762 | 1203 | 1.325 | 0.170 | 1.773 | 0.132 | 0.747 | 0.0231 |
| 826.7069 | 1204 | 2.424 | 0.137 | 2.731 | 0.099 | 0.887 | 0.0242 |
| 419.8773 | 1101 | 1.946 | 0.176 | 1.305 | 0.194 | 1.491 | 0.0243 |
| 440.3532 | 1204 | 1.481 | 0.134 | 0.945 | 0.180 | 1.567 | 0.0247 |
| 831.7387 | 1204 | 3.137 | 0.164 | 3.534 | 0.150 | 0.888 | 0.0248 |
| 310.2883 | 1204 | 2.448 | 0.085 | 2.607 | 0.062 | 0.939 | 0.0256 |
| 481.3172 | 1202 | 3.978 | 0.053 | 4.029 | 0.060 | 0.987 | 0.0259 |
| 205.8865 | 1101 | 3.759 | 0.234 | 2.793 | 0.319 | 1.346 | 0.0271 |
| 513.4122 | 1204 | 1.142 | 0.153 | 0.623 | 0.163 | 1.833 | 0.0279 |
| 839.6031 | 1202 | 3.895 | 0.051 | 3.609 | 0.057 | 1.079 | 0.0286 |
| 865.7487 | 1204 | 4.847 | 0.188 | 5.275 | 0.193 | 0.919 | 0.029 |
| 579.5325 | 1203 | 4.188 | 0.154 | 4.491 | 0.127 | 0.933 | 0.0292 |
| 807.59 | 1202 | 2.477 | 0.072 | 2.633 | 0.082 | 0.941 | 0.0293 |
| 351.8903 | 1101 | 2.359 | 0.220 | 1.567 | 0.256 | 1.506 | 0.0296 |
| 782.5085 | 1204 | 3.596 | 0.062 | 3.662 | 0.055 | 0.982 | 0.0297 |
| 859.7696 | 1203 | 5.853 | 0.104 | 5.972 | 0.093 | 0.980 | 0.0298 |
| 409.8484 | 1101 | 2.107 | 0.192 | 1.437 | 0.210 | 1.466 | 0.0304 |
| 577.5137 | 1203 | 8.099 | 0.104 | 8.148 | 0.094 | 0.994 | 0.0305 |
| 1018.942 | 1203 | 3.468 | 0.142 | 3.767 | 0.126 | 0.921 | 0.0305 |
| 703.5709 | 1101 | 3.024 | 0.090 | 3.185 | 0.079 | 0.949 | 0.0314 |
| 484.3794 | 1204 | 2.234 | 0.118 | 1.721 | 0.178 | 1.298 | 0.0315 |
| 283.2602 | 1204 | 6.622 | 0.070 | 6.621 | 0.067 | 1.000 | 0.0316 |
| 401.8166 | 1101 | 1.696 | 0.161 | 1.139 | 0.177 | 1.489 | 0.0316 |
| 832.7492 | 1204 | 3.251 | 0.195 | 3.728 | 0.190 | 0.872 | 0.0316 |
| 190.033 | 1101 | 3.264 | 0.233 | 2.384 | 0.289 | 1.369 | 0.0317 |
| 806.5873 | 1202 | 4.367 | 0.082 | 4.490 | 0.092 | 0.973 | 0.032 |
| 282.2573 | 1204 | 9.088 | 0.073 | 9.019 | 0.071 | 1.008 | 0.0327 |
| 195.8577 | 1101 | 3.161 | 0.202 | 2.370 | 0.266 | 1.334 | 0.0328 |
| 744.4956 | 1204 | 3.941 | 0.058 | 3.988 | 0.058 | 0.988 | 0.0332 |
| 866.7532 | 1204 | 4.123 | 0.184 | 4.547 | 0.189 | 0.907 | 0.0334 |
| 215.9153 | 1101 | 5.221 | 0.247 | 4.183 | 0.346 | 1.248 | 0.0335 |
| 825.6926 | 1203 | 1.767 | 0.173 | 2.165 | 0.124 | 0.816 | 0.0339 |
| 469.8042 | 1101 | 1.617 | 0.150 | 1.096 | 0.170 | 1.475 | 0.0344 |
| 874.7645 | 1204 | 3.091 | 0.144 | 3.377 | 0.111 | 0.915 | 0.0345 |
| 494.4343 | 1203 | 2.119 | 0.275 | 2.809 | 0.232 | 0.754 | 0.0346 |
| 399.8196 | 1101 | 1.827 | 0.171 | 1.249 | 0.184 | 1.463 | 0.0348 |
| 802.7056 | 1204 | 1.701 | 0.206 | 2.248 | 0.202 | 0.756 | 0.0348 |
| 576.5098 | 1203 | 9.446 | 0.111 | 9.460 | 0.099 | 0.999 | 0.0355 |
| 382.1082 | 1101 | 2.222 | 0.229 | 1.494 | 0.220 | 1.487 | 0.0356 |
| 720.6438 | 1204 | 2.962 | 0.180 | 3.293 | 0.083 | 0.900 | 0.036 |
| 805.5839 | 1202 | 5.574 | 0.081 | 5.658 | 0.097 | 0.985 | 0.0365 |
| 779.5441 | 1201 | 7.096 | 0.041 | 7.010 | 0.053 | 1.012 | 0.0368 |
| 231.8893 | 1101 | 2.592 | 0.233 | 1.800 | 0.259 | 1.440 | 0.0372 |
| 686.4877 | 1204 | 2.721 | 0.054 | 2.791 | 0.052 | 0.975 | 0.0374 |
| 429.3749 | 1204 | 2.601 | 0.098 | 2.777 | 0.077 | 0.937 | 0.0378 |
| 265.8423 | 1101 | 2.499 | 0.220 | 1.743 | 0.252 | 1.433 | 0.0384 |
| 722.6424 | 1204 | 3.726 | 0.167 | 4.006 | 0.086 | 0.930 | 0.0385 |
| 780.5474 | 1201 | 6.022 | 0.043 | 5.972 | 0.054 | 1.008 | 0.0396 |
| 599.4936 | 1204 | 1.373 | 0.191 | 1.873 | 0.188 | 0.733 | 0.04 |
| 536.4794 | 1203 | 2.280 | 0.202 | 2.711 | 0.143 | 0.841 | 0.0422 |
| 244.0559 | 1101 | 3.574 | 0.126 | 3.098 | 0.132 | 1.153 | 0.0424 |
| 202.0453 | 1101 | 5.561 | 0.180 | 4.832 | 0.215 | 1.151 | 0.0425 |
| 535.7944 | 1101 | 1.480 | 0.143 | 1.018 | 0.153 | 1.455 | 0.0425 |
| 758.5092 | 1204 | 4.670 | 0.051 | 4.658 | 0.042 | 1.003 | 0.0426 |
| 626.5104 | 1204 | 2.100 | 0.135 | 2.391 | 0.114 | 0.878 | 0.0427 |
| 847.5316 | 1101 | 2.815 | 0.104 | 2.994 | 0.083 | 0.940 | 0.0432 |
| 592.3571 | 1202 | 2.375 | 0.065 | 2.480 | 0.062 | 0.958 | 0.0437 |
| 569.4784 | 1204 | 1.175 | 0.183 | 0.634 | 0.178 | 1.853 | 0.0447 |
| 721.639 | 1204 | 4.879 | 0.142 | 5.064 | 0.088 | 0.963 | 0.0447 |
| 752.5583 | 1204 | 4.284 | 0.070 | 3.966 | 0.061 | 1.080 | 0.0451 |
| 507.7055 | 1101 | 1.487 | 0.126 | 1.052 | 0.154 | 1.413 | 0.0454 |
| 827.7086 | 1203 | 3.916 | 0.119 | 4.098 | 0.096 | 0.956 | 0.046 |
| 784.5237 | 1204 | 3.464 | 0.056 | 3.490 | 0.037 | 0.993 | 0.0461 |
| 755.486 | 1204 | 3.395 | 0.059 | 3.450 | 0.057 | 0.984 | 0.0471 |
| 628.5237 | 1204 | 2.627 | 0.158 | 2.955 | 0.136 | 0.889 | 0.0472 |
| 218.0192 | 1101 | 3.591 | 0.258 | 2.716 | 0.302 | 1.322 | 0.049 |

TABLE 6

Accurate mass features differing between clinically diagnosed AD patients with a mild cognitive impairment and non-demented controls ($p < 0.05$, log2 transformed).

| Detected Mass | Analysis Mode | AVG (log2) AD noCog | SEM AD noCog | Avg (log2) Normal | SEM Normal | log(2) Ratio | P Value |
|---|---|---|---|---|---|---|---|
| 723.5197 | 1204 | 3.576 | 0.058 | 4.350 | 0.056 | 0.822 | 6.42E−14 |
| 723.5195 | 1202 | 2.181 | 0.056 | 2.892 | 0.052 | 0.754 | 2.49E−13 |
| 751.5529 | 1202 | 3.293 | 0.050 | 3.920 | 0.050 | 0.840 | 1.39E−12 |
| 724.5257 | 1204 | 2.883 | 0.044 | 3.463 | 0.055 | 0.833 | 9.96E−12 |
| 749.5367 | 1202 | 3.168 | 0.051 | 3.714 | 0.041 | 0.853 | 1.33E−11 |
| 752.5564 | 1202 | 2.216 | 0.057 | 2.836 | 0.050 | 0.781 | 1.91E−11 |
| 751.5555 | 1204 | 4.553 | 0.060 | 5.248 | 0.060 | 0.868 | 1.96E−11 |
| 750.5402 | 1202 | 2.175 | 0.054 | 2.704 | 0.044 | 0.804 | 2.92E−10 |
| 752.5583 | 1204 | 3.453 | 0.063 | 4.094 | 0.061 | 0.844 | 6.11E−10 |
| 750.544 | 1204 | 3.299 | 0.052 | 3.858 | 0.063 | 0.855 | 3.31E−09 |
| 749.5407 | 1204 | 4.429 | 0.061 | 5.012 | 0.064 | 0.884 | 9.50E−09 |
| 699.5198 | 1204 | 2.309 | 0.047 | 2.775 | 0.054 | 0.832 | 1.20E−08 |
| 725.5385 | 1204 | 2.958 | 0.060 | 3.417 | 0.054 | 0.866 | 4.59E−07 |
| 727.5568 | 1204 | 3.588 | 0.050 | 3.986 | 0.060 | 0.900 | 3.00E−06 |
| 812.5762 | 1202 | 1.571 | 0.087 | 2.084 | 0.058 | 0.754 | 1.13E−05 |
| 541.3432 | 1102 | 3.518 | 0.039 | 3.798 | 0.048 | 0.926 | 2.42E−05 |
| 813.5885 | 1202 | 2.992 | 0.041 | 3.276 | 0.048 | 0.913 | 2.68E−05 |
| 811.5732 | 1202 | 2.683 | 0.055 | 3.027 | 0.055 | 0.886 | 3.92E−05 |
| 726.5461 | 1204 | 2.869 | 0.047 | 3.150 | 0.050 | 0.911 | 0.0001 |
| 814.5917 | 1202 | 2.028 | 0.040 | 2.289 | 0.051 | 0.886 | 0.0001 |
| 632.5762 | 1203 | 0.944 | 0.175 | 1.830 | 0.132 | 0.516 | 0.0002 |
| 728.5627 | 1204 | 2.998 | 0.045 | 3.281 | 0.060 | 0.914 | 0.0003 |
| 782.5085 | 1204 | 3.435 | 0.071 | 3.780 | 0.055 | 0.909 | 0.0003 |
| 569.3687 | 1102 | 2.479 | 0.045 | 2.724 | 0.048 | 0.910 | 0.0004 |
| 803.5445 | 1101 | 5.324 | 0.070 | 5.655 | 0.059 | 0.941 | 0.0007 |
| 804.5476 | 1101 | 4.370 | 0.073 | 4.703 | 0.060 | 0.929 | 0.0009 |
| 817.5377 | 1102 | 2.405 | 0.066 | 2.712 | 0.057 | 0.887 | 0.001 |
| 787.5729 | 1202 | 1.864 | 0.058 | 2.145 | 0.057 | 0.869 | 0.0011 |
| 747.5245 | 1204 | 3.521 | 0.063 | 3.886 | 0.090 | 0.906 | 0.0013 |
| 775.5533 | 1202 | 2.140 | 0.062 | 2.449 | 0.068 | 0.874 | 0.0013 |
| 746.5717 | 1204 | 3.117 | 0.043 | 3.362 | 0.061 | 0.927 | 0.0014 |
| 827.57 | 1102 | 4.337 | 0.063 | 4.630 | 0.062 | 0.937 | 0.0017 |
| 745.5658 | 1204 | 3.989 | 0.041 | 4.242 | 0.068 | 0.940 | 0.0018 |
| 828.5737 | 1102 | 3.313 | 0.063 | 3.590 | 0.061 | 0.923 | 0.0025 |
| 542.3173 | 1101 | 2.344 | 0.067 | 2.687 | 0.089 | 0.872 | 0.0027 |
| 760.5216 | 1204 | 4.140 | 0.052 | 4.347 | 0.039 | 0.952 | 0.0028 |
| 748.5287 | 1204 | 2.319 | 0.131 | 2.820 | 0.088 | 0.822 | 0.003 |
| 774.0316 | 1204 | 2.044 | 0.199 | 1.167 | 0.203 | 1.752 | 0.0031 |
| 784.5237 | 1204 | 3.405 | 0.052 | 3.603 | 0.037 | 0.945 | 0.0035 |
| 775.5528 | 1204 | 3.221 | 0.065 | 3.537 | 0.085 | 0.911 | 0.004 |
| 744.5536 | 1204 | 4.388 | 0.046 | 4.605 | 0.058 | 0.953 | 0.0042 |
| 482.3215 | 1202 | 2.001 | 0.057 | 2.251 | 0.062 | 0.889 | 0.0043 |
| 768.5539 | 1204 | 3.995 | 0.060 | 4.279 | 0.077 | 0.934 | 0.0044 |
| 506.2851 | 1201 | 3.210 | 0.100 | 2.656 | 0.165 | 1.209 | 0.0045 |
| 747.5201 | 1202 | 2.006 | 0.060 | 2.313 | 0.088 | 0.867 | 0.0045 |
| 755.486 | 1204 | 3.295 | 0.069 | 3.561 | 0.057 | 0.925 | 0.0047 |
| 781.5617 | 1101 | 6.305 | 0.075 | 6.610 | 0.072 | 0.954 | 0.005 |
| 786.5416 | 1204 | 3.903 | 0.046 | 4.087 | 0.043 | 0.955 | 0.0052 |
| 804.5713 | 1102 | 4.426 | 0.054 | 4.610 | 0.033 | 0.960 | 0.0064 |
| 743.5471 | 1204 | 5.349 | 0.054 | 5.579 | 0.063 | 0.959 | 0.0066 |
| 541.3139 | 1101 | 4.172 | 0.067 | 4.494 | 0.096 | 0.928 | 0.0069 |
| 767.5495 | 1204 | 5.085 | 0.063 | 5.369 | 0.082 | 0.947 | 0.0072 |
| 782.565 | 1101 | 5.279 | 0.080 | 5.589 | 0.078 | 0.945 | 0.0074 |
| 555.3102 | 1102 | 2.033 | 0.059 | 2.240 | 0.046 | 0.908 | 0.0086 |
| 567.3547 | 1102 | 3.031 | 0.045 | 3.218 | 0.054 | 0.942 | 0.0089 |
| 565.3394 | 1102 | 3.728 | 0.064 | 3.958 | 0.055 | 0.942 | 0.0094 |
| 582.2473 | 1201 | 3.346 | 0.151 | 2.793 | 0.141 | 1.198 | 0.0099 |
| 803.568 | 1102 | 5.656 | 0.057 | 5.838 | 0.035 | 0.969 | 0.0108 |
| 779.5444 | 1101 | 6.654 | 0.070 | 6.874 | 0.043 | 0.968 | 0.0113 |
| 796.5876 | 1204 | 2.630 | 0.063 | 2.860 | 0.062 | 0.919 | 0.0117 |
| 758.5092 | 1204 | 4.652 | 0.043 | 4.808 | 0.042 | 0.968 | 0.0126 |
| 783.5148 | 1204 | 3.344 | 0.068 | 3.574 | 0.056 | 0.936 | 0.0126 |
| 748.5735 | 1202 | 3.893 | 0.045 | 3.722 | 0.050 | 1.046 | 0.0135 |
| 529.3167 | 1202 | 3.028 | 0.064 | 3.265 | 0.069 | 0.927 | 0.0138 |
| 781.562 | 1201 | 7.406 | 0.060 | 7.638 | 0.071 | 0.970 | 0.0144 |
| 780.5474 | 1101 | 5.661 | 0.070 | 5.875 | 0.043 | 0.964 | 0.0145 |
| 810.5399 | 1204 | 2.905 | 0.069 | 3.145 | 0.066 | 0.923 | 0.0147 |
| 837.5881 | 1202 | 2.412 | 0.040 | 2.577 | 0.053 | 0.936 | 0.0147 |
| 590.343 | 1202 | 4.042 | 0.072 | 4.304 | 0.076 | 0.939 | 0.0149 |
| 580.5351 | 1203 | 1.531 | 0.200 | 2.192 | 0.174 | 0.699 | 0.0166 |
| 789.5892 | 1202 | 1.755 | 0.049 | 1.952 | 0.065 | 0.899 | 0.0167 |
| 887.7352 | 1204 | 6.359 | 0.115 | 5.963 | 0.113 | 1.066 | 0.0174 |
| 828.5743 | 1202 | 5.301 | 0.087 | 5.598 | 0.085 | 0.947 | 0.0178 |

TABLE 6-continued

Accurate mass features differing between clinically diagnosed AD patients with a mild cognitive impairment and non-demented controls (p < 0.05, log2 transformed).

| Detected Mass | Analysis Mode | AVG (log2) AD noCog | SEM AD noCog | Avg (log2) Normal | SEM Normal | log(2) Ratio | P Value |
|---|---|---|---|---|---|---|---|
| 916.7743 | 1204 | 5.952 | 0.113 | 5.571 | 0.107 | 1.068 | 0.0178 |
| 856.672 | 1202 | 2.753 | 0.058 | 2.553 | 0.057 | 1.078 | 0.0179 |
| 827.5701 | 1202 | 6.362 | 0.095 | 6.684 | 0.092 | 0.952 | 0.0187 |
| 942.7879 | 1204 | 3.531 | 0.102 | 3.195 | 0.092 | 1.105 | 0.019 |
| 523.4679 | 1203 | 3.471 | 0.153 | 4.011 | 0.165 | 0.865 | 0.0194 |
| 915.7681 | 1204 | 6.365 | 0.115 | 5.972 | 0.116 | 1.066 | 0.0194 |
| 517.314 | 1101 | 5.547 | 0.055 | 5.755 | 0.069 | 0.964 | 0.0195 |
| 777.553 | 1202 | 2.002 | 0.098 | 2.384 | 0.130 | 0.840 | 0.0204 |
| 744.4956 | 1204 | 3.916 | 0.061 | 4.117 | 0.058 | 0.951 | 0.0206 |
| 440.3532 | 1204 | 1.502 | 0.136 | 0.975 | 0.180 | 1.539 | 0.021 |
| 782.5653 | 1201 | 6.382 | 0.065 | 6.614 | 0.076 | 0.965 | 0.0222 |
| 494.4343 | 1203 | 2.145 | 0.226 | 2.900 | 0.232 | 0.740 | 0.0232 |
| 303.1079 | 1202 | 5.646 | 0.048 | 5.802 | 0.047 | 0.973 | 0.0233 |
| 771.5814 | 1204 | 4.208 | 0.050 | 4.367 | 0.046 | 0.964 | 0.0236 |
| 521.4522 | 1203 | 2.482 | 0.173 | 3.028 | 0.158 | 0.820 | 0.0242 |
| 793.5681 | 1204 | 3.191 | 0.055 | 3.372 | 0.055 | 0.946 | 0.0244 |
| 832.6026 | 1102 | 3.662 | 0.042 | 3.795 | 0.040 | 0.965 | 0.0252 |
| 589.3403 | 1202 | 5.900 | 0.084 | 6.171 | 0.085 | 0.956 | 0.026 |
| 732.4938 | 1204 | 4.319 | 0.061 | 4.511 | 0.057 | 0.957 | 0.0263 |
| 783.5672 | 1101 | 3.993 | 0.085 | 4.259 | 0.079 | 0.938 | 0.0265 |
| 569.369 | 1202 | 4.947 | 0.042 | 5.089 | 0.047 | 0.972 | 0.0273 |
| 522.4635 | 1203 | 4.938 | 0.167 | 5.485 | 0.176 | 0.900 | 0.0277 |
| 795.5181 | 1101 | 2.823 | 0.073 | 3.044 | 0.064 | 0.927 | 0.0287 |
| 888.7394 | 1204 | 5.759 | 0.115 | 5.400 | 0.110 | 1.066 | 0.0287 |
| 490.3641 | 1203 | 1.864 | 0.138 | 1.397 | 0.159 | 1.334 | 0.029 |
| 914.7583 | 1204 | 5.125 | 0.112 | 4.763 | 0.118 | 1.076 | 0.0294 |
| 520.4499 | 1203 | 4.141 | 0.131 | 4.577 | 0.148 | 0.905 | 0.03 |
| 805.5832 | 1102 | 4.292 | 0.055 | 4.485 | 0.068 | 0.957 | 0.0301 |
| 795.5838 | 1204 | 3.558 | 0.070 | 3.769 | 0.063 | 0.944 | 0.0305 |
| 575.2728 | 1101 | 2.532 | 0.060 | 2.739 | 0.074 | 0.925 | 0.0324 |
| 831.5997 | 1102 | 4.774 | 0.042 | 4.903 | 0.040 | 0.974 | 0.0325 |
| 518.3174 | 1101 | 3.523 | 0.054 | 3.717 | 0.073 | 0.948 | 0.0338 |
| 520.3354 | 1101 | 2.271 | 0.117 | 2.646 | 0.130 | 0.858 | 0.0354 |
| 573.4852 | 1203 | 4.919 | 0.063 | 4.740 | 0.053 | 1.038 | 0.0354 |
| 579.5325 | 1203 | 4.235 | 0.135 | 4.636 | 0.127 | 0.913 | 0.0355 |
| 570.3725 | 1202 | 3.021 | 0.043 | 3.155 | 0.045 | 0.958 | 0.0359 |
| 793.5386 | 1102 | 3.799 | 0.057 | 3.950 | 0.039 | 0.962 | 0.0359 |
| 481.3172 | 1202 | 3.980 | 0.058 | 4.159 | 0.060 | 0.957 | 0.0361 |
| 831.5759 | 1101 | 4.485 | 0.066 | 4.677 | 0.060 | 0.959 | 0.0365 |
| 913.7513 | 1204 | 5.358 | 0.113 | 5.006 | 0.120 | 1.070 | 0.037 |
| 772.5862 | 1204 | 3.306 | 0.045 | 3.437 | 0.042 | 0.962 | 0.0378 |
| 304.241 | 1204 | 4.898 | 0.062 | 5.088 | 0.066 | 0.963 | 0.0397 |
| 746.557 | 1202 | 2.177 | 0.042 | 2.057 | 0.037 | 1.058 | 0.0399 |
| 519.3321 | 1101 | 4.014 | 0.116 | 4.382 | 0.133 | 0.916 | 0.0405 |
| 833.7551 | 1204 | 2.611 | 0.191 | 3.140 | 0.161 | 0.831 | 0.0406 |
| 889.7492 | 1204 | 7.711 | 0.122 | 7.365 | 0.110 | 1.047 | 0.0415 |
| 614.4914 | 1203 | 2.747 | 0.091 | 2.448 | 0.114 | 1.122 | 0.0418 |
| 618.4829 | 1201 | 1.844 | 0.179 | 1.310 | 0.185 | 1.407 | 0.0429 |
| 601.5164 | 1203 | 7.639 | 0.052 | 7.463 | 0.069 | 1.024 | 0.0431 |
| 671.5723 | 1204 | 2.349 | 0.088 | 2.604 | 0.087 | 0.902 | 0.0435 |
| 794.5421 | 1102 | 2.703 | 0.059 | 2.853 | 0.040 | 0.948 | 0.0438 |
| 731.4916 | 1204 | 5.555 | 0.068 | 5.746 | 0.063 | 0.967 | 0.0444 |
| 512.4082 | 1204 | 2.523 | 0.180 | 1.954 | 0.215 | 1.292 | 0.0451 |
| 768.5503 | 1202 | 2.028 | 0.082 | 2.277 | 0.090 | 0.891 | 0.0453 |
| 665.501 | 1204 | 3.429 | 0.105 | 3.074 | 0.142 | 1.116 | 0.0454 |
| 890.7535 | 1204 | 7.055 | 0.116 | 6.731 | 0.106 | 1.048 | 0.0454 |
| 759.5163 | 1204 | 4.804 | 0.055 | 4.954 | 0.048 | 0.970 | 0.0455 |
| 605.5457 | 1203 | 5.235 | 0.100 | 5.509 | 0.089 | 0.950 | 0.0473 |
| 541.4425 | 1204 | 2.234 | 0.148 | 1.745 | 0.198 | 1.280 | 0.0488 |
| 572.4816 | 1203 | 6.271 | 0.061 | 6.108 | 0.052 | 1.027 | 0.049 |
| 743.5466 | 1203 | 1.977 | 0.103 | 2.266 | 0.099 | 0.873 | 0.0492 |

TABLE 7

Accurate mass features differing between dementia patients with
a significant cognitive impairment (ADAS ≧ 16) and dementia
patients with a mild cognitive impairment (ADAS ≦ 15)
($p < 0.05$, log2 transformed).

| Detected Mass | Analysis Mode | AVG (log2) ADAS high | SEM ADAS HIGH | Avg (log2) ADAS LOW | SEM ADAS LOW | log(2) Ratio | P Value |
|---|---|---|---|---|---|---|---|
| 541.3432 | 1102 | 3.155 | 0.038 | 3.581 | 0.054 | 0.881 | 6.71E-09 |
| 567.3547 | 1102 | 2.633 | 0.052 | 3.122 | 0.058 | 0.843 | 3.84E-08 |
| 569.3687 | 1102 | 2.079 | 0.053 | 2.526 | 0.054 | 0.823 | 2.41E-07 |
| 829.5856 | 1102 | 3.861 | 0.057 | 4.303 | 0.059 | 0.897 | 1.71E-06 |
| 565.3394 | 1102 | 3.268 | 0.064 | 3.784 | 0.081 | 0.864 | 3.73E-06 |
| 837.5027 | 1101 | 3.373 | 0.056 | 3.818 | 0.070 | 0.884 | 4.53E-06 |
| 804.5713 | 1102 | 4.022 | 0.051 | 4.414 | 0.060 | 0.911 | 5.01E-06 |
| 831.5997 | 1102 | 4.379 | 0.055 | 4.761 | 0.046 | 0.920 | 5.17E-06 |
| 832.6026 | 1102 | 3.278 | 0.055 | 3.658 | 0.046 | 0.896 | 5.66E-06 |
| 803.568 | 1102 | 5.252 | 0.052 | 5.640 | 0.065 | 0.931 | 1.42E-05 |
| 805.5832 | 1102 | 3.894 | 0.056 | 4.293 | 0.063 | 0.907 | 1.48E-05 |
| 871.5528 | 1102 | 2.886 | 0.051 | 3.244 | 0.059 | 0.890 | 2.25E-05 |
| 555.3102 | 1102 | 1.669 | 0.053 | 2.070 | 0.074 | 0.806 | 2.34E-05 |
| 853.5854 | 1102 | 2.473 | 0.058 | 2.824 | 0.040 | 0.876 | 2.85E-05 |
| 886.5582 | 1102 | 2.898 | 0.036 | 3.166 | 0.051 | 0.916 | 4.34E-05 |
| 808.5792 | 1101 | 4.475 | 0.071 | 4.922 | 0.068 | 0.909 | 4.77E-05 |
| 780.5474 | 1101 | 5.229 | 0.067 | 5.665 | 0.086 | 0.923 | 0.0001 |
| 805.5605 | 1101 | 5.210 | 0.072 | 5.655 | 0.078 | 0.921 | 0.0001 |
| 807.5758 | 1101 | 5.522 | 0.071 | 5.962 | 0.069 | 0.926 | 0.0001 |
| 543.3296 | 1101 | 3.594 | 0.055 | 3.948 | 0.075 | 0.910 | 0.0002 |
| 779.5444 | 1101 | 6.228 | 0.067 | 6.660 | 0.086 | 0.935 | 0.0002 |
| 806.5639 | 1101 | 4.213 | 0.074 | 4.656 | 0.079 | 0.905 | 0.0002 |
| 829.5604 | 1101 | 3.368 | 0.070 | 3.766 | 0.069 | 0.894 | 0.0002 |
| 755.5468 | 1101 | 2.034 | 0.091 | 2.551 | 0.098 | 0.797 | 0.0003 |
| 819.5551 | 1102 | 2.270 | 0.062 | 2.611 | 0.062 | 0.869 | 0.0003 |
| 915.5191 | 1101 | 2.209 | 0.066 | 2.603 | 0.082 | 0.849 | 0.0004 |
| 794.5421 | 1102 | 2.389 | 0.054 | 2.705 | 0.073 | 0.883 | 0.0007 |
| 832.5791 | 1101 | 3.221 | 0.066 | 3.564 | 0.066 | 0.904 | 0.0007 |
| 793.5386 | 1102 | 3.462 | 0.057 | 3.778 | 0.069 | 0.916 | 0.0008 |
| 803.5445 | 1101 | 4.995 | 0.065 | 5.351 | 0.078 | 0.933 | 0.0008 |
| 804.5476 | 1101 | 4.045 | 0.064 | 4.402 | 0.080 | 0.919 | 0.0008 |
| 731.5464 | 1101 | 1.574 | 0.132 | 2.200 | 0.109 | 0.716 | 0.0011 |
| 827.57 | 1102 | 4.055 | 0.057 | 4.341 | 0.062 | 0.934 | 0.0014 |
| 722.5335 | 1101 | 2.379 | 0.064 | 2.687 | 0.064 | 0.885 | 0.0015 |
| 831.5759 | 1101 | 4.163 | 0.072 | 4.510 | 0.070 | 0.923 | 0.0015 |
| 517.314 | 1101 | 5.343 | 0.057 | 5.631 | 0.068 | 0.949 | 0.0019 |
| 757.4991 | 1101 | 3.393 | 0.086 | 3.828 | 0.102 | 0.886 | 0.0019 |
| 783.5672 | 1101 | 3.547 | 0.087 | 3.974 | 0.097 | 0.893 | 0.002 |
| 545.3453 | 1101 | 3.457 | 0.072 | 3.795 | 0.073 | 0.911 | 0.0022 |
| 518.3174 | 1101 | 3.321 | 0.056 | 3.600 | 0.068 | 0.922 | 0.0023 |
| 760.5811 | 1101 | 4.181 | 0.092 | 4.609 | 0.101 | 0.907 | 0.003 |
| 784.5811 | 1101 | 4.155 | 0.104 | 4.630 | 0.111 | 0.897 | 0.0033 |
| 546.3485 | 1101 | 1.883 | 0.067 | 2.196 | 0.078 | 0.857 | 0.0034 |
| 759.5779 | 1101 | 5.313 | 0.091 | 5.727 | 0.098 | 0.928 | 0.0034 |
| 855.6016 | 1102 | 3.447 | 0.060 | 3.709 | 0.056 | 0.929 | 0.0034 |
| 847.5316 | 1101 | 2.627 | 0.075 | 3.004 | 0.106 | 0.874 | 0.0037 |
| 781.5617 | 1101 | 5.942 | 0.079 | 6.291 | 0.082 | 0.945 | 0.0039 |
| 575.2728 | 1101 | 2.359 | 0.070 | 2.663 | 0.069 | 0.886 | 0.0042 |
| 828.5737 | 1102 | 3.070 | 0.054 | 3.317 | 0.064 | 0.926 | 0.0047 |
| 795.555 | 1102 | 2.558 | 0.065 | 2.831 | 0.063 | 0.904 | 0.0053 |
| 821.5712 | 1102 | 2.952 | 0.058 | 3.195 | 0.057 | 0.924 | 0.0053 |
| 833.5932 | 1101 | 3.069 | 0.092 | 3.444 | 0.083 | 0.891 | 0.0053 |
| 782.565 | 1101 | 4.918 | 0.082 | 5.266 | 0.085 | 0.934 | 0.0056 |
| 795.5181 | 1101 | 2.462 | 0.075 | 2.793 | 0.090 | 0.882 | 0.0066 |
| 725.5527 | 1101 | 3.222 | 0.073 | 3.500 | 0.057 | 0.921 | 0.0068 |
| 761.5843 | 1101 | 2.194 | 0.095 | 2.580 | 0.098 | 0.850 | 0.0078 |
| 738.5448 | 1102 | 2.493 | 0.076 | 2.766 | 0.047 | 0.901 | 0.0083 |
| 811.6096 | 1101 | 2.869 | 0.106 | 3.277 | 0.096 | 0.876 | 0.0088 |
| 758.5656 | 1101 | 5.459 | 0.101 | 5.870 | 0.112 | 0.930 | 0.0092 |
| 785.5933 | 1101 | 5.643 | 0.108 | 6.049 | 0.097 | 0.933 | 0.0103 |
| 458.2405 | 1101 | 1.635 | 0.057 | 1.880 | 0.075 | 0.870 | 0.0104 |
| 757.5626 | 1101 | 6.418 | 0.100 | 6.815 | 0.112 | 0.942 | 0.0112 |
| 541.3139 | 1101 | 3.968 | 0.074 | 4.278 | 0.096 | 0.928 | 0.0116 |
| 786.5967 | 1101 | 4.570 | 0.109 | 4.973 | 0.099 | 0.919 | 0.012 |
| 748.5721 | 1102 | 3.811 | 0.069 | 4.050 | 0.055 | 0.941 | 0.0137 |
| 749.5761 | 1102 | 2.699 | 0.066 | 2.929 | 0.053 | 0.922 | 0.0156 |
| 501.3212 | 1201 | 1.903 | 0.052 | 2.108 | 0.066 | 0.903 | 0.0176 |
| 809.5936 | 1101 | 4.792 | 0.099 | 5.124 | 0.084 | 0.935 | 0.0194 |
| 810.5969 | 1101 | 3.785 | 0.102 | 4.126 | 0.086 | 0.917 | 0.0199 |
| 542.3173 | 1101 | 2.183 | 0.077 | 2.464 | 0.091 | 0.886 | 0.0228 |
| 724.5493 | 1101 | 4.493 | 0.076 | 4.734 | 0.059 | 0.949 | 0.0232 |
| 723.5197 | 1204 | 3.966 | 0.083 | 3.699 | 0.091 | 1.072 | 0.0362 |

TABLE 7-continued

Accurate mass features differing between dementia patients with a significant cognitive impairment (ADAS ≧ 16) and dementia patients with a mild cognitive impairment (ADAS ≦ 15) (p < 0.05, log2 transformed).

| Detected Mass | Analysis Mode | AVG (log2) ADAS high | SEM ADAS HIGH | Avg (log2) ADAS LOW | SEM ADAS LOW | log(2) Ratio | P Value |
|---|---|---|---|---|---|---|---|
| 521.3477 | 1101 | 3.545 | 0.086 | 3.863 | 0.130 | 0.918 | 0.0374 |
| 1098.974 | 1204 | 3.016 | 0.105 | 2.552 | 0.219 | 1.182 | 0.039 |
| 523.3634 | 1101 | 3.263 | 0.100 | 3.596 | 0.130 | 0.907 | 0.0433 |
| 807.5768 | 1201 | 6.721 | 0.033 | 6.816 | 0.031 | 0.986 | 0.0452 |
| 826.7069 | 1204 | 2.385 | 0.134 | 2.766 | 0.113 | 0.862 | 0.0462 |
| 931.7695 | 1203 | 2.852 | 0.090 | 2.495 | 0.169 | 1.143 | 0.0475 |
| 183.0661 | 1101 | 2.358 | 0.139 | 2.748 | 0.116 | 0.858 | 0.0485 |
| 504.3814 | 1203 | 1.818 | 0.065 | 1.573 | 0.113 | 1.156 | 0.0489 |

TABLE 8

Accurate mass features differing between patients with mild cognitive impairment (MMSE 18-23), severe cognitive impairment (MMSE ≦ 17) and normal cognitive ability (MMSE ≧ 28) as measured on the MMSE.

| Detected Mass | Analysis Mode | AVG (log2) mild MMSE | SEM (log2) mild MMSE | AVG (log2) severe MMSE | SEM (log2) severe MMSE | AVG (log2) Normal | SEM (log2) Normal | log (2) Ratio mild/ normal | log (2) Ratio severe/ normal | log (2) Ratio mild/ severe | P Value |
|---|---|---|---|---|---|---|---|---|---|---|---|
| 726.5461 | 1204 | 3.125 | 0.058 | 2.729 | 0.053 | 2.981 | 0.067 | 1.048 | 0.916 | 1.145 | 0.0002 |
| 675.6377 | 1204 | 4.131 | 0.049 | 3.856 | 0.082 | 4.124 | 0.061 | 1.002 | 0.935 | 1.071 | 0.0102 |
| 801.555* | 1202 | 2.733 | 0.144 | 2.602 | 0.110 | 3.052 | 0.077 | 0.895 | 0.853 | 1.050 | 0.0108 |
| 570.3725 | 1202 | 3.071 | 0.067 | 2.895 | 0.054 | 3.130 | 0.054 | 0.981 | 0.925 | 1.061 | 0.0116 |
| 597.484 | 1203 | 2.915 | 0.146 | 2.582 | 0.101 | 3.046 | 0.110 | 0.957 | 0.848 | 1.129 | 0.0138 |
| 246.1472 | 1204 | 2.437 | 0.187 | 3.031 | 0.161 | 2.974 | 0.067 | 0.819 | 1.019 | 0.804 | 0.0161 |
| 565.3394* | 1202 | 7.087 | 0.132 | 6.908 | 0.090 | 7.304 | 0.087 | 0.970 | 0.946 | 1.026 | 0.0171 |
| 596.4791 | 1203 | 4.125 | 0.172 | 3.792 | 0.112 | 4.283 | 0.111 | 0.963 | 0.886 | 1.088 | 0.0188 |
| 246.1465 | 1202 | 3.577 | 0.208 | 4.046 | 0.123 | 4.169 | 0.104 | 0.858 | 0.970 | 0.884 | 0.0199 |
| 432.3254 | 1204 | 2.540 | 0.059 | 2.325 | 0.058 | 2.495 | 0.047 | 1.018 | 0.932 | 1.092 | 0.0201 |
| 569.369* | 1202 | 5.009 | 0.056 | 4.834 | 0.050 | 5.032 | 0.063 | 0.995 | 0.961 | 1.036 | 0.0285 |
| 661.6233 | 1204 | 2.783 | 0.091 | 2.448 | 0.090 | 2.683 | 0.079 | 1.037 | 0.912 | 1.137 | 0.0307 |
| 857.6186* | 1202 | 3.923 | 0.122 | 3.699 | 0.104 | 4.090 | 0.101 | 0.959 | 0.904 | 1.061 | 0.0332 |
| 804.5718 | 1202 | 5.940 | 0.135 | 5.776 | 0.088 | 6.170 | 0.112 | 0.963 | 0.936 | 1.028 | 0.0334 |
| 803.5677 | 1202 | 7.274 | 0.174 | 7.084 | 0.116 | 7.570 | 0.131 | 0.961 | 0.936 | 1.027 | 0.0359 |
| 542.3461 | 1202 | 3.898 | 0.134 | 3.773 | 0.071 | 4.124 | 0.104 | 0.945 | 0.915 | 1.033 | 0.037 |
| 810.5399 | 1204 | 3.152 | 0.104 | 2.749 | 0.088 | 2.959 | 0.113 | 1.065 | 0.929 | 1.146 | 0.0374 |
| 728.5627 | 1204 | 3.233 | 0.078 | 2.954 | 0.065 | 3.054 | 0.071 | 1.059 | 0.967 | 1.094 | 0.0404 |
| 566.3434 | 1202 | 5.338 | 0.100 | 5.142 | 0.093 | 5.460 | 0.082 | 0.978 | 0.942 | 1.038 | 0.0417 |
| 481.3172 | 1202 | 3.940 | 0.088 | 3.875 | 0.069 | 4.136 | 0.077 | 0.953 | 0.937 | 1.017 | 0.0436 |
| 724.5257 | 1204 | 3.168 | 0.102 | 2.875 | 0.079 | 2.961 | 0.055 | 1.070 | 0.971 | 1.102 | 0.0447 |
| 825.5544 | 1202 | 2.933 | 0.173 | 2.605 | 0.144 | 3.160 | 0.171 | 0.928 | 0.824 | 1.126 | 0.0474 |
| 826.5581 | 1202 | 2.005 | 0.151 | 1.579 | 0.156 | 2.139 | 0.188 | 0.937 | 0.738 | 1.270 | 0.0488 |

TABLE 9

Grouping of patients into one of 8 groups based on the presence of AD pathology, ADAS score and MMSE score. A score of 1 was given for the presence of AD pathology, high ADAS score (≧16), or low MMSE score (≦23); a score of 0 was given in the absence of AD pathology, low ADAS score (≦15), or high MMSE score (≧28).

| Patient ID | AD Pathology | ADAS | MMSE |
|---|---|---|---|
| 7001 | 1 | 1 | 1 |
| 7002 | 0 | 1 | 1 |
| 7006 | 1 | 0 | 1 |
| 7007 | 1 | 1 | 1 |
| 7008 | 1 | 0 | 1 |
| 7009 | 1 | 0 | 1 |
| 7010 | 1 | 0 | 1 |
| 7011 | 1 | 0 | 1 |
| 7014 | 1 | 0 | 1 |
| 7015 | 0 | 1 | 1 |
| 7016 | 1 | 1 | 1 |
| 7017 | 1 | 1 | 1 |
| 7022 | 1 | 1 | 1 |
| 7023 | 1 | 1 | 1 |
| 7024 | 1 | 0 | 1 |
| 7025 | 1 | 0 | 1 |
| 7027 | 1 | 0 | 1 |
| 7028 | 1 | 1 | 1 |
| 7029 | 1 | 1 | 1 |
| 7030 | 1 | 0 | 1 |

TABLE 9-continued

Grouping of patients into one of 8 groups based on the presence of AD pathology, ADAS score and MMSE score. A score of 1 was given for the presence of AD pathology, high ADAS score ($\geq 16$), or low MMSE score ($\leq 23$); a score of 0 was given in the absence of AD pathology, low ADAS score ($\leq 15$), or high MMSE score ($\geq 28$).

| Patient ID | AD Pathology | ADAS | MMSE |
|---|---|---|---|
| 7031 | 1 | 0 | 1 |
| 7033 | 0 | 1 | 1 |
| 7034 | 1 | 0 | 1 |
| 7035 | 0 | 1 | 1 |
| 7037 | 1 | 1 | 1 |
| 7039 | 1 | 0 | 1 |
| 7042 | 1 | 0 | 1 |
| 7043 | 0 | 1 | 1 |
| 7044 | 1 | 1 | 1 |
| 7045 | 1 | 0 | 1 |
| 7046 | 1 | 1 | 1 |
| 7047 | 0 | 1 | 1 |
| 7048 | 1 | 0 | 1 |
| 7049 | 1 | 0 | 1 |
| 7050 | 0 | 1 | 1 |
| 7051 | 1 | 0 | 1 |
| 7052 | 1 | 0 | 1 |
| 7053 | 1 | 0 | 1 |
| 7055 | 0 | 1 | 1 |
| 7056 | 1 | 1 | 1 |
| 7057 | 1 | 0 | 1 |
| 7058 | 1 | 0 | 1 |
| 7059 | 0 | 1 | 1 |
| 7062 | 0 | 0 | 0 |
| 7063 | 1 | 1 | 1 |
| 7064 | 0 | 0 | 0 |
| 7066 | 0 | 0 | 1 |
| 7067 | 1 | 1 | 1 |
| 7070 | 0 | 0 | 0 |
| 7074 | 0 | 1 | 1 |
| 7075 | 1 | 1 | 1 |
| 7076 | 0 | 1 | 1 |
| 7077 | 1 | 1 | 1 |
| 7078 | 1 | 0 | 1 |
| 7079 | 0 | 1 | 1 |
| 7080 | 0 | 1 | 1 |
| 7081 | 1 | 1 | 1 |
| 7082 | 1 | 1 | 1 |
| 7084 | 1 | 1 | 1 |
| 7085 | 1 | 0 | 1 |
| 7086 | 0 | 1 | 1 |
| 7087 | 0 | 1 | 1 |
| 7088 | 1 | 1 | 1 |
| 7089 | 1 | 1 | 1 |
| 7090 | 1 | 1 | 1 |
| 7091 | 0 | 1 | 1 |
| 7093 | 1 | 0 | 1 |
| 7094 | 0 | 1 | 1 |
| 7095 | 0 | 1 | 1 |
| 7096 | 1 | 0 | 1 |
| 7097 | 1 | 0 | 1 |
| 7098 | 0 | 0 | 0 |
| 7101 | 0 | 0 | 0 |
| 7102 | 1 | 0 | 0 |
| 7103 | 0 | 1 | 0 |
| 7104 | 0 | 1 | 0 |
| 7105 | 0 | 1 | 0 |
| 7106 | 1 | 1 | 0 |
| 7108 | 0 | 0 | 0 |
| 7109 | 0 | 0 | 0 |
| 7110 | 0 | 1 | 0 |
| 7111 | 0 | 0 | 0 |
| 7112 | 1 | 1 | 0 |
| 7113 | 1 | 1 | 0 |
| 7114 | 1 | 0 | 0 |
| 7115 | 0 | 1 | 0 |
| 7116 | 1 | 1 | 0 |
| 7117 | 0 | 1 | 0 |
| 7118 | 0 | 0 | 0 |
| 7119 | 0 | 0 | 0 |
| 7120 | 0 | 0 | 0 |
| 7124 | 1 | 1 | 0 |
| 7125 | 1 | 1 | 0 |
| 7126 | 0 | 0 | 0 |
| 7127 | 0 | 0 | 0 |
| 7128 | 0 | 1 | 0 |
| 7129 | 1 | 0 | 0 |
| 7130 | 0 | 0 | 0 |
| 7131 | 0 | 0 | 0 |
| 7133 | 0 | 1 | 0 |
| 7134 | 0 | 1 | 0 |
| 7135 | 0 | 0 | 0 |
| 7136 | 1 | 0 | 0 |
| 7137 | 0 | 0 | 0 |
| 7138 | 0 | 0 | 0 |
| 7139 | 0 | 1 | 0 |
| 7140 | 1 | 0 | 0 |
| 7141 | 1 | 1 | 0 |
| 7142 | 1 | 1 | 0 |
| 7143 | 1 | 0 | 0 |
| 7144 | 1 | 0 | 0 |
| 7145 | 0 | 1 | 0 |
| 7146 | 0 | 1 | 0 |
| 7147 | 0 | 1 | 0 |
| 7150 | 1 | 0 | 0 |
| 7151 | 1 | 0 | 0 |
| 7152 | 0 | 1 | 0 |
| 7153 | 0 | 0 | 0 |
| 7154 | 1 | 1 | 0 |
| 7155 | 1 | 1 | 0 |
| 7156 | 0 | 0 | 0 |
| 7157 | 1 | 0 | 0 |
| 7158 | 1 | 0 | 0 |
| 7309 | 1 | 0 | 1 |
| 7310 | 1 | 0 | 0 |
| 7315 | 1 | 0 | 1 |
| 7802 | 0 | 0 | 0 |
| 7811 | 0 | 0 | 0 |
| 7814 | 1 | 0 | 0 |
| 7817 | 1 | 0 | 0 |
| 7818 | 0 | 0 | 0 |
| 7819 | 0 | 1 | 0 |
| 7823 | 1 | 0 | 0 |
| 7831 | 0 | 0 | 0 |
| 7832 | 1 | 0 | 0 |
| 7833 | 1 | 0 | 0 |

TABLE 10

Accurate mass features differing between patients showing the best discrimination between AD and non-AD pathology ($p < 0.05$, log2 transformed).

| Detected Mass | Analysis Mode | AVG (log2) AD | SEM AD | AVG (log2) non-AD | SEM AD | log(2) Ratio | P Value |
|---|---|---|---|---|---|---|---|
| 699.5199 | 1204 | 1.985 | 0.043 | 2.956 | 0.067 | 0.672 | 1.24E−14 |
| 723.5195 | 1204 | 3.281 | 0.070 | 4.702 | 0.101 | 0.698 | 4.86E−14 |
| 723.5194 | 1202 | 2.039 | 0.077 | 3.191 | 0.069 | 0.639 | 1.59E−13 |
| 751.5553 | 1204 | 4.290 | 0.074 | 5.450 | 0.093 | 0.787 | 5.86E−12 |
| 724.5258 | 1204 | 2.667 | 0.062 | 3.750 | 0.092 | 0.711 | 6.50E−12 |
| 751.5529 | 1202 | 3.197 | 0.068 | 4.076 | 0.062 | 0.784 | 1.03E−11 |
| 752.5564 | 1202 | 2.126 | 0.069 | 3.010 | 0.061 | 0.706 | 1.16E−11 |
| 749.5367 | 1202 | 3.061 | 0.062 | 3.861 | 0.056 | 0.793 | 1.22E−11 |
| 752.5581 | 1204 | 3.170 | 0.072 | 4.292 | 0.094 | 0.739 | 1.52E−11 |
| 749.5406 | 1204 | 4.177 | 0.067 | 5.235 | 0.095 | 0.798 | 4.77E−11 |

TABLE 10-continued

Accurate mass features differing between patients showing the best discrimination between AD and non-AD pathology (p < 0.05, log2 transformed).

| Detected Mass | Analysis Mode | AVG (log2) AD | SEM AD | AVG (log2) non-AD | SEM AD | log(2) Ratio | P Value |
|---|---|---|---|---|---|---|---|
| 750.5403 | 1202 | 2.081 | 0.074 | 2.886 | 0.051 | 0.721 | 6.77E−11 |
| 750.5438 | 1204 | 3.060 | 0.068 | 4.067 | 0.091 | 0.752 | 7.99E−11 |
| 727.5567 | 1204 | 3.305 | 0.074 | 4.064 | 0.053 | 0.813 | 4.71E−10 |
| 725.5385 | 1204 | 2.654 | 0.094 | 3.590 | 0.079 | 0.739 | 3.99E−09 |
| 728.5629 | 1204 | 2.813 | 0.063 | 3.345 | 0.057 | 0.841 | 2.54E−07 |
| 726.5462 | 1204 | 2.753 | 0.064 | 3.215 | 0.062 | 0.856 | 7.09E−06 |
| 768.5538 | 1204 | 3.755 | 0.060 | 4.250 | 0.084 | 0.884 | 2.34E−05 |
| 747.5244 | 1204 | 3.263 | 0.092 | 3.999 | 0.123 | 0.816 | 2.45E−05 |
| 744.5535 | 1204 | 4.147 | 0.050 | 4.492 | 0.053 | 0.923 | 3.13E−05 |
| 813.5885 | 1202 | 2.969 | 0.051 | 3.362 | 0.067 | 0.883 | 3.58E−05 |
| 743.547 | 1204 | 5.096 | 0.053 | 5.455 | 0.059 | 0.934 | 0.0001 |
| 767.5494 | 1204 | 4.835 | 0.065 | 5.337 | 0.092 | 0.906 | 0.0001 |
| 775.5527 | 1204 | 2.993 | 0.100 | 3.645 | 0.105 | 0.821 | 0.0001 |
| 775.5533 | 1202 | 1.993 | 0.078 | 2.525 | 0.088 | 0.789 | 0.0001 |
| 811.5732 | 1202 | 2.590 | 0.072 | 3.025 | 0.071 | 0.856 | 0.0001 |
| 812.5761 | 1202 | 1.599 | 0.064 | 2.057 | 0.084 | 0.777 | 0.0001 |
| 817.5376 | 1102 | 1.992 | 0.073 | 2.490 | 0.081 | 0.800 | 0.0001 |
| 747.5201 | 1202 | 1.829 | 0.090 | 2.412 | 0.110 | 0.758 | 0.0002 |
| 795.5837 | 1204 | 3.418 | 0.073 | 3.810 | 0.062 | 0.897 | 0.0002 |
| 796.5874 | 1204 | 2.468 | 0.051 | 2.839 | 0.074 | 0.869 | 0.0002 |
| 748.5286 | 1204 | 1.812 | 0.247 | 2.917 | 0.126 | 0.621 | 0.0003 |
| 810.54 | 1204 | 2.627 | 0.088 | 3.116 | 0.083 | 0.843 | 0.0003 |
| 782.5084 | 1204 | 3.308 | 0.060 | 3.687 | 0.078 | 0.897 | 0.0004 |
| 755.486 | 1204 | 3.069 | 0.080 | 3.477 | 0.073 | 0.883 | 0.0005 |
| 758.5092 | 1204 | 4.418 | 0.065 | 4.707 | 0.043 | 0.939 | 0.0007 |
| 771.5813 | 1204 | 3.965 | 0.074 | 4.288 | 0.046 | 0.925 | 0.0007 |
| 304.241 | 1204 | 4.716 | 0.057 | 5.013 | 0.062 | 0.941 | 0.0011 |
| 814.5919 | 1202 | 1.988 | 0.046 | 2.307 | 0.077 | 0.862 | 0.0011 |
| 786.5415 | 1204 | 3.671 | 0.074 | 3.979 | 0.050 | 0.923 | 0.0013 |
| 787.5728 | 1202 | 1.743 | 0.085 | 2.136 | 0.075 | 0.816 | 0.0013 |
| 793.5386 | 1102 | 3.337 | 0.086 | 3.690 | 0.057 | 0.904 | 0.0015 |
| 783.5147 | 1204 | 3.166 | 0.071 | 3.512 | 0.077 | 0.901 | 0.0022 |
| 828.5736 | 1102 | 2.906 | 0.080 | 3.292 | 0.087 | 0.883 | 0.0023 |
| 828.5743 | 1202 | 5.132 | 0.073 | 5.485 | 0.081 | 0.936 | 0.0024 |
| 743.5468 | 1203 | 1.812 | 0.118 | 2.235 | 0.061 | 0.811 | 0.0029 |
| 784.5235 | 1204 | 3.196 | 0.081 | 3.490 | 0.045 | 0.916 | 0.003 |
| 760.5215 | 1204 | 3.910 | 0.072 | 4.200 | 0.058 | 0.931 | 0.0032 |
| 787.5464 | 1204 | 2.617 | 0.090 | 2.937 | 0.050 | 0.891 | 0.0037 |
| 827.57 | 1102 | 3.933 | 0.078 | 4.313 | 0.096 | 0.912 | 0.0039 |
| 305.2438 | 1204 | 2.384 | 0.064 | 2.648 | 0.058 | 0.900 | 0.0041 |
| 794.5421 | 1102 | 2.275 | 0.090 | 2.601 | 0.058 | 0.875 | 0.0041 |
| 827.5701 | 1202 | 6.193 | 0.081 | 6.559 | 0.090 | 0.944 | 0.0046 |
| 590.343 | 1202 | 3.939 | 0.055 | 4.216 | 0.074 | 0.934 | 0.0047 |
| 589.3404 | 1202 | 5.769 | 0.061 | 6.076 | 0.085 | 0.950 | 0.0057 |
| 789.5893 | 1202 | 1.673 | 0.064 | 1.967 | 0.077 | 0.851 | 0.0057 |
| 670.5689 | 1204 | 3.048 | 0.095 | 3.510 | 0.127 | 0.868 | 0.006 |
| 855.6016 | 1102 | 3.325 | 0.079 | 3.646 | 0.079 | 0.912 | 0.0064 |
| 759.5162 | 1204 | 4.510 | 0.086 | 4.811 | 0.060 | 0.937 | 0.0065 |
| 671.5722 | 1204 | 2.157 | 0.123 | 2.635 | 0.111 | 0.819 | 0.0066 |
| 769.5654 | 1204 | 3.829 | 0.065 | 4.086 | 0.063 | 0.937 | 0.0069 |
| 856.6063 | 1202 | 4.446 | 0.076 | 4.777 | 0.087 | 0.931 | 0.007 |
| 409.0208 | 1202 | 2.638 | 0.057 | 2.899 | 0.073 | 0.910 | 0.0072 |
| 774.0313 | 1204 | 2.317 | 0.202 | 1.370 | 0.268 | 1.691 | 0.0076 |
| 804.5713 | 1102 | 3.964 | 0.086 | 4.276 | 0.071 | 0.927 | 0.008 |
| 855.6025 | 1202 | 5.437 | 0.074 | 5.749 | 0.085 | 0.946 | 0.0083 |
| 530.382 | 1204 | 2.991 | 0.089 | 2.097 | 0.309 | 1.426 | 0.0085 |
| 626.5278 | 1203 | 3.676 | 0.068 | 3.915 | 0.053 | 0.939 | 0.0087 |
| 731.4914 | 1204 | 5.281 | 0.086 | 5.589 | 0.073 | 0.945 | 0.0093 |
| 732.4937 | 1204 | 4.050 | 0.083 | 4.348 | 0.070 | 0.931 | 0.0093 |
| 517.3722 | 1204 | 2.189 | 0.112 | 1.465 | 0.241 | 1.494 | 0.0096 |
| 741.5307 | 1204 | 2.754 | 0.086 | 3.117 | 0.105 | 0.884 | 0.0109 |
| 803.5681 | 1102 | 5.187 | 0.087 | 5.491 | 0.073 | 0.945 | 0.0111 |
| 746.5714 | 1204 | 2.962 | 0.065 | 3.228 | 0.076 | 0.918 | 0.0113 |
| 627.5304 | 1203 | 2.544 | 0.068 | 2.783 | 0.058 | 0.914 | 0.0118 |
| 544.397 | 1204 | 3.249 | 0.120 | 2.323 | 0.341 | 1.399 | 0.0145 |
| 745.5656 | 1204 | 3.812 | 0.071 | 4.091 | 0.083 | 0.932 | 0.0148 |
| 739.5142 | 1204 | 2.576 | 0.105 | 3.009 | 0.137 | 0.856 | 0.0162 |
| 570.3725 | 1202 | 2.879 | 0.050 | 3.071 | 0.057 | 0.938 | 0.0164 |
| 686.4877 | 1204 | 2.527 | 0.068 | 2.757 | 0.064 | 0.917 | 0.0179 |
| 517.3136 | 1201 | 2.907 | 0.104 | 2.575 | 0.088 | 1.129 | 0.0193 |
| 744.4956 | 1204 | 3.741 | 0.073 | 3.988 | 0.070 | 0.938 | 0.0202 |
| 529.3167 | 1202 | 2.929 | 0.057 | 3.199 | 0.095 | 0.916 | 0.0203 |
| 821.5713 | 1102 | 2.825 | 0.089 | 3.091 | 0.065 | 0.914 | 0.0207 |
| 819.5641 | 1202 | 2.632 | 0.117 | 3.063 | 0.136 | 0.859 | 0.0209 |
| 667.5474 | 1204 | 3.336 | 0.118 | 2.882 | 0.150 | 1.158 | 0.0222 |
| 886.5582 | 1102 | 2.820 | 0.064 | 3.038 | 0.067 | 0.928 | 0.0232 |
| 796.529 | 1204 | 2.815 | 0.070 | 3.063 | 0.078 | 0.919 | 0.0234 |
| 306.2569 | 1204 | 2.848 | 0.083 | 3.103 | 0.074 | 0.918 | 0.0256 |
| 581.3344 | 1202 | 1.676 | 0.132 | 2.082 | 0.115 | 0.805 | 0.0261 |
| 817.584 | 1202 | 2.181 | 0.064 | 2.383 | 0.060 | 0.915 | 0.0261 |
| 685.5538 | 1204 | 1.862 | 0.132 | 2.222 | 0.083 | 0.838 | 0.0263 |
| 555.3101 | 1102 | 1.640 | 0.094 | 1.944 | 0.093 | 0.844 | 0.0277 |
| 666.5455 | 1204 | 4.533 | 0.128 | 4.059 | 0.168 | 1.117 | 0.0301 |
| 820.5677 | 1202 | 1.550 | 0.163 | 2.037 | 0.145 | 0.761 | 0.031 |
| 773.5368 | 1202 | 1.455 | 0.109 | 1.808 | 0.114 | 0.805 | 0.0324 |
| 541.3432 | 1102 | 3.148 | 0.073 | 3.377 | 0.073 | 0.932 | 0.0328 |
| 767.547 | 1202 | 2.917 | 0.095 | 3.237 | 0.111 | 0.901 | 0.0345 |
| 569.369 | 1202 | 4.824 | 0.048 | 4.987 | 0.057 | 0.967 | 0.0352 |
| 871.5935 | 1202 | 1.702 | 0.068 | 2.049 | 0.145 | 0.830 | 0.0362 |
| 1226.0968 | 1203 | 3.089 | 0.116 | 2.709 | 0.130 | 1.140 | 0.0365 |
| 793.5679 | 1204 | 3.022 | 0.067 | 3.237 | 0.075 | 0.934 | 0.0407 |
| 411.3211 | 1202 | 2.817 | 0.068 | 2.988 | 0.042 | 0.943 | 0.0408 |
| 684.5491 | 1204 | 2.304 | 0.087 | 2.600 | 0.110 | 0.886 | 0.041 |
| 768.5504 | 1202 | 1.786 | 0.141 | 2.160 | 0.106 | 0.827 | 0.041 |
| 743.5469 | 1202 | 2.894 | 0.076 | 3.173 | 0.109 | 0.912 | 0.0417 |
| 482.3215 | 1202 | 1.866 | 0.054 | 2.056 | 0.072 | 0.908 | 0.0424 |
| 574.4637 | 1202 | 1.059 | 0.201 | 1.653 | 0.204 | 0.640 | 0.0444 |
| 509.3493 | 1202 | 2.290 | 0.057 | 2.490 | 0.079 | 0.919 | 0.0446 |
| 772.586 | 1204 | 3.167 | 0.062 | 3.330 | 0.050 | 0.951 | 0.0458 |
| 383.3283 | 1204 | 1.280 | 0.142 | 1.662 | 0.119 | 0.770 | 0.0462 |
| 664.5322 | 1204 | 4.643 | 0.145 | 4.176 | 0.173 | 1.112 | 0.0465 |
| 312.2312 | 1204 | 2.771 | 0.059 | 2.583 | 0.070 | 1.073 | 0.0467 |
| 481.3172 | 1204 | 3.803 | 0.057 | 3.982 | 0.065 | 0.955 | 0.0468 |
| 765.5335 | 1204 | 3.065 | 0.107 | 3.418 | 0.137 | 0.897 | 0.0491 |
| 847.5953 | 1202 | 2.162 | 0.114 | 2.518 | 0.134 | 0.858 | 0.0492 |
| 624.5131 | 1203 | 3.900 | 0.068 | 4.084 | 0.061 | 0.955 | 0.0497 |

TABLE 11

Accurate mass features differing between patients showing the best discrimination between high ADAS score and low ADAS score (p < 0.05, log2 transformed).

| Detected Mass | Analysis Mode | AVG (log2) high ADAS | SEM high ADAS | Avg (log2) low ADAS | SEM low ADAS | log(2) Ratio | P Value |
|---|---|---|---|---|---|---|---|
| 541.3435 | 1102 | 3.007 | 0.047 | 3.741 | 0.083 | 0.804 | 5.76E−09 |
| 569.3685 | 1102 | 1.862 | 0.065 | 2.686 | 0.070 | 0.693 | 9.27E−09 |
| 804.5713 | 1102 | 3.915 | 0.047 | 4.494 | 0.080 | 0.871 | 3.59E−07 |
| 803.5681 | 1102 | 5.145 | 0.046 | 5.720 | 0.084 | 0.899 | 5.31E−07 |
| 837.5027 | 1101 | 3.257 | 0.058 | 3.866 | 0.070 | 0.842 | 5.33E−07 |
| 807.5758 | 1101 | 5.318 | 0.076 | 6.045 | 0.065 | 0.880 | 5.92E−07 |

TABLE 11-continued

Accurate mass features differing between patients showing the best discrimination between high ADAS score and low ADAS score ($p < 0.05$, log2 transformed).

| Detected Mass | Analysis Mode | AVG (log2) high ADAS | SEM high ADAS | Avg (log2) low ADAS | SEM low ADAS | log(2) Ratio | P Value |
|---|---|---|---|---|---|---|---|
| 808.5792 | 1101 | 4.265 | 0.076 | 4.992 | 0.069 | 0.854 | 7.70E−07 |
| 832.6024 | 1102 | 3.129 | 0.065 | 3.740 | 0.063 | 0.837 | 1.34E−06 |
| 779.5444 | 1101 | 6.061 | 0.061 | 6.691 | 0.082 | 0.906 | 1.39E−06 |
| 780.5474 | 1101 | 5.073 | 0.063 | 5.714 | 0.083 | 0.888 | 1.42E−06 |
| 831.5995 | 1102 | 4.245 | 0.068 | 4.850 | 0.061 | 0.875 | 2.37E−06 |
| 546.3486 | 1101 | 1.593 | 0.073 | 2.250 | 0.084 | 0.708 | 5.48E−06 |
| 871.5529 | 1102 | 2.778 | 0.050 | 3.307 | 0.090 | 0.840 | 6.59E−06 |
| 567.3545 | 1102 | 2.637 | 0.079 | 3.305 | 0.081 | 0.798 | 8.54E−06 |
| 545.3453 | 1101 | 3.142 | 0.085 | 3.836 | 0.077 | 0.819 | 9.04E−06 |
| 805.5604 | 1101 | 5.013 | 0.074 | 5.685 | 0.099 | 0.882 | 9.51E−06 |
| 794.5422 | 1102 | 2.287 | 0.056 | 2.795 | 0.079 | 0.818 | 1.22E−05 |
| 886.5584 | 1102 | 2.853 | 0.053 | 3.354 | 0.081 | 0.851 | 1.32E−05 |
| 827.57 | 1102 | 3.893 | 0.063 | 4.438 | 0.079 | 0.877 | 1.41E−05 |
| 828.5737 | 1102 | 2.920 | 0.061 | 3.425 | 0.069 | 0.852 | 1.56E−05 |
| 805.5831 | 1102 | 3.821 | 0.058 | 4.385 | 0.100 | 0.871 | 1.61E−05 |
| 829.5856 | 1102 | 3.781 | 0.076 | 4.393 | 0.077 | 0.861 | 1.68E−05 |
| 915.5191 | 1101 | 2.144 | 0.053 | 2.621 | 0.078 | 0.818 | 1.99E−05 |
| 793.5387 | 1102 | 3.352 | 0.056 | 3.854 | 0.086 | 0.870 | 2.76E−05 |
| 806.5637 | 1101 | 4.001 | 0.078 | 4.667 | 0.107 | 0.857 | 2.85E−05 |
| 821.5713 | 1102 | 2.834 | 0.067 | 3.309 | 0.046 | 0.856 | 3.30E−05 |
| 565.3396 | 1102 | 3.216 | 0.096 | 3.992 | 0.121 | 0.806 | 3.57E−05 |
| 555.3098 | 1102 | 1.608 | 0.081 | 2.242 | 0.094 | 0.717 | 4.04E−05 |
| 757.4989 | 1101 | 3.119 | 0.086 | 3.849 | 0.148 | 0.810 | 0.0001 |
| 832.5792 | 1101 | 3.024 | 0.092 | 3.662 | 0.085 | 0.826 | 0.0001 |
| 855.6015 | 1102 | 3.274 | 0.068 | 3.795 | 0.093 | 0.862 | 0.0001 |
| 458.2404 | 1101 | 1.430 | 0.076 | 1.984 | 0.109 | 0.721 | 0.0002 |
| 783.5671 | 1101 | 3.275 | 0.105 | 4.025 | 0.141 | 0.813 | 0.0002 |
| 803.5445 | 1101 | 4.778 | 0.095 | 5.397 | 0.079 | 0.885 | 0.0002 |
| 804.5475 | 1101 | 3.844 | 0.095 | 4.459 | 0.075 | 0.862 | 0.0002 |
| 831.576 | 1101 | 3.924 | 0.100 | 4.575 | 0.095 | 0.858 | 0.0002 |
| 518.3174 | 1101 | 3.093 | 0.072 | 3.609 | 0.101 | 0.857 | 0.0003 |
| 781.5616 | 1101 | 5.679 | 0.096 | 6.315 | 0.110 | 0.899 | 0.0003 |
| 517.314 | 1101 | 5.122 | 0.077 | 5.642 | 0.104 | 0.908 | 0.0004 |
| 782.5649 | 1101 | 4.649 | 0.100 | 5.296 | 0.118 | 0.878 | 0.0004 |
| 785.5933 | 1101 | 5.333 | 0.121 | 6.107 | 0.132 | 0.873 | 0.0004 |
| 786.5967 | 1101 | 4.256 | 0.124 | 5.039 | 0.133 | 0.844 | 0.0004 |
| 833.5932 | 1101 | 2.746 | 0.113 | 3.494 | 0.134 | 0.786 | 0.0004 |
| 853.5855 | 1102 | 2.333 | 0.088 | 2.875 | 0.080 | 0.811 | 0.0004 |
| 755.5468 | 1101 | 1.879 | 0.101 | 2.593 | 0.157 | 0.725 | 0.0005 |
| 811.6096 | 1101 | 2.512 | 0.140 | 3.375 | 0.152 | 0.744 | 0.0006 |
| 809.5936 | 1101 | 4.448 | 0.126 | 5.177 | 0.119 | 0.859 | 0.0007 |
| 761.5843 | 1101 | 1.993 | 0.094 | 2.654 | 0.160 | 0.751 | 0.0008 |
| 810.5969 | 1101 | 3.451 | 0.128 | 4.183 | 0.115 | 0.825 | 0.0008 |
| 847.5316 | 1101 | 2.543 | 0.093 | 3.082 | 0.092 | 0.825 | 0.0008 |
| 757.5626 | 1101 | 6.144 | 0.104 | 6.825 | 0.155 | 0.900 | 0.0009 |
| 758.5656 | 1101 | 5.185 | 0.107 | 5.885 | 0.158 | 0.881 | 0.0009 |
| 543.3296 | 1101 | 3.486 | 0.084 | 4.025 | 0.125 | 0.866 | 0.001 |
| 759.5779 | 1101 | 5.080 | 0.100 | 5.759 | 0.169 | 0.882 | 0.0011 |
| 760.5811 | 1101 | 3.952 | 0.102 | 4.645 | 0.177 | 0.851 | 0.0012 |
| 795.5551 | 1102 | 2.493 | 0.075 | 2.937 | 0.092 | 0.849 | 0.0012 |
| 829.5604 | 1101 | 3.200 | 0.098 | 3.759 | 0.106 | 0.851 | 0.0012 |
| 523.3635 | 1101 | 2.882 | 0.117 | 3.595 | 0.163 | 0.801 | 0.0014 |
| 575.2728 | 1101 | 2.204 | 0.078 | 2.673 | 0.104 | 0.824 | 0.0014 |
| 784.581 | 1101 | 3.921 | 0.129 | 4.667 | 0.171 | 0.840 | 0.0018 |
| 819.5553 | 1102 | 2.210 | 0.089 | 2.665 | 0.085 | 0.829 | 0.0025 |
| 817.5378 | 1102 | 2.089 | 0.088 | 2.491 | 0.068 | 0.839 | 0.0047 |
| 731.5463 | 1101 | 1.373 | 0.174 | 2.218 | 0.197 | 0.619 | 0.0052 |
| 795.5183 | 1101 | 2.270 | 0.081 | 2.725 | 0.140 | 0.833 | 0.0058 |
| 722.5334 | 1101 | 2.190 | 0.085 | 2.598 | 0.111 | 0.843 | 0.0083 |
| 760.5217 | 1204 | 4.084 | 0.063 | 4.331 | 0.042 | 0.943 | 0.0118 |
| 833.757 | 1203 | 2.531 | 0.161 | 3.274 | 0.231 | 0.773 | 0.0132 |
| 429.3749 | 1204 | 2.703 | 0.080 | 3.137 | 0.167 | 0.861 | 0.0143 |
| 722.4789 | 1201 | 1.895 | 0.093 | 2.247 | 0.064 | 0.843 | 0.0145 |
| 1228.1111 | 1203 | 2.699 | 0.127 | 3.291 | 0.194 | 0.820 | 0.0146 |
| 541.3139 | 1101 | 3.909 | 0.116 | 4.412 | 0.152 | 0.886 | 0.0158 |
| 860.7753 | 1203 | 4.152 | 0.110 | 4.647 | 0.161 | 0.893 | 0.016 |
| 703.5709 | 1101 | 2.858 | 0.095 | 3.216 | 0.072 | 0.888 | 0.0163 |
| 579.5325 | 1203 | 3.776 | 0.177 | 4.492 | 0.191 | 0.841 | 0.0166 |
| 858.686 | 1202 | 3.030 | 0.064 | 2.781 | 0.057 | 1.090 | 0.0166 |
| 831.7408 | 1203 | 3.708 | 0.137 | 4.286 | 0.176 | 0.865 | 0.0175 |
| 484.3041 | 1203 | 2.257 | 0.120 | 1.475 | 0.348 | 1.530 | 0.0176 |
| 580.5352 | 1203 | 1.310 | 0.222 | 2.135 | 0.172 | 0.614 | 0.0181 |
| 830.7362 | 1203 | 4.568 | 0.137 | 5.156 | 0.187 | 0.886 | 0.0182 |

TABLE 11-continued

Accurate mass features differing between patients showing the best discrimination between high ADAS score and low ADAS score (p < 0.05, log2 transformed).

| Detected Mass | Analysis Mode | AVG (log2) high ADAS | SEM high ADAS | Avg (log2) low ADAS | SEM low ADAS | log(2) Ratio | P Value |
|---|---|---|---|---|---|---|---|
| 495.332 | 1101 | 4.769 | 0.114 | 5.305 | 0.195 | 0.899 | 0.0186 |
| 183.0662 | 1101 | 1.868 | 0.215 | 2.671 | 0.183 | 0.699 | 0.0191 |
| 702.5677 | 1101 | 4.033 | 0.104 | 4.409 | 0.074 | 0.915 | 0.0194 |
| 887.8001 | 1203 | 2.884 | 0.137 | 3.396 | 0.122 | 0.849 | 0.0199 |
| 886.7916 | 1203 | 4.153 | 0.131 | 4.631 | 0.120 | 0.897 | 0.0232 |
| 759.5164 | 1204 | 4.697 | 0.077 | 4.975 | 0.066 | 0.944 | 0.0236 |
| 725.5527 | 1101 | 3.123 | 0.108 | 3.499 | 0.079 | 0.892 | 0.0244 |
| 832.7522 | 1203 | 3.418 | 0.170 | 4.119 | 0.245 | 0.830 | 0.0255 |
| 828.7207 | 1203 | 5.336 | 0.130 | 5.867 | 0.187 | 0.909 | 0.0263 |
| 496.3355 | 1101 | 2.972 | 0.113 | 3.473 | 0.195 | 0.856 | 0.0264 |
| 604.5432 | 1203 | 6.338 | 0.149 | 6.863 | 0.137 | 0.924 | 0.0283 |
| 864.738 | 1204 | 4.641 | 0.166 | 5.295 | 0.232 | 0.876 | 0.0298 |
| 680.5623 | 1204 | 3.590 | 0.125 | 4.126 | 0.214 | 0.870 | 0.0305 |
| 627.5201 | 1204 | 3.756 | 0.157 | 4.380 | 0.227 | 0.858 | 0.0315 |
| 1019.3838 | 1102 | 3.116 | 0.042 | 2.950 | 0.063 | 1.056 | 0.0323 |
| 825.6927 | 1203 | 1.408 | 0.212 | 2.138 | 0.204 | 0.658 | 0.0331 |
| 863.7336 | 1204 | 5.382 | 0.170 | 6.035 | 0.237 | 0.892 | 0.0338 |
| 521.3477 | 1101 | 3.368 | 0.126 | 3.890 | 0.213 | 0.866 | 0.0349 |
| 731.4916 | 1204 | 5.513 | 0.065 | 5.746 | 0.076 | 0.959 | 0.0351 |
| 542.3173 | 1101 | 2.116 | 0.120 | 2.565 | 0.157 | 0.825 | 0.0352 |
| 829.7242 | 1204 | 2.575 | 0.161 | 3.185 | 0.221 | 0.809 | 0.0356 |
| 835.6998 | 1204 | 2.285 | 0.247 | 3.153 | 0.271 | 0.725 | 0.0356 |
| 276.2095 | 1204 | 2.479 | 0.091 | 2.885 | 0.179 | 0.859 | 0.0358 |
| 653.536 | 1204 | 4.096 | 0.154 | 4.679 | 0.218 | 0.875 | 0.0368 |
| 523.4678 | 1203 | 2.747 | 0.238 | 3.609 | 0.295 | 0.761 | 0.0372 |
| 829.7246 | 1203 | 4.606 | 0.121 | 5.065 | 0.173 | 0.909 | 0.0376 |
| 921.8142 | 1204 | 2.618 | 0.338 | 3.654 | 0.184 | 0.716 | 0.039 |
| 605.5456 | 1203 | 4.920 | 0.154 | 5.420 | 0.131 | 0.908 | 0.0392 |
| 549.4844 | 1203 | 5.315 | 0.129 | 5.753 | 0.137 | 0.924 | 0.0398 |
| 732.4939 | 1204 | 4.258 | 0.065 | 4.480 | 0.069 | 0.950 | 0.04 |
| 365.3159 | 1203 | 1.907 | 0.098 | 1.449 | 0.217 | 1.316 | 0.0402 |
| 867.7581 | 1204 | 2.358 | 0.280 | 3.299 | 0.284 | 0.715 | 0.0402 |
| 738.5445 | 1102 | 2.458 | 0.122 | 2.825 | 0.059 | 0.870 | 0.0409 |
| 859.7695 | 1203 | 5.769 | 0.102 | 6.185 | 0.179 | 0.933 | 0.0414 |
| 625.5075 | 1204 | 3.271 | 0.138 | 3.811 | 0.224 | 0.858 | 0.0422 |
| 512.3356 | 1203 | 2.602 | 0.095 | 2.151 | 0.223 | 1.210 | 0.0432 |
| 842.7387 | 1203 | 2.626 | 0.103 | 2.998 | 0.139 | 0.876 | 0.0432 |
| 552.5021 | 1203 | 2.742 | 0.161 | 3.315 | 0.213 | 0.827 | 0.0444 |
| 724.5493 | 1101 | 4.410 | 0.105 | 4.736 | 0.081 | 0.931 | 0.0447 |
| 626.5108 | 1204 | 2.117 | 0.159 | 2.677 | 0.209 | 0.791 | 0.0454 |
| 928.7505 | 1203 | 2.869 | 0.168 | 2.238 | 0.265 | 1.282 | 0.0473 |
| 894.781 | 1204 | 3.884 | 0.196 | 4.542 | 0.228 | 0.855 | 0.048 |
| 866.7533 | 1204 | 3.905 | 0.219 | 4.667 | 0.292 | 0.837 | 0.0492 |
| 278.2255 | 1204 | 4.693 | 0.070 | 5.006 | 0.156 | 0.937 | 0.0494 |
| 865.7486 | 1204 | 4.644 | 0.223 | 5.419 | 0.296 | 0.857 | 0.0497 |

TABLE 12

Accurate mass features differing between patients showing the best discrimination between high MMSE score and low MMSE score (p < 0.05, log2 transformed).

| Detected Mass | Analysis Mode | AVG (log2) low MMSE | SEM low MMSE | Avg (log2) high MMSE | SEM high MMSE | log(2) Ratio | P Value |
|---|---|---|---|---|---|---|---|
| 505.3229 | 1202 | 3.585 | 0.045 | 4.514 | 0.053 | 0.794 | 3.90E−15 |
| 857.6186 | 1202 | 3.339 | 0.058 | 4.298 | 0.053 | 0.777 | 5.05E−14 |
| 803.5678 | 1202 | 6.747 | 0.056 | 7.962 | 0.082 | 0.847 | 5.19E−14 |
| 858.6211 | 1202 | 2.300 | 0.058 | 3.221 | 0.059 | 0.714 | 6.73E−13 |
| 566.3434 | 1202 | 4.856 | 0.055 | 5.682 | 0.055 | 0.855 | 1.90E−12 |
| 801.555 | 1202 | 2.220 | 0.057 | 3.128 | 0.064 | 0.710 | 2.89E−12 |
| 832.6036 | 1202 | 4.692 | 0.057 | 5.569 | 0.061 | 0.842 | 3.64E−12 |
| 804.5718 | 1202 | 5.516 | 0.047 | 6.475 | 0.080 | 0.852 | 4.63E−12 |
| 565.3393 | 1202 | 6.629 | 0.054 | 7.462 | 0.062 | 0.888 | 9.30E−12 |
| 506.3214 | 1202 | 2.237 | 0.051 | 2.908 | 0.044 | 0.769 | 1.26E−11 |
| 743.5467 | 1202 | 2.635 | 0.077 | 3.621 | 0.066 | 0.728 | 2.57E−11 |
| 831.6 | 1202 | 5.793 | 0.055 | 6.774 | 0.087 | 0.855 | 4.69E−11 |
| 744.55 | 1202 | 1.608 | 0.082 | 2.504 | 0.056 | 0.642 | 1.72E−10 |
| 570.3724 | 1202 | 2.702 | 0.042 | 3.289 | 0.052 | 0.821 | 4.09E−10 |
| 829.5859 | 1202 | 5.572 | 0.065 | 6.476 | 0.085 | 0.860 | 8.42E−10 |

TABLE 12-continued

Accurate mass features differing between patients showing the best discrimination between high MMSE score and low MMSE score ($p < 0.05$, log2 transformed).

| Detected Mass | Analysis Mode | AVG (log2) low MMSE | SEM low MMSE | Avg (log2) high MMSE | SEM high MMSE | log(2) Ratio | P Value |
| --- | --- | --- | --- | --- | --- | --- | --- |
| 830.5894 | 1202 | 4.477 | 0.061 | 5.311 | 0.078 | 0.843 | 1.01E−09 |
| 509.3494 | 1202 | 2.113 | 0.042 | 2.685 | 0.059 | 0.787 | 4.17E−09 |
| 542.3461 | 1202 | 3.562 | 0.047 | 4.292 | 0.082 | 0.830 | 6.29E−09 |
| 711.2577 | 1202 | 1.891 | 0.072 | 2.585 | 0.057 | 0.731 | 1.12E−08 |
| 709.2595 | 1202 | 1.864 | 0.079 | 2.546 | 0.047 | 0.732 | 1.49E−08 |
| 481.3172 | 1202 | 3.642 | 0.055 | 4.233 | 0.060 | 0.860 | 2.74E−08 |
| 569.369 | 1202 | 4.664 | 0.046 | 5.203 | 0.063 | 0.897 | 7.82E−08 |
| 805.5839 | 1202 | 5.216 | 0.051 | 5.867 | 0.082 | 0.889 | 1.16E−07 |
| 806.5873 | 1202 | 4.024 | 0.052 | 4.658 | 0.078 | 0.864 | 1.16E−07 |
| 856.6061 | 1202 | 4.179 | 0.069 | 5.099 | 0.121 | 0.819 | 1.81E−07 |
| 743.5469 | 1204 | 5.166 | 0.051 | 5.635 | 0.049 | 0.917 | 1.96E−07 |
| 793.5386 | 1102 | 2.966 | 0.065 | 3.468 | 0.043 | 0.855 | 2.63E−07 |
| 855.6023 | 1202 | 5.166 | 0.065 | 6.090 | 0.128 | 0.848 | 2.81E−07 |
| 482.3215 | 1202 | 1.742 | 0.057 | 2.291 | 0.066 | 0.761 | 4.15E−07 |
| 541.3433 | 1202 | 5.318 | 0.067 | 6.197 | 0.123 | 0.858 | 4.56E−07 |
| 744.5535 | 1204 | 4.203 | 0.048 | 4.631 | 0.048 | 0.908 | 4.68E−07 |
| 807.5899 | 1202 | 2.124 | 0.071 | 2.730 | 0.070 | 0.778 | 8.81E−07 |
| 827.5701 | 1202 | 5.937 | 0.077 | 6.931 | 0.147 | 0.857 | 1.20E−06 |
| 847.5954 | 1202 | 2.030 | 0.095 | 2.867 | 0.104 | 0.708 | 1.37E−06 |
| 828.5742 | 1202 | 4.908 | 0.074 | 5.818 | 0.137 | 0.844 | 1.67E−06 |
| 787.5464 | 1204 | 2.601 | 0.059 | 3.069 | 0.056 | 0.847 | 2.17E−06 |
| 591.3542 | 1202 | 3.749 | 0.081 | 4.387 | 0.078 | 0.855 | 3.05E−06 |
| 794.5422 | 1102 | 1.910 | 0.065 | 2.338 | 0.040 | 0.817 | 3.76E−06 |
| 804.5713 | 1102 | 3.619 | 0.065 | 4.092 | 0.056 | 0.885 | 4.94E−06 |
| 803.568 | 1102 | 4.829 | 0.068 | 5.317 | 0.057 | 0.908 | 5.22E−06 |
| 758.5094 | 1204 | 4.437 | 0.052 | 4.813 | 0.046 | 0.922 | 5.89E−06 |
| 592.3571 | 1202 | 2.013 | 0.084 | 2.634 | 0.079 | 0.764 | 7.14E−06 |
| 760.5216 | 1204 | 3.930 | 0.056 | 4.313 | 0.045 | 0.911 | 8.02E−06 |
| 759.5165 | 1204 | 4.558 | 0.067 | 5.001 | 0.050 | 0.911 | 9.01E−06 |
| 767.5469 | 1202 | 2.700 | 0.119 | 3.526 | 0.101 | 0.766 | 9.49E−06 |
| 786.5416 | 1204 | 3.664 | 0.051 | 4.093 | 0.064 | 0.895 | 1.12E−05 |
| 784.5239 | 1204 | 3.102 | 0.069 | 3.575 | 0.060 | 0.868 | 1.23E−05 |
| 821.5711 | 1102 | 2.415 | 0.067 | 2.863 | 0.055 | 0.843 | 1.25E−05 |
| 819.5641 | 1202 | 2.451 | 0.109 | 3.287 | 0.126 | 0.746 | 2.03E−05 |
| 777.5531 | 1202 | 1.473 | 0.133 | 2.257 | 0.083 | 0.653 | 2.21E−05 |
| 853.5862 | 1202 | 4.524 | 0.069 | 5.222 | 0.126 | 0.866 | 3.29E−05 |
| 507.3316 | 1202 | 2.653 | 0.056 | 3.061 | 0.064 | 0.867 | 3.70E−05 |
| 731.4917 | 1204 | 5.356 | 0.062 | 5.744 | 0.053 | 0.932 | 4.18E−05 |
| 831.5998 | 1102 | 3.958 | 0.081 | 4.429 | 0.057 | 0.894 | 4.26E−05 |
| 854.5902 | 1202 | 3.521 | 0.075 | 4.231 | 0.130 | 0.832 | 4.70E−05 |
| 630.5586 | 1203 | 2.845 | 0.054 | 3.242 | 0.069 | 0.877 | 0.0001 |
| 732.494 | 1204 | 4.127 | 0.062 | 4.492 | 0.050 | 0.919 | 0.0001 |
| 741.5307 | 1204 | 2.661 | 0.099 | 3.337 | 0.105 | 0.797 | 0.0001 |
| 771.5815 | 1204 | 4.036 | 0.064 | 4.423 | 0.055 | 0.913 | 0.0001 |
| 819.5552 | 1102 | 1.733 | 0.081 | 2.149 | 0.045 | 0.806 | 0.0001 |
| 832.6027 | 1102 | 2.864 | 0.081 | 3.318 | 0.056 | 0.863 | 0.0001 |
| 871.5527 | 1102 | 2.467 | 0.073 | 2.914 | 0.066 | 0.846 | 0.0001 |
| 871.5935 | 1202 | 1.550 | 0.108 | 2.224 | 0.110 | 0.697 | 0.0001 |
| 886.7917 | 1203 | 3.826 | 0.095 | 4.459 | 0.099 | 0.858 | 0.0001 |
| 910.7968 | 1203 | 3.257 | 0.083 | 3.757 | 0.079 | 0.867 | 0.0001 |
| 529.3166 | 1202 | 2.771 | 0.071 | 3.332 | 0.112 | 0.832 | 0.0002 |
| 589.3404 | 1202 | 5.578 | 0.072 | 6.318 | 0.155 | 0.883 | 0.0002 |
| 768.5503 | 1202 | 1.668 | 0.144 | 2.412 | 0.103 | 0.691 | 0.0002 |
| 884.7801 | 1203 | 6.076 | 0.082 | 6.639 | 0.104 | 0.915 | 0.0002 |
| 568.3574 | 1202 | 3.760 | 0.055 | 4.144 | 0.074 | 0.907 | 0.0003 |
| 685.2601 | 1202 | 1.483 | 0.102 | 2.052 | 0.093 | 0.723 | 0.0003 |
| 765.5313 | 1202 | 1.447 | 0.148 | 2.219 | 0.120 | 0.652 | 0.0003 |
| 772.5863 | 1204 | 3.177 | 0.051 | 3.466 | 0.050 | 0.917 | 0.0003 |
| 829.5856 | 1102 | 3.407 | 0.088 | 3.862 | 0.064 | 0.882 | 0.0003 |
| 911.8032 | 1203 | 2.388 | 0.077 | 2.794 | 0.064 | 0.855 | 0.0003 |
| 786.5967 | 1101 | 4.302 | 0.096 | 4.955 | 0.132 | 0.868 | 0.0004 |
| 885.7854 | 1203 | 5.116 | 0.080 | 5.615 | 0.095 | 0.911 | 0.0004 |
| 174.1409 | 1203 | 1.904 | 0.122 | 2.872 | 0.212 | 0.663 | 0.0005 |
| 590.3431 | 1202 | 3.790 | 0.071 | 4.415 | 0.142 | 0.858 | 0.0005 |
| 604.5432 | 1203 | 6.172 | 0.114 | 6.803 | 0.113 | 0.907 | 0.0005 |
| 757.5626 | 1101 | 6.170 | 0.099 | 6.804 | 0.129 | 0.907 | 0.0005 |
| 879.5999 | 1202 | 2.601 | 0.104 | 3.235 | 0.124 | 0.804 | 0.0005 |
| 605.5456 | 1203 | 4.762 | 0.115 | 5.393 | 0.118 | 0.883 | 0.0006 |
| 757.5016 | 1204 | 3.549 | 0.094 | 3.977 | 0.057 | 0.893 | 0.0006 |
| 581.3345 | 1202 | 1.572 | 0.124 | 2.253 | 0.131 | 0.698 | 0.0007 |
| 628.5421 | 1203 | 3.231 | 0.070 | 3.606 | 0.070 | 0.896 | 0.0007 |
| 723.5195 | 1202 | 2.196 | 0.085 | 2.730 | 0.110 | 0.805 | 0.0007 |
| 749.5365 | 1202 | 3.146 | 0.084 | 3.579 | 0.078 | 0.879 | 0.0007 |

TABLE 12-continued

Accurate mass features differing between patients showing the best discrimination between high MMSE score and low MMSE score (p < 0.05, log2 transformed).

| Detected Mass | Analysis Mode | AVG (log2) low MMSE | SEM low MMSE | Avg (log2) high MMSE | SEM high MMSE | log(2) Ratio | P Value |
|---|---|---|---|---|---|---|---|
| 785.5933 | 1101 | 5.382 | 0.098 | 6.025 | 0.137 | 0.893 | 0.0007 |
| 887.7999 | 1203 | 2.493 | 0.171 | 3.227 | 0.087 | 0.773 | 0.0007 |
| 886.8012 | 1204 | 3.209 | 0.117 | 3.782 | 0.096 | 0.849 | 0.0008 |
| 186.1408 | 1203 | 1.539 | 0.100 | 2.279 | 0.172 | 0.675 | 0.0009 |
| 200.1564 | 1203 | 2.724 | 0.075 | 3.280 | 0.129 | 0.830 | 0.0009 |
| 769.5655 | 1204 | 3.833 | 0.075 | 4.197 | 0.063 | 0.913 | 0.0009 |
| 817.5838 | 1202 | 2.041 | 0.086 | 2.452 | 0.070 | 0.833 | 0.0009 |
| 715.5169 | 1204 | 2.238 | 0.200 | 3.073 | 0.108 | 0.728 | 0.001 |
| 699.52 | 1204 | 2.223 | 0.082 | 2.690 | 0.099 | 0.826 | 0.0011 |
| 758.5656 | 1101 | 5.231 | 0.101 | 5.844 | 0.134 | 0.895 | 0.0011 |
| 795.5182 | 1101 | 2.324 | 0.087 | 2.800 | 0.098 | 0.830 | 0.0011 |
| 772.528 | 1204 | 3.202 | 0.075 | 3.531 | 0.053 | 0.907 | 0.0012 |
| 739.5164 | 1202 | 1.109 | 0.170 | 1.859 | 0.124 | 0.597 | 0.0014 |
| 779.5444 | 1101 | 6.186 | 0.098 | 6.639 | 0.083 | 0.932 | 0.0014 |
| 244.2187 | 1203 | 2.645 | 0.062 | 3.037 | 0.093 | 0.871 | 0.0015 |
| 508.3356 | 1202 | 0.969 | 0.088 | 1.386 | 0.078 | 0.700 | 0.0015 |
| 811.6096 | 1101 | 2.569 | 0.101 | 3.204 | 0.152 | 0.802 | 0.0017 |
| 882.766 | 1203 | 7.238 | 0.092 | 7.755 | 0.117 | 0.933 | 0.0017 |
| 744.4954 | 1204 | 3.832 | 0.067 | 4.118 | 0.049 | 0.930 | 0.0018 |
| 884.7877 | 1204 | 4.658 | 0.101 | 5.127 | 0.092 | 0.909 | 0.0018 |
| 262.2293 | 1203 | 2.639 | 0.059 | 2.992 | 0.084 | 0.882 | 0.002 |
| 784.5811 | 1101 | 3.896 | 0.100 | 4.493 | 0.143 | 0.867 | 0.002 |
| 817.5375 | 1102 | 1.715 | 0.076 | 2.148 | 0.101 | 0.798 | 0.002 |
| 723.5197 | 1204 | 3.643 | 0.087 | 4.211 | 0.143 | 0.865 | 0.0021 |
| 810.5401 | 1204 | 2.693 | 0.070 | 3.119 | 0.104 | 0.863 | 0.0021 |
| 880.6035 | 1202 | 1.837 | 0.084 | 2.351 | 0.126 | 0.782 | 0.0021 |
| 807.5757 | 1101 | 5.434 | 0.097 | 5.912 | 0.102 | 0.919 | 0.0022 |
| 883.7705 | 1203 | 6.396 | 0.085 | 6.870 | 0.111 | 0.931 | 0.0022 |
| 749.576 | 1102 | 2.516 | 0.057 | 2.174 | 0.084 | 1.157 | 0.0023 |
| 852.5738 | 1202 | 3.365 | 0.120 | 3.968 | 0.135 | 0.848 | 0.0025 |
| 752.5564 | 1202 | 2.277 | 0.101 | 2.730 | 0.092 | 0.834 | 0.0027 |
| 783.5672 | 1101 | 3.273 | 0.106 | 3.856 | 0.141 | 0.849 | 0.0027 |
| 808.5792 | 1101 | 4.393 | 0.099 | 4.868 | 0.104 | 0.902 | 0.0027 |
| 755.5468 | 1101 | 1.885 | 0.107 | 2.412 | 0.121 | 0.782 | 0.0031 |
| 780.5475 | 1101 | 5.202 | 0.096 | 5.629 | 0.089 | 0.924 | 0.0031 |
| 826.707 | 1204 | 2.266 | 0.118 | 2.743 | 0.086 | 0.826 | 0.0031 |
| 851.5698 | 1202 | 4.297 | 0.118 | 4.898 | 0.142 | 0.877 | 0.0031 |
| 631.5619 | 1203 | 1.475 | 0.132 | 1.956 | 0.066 | 0.754 | 0.0033 |
| 755.4861 | 1204 | 3.019 | 0.074 | 3.424 | 0.102 | 0.882 | 0.0034 |
| 188.1566 | 1203 | 2.272 | 0.134 | 2.926 | 0.154 | 0.777 | 0.0035 |
| 883.7765 | 1204 | 4.148 | 0.099 | 4.589 | 0.095 | 0.904 | 0.0035 |
| 726.5459 | 1204 | 2.790 | 0.064 | 3.090 | 0.069 | 0.903 | 0.0038 |
| 750.5403 | 1202 | 2.185 | 0.089 | 2.549 | 0.073 | 0.857 | 0.0038 |
| 627.5302 | 1203 | 2.497 | 0.080 | 2.845 | 0.075 | 0.878 | 0.0039 |
| 885.7922 | 1204 | 3.954 | 0.103 | 4.382 | 0.089 | 0.902 | 0.0039 |
| 675.6357 | 1203 | 1.815 | 0.210 | 0.815 | 0.240 | 2.228 | 0.0042 |
| 751.5529 | 1202 | 3.374 | 0.098 | 3.787 | 0.090 | 0.891 | 0.0043 |
| 882.7723 | 1204 | 4.984 | 0.102 | 5.422 | 0.096 | 0.919 | 0.0043 |
| 530.3213 | 1202 | 1.209 | 0.089 | 1.698 | 0.129 | 0.712 | 0.0044 |
| 380.3096 | 1204 | 1.432 | 0.107 | 1.867 | 0.092 | 0.767 | 0.0046 |
| 783.5148 | 1204 | 3.121 | 0.064 | 3.517 | 0.111 | 0.887 | 0.0048 |
| 202.172 | 1203 | 3.048 | 0.112 | 3.631 | 0.153 | 0.839 | 0.0049 |
| 748.5721 | 1102 | 3.632 | 0.058 | 3.325 | 0.082 | 1.092 | 0.0049 |
| 603.5317 | 1203 | 7.585 | 0.077 | 7.883 | 0.060 | 0.962 | 0.005 |
| 243.0718 | 1101 | 4.430 | 0.144 | 3.210 | 0.373 | 1.380 | 0.0052 |
| 582.2473 | 1201 | 3.377 | 0.132 | 2.673 | 0.191 | 1.264 | 0.0055 |
| 739.5141 | 1204 | 2.498 | 0.195 | 3.173 | 0.109 | 0.787 | 0.0056 |
| 879.7454 | 1204 | 3.291 | 0.124 | 3.749 | 0.088 | 0.878 | 0.0057 |
| 494.4342 | 1203 | 1.382 | 0.353 | 2.777 | 0.303 | 0.497 | 0.0059 |
| 782.5086 | 1204 | 3.266 | 0.073 | 3.662 | 0.110 | 0.892 | 0.0059 |
| 855.6016 | 1102 | 2.984 | 0.080 | 3.363 | 0.097 | 0.887 | 0.006 |
| 921.8153 | 1204 | 2.175 | 0.312 | 3.187 | 0.131 | 0.682 | 0.006 |
| 724.5256 | 1204 | 2.877 | 0.077 | 3.324 | 0.128 | 0.866 | 0.0061 |
| 183.0661 | 1101 | 2.155 | 0.151 | 2.748 | 0.130 | 0.784 | 0.0065 |
| 522.4634 | 1203 | 4.325 | 0.238 | 5.237 | 0.198 | 0.826 | 0.0067 |
| 853.7296 | 1204 | 3.607 | 0.109 | 4.012 | 0.083 | 0.899 | 0.0068 |
| 216.1877 | 1203 | 2.796 | 0.092 | 3.282 | 0.140 | 0.852 | 0.0076 |
| 779.5442 | 1201 | 7.005 | 0.079 | 7.301 | 0.065 | 0.959 | 0.0076 |
| 777.5288 | 1201 | 2.657 | 0.093 | 3.009 | 0.079 | 0.883 | 0.0077 |
| 523.468 | 1203 | 2.895 | 0.227 | 3.731 | 0.183 | 0.776 | 0.0083 |
| 569.3687 | 1102 | 1.734 | 0.098 | 2.075 | 0.067 | 0.836 | 0.0085 |
| 775.5535 | 1202 | 2.112 | 0.083 | 2.438 | 0.079 | 0.866 | 0.0087 |
| 632.5035 | 1204 | 4.858 | 0.122 | 5.325 | 0.110 | 0.912 | 0.0088 |

TABLE 12-continued

Accurate mass features differing between patients showing the best discrimination between high MMSE score and low MMSE score (p < 0.05, log2 transformed).

| Detected Mass | Analysis Mode | AVG (log2) low MMSE | SEM low MMSE | Avg (log2) high MMSE | SEM high MMSE | log(2) Ratio | P Value |
|---|---|---|---|---|---|---|---|
| 805.5604 | 1101 | 5.112 | 0.099 | 5.504 | 0.097 | 0.929 | 0.0089 |
| 313.269 | 1203 | 1.592 | 0.175 | 2.180 | 0.112 | 0.730 | 0.009 |
| 743.5464 | 1203 | 1.703 | 0.150 | 2.156 | 0.056 | 0.790 | 0.009 |
| 768.5539 | 1204 | 3.881 | 0.077 | 4.240 | 0.100 | 0.915 | 0.009 |
| 686.488 | 1204 | 2.671 | 0.054 | 2.872 | 0.047 | 0.930 | 0.0092 |
| 886.5582 | 1102 | 2.503 | 0.058 | 2.781 | 0.079 | 0.900 | 0.0092 |
| 602.5282 | 1203 | 8.833 | 0.081 | 9.116 | 0.059 | 0.969 | 0.0093 |
| 558.4667 | 1202 | 1.932 | 0.201 | 2.652 | 0.159 | 0.728 | 0.0095 |
| 809.5936 | 1101 | 4.523 | 0.112 | 5.054 | 0.155 | 0.895 | 0.0101 |
| 881.7616 | 1204 | 4.015 | 0.111 | 4.427 | 0.099 | 0.907 | 0.0101 |
| 833.7558 | 1204 | 1.919 | 0.311 | 2.863 | 0.138 | 0.670 | 0.0103 |
| 864.7596 | 1203 | 2.184 | 0.067 | 2.468 | 0.078 | 0.885 | 0.0103 |
| 613.3405 | 1202 | 3.422 | 0.124 | 3.963 | 0.150 | 0.863 | 0.0104 |
| 626.5277 | 1203 | 3.649 | 0.073 | 3.946 | 0.079 | 0.925 | 0.0105 |
| 629.5449 | 1203 | 2.015 | 0.088 | 2.370 | 0.093 | 0.850 | 0.0106 |
| 767.5494 | 1204 | 4.975 | 0.083 | 5.343 | 0.104 | 0.931 | 0.0106 |
| 517.3722 | 1204 | 2.176 | 0.149 | 1.408 | 0.235 | 1.545 | 0.0107 |
| 773.5347 | 1204 | 3.151 | 0.056 | 3.426 | 0.082 | 0.920 | 0.0108 |
| 806.5638 | 1101 | 4.113 | 0.100 | 4.498 | 0.097 | 0.914 | 0.0109 |
| 204.1876 | 1203 | 2.205 | 0.099 | 2.682 | 0.143 | 0.822 | 0.0113 |
| 837.5027 | 1101 | 3.439 | 0.075 | 3.734 | 0.078 | 0.921 | 0.0116 |
| 595.4932 | 1202 | 1.393 | 0.217 | 2.170 | 0.185 | 0.642 | 0.0117 |
| 915.5192 | 1101 | 2.301 | 0.087 | 2.588 | 0.060 | 0.889 | 0.0117 |
| 257.8105 | 1101 | 3.636 | 0.084 | 2.677 | 0.344 | 1.358 | 0.0121 |
| 541.343 | 1102 | 2.816 | 0.087 | 3.105 | 0.062 | 0.907 | 0.0121 |
| 745.5656 | 1204 | 3.838 | 0.051 | 4.054 | 0.062 | 0.947 | 0.0125 |
| 749.5408 | 1204 | 4.465 | 0.071 | 4.865 | 0.130 | 0.918 | 0.0126 |
| 725.5385 | 1204 | 2.932 | 0.068 | 3.293 | 0.115 | 0.890 | 0.0128 |
| 757.4993 | 1101 | 3.262 | 0.095 | 3.716 | 0.140 | 0.878 | 0.0128 |
| 852.725 | 1204 | 3.774 | 0.105 | 4.122 | 0.076 | 0.916 | 0.0128 |
| 780.5474 | 1201 | 5.941 | 0.081 | 6.223 | 0.067 | 0.955 | 0.0129 |
| 880.7516 | 1203 | 7.205 | 0.107 | 7.651 | 0.127 | 0.942 | 0.0129 |
| 881.7558 | 1203 | 6.471 | 0.103 | 6.883 | 0.116 | 0.940 | 0.0132 |
| 338.2821 | 1203 | 4.474 | 0.095 | 4.792 | 0.073 | 0.934 | 0.0135 |
| 827.5699 | 1102 | 3.597 | 0.089 | 3.987 | 0.116 | 0.902 | 0.0136 |
| 880.7566 | 1204 | 4.483 | 0.117 | 4.882 | 0.094 | 0.918 | 0.0138 |
| 572.4468 | 1204 | 1.726 | 0.131 | 2.213 | 0.129 | 0.780 | 0.014 |
| 336.2662 | 1203 | 3.181 | 0.097 | 3.518 | 0.083 | 0.904 | 0.0141 |
| 615.3539 | 1202 | 2.263 | 0.089 | 2.598 | 0.092 | 0.871 | 0.0146 |
| 544.4479 | 1203 | 1.928 | 0.085 | 2.273 | 0.100 | 0.848 | 0.0148 |
| 579.5325 | 1203 | 3.737 | 0.170 | 4.362 | 0.166 | 0.857 | 0.0148 |
| 520.45 | 1203 | 3.613 | 0.209 | 4.378 | 0.204 | 0.825 | 0.0149 |
| 633.5078 | 1204 | 3.891 | 0.128 | 4.347 | 0.118 | 0.895 | 0.0149 |
| 519.3321 | 1101 | 3.416 | 0.099 | 3.875 | 0.146 | 0.881 | 0.0151 |
| 547.6031 | 1101 | 2.454 | 0.114 | 1.714 | 0.259 | 1.432 | 0.0152 |
| 727.5569 | 1204 | 3.548 | 0.077 | 3.866 | 0.093 | 0.918 | 0.0152 |
| 339.285 | 1203 | 2.242 | 0.107 | 2.601 | 0.087 | 0.862 | 0.0154 |
| 746.5719 | 1204 | 3.004 | 0.054 | 3.196 | 0.050 | 0.940 | 0.0154 |
| 828.5736 | 1102 | 2.605 | 0.083 | 2.966 | 0.111 | 0.878 | 0.0154 |
| 798.6742 | 1203 | 1.685 | 0.154 | 2.329 | 0.192 | 0.723 | 0.0155 |
| 860.7753 | 1203 | 4.054 | 0.129 | 4.507 | 0.117 | 0.899 | 0.0156 |
| 521.4522 | 1203 | 1.837 | 0.271 | 2.786 | 0.244 | 0.660 | 0.0158 |
| 594.4878 | 1202 | 2.699 | 0.253 | 3.523 | 0.191 | 0.766 | 0.0158 |
| 781.5617 | 1101 | 5.737 | 0.110 | 6.187 | 0.134 | 0.927 | 0.0158 |
| 810.5969 | 1101 | 3.498 | 0.121 | 4.023 | 0.161 | 0.870 | 0.0158 |
| 631.4902 | 1204 | 2.690 | 0.150 | 3.208 | 0.132 | 0.839 | 0.0163 |
| 518.4346 | 1203 | 1.198 | 0.238 | 2.121 | 0.267 | 0.565 | 0.0164 |
| 244.0559 | 1101 | 3.875 | 0.099 | 3.359 | 0.174 | 1.153 | 0.0165 |
| 751.5556 | 1204 | 4.690 | 0.092 | 5.091 | 0.126 | 0.921 | 0.0165 |
| 825.5544 | 1202 | 2.647 | 0.146 | 3.202 | 0.159 | 0.827 | 0.017 |
| 520.3353 | 1101 | 1.661 | 0.103 | 2.114 | 0.144 | 0.786 | 0.0176 |
| 858.7632 | 1203 | 6.769 | 0.125 | 7.244 | 0.137 | 0.935 | 0.0178 |
| 861.7801 | 1203 | 2.123 | 0.171 | 2.681 | 0.138 | 0.792 | 0.0179 |
| 646.4837 | 1204 | 1.688 | 0.192 | 2.245 | 0.108 | 0.752 | 0.0184 |
| 489.6451 | 1101 | 2.555 | 0.109 | 1.822 | 0.269 | 1.402 | 0.0186 |
| 255.8135 | 1101 | 4.518 | 0.090 | 3.502 | 0.393 | 1.290 | 0.019 |
| 260.2135 | 1203 | 1.422 | 0.129 | 1.878 | 0.128 | 0.757 | 0.0193 |
| 833.5931 | 1101 | 2.952 | 0.114 | 3.347 | 0.109 | 0.882 | 0.0197 |
| 831.5759 | 1101 | 4.038 | 0.114 | 4.451 | 0.121 | 0.907 | 0.0201 |
| 544.3971 | 1204 | 3.313 | 0.158 | 2.377 | 0.342 | 1.394 | 0.0203 |
| 294.2207 | 1204 | 5.248 | 0.117 | 5.652 | 0.112 | 0.929 | 0.0205 |
| 724.5493 | 1101 | 4.674 | 0.050 | 4.395 | 0.101 | 1.063 | 0.0205 |
| 663.487 | 1204 | 1.733 | 0.223 | 2.369 | 0.128 | 0.731 | 0.0207 |

TABLE 12-continued

Accurate mass features differing between patients showing the best discrimination between high MMSE score and low MMSE score (p < 0.05, log2 transformed).

| Detected Mass | Analysis Mode | AVG (log2) low MMSE | SEM low MMSE | Avg (log2) high MMSE | SEM high MMSE | log(2) Ratio | P Value |
| --- | --- | --- | --- | --- | --- | --- | --- |
| 860.7753 | 1204 | 3.460 | 0.170 | 3.955 | 0.104 | 0.875 | 0.0207 |
| 246.1465 | 1202 | 3.707 | 0.141 | 4.188 | 0.134 | 0.885 | 0.0209 |
| 606.4869 | 1204 | 4.562 | 0.137 | 5.023 | 0.126 | 0.908 | 0.0215 |
| 576.5097 | 1203 | 9.304 | 0.133 | 9.756 | 0.127 | 0.954 | 0.0216 |
| 311.775 | 1101 | 2.594 | 0.152 | 1.849 | 0.264 | 1.403 | 0.022 |
| 566.413 | 1204 | 2.026 | 0.190 | 2.553 | 0.100 | 0.794 | 0.0221 |
| 577.5136 | 1203 | 7.959 | 0.125 | 8.392 | 0.124 | 0.948 | 0.0224 |
| 835.7001 | 1204 | 2.246 | 0.249 | 3.007 | 0.187 | 0.747 | 0.0226 |
| 665.501 | 1204 | 2.974 | 0.116 | 3.370 | 0.114 | 0.883 | 0.0227 |
| 675.6377 | 1204 | 3.825 | 0.077 | 4.086 | 0.075 | 0.936 | 0.023 |
| 600.5127 | 1203 | 8.597 | 0.082 | 8.866 | 0.075 | 0.970 | 0.0232 |
| 752.5583 | 1204 | 3.555 | 0.096 | 3.939 | 0.126 | 0.902 | 0.0241 |
| 161.1053 | 1101 | 4.011 | 0.148 | 2.977 | 0.402 | 1.347 | 0.0242 |
| 616.4673 | 1201 | 1.329 | 0.218 | 2.031 | 0.193 | 0.654 | 0.0245 |
| 253.8163 | 1101 | 4.184 | 0.090 | 3.283 | 0.364 | 1.274 | 0.0248 |
| 878.74 | 1204 | 3.665 | 0.118 | 4.001 | 0.074 | 0.916 | 0.025 |
| 580.535 | 1203 | 1.221 | 0.219 | 1.936 | 0.203 | 0.631 | 0.0252 |
| 859.7694 | 1203 | 5.668 | 0.122 | 6.076 | 0.119 | 0.933 | 0.0252 |
| 538.4224 | 1202 | 1.087 | 0.172 | 1.689 | 0.184 | 0.643 | 0.0256 |
| 804.723 | 1203 | 1.425 | 0.264 | 2.238 | 0.214 | 0.637 | 0.0256 |
| 833.7571 | 1203 | 2.599 | 0.192 | 3.201 | 0.165 | 0.812 | 0.0261 |
| 530.382 | 1204 | 2.988 | 0.204 | 2.114 | 0.305 | 1.413 | 0.0262 |
| 908.7832 | 1203 | 5.011 | 0.090 | 5.309 | 0.088 | 0.944 | 0.027 |
| 653.5361 | 1204 | 3.973 | 0.129 | 4.367 | 0.107 | 0.910 | 0.0273 |
| 559.47 | 1202 | 0.812 | 0.174 | 1.388 | 0.171 | 0.585 | 0.0274 |
| 748.5735 | 1202 | 3.935 | 0.071 | 3.726 | 0.054 | 1.056 | 0.0279 |
| 803.5445 | 1101 | 4.899 | 0.121 | 5.305 | 0.124 | 0.924 | 0.028 |
| 832.7521 | 1203 | 3.434 | 0.205 | 4.059 | 0.169 | 0.846 | 0.0283 |
| 320.2357 | 1204 | 1.225 | 0.148 | 1.609 | 0.071 | 0.761 | 0.0284 |
| 728.5626 | 1204 | 2.941 | 0.066 | 3.161 | 0.067 | 0.930 | 0.0284 |
| 795.555 | 1102 | 2.053 | 0.080 | 2.292 | 0.062 | 0.896 | 0.0285 |
| 838.7232 | 1204 | 2.011 | 0.253 | 2.753 | 0.191 | 0.730 | 0.0285 |
| 782.565 | 1101 | 4.709 | 0.114 | 5.143 | 0.147 | 0.916 | 0.0286 |
| 750.544 | 1204 | 3.351 | 0.066 | 3.678 | 0.124 | 0.911 | 0.0287 |
| 783.4315 | 1101 | 2.505 | 0.125 | 1.807 | 0.271 | 1.386 | 0.029 |
| 214.172 | 1203 | 3.549 | 0.090 | 3.910 | 0.126 | 0.908 | 0.0292 |
| 312.2663 | 1203 | 3.879 | 0.140 | 4.315 | 0.126 | 0.899 | 0.03 |
| 857.7531 | 1203 | 7.332 | 0.109 | 7.738 | 0.138 | 0.947 | 0.03 |
| 202.0453 | 1101 | 5.911 | 0.122 | 5.238 | 0.266 | 1.128 | 0.0305 |
| 763.5157 | 1202 | 1.570 | 0.175 | 2.098 | 0.147 | 0.748 | 0.0306 |
| 218.0192 | 1101 | 4.023 | 0.134 | 3.143 | 0.357 | 1.280 | 0.0307 |
| 856.7481 | 1203 | 8.173 | 0.118 | 8.608 | 0.151 | 0.949 | 0.032 |
| 795.5839 | 1204 | 3.545 | 0.061 | 3.800 | 0.093 | 0.933 | 0.0321 |
| 565.4104 | 1204 | 3.353 | 0.123 | 3.754 | 0.127 | 0.893 | 0.0332 |
| 313.7722 | 1101 | 3.080 | 0.178 | 2.250 | 0.319 | 1.369 | 0.0334 |
| 909.7882 | 1203 | 4.177 | 0.092 | 4.456 | 0.081 | 0.938 | 0.0337 |
| 429.6888 | 1101 | 2.475 | 0.093 | 1.833 | 0.268 | 1.351 | 0.0341 |
| 431.957 | 1202 | 1.847 | 0.154 | 2.312 | 0.136 | 0.799 | 0.0341 |
| 607.4919 | 1204 | 2.906 | 0.259 | 3.579 | 0.147 | 0.812 | 0.0341 |
| 294.1443 | 1201 | 2.449 | 0.210 | 1.795 | 0.201 | 1.364 | 0.0348 |
| 598.4965 | 1203 | 6.590 | 0.104 | 6.923 | 0.106 | 0.952 | 0.035 |
| 549.6005 | 1101 | 2.027 | 0.167 | 1.424 | 0.212 | 1.424 | 0.0351 |
| 283.9028 | 1101 | 3.018 | 0.076 | 2.397 | 0.267 | 1.259 | 0.0353 |
| 820.5679 | 1202 | 1.438 | 0.153 | 2.061 | 0.231 | 0.698 | 0.0353 |
| 574.4597 | 1204 | 3.354 | 0.210 | 3.994 | 0.196 | 0.840 | 0.0359 |
| 826.7048 | 1203 | 4.509 | 0.145 | 4.950 | 0.134 | 0.911 | 0.0361 |
| 805.5832 | 1102 | 3.502 | 0.085 | 3.742 | 0.066 | 0.936 | 0.0364 |
| 550.4956 | 1203 | 6.603 | 0.188 | 7.165 | 0.167 | 0.922 | 0.0365 |
| 630.4861 | 1204 | 3.807 | 0.132 | 4.238 | 0.142 | 0.898 | 0.0369 |
| 551.4985 | 1203 | 5.182 | 0.182 | 5.733 | 0.167 | 0.904 | 0.0371 |
| 549.4845 | 1203 | 5.363 | 0.140 | 5.765 | 0.115 | 0.930 | 0.0372 |
| 827.7083 | 1203 | 3.751 | 0.145 | 4.174 | 0.124 | 0.899 | 0.0374 |
| 306.2569 | 1204 | 2.821 | 0.075 | 3.051 | 0.072 | 0.925 | 0.0375 |
| 775.553 | 1204 | 3.272 | 0.071 | 3.577 | 0.119 | 0.915 | 0.0377 |
| 242.203 | 1203 | 4.260 | 0.087 | 4.573 | 0.113 | 0.932 | 0.0382 |
| 828.7202 | 1204 | 3.465 | 0.158 | 3.906 | 0.122 | 0.887 | 0.0385 |
| 232.2188 | 1203 | 3.156 | 0.098 | 3.499 | 0.122 | 0.902 | 0.0387 |
| 722.4789 | 1201 | 1.873 | 0.084 | 2.132 | 0.082 | 0.879 | 0.0389 |
| 530.3471 | 1202 | 2.566 | 0.117 | 2.910 | 0.103 | 0.882 | 0.0393 |
| 264.2452 | 1203 | 1.753 | 0.138 | 2.114 | 0.090 | 0.829 | 0.0397 |
| 858.7663 | 1204 | 5.791 | 0.140 | 6.169 | 0.100 | 0.939 | 0.0401 |
| 759.5779 | 1101 | 5.093 | 0.108 | 5.471 | 0.136 | 0.931 | 0.0404 |
| 559.469 | 1204 | 2.761 | 0.191 | 3.288 | 0.149 | 0.840 | 0.0406 |

TABLE 12-continued

Accurate mass features differing between patients showing the
best discrimination between high MMSE score and low MMSE
score (p < 0.05, log2 transformed).

| Detected Mass | Analysis Mode | AVG (log2) low MMSE | SEM low MMSE | Avg (log2) high MMSE | SEM high MMSE | log(2) Ratio | P Value |
|---|---|---|---|---|---|---|---|
| 593.4743 | 1204 | 2.069 | 0.240 | 2.728 | 0.184 | 0.758 | 0.0406 |
| 392.2938 | 1204 | 1.941 | 0.277 | 2.718 | 0.225 | 0.714 | 0.041 |
| 575.499 | 1203 | 7.133 | 0.096 | 7.452 | 0.112 | 0.957 | 0.0414 |
| 826.5581 | 1202 | 1.759 | 0.125 | 2.203 | 0.163 | 0.798 | 0.0417 |
| 719.6233 | 1204 | 4.578 | 0.094 | 4.279 | 0.102 | 1.070 | 0.0419 |
| 295.2287 | 1204 | 2.883 | 0.203 | 3.414 | 0.138 | 0.844 | 0.0422 |
| 555.3101 | 1102 | 1.310 | 0.070 | 1.541 | 0.080 | 0.850 | 0.0424 |
| 830.7355 | 1204 | 3.947 | 0.183 | 4.447 | 0.141 | 0.888 | 0.0427 |
| 474.3706 | 1203 | 0.868 | 0.128 | 1.234 | 0.112 | 0.704 | 0.0433 |
| 203.1157 | 1101 | 3.694 | 0.116 | 2.965 | 0.319 | 1.246 | 0.0437 |
| 295.2239 | 1204 | 3.109 | 0.123 | 3.476 | 0.119 | 0.894 | 0.0437 |
| 855.7417 | 1204 | 4.834 | 0.122 | 5.184 | 0.107 | 0.932 | 0.0438 |
| 760.5811 | 1101 | 3.973 | 0.109 | 4.349 | 0.138 | 0.913 | 0.0441 |
| 625.5076 | 1204 | 3.218 | 0.140 | 3.624 | 0.126 | 0.888 | 0.0443 |
| 270.2343 | 1203 | 1.714 | 0.106 | 2.018 | 0.095 | 0.850 | 0.0444 |
| 661.6233 | 1204 | 2.375 | 0.073 | 2.644 | 0.103 | 0.898 | 0.0445 |
| 446.3403 | 1202 | 0.751 | 0.166 | 1.275 | 0.181 | 0.589 | 0.0446 |
| 521.3474 | 1201 | 2.493 | 0.169 | 2.031 | 0.137 | 1.228 | 0.0451 |
| 837.718 | 1204 | 2.369 | 0.329 | 3.272 | 0.267 | 0.724 | 0.0451 |
| 228.1877 | 1203 | 2.954 | 0.108 | 3.313 | 0.131 | 0.892 | 0.0458 |
| 832.7495 | 1204 | 2.994 | 0.226 | 3.588 | 0.164 | 0.834 | 0.0458 |
| 576.477 | 1202 | 1.734 | 0.213 | 2.337 | 0.187 | 0.742 | 0.0459 |
| 1085.3294 | 1101 | 3.756 | 0.022 | 3.463 | 0.136 | 1.085 | 0.0467 |
| 444.2717 | 1202 | 1.195 | 0.096 | 1.496 | 0.105 | 0.799 | 0.0473 |
| 545.6062 | 1101 | 1.955 | 0.134 | 1.427 | 0.213 | 1.370 | 0.0477 |
| 651.5221 | 1204 | 3.677 | 0.131 | 4.039 | 0.111 | 0.910 | 0.0482 |
| 829.7244 | 1203 | 4.651 | 0.135 | 5.044 | 0.130 | 0.922 | 0.0482 |
| 859.7706 | 1204 | 4.962 | 0.145 | 5.331 | 0.100 | 0.931 | 0.0482 |
| 575.4632 | 1204 | 2.109 | 0.207 | 2.692 | 0.185 | 0.783 | 0.0485 |
| 804.5476 | 1101 | 3.984 | 0.119 | 4.353 | 0.130 | 0.915 | 0.0485 |
| 725.5527 | 1101 | 3.407 | 0.058 | 3.160 | 0.102 | 1.078 | 0.0486 |
| 350.2423 | 1202 | 2.544 | 0.227 | 1.901 | 0.207 | 1.338 | 0.0489 |
| 382.1083 | 1101 | 2.600 | 0.210 | 1.858 | 0.286 | 1.399 | 0.049 |
| 836.7076 | 1204 | 1.427 | 0.242 | 2.163 | 0.256 | 0.660 | 0.0493 |
| 671.5726 | 1204 | 2.055 | 0.138 | 2.458 | 0.136 | 0.836 | 0.0495 |
| 197.8549 | 1101 | 3.431 | 0.102 | 2.697 | 0.337 | 1.272 | 0.0499 |
| 773.537 | 1202 | 1.569 | 0.078 | 1.805 | 0.082 | 0.869 | 0.0499 |

TABLE 13

Accurate mass features differing between clinically diagnosed
AD and non-AD patients in CSF (p < 0.05, log2 transformed).

| Detected Mass | Analysis Mode | AVG (log2) AD | SEM AD | AVG (log2) non-AD | SEM non-AD | log(2) Ratio | P Value |
|---|---|---|---|---|---|---|---|
| 742.2972 | 1203 | 1.187 | 0.130 | 0.000 | 0.000 | 1.187 | 1.69E−05 |
| 562.46 | 1203 | 1.080 | 0.134 | 0.000 | 0.000 | 1.080 | 4.84E−05 |
| 731.653 | 1203 | 0.905 | 0.193 | 0.000 | 0.000 | 0.905 | 0.0022 |
| 432.1532 | 1203 | 1.445 | 0.125 | 0.880 | 0.053 | 0.609 | 0.0037 |
| 487.6482 | 1101 | 2.388 | 0.044 | 2.668 | 0.057 | 1.117 | 0.0037 |
| 275.8712 | 1101 | 2.362 | 0.057 | 2.664 | 0.058 | 1.128 | 0.0045 |
| 371.7311 | 1101 | 3.417 | 0.098 | 3.818 | 0.022 | 1.117 | 0.0053 |
| 622.2539 | 1203 | 2.667 | 0.110 | 2.166 | 0.074 | 0.812 | 0.0056 |
| 485.6503 | 1101 | 1.758 | 0.051 | 1.976 | 0.024 | 1.124 | 0.0058 |
| 207.0822 | 1203 | 1.010 | 0.126 | 0.198 | 0.198 | 0.196 | 0.006 |
| 640.2637 | 1203 | 3.557 | 0.152 | 2.876 | 0.106 | 0.809 | 0.0063 |
| 373.728 | 1101 | 3.013 | 0.086 | 3.358 | 0.037 | 1.114 | 0.0071 |
| 656.2587 | 1203 | 0.977 | 0.080 | 0.322 | 0.199 | 0.330 | 0.0097 |
| 730.6493 | 1203 | 1.888 | 0.139 | 0.948 | 0.278 | 0.502 | 0.0109 |
| 220.0798 | 1101 | 2.252 | 0.078 | 2.556 | 0.044 | 1.135 | 0.011 |
| 641.2661 | 1203 | 1.915 | 0.148 | 1.010 | 0.282 | 0.527 | 0.0152 |
| 779.4393 | 1101 | 3.612 | 0.032 | 3.728 | 0.022 | 1.032 | 0.0167 |
| 782.5647 | 1201 | 1.898 | 0.208 | 1.128 | 0.142 | 0.594 | 0.0172 |
| 313.7721 | 1101 | 4.045 | 0.096 | 4.350 | 0.031 | 1.075 | 0.0215 |
| 785.4288 | 1101 | 3.273 | 0.039 | 3.410 | 0.033 | 1.042 | 0.0253 |
| 777.4426 | 1101 | 2.495 | 0.017 | 2.614 | 0.044 | 1.048 | 0.0279 |
| 341.8614 | 1101 | 2.747 | 0.069 | 2.990 | 0.061 | 1.089 | 0.0305 |
| 250.0366 | 1101 | 3.122 | 0.115 | 3.462 | 0.049 | 1.109 | 0.0309 |
| 315.7693 | 1101 | 3.347 | 0.090 | 3.618 | 0.044 | 1.081 | 0.0311 |
| 253.8164 | 1101 | 4.237 | 0.108 | 4.542 | 0.030 | 1.072 | 0.033 |
| 369.7338 | 1101 | 2.713 | 0.148 | 3.132 | 0.035 | 1.154 | 0.034 |
| 781.5607 | 1201 | 2.728 | 0.234 | 2.048 | 0.095 | 0.751 | 0.0345 |
| 206.0789 | 1203 | 4.178 | 0.147 | 3.484 | 0.253 | 0.834 | 0.0357 |
| 429.689 | 1101 | 3.232 | 0.042 | 3.392 | 0.051 | 1.050 | 0.0358 |
| 638.2465 | 1203 | 1.927 | 0.188 | 1.372 | 0.095 | 0.712 | 0.0362 |
| 578.1574 | 1101 | 1.828 | 0.042 | 1.674 | 0.046 | 0.916 | 0.0368 |
| 262.0777 | 1101 | 4.738 | 0.114 | 5.072 | 0.052 | 1.070 | 0.0371 |
| 265.8423 | 1101 | 3.682 | 0.101 | 3.960 | 0.028 | 1.076 | 0.0395 |
| 582.6334 | 1101 | 1.702 | 0.051 | 1.526 | 0.052 | 0.897 | 0.0395 |
| 255.8135 | 1101 | 4.678 | 0.113 | 4.978 | 0.029 | 1.064 | 0.0418 |
| 321.8039 | 1101 | 3.190 | 0.098 | 3.480 | 0.062 | 1.091 | 0.0423 |
| 514.6879 | 1101 | 2.650 | 0.037 | 2.534 | 0.032 | 0.956 | 0.0424 |
| 262.0221 | 1101 | 3.633 | 0.126 | 3.964 | 0.026 | 1.091 | 0.0435 |
| 746.621 | 1101 | 1.015 | 0.225 | 0.306 | 0.190 | 0.301 | 0.0438 |
| 781.4354 | 1101 | 4.163 | 0.028 | 4.254 | 0.025 | 1.022 | 0.045 |
| 311.775 | 1101 | 3.457 | 0.111 | 3.764 | 0.053 | 1.089 | 0.0461 |
| 257.8105 | 1101 | 3.753 | 0.115 | 4.056 | 0.036 | 1.081 | 0.0472 |

TABLE 14

Retention Time of Six Biomarkers

| FT Accurate Neutral Mass | Formula | Theoretical Neutral Mass | Q-Star Mass (M − H) ion | Retention Time (min) |
|---|---|---|---|---|
| 541.3432 | C25H52NO9P | 541.3379 | 540.3616 | 29.4 |
| 569.3687 | C27H56NO9P | 569.3692 | 568.3979 | 31.0 |
| 699.5198 | C39H74NO7P | 699.5202 | 698.5392 | 40.5 |
| 723.5195 | C41H74NO7P | 723.5202 | 722.5331 | 40.2 |
| 751.5555 | C43H78NO7P | 751.5515 | 750.5667 | 41.9 |
| 803.568 | C43H82NO10P | 803.5676 | 802.5575 | 38.6 |

TABLE 15

Metabolite 541.3432 Fragments

| Frag Formula | Theoretical | Q-Star Detected | Delta | Diff | Loss |
|---|---|---|---|---|---|
| C25H51NO9P | 540.33014 | 540.3616 | 0.0315 | — | — |
| C23H47NO7P | 480.30901 | 480.3313 | 0.0223 | 60.02112 | C2H4O2 |
| C16H31O2 | 255.23240 | 255.2521 | 0.0197 | 292.15251 | C9H27NO7P |
| C7H15NO5P | 224.06878 | 224.0904 | 0.0216 | 300.26644 | C18H36O3 |
| O3P | 78.95850 | 78.975 | 0.0165 | 461.37163 | C25H51NO6 |

Legend:
frag formula: The putative computationally derived molecular formula of the fragment neutral mass.
theoretical: The theoretical mass of the formulas shown in the frag formula column.
Qstar-detected: The detected mass from the ABI Q-Star XL.
delta: The difference between the theoretical and neutral mass.
diff: The mass difference between the Qstar-detected parent ion mass and the Qstar-detected fragmant ion mass.
Loss: The putative molecular formulas of the "diff" column
Note:
These are only predicted formulas for each fragment and are not necessarily the actual formulas.

TABLE 16

Metabolite 569.3687 Fragments

| Frag Formula | Theoretical | Q-Star Detected | Delta | Diff | Loss |
|---|---|---|---|---|---|
| C27H55NO9P | 568.3614 | 568.3979 | 0.0365 | — | — |
| C25H51NO7P | 508.34031 | 508.3612 | 0.0209 | 60.02112 | C2H4O2 |
| C18H35O2 | 283.26370 | 283.2900 | 0.0263 | 285.09773 | C9H20NO7P |
| C7H15NO5P | 224.06878 | 224.0899 | 0.0211 | 344.23266 | C20H40O4 |
| C4H11NO4P | 168.04256 | 168.0668 | 0.0242 | 400.31887 | C23H44O5 |
| C3H6PO5 | 152.99528 | 153.0196 | 0.0243 | 446.33992 | C24H49NO4P |
| O3P | 78.95850 | 78.975 | 0.0165 | 489.40293 | C27H55NO6 |

Legend:
frag formula: The putative computationally derived molecular formula of the fragment neutral mass.
theoretical: The theoretical mass of the formulas shown in the frag formula column.
Qstar-detected: The detected mass from the ABI Q-Star XL.
delta: The difference between the theoretical and neutral mass.
diff: The mass difference between the Qstar-detected parent ion mass and the Qstar-detected fragmant ion mass.
Loss: The putative molecular formulas of the "diff" column
Note:
These are only predicted formulas for each fragment and are not necessarily the actual formulas.

TABLE 17

Metabolite 803.568 Fragments

| Frag Formula | Theoretical | Q-Star Detected | Delta | Differences | Loss |
|---|---|---|---|---|---|
| C43H81NO10P | 802.55980 | 802.5575 | −0.0023 | — | — |
| C41H77NO8P | 742.53868 | 742.5526 | 0.0139 | 76.01604 | C2H4O3 |
| C23H47NO7P | 480.30901 | 480.3248 | 0.0158 | 322.25079 | C20H34O3 |
| C18H32O2 | 279.23240 | 279.2485 | 0.0161 | 522.31957 | C25H49NO89 |
| C16H31O2 | 255.23240 | 255.2469 | 0.0145 | 547.32740 | C27H50NO8P |

TABLE 17-continued

Metabolite 803.568 Fragments

| Frag Formula | Theoretical | Q-Star Detected | Delta | Differences | Loss |
|---|---|---|---|---|---|
| C7H15NO5P | 224.06878 | 224.0853 | 0.0165 | 578.49102 | C36H66O5 |
| C4H11NO4P | 168.04256 | 168.0629 | 0.0203 | 634.51724 | C39H70O6 |

Legend:
frag formula: The putative computationally derived molecular formula of the fragment neutral mass.
theoretical: The theoretical mass of the formulas shown in the frag formula column.
Qstar-detected: The detected mass from the ABI Q-Star XL.
delta: The difference between the theoretical and neutral mass.
diff: The mass difference between the Qstar-detected parent ion mass and the Qstar-detected fragmant ion mass.
Loss: The putative molecular formulas of the "diff" column
Note:
These are only predicted formulas for each fragment and are not necessarily the actual formulas.

TABLE 18

List of Preferred List of Metabolites

| Metabolite Code | Metabolite Name | Molecular Formula | Parent Mass | M-H Mass | Diagnostic Fragment Mass | MS/MS Transition |
|---|---|---|---|---|---|---|
| M01 | PtdEt 16:0/18:0 | C39H78N1O8P1 | 719.54648 | 718.5 | R1 (C16H31O2)-255 | 718.0/255.0 |
| M02 | PtdEt 16:0/18:1 | C39H76N1O8P1 | 717.53083 | 716.5 | R1 (C16H31O2)-255 | 716.0/255.0 |
| M03 | PtdEt 18:0/18:0 | C41H82N1O8P1 | 747.57777 | 746.5 | R1 (C18H35O2)-283 | 746.0/283.0 |
| M04 | PtdEt 18:0/18:1 | C41H80N1O8P1 | 745.56213 | 744.5 | R1 (C18H35O2)-283 | 744.0/283.0 |
| M05 | Plasmanyl 16:0/18:1 | C39H78N1O7P1 | 703.55156 | 702.5 | R2 (C18H33O2)-281 | 702.0/281.0 |
| M06 | Plasmanyl 16:0/18:2 | C39H76N1O7P1 | 701.53591 | 700.5 | R2 (C18H31O2)-279 | 700.0/279.0 |
| M07 | Plasmanyl 16:0/20:4 | C41H76N1O7P1 | 725.53591 | 724.5 | R2 (C20H31O2)-303 | 724.0/303.0 |
| M08 | Plasmanyl 16:0/22:4 | C43H80N1O7P1 | 753.56721 | 752.5 | R2 (C22H35O2)-331 | 752.0/331.0 |
| M09 | Plasmanyl 16:0/22:6 | C43H76N1O7P1 | 749.53591 | 748.5 | R2 (C22H31O2)-327 | 748.0/327.0 |
| M10 | Plasmanyl 18:0/18:1 | C41H82N1O7P1 | 731.58286 | 730.5 | R2 (C18H33O2)-281 | 730.0/281.0 |
| M11 | Plasmanyl 18:0/18:2 | C41H80N1O7P1 | 729.56721 | 728.5 | R2 (C18H31O2)-279 | 728.0/279.0 |
| M12 | Plasmanyl 18:0/20:4 | C43H80N1O7P1 | 753.56721 | 752.5 | R2 (C20H31O2)-303 | 752.0/303.0 |
| M13 | Plasmanyl 18:0/22:4 | C45H84N1O7P1 | 781.59851 | 780.5 | R2 (C22H35O2)-331 | 780.0/331.0 |
| M14 | Plasmanyl 18:0/22:6 | C45H80N1O7P1 | 777.56721 | 776.5 | R2 (C22H31O2)-327 | 776.0/327.0 |
| M15 | Plasmenyl 16:0/18:1 | C39H76N1O7P1 | 701.53591 | 700.5 | R2 (C18H33O2)-281 | 700.0/281.0 |
| M16 | Plasmenyl 16:0/18:2 | C39H74N1O7P1 | 699.52026 | 698.5 | R2 (C18H31O2)-279 | 698.0/279.0 |
| M17 | Plasmenyl 16:0/20:4 | C41H74N1O7P1 | 723.52026 | 722.5 | R2 (C20H31O2)-303 | 722.0/303.0 |
| M18 | Plasmenyl 16:0/22:4 | C43H78N1O7P1 | 751.55156 | 750.5 | R2 (C22H35O2)-331 | 750.0/331.0 |
| M19 | Plasmenyl 16:0/22:6 | C43H74N1O7P1 | 747.52026 | 746.5 | R2 (C22H31O2)-327 | 746.0/327.0 |
| M20 | Plasmenyl 18:0/18:1 | C41H80N1O7P1 | 729.56721 | 728.5 | R2 (C18H33O2)-281 | 728.0/281.0 |
| M21 | Plasmenyl 18:0/18:2 | C41H78N1O7P1 | 727.55156 | 726.5 | R2 (C18H31O2)-279 | 726.0/279.0 |
| M22 | Plasmenyl 18:0/20:4 | C43H78N1O7P1 | 751.55156 | 750.5 | R2 (C20H31O2)-303 | 750.6/303.2 |
| M23 | Plasmenyl 18:0/22:4 | C45H82N1O7P1 | 779.58286 | 778.5 | R2 (C22H35O2)-331 | 778.0/331.0 |
| M24 | Plasmenyl 18:0/22:6 | C45H78N1O7P1 | 775.55156 | 774.5 | R2 (C22H31O2)-327 | 774.0/327.0 |
| M25 | Free 22:6 | C22H32O2 | 328.24022 | 327.2 | (C21H31)-283 | 327.2/283.0 |
| M26 | Free 20:4 | C20H32O2 | 304.24022 | 303.2 | (C19H31)-259 | 303.2/259.5 |

TABLE 19

Clinical Data on Subject Cohorts

| Population | n | Age Mean | Age SEM | MMSE Mean | MMSE SEM | ADAS-cog Mean | ADAS-cog SEM |
|---|---|---|---|---|---|---|---|
| Age Ctl, 30-39, Female | 14 | 36.4 | 0.9 | | | | |
| Age Ctl, 30-39, Male | 11 | 35.2 | 1.0 | | | | |
| Age Ctl, 40-49, Female | 44 | 44.8 | 0.5 | | | | |
| Age Ctl, 40-49, Male | 27 | 44.7 | 0.6 | | | | |
| Age Ctl, 50-59, Female | 107 | 54.2 | 0.3 | | | | |
| Age Ctl, 50-59, Male | 59 | 54.1 | 0.4 | | | | |
| Age Ctl, 60-69, Female | 55 | 63.4 | 0.3 | | | | |
| Age Ctl, 60-69, Male | 34 | 64.4 | 0.5 | | | | |
| Age Ctl, 70+_Female | 27 | 79.7 | 1.2 | | | | |
| Age Ctl, 70+_Male | 35 | 75.5 | 0.7 | | | | |
| Cognitive Normal, Female | 36 | 77.6 | 1.1 | 29.6 | 0.1 | | |
| Cognitive Normal, Male | 32 | 76.8 | 1.1 | 29.3 | 0.1 | | |
| SDAT_all, Female | 140 | 80.0 | 0.6 | 12.6 | 0.7 | 34.2 | 1.6 |
| SDAT_all, Male | 117 | 79.8 | 0.7 | 15.3 | 0.5 | 27.4 | 1.3 |
| SDAT, ADAS 5-19, Female | 38 | 79.6 | 1.2 | 17.6 | 0.7 | 15.2 | 0.6 |
| SDAT, ADAS 20-39, Female | 54 | 78.6 | 1.0 | 16.6 | 0.7 | 27.0 | 0.8 |
| SDAT, ADAS 40-70, Female | 48 | 81.9 | 1.1 | 4.2 | 0.7 | 57.3 | 1.5 |
| SDAT, ADAS 5-19, Male | 40 | 79.0 | 1.1 | 17.3 | 0.7 | 15.3 | 0.5 |
| SDAT, ADAS 20-39, Male | 58 | 79.6 | 0.9 | 16.8 | 0.6 | 27.5 | 0.7 |

TABLE 19-continued

Clinical Data on Subject Cohorts

| Population | n | Age Mean | Age SEM | MMSE Mean | MMSE SEM | ADAS-cog Mean | ADAS-cog SEM |
|---|---|---|---|---|---|---|---|
| SDAT, ADAS 40-70, Male | 18 | 82.6 | 2.1 | 6.2 | 1.1 | 53.2 | 2.2 |
| Post Mortem SDAT Male | 10 | 80.1 | 1.4 | | | | |
| Post Mortem SDAT Female | 10 | 77.6 | 1.5 | | | | |
| Post Mortem Ctl, Female | 9 | 84.4 | 1.8 | | | | |
| Post Mortem Ctl, Male | 10 | 77.9 | 1.4 | | | | |

TABLE 20

Effect of Age on Serum Ethanolamine Phospholipid Levels in Males

| Metabolite Code | Age Ctl, 30-39, Male Mean | SEM | Age Ctl, 40-49, Male Mean | SEM | Age Ctl, 50-59, Male Mean | SEM | Age Ctl, 60-69, Male Mean | SEM | Age Ctl, 70+ Male Mean | SEM |
|---|---|---|---|---|---|---|---|---|---|---|
| M01 | 0.122 | 0.017 | 0.119 | 0.008 | 0.113 | 0.006 | 0.132 | 0.007 | 0.130 | 0.006 |
| M02 | 0.056 | 0.008 | 0.058 | 0.006 | 0.058 | 0.004 | 0.059 | 0.007 | 0.056 | 0.005 |
| M03 | 0.102 | 0.014 | 0.085 | 0.006 | 0.095 | 0.005 | 0.103 | 0.008 | 0.110 | 0.010 |
| M04 | 0.026 | 0.004 | 0.027 | 0.003 | 0.025 | 0.002 | 0.027 | 0.003 | 0.027 | 0.003 |
| M05 | 0.014 | 0.002 | 0.012 | 0.001 | 0.011 | 0.001 | 0.012 | 0.001 | 0.011 | 0.001 |
| M06 | 0.032 | 0.005 | 0.026 | 0.002 | 0.026 | 0.001 | 0.025 | 0.002 | 0.027 | 0.002 |
| M07 | 0.078 | 0.015 | 0.053 | 0.007 | 0.063 | 0.005 | 0.061 | 0.007 | 0.060 | 0.006 |
| M08 | 0.010 | 0.002 | 0.007 | 0.001 | 0.007 | 0.001 | 0.007 | 0.001 | 0.006 | 0.001 |
| M09 | 0.019 | 0.004 | 0.013 | 0.002 | 0.019 | 0.002 | 0.019 | 0.002 | 0.022 | 0.003 |
| M10 | 0.058 | 0.009 | 0.052 | 0.004 | 0.049 | 0.003 | 0.055 | 0.004 | 0.053 | 0.003 |
| M11 | 0.131 | 0.021 | 0.099 | 0.007 | 0.098 | 0.005 | 0.099 | 0.007 | 0.104 | 0.007 |
| M12 | 0.244 | 0.037 | 0.186 | 0.015 | 0.210 | 0.012 | 0.213 | 0.017 | 0.202 | 0.016 |
| M13 | 0.015 | 0.002 | 0.013 | 0.001 | 0.013 | 0.001 | 0.013 | 0.001 | 0.012 | 0.001 |
| M14 | 0.034 | 0.005 | 0.026 | 0.003 | 0.036 | 0.002 | 0.040 | 0.004 | 0.047 | 0.006 |
| M15 | 0.085 | 0.012 | 0.075 | 0.005 | 0.074 | 0.004 | 0.074 | 0.006 | 0.076 | 0.005 |
| M16 | 0.291 | 0.043 | 0.220 | 0.016 | 0.244 | 0.013 | 0.223 | 0.018 | 0.246 | 0.018 |
| M17 | 0.489 | 0.102 | 0.332 | 0.035 | 0.429 | 0.029 | 0.412 | 0.048 | 0.410 | 0.044 |
| M18 | 0.032 | 0.005 | 0.025 | 0.003 | 0.027 | 0.002 | 0.026 | 0.004 | 0.023 | 0.002 |
| M19 | 0.086 | 0.014 | 0.063 | 0.008 | 0.094 | 0.008 | 0.098 | 0.012 | 0.114 | 0.017 |
| M20 | 0.086 | 0.013 | 0.070 | 0.006 | 0.068 | 0.004 | 0.069 | 0.006 | 0.071 | 0.006 |
| M21 | 0.294 | 0.044 | 0.236 | 0.017 | 0.247 | 0.014 | 0.222 | 0.018 | 0.236 | 0.018 |
| M22 | 1.054 | 0.220 | 0.788 | 0.079 | 0.930 | 0.067 | 0.933 | 0.102 | 0.906 | 0.104 |
| M23 | 0.022 | 0.003 | 0.019 | 0.001 | 0.019 | 0.001 | 0.020 | 0.003 | 0.017 | 0.001 |
| M24 | 0.077 | 0.014 | 0.063 | 0.008 | 0.086 | 0.007 | 0.088 | 0.010 | 0.103 | 0.016 |
| M25 | 0.205 | 0.014 | 0.195 | 0.017 | 0.274 | 0.018 | 0.310 | 0.025 | 0.374 | 0.031 |
| M26 | 0.091 | 0.011 | 0.082 | 0.005 | 0.096 | 0.003 | 0.109 | 0.009 | 0.114 | 0.009 |

TABLE 21

Ratio and T-test values between males of different ages

| Metabolite Code | 50-59 vs. 40-49, Male Ratio | ttest | 60-69 vs. 40-49, Male Ratio | ttest | 70+ vs. 40-49, Male Ratio | ttest |
|---|---|---|---|---|---|---|
| M01 | 0.955 | 6.0E−01 | 1.110 | 2.2E−01 | 1.097 | 2.4E−01 |
| M02 | 0.998 | 9.9E−01 | 1.024 | 8.8E−01 | 0.965 | 8.1E−01 |
| M03 | 1.125 | 2.3E−01 | 1.213 | 9.4E−02 | 1.296 | 5.0E−02 |
| M04 | 0.954 | 7.0E−01 | 1.019 | 9.1E−01 | 1.015 | 9.3E−01 |
| M05 | 0.953 | 6.3E−01 | 1.011 | 9.3E−01 | 0.979 | 8.5E−01 |
| M06 | 1.031 | 7.5E−01 | 0.976 | 8.3E−01 | 1.054 | 6.2E−01 |
| M07 | 1.198 | 2.4E−01 | 1.164 | 4.1E−01 | 1.133 | 4.8E−01 |
| M08 | 1.031 | 8.2E−01 | 1.014 | 9.4E−01 | 0.907 | 5.4E−01 |
| M09 | 1.443 | 2.7E−02 | 1.473 | 4.5E−02 | 1.701 | 2.1E−02 |
| M10 | 0.953 | 5.9E−01 | 1.061 | 5.9E−01 | 1.013 | 8.9E−01 |
| M11 | 0.992 | 9.3E−01 | 1.004 | 9.7E−01 | 1.058 | 5.6E−01 |
| M12 | 1.128 | 2.5E−01 | 1.147 | 2.5E−01 | 1.085 | 4.8E−01 |
| M13 | 1.007 | 9.4E−01 | 1.032 | 8.0E−01 | 0.921 | 4.4E−01 |
| M14 | 1.383 | 1.5E−02 | 1.536 | 7.0E−03 | 1.802 | 2.8E−03 |
| M15 | 0.987 | 8.9E−01 | 0.985 | 8.9E−01 | 1.020 | 8.5E−01 |
| M16 | 1.109 | 2.7E−01 | 1.013 | 9.1E−01 | 1.118 | 2.9E−01 |
| M17 | 1.291 | 5.4E−02 | 1.241 | 2.1E−01 | 1.235 | 1.9E−01 |
| M18 | 1.055 | 6.6E−01 | 1.032 | 8.7E−01 | 0.904 | 4.9E−01 |
| M19 | 1.484 | 1.9E−02 | 1.540 | 2.6E−02 | 1.789 | 1.9E−02 |
| M20 | 0.971 | 7.8E−01 | 0.976 | 8.4E−01 | 1.014 | 9.0E−01 |
| M21 | 1.048 | 6.3E−01 | 0.941 | 5.8E−01 | 1.000 | 1.0E+00 |
| M22 | 1.179 | 2.1E−01 | 1.183 | 2.9E−01 | 1.149 | 3.9E−01 |
| M23 | 1.008 | 9.3E−01 | 1.066 | 7.5E−01 | 0.900 | 3.6E−01 |
| M24 | 1.365 | 5.2E−02 | 1.403 | 6.0E−02 | 1.642 | 4.7E−02 |
| M25 | 1.405 | 9.0E−03 | 1.589 | 6.7E−04 | 1.912 | 1.7E−05 |
| M26 | 1.175 | 1.8E−02 | 1.324 | 1.7E−02 | 1.389 | 6.3E−03 |

TABLE 22

Effect of Age on Serum Ethanolamine Phospholipid Levels in Females

| Metabolite Code | Age Ctl, 30-39, Female Mean | SEM | Age Ctl, 40-49, Female Mean | SEM | Age Ctl, 50-59, Female Mean | SEM | Age Ctl, 60-69, Female Mean | SEM | Age Ctl, 70+ Female Mean | SEM |
|---|---|---|---|---|---|---|---|---|---|---|
| M01 | 0.103 | 0.012 | 0.114 | 0.006 | 0.105 | 0.006 | 0.127 | 0.007 | 0.126 | 0.009 |
| M02 | 0.047 | 0.006 | 0.069 | 0.006 | 0.058 | 0.004 | 0.058 | 0.004 | 0.056 | 0.004 |
| M03 | 0.095 | 0.015 | 0.101 | 0.007 | 0.093 | 0.005 | 0.091 | 0.006 | 0.100 | 0.005 |
| M04 | 0.028 | 0.005 | 0.033 | 0.003 | 0.025 | 0.002 | 0.023 | 0.002 | 0.026 | 0.002 |
| M05 | 0.011 | 0.002 | 0.013 | 0.001 | 0.010 | 0.000 | 0.010 | 0.001 | 0.011 | 0.001 |
| M06 | 0.031 | 0.005 | 0.031 | 0.002 | 0.025 | 0.001 | 0.023 | 0.001 | 0.025 | 0.002 |
| M07 | 0.061 | 0.010 | 0.071 | 0.007 | 0.057 | 0.003 | 0.051 | 0.005 | 0.052 | 0.005 |
| M08 | 0.008 | 0.001 | 0.010 | 0.001 | 0.007 | 0.000 | 0.006 | 0.001 | 0.006 | 0.001 |
| M09 | 0.021 | 0.004 | 0.021 | 0.002 | 0.020 | 0.001 | 0.017 | 0.002 | 0.019 | 0.002 |
| M10 | 0.050 | 0.007 | 0.059 | 0.003 | 0.049 | 0.002 | 0.052 | 0.003 | 0.051 | 0.003 |
| M11 | 0.120 | 0.018 | 0.119 | 0.008 | 0.100 | 0.004 | 0.099 | 0.006 | 0.100 | 0.008 |
| M12 | 0.196 | 0.022 | 0.222 | 0.015 | 0.191 | 0.009 | 0.181 | 0.011 | 0.188 | 0.013 |
| M13 | 0.013 | 0.001 | 0.015 | 0.001 | 0.012 | 0.001 | 0.011 | 0.001 | 0.012 | 0.001 |
| M14 | 0.040 | 0.007 | 0.043 | 0.004 | 0.042 | 0.003 | 0.041 | 0.003 | 0.049 | 0.004 |
| M15 | 0.071 | 0.009 | 0.079 | 0.005 | 0.068 | 0.003 | 0.066 | 0.004 | 0.069 | 0.004 |
| M16 | 0.274 | 0.044 | 0.268 | 0.021 | 0.226 | 0.011 | 0.210 | 0.013 | 0.232 | 0.017 |
| M17 | 0.419 | 0.076 | 0.458 | 0.053 | 0.392 | 0.024 | 0.354 | 0.036 | 0.360 | 0.033 |
| M18 | 0.028 | 0.004 | 0.032 | 0.003 | 0.025 | 0.002 | 0.019 | 0.002 | 0.023 | 0.003 |
| M19 | 0.107 | 0.024 | 0.100 | 0.012 | 0.099 | 0.007 | 0.087 | 0.009 | 0.103 | 0.008 |
| M20 | 0.074 | 0.013 | 0.075 | 0.006 | 0.063 | 0.003 | 0.063 | 0.004 | 0.068 | 0.005 |
| M21 | 0.294 | 0.057 | 0.275 | 0.024 | 0.228 | 0.012 | 0.210 | 0.014 | 0.229 | 0.020 |
| M22 | 0.938 | 0.170 | 1.025 | 0.108 | 0.853 | 0.055 | 0.759 | 0.068 | 0.837 | 0.096 |
| M23 | 0.021 | 0.003 | 0.022 | 0.002 | 0.017 | 0.001 | 0.015 | 0.001 | 0.017 | 0.002 |
| M24 | 0.102 | 0.025 | 0.093 | 0.011 | 0.089 | 0.006 | 0.081 | 0.008 | 0.096 | 0.008 |
| M25 | 0.239 | 0.023 | 0.236 | 0.014 | 0.277 | 0.012 | 0.326 | 0.022 | 0.373 | 0.020 |
| M26 | 0.091 | 0.012 | 0.093 | 0.006 | 0.093 | 0.003 | 0.094 | 0.004 | 0.107 | 0.007 |

TABLE 23

Ratio and T-test values between females of different ages

| Metabolite Code | 50-59 vs. 40-49, Female Ratio | ttest | 60-69 vs. 40-49, Female Ratio | ttest | 70+ vs. 40-49, Female Ratio | ttest |
|---|---|---|---|---|---|---|
| M01 | 0.925 | 3.7E−01 | 1.118 | 1.8E−01 | 1.110 | 2.6E−01 |
| M02 | 0.838 | 1.3E−01 | 0.835 | 9.5E−02 | 0.812 | 1.1E−01 |
| M03 | 0.927 | 4.0E−01 | 0.906 | 2.9E−01 | 0.989 | 9.0E−01 |
| M04 | 0.772 | 2.1E−02 | 0.709 | 5.1E−03 | 0.811 | 1.2E−01 |
| M05 | 0.811 | 1.1E−02 | 0.798 | 2.0E−02 | 0.832 | 8.7E−02 |
| M06 | 0.815 | 1.1E−02 | 0.731 | 1.5E−03 | 0.805 | 5.7E−02 |
| M07 | 0.798 | 3.4E−02 | 0.718 | 1.9E−02 | 0.726 | 4.9E−02 |
| M08 | 0.721 | 4.2E−03 | 0.569 | 1.3E−04 | 0.640 | 1.9E−02 |
| M09 | 0.934 | 5.8E−01 | 0.784 | 9.4E−02 | 0.912 | 5.6E−01 |
| M10 | 0.841 | 3.1E−02 | 0.882 | 1.3E−01 | 0.863 | 1.1E−01 |
| M11 | 0.843 | 2.3E−02 | 0.832 | 3.5E−02 | 0.843 | 1.1E−01 |
| M12 | 0.862 | 6.2E−02 | 0.815 | 2.5E−02 | 0.848 | 1.2E−01 |
| M13 | 0.806 | 8.8E−03 | 0.737 | 2.0E−03 | 0.839 | 1.3E−01 |
| M14 | 0.981 | 8.6E−01 | 0.953 | 6.9E−01 | 1.149 | 2.6E−01 |
| M15 | 0.864 | 5.6E−02 | 0.841 | 3.7E−02 | 0.871 | 1.5E−01 |
| M16 | 0.846 | 5.3E−02 | 0.786 | 1.5E−02 | 0.867 | 2.3E−01 |
| M17 | 0.856 | 2.0E−01 | 0.773 | 1.0E−01 | 0.786 | 1.9E−01 |
| M18 | 0.778 | 2.4E−02 | 0.594 | 1.8E−04 | 0.733 | 7.4E−02 |
| M19 | 0.986 | 9.2E−01 | 0.872 | 3.8E−01 | 1.030 | 8.5E−01 |
| M20 | 0.843 | 5.6E−02 | 0.842 | 9.5E−02 | 0.905 | 4.0E−01 |
| M21 | 0.829 | 5.0E−02 | 0.763 | 1.8E−02 | 0.832 | 1.9E−01 |
| M22 | 0.832 | 1.2E−01 | 0.741 | 3.3E−02 | 0.817 | 2.3E−01 |
| M23 | 0.797 | 1.5E−02 | 0.663 | 3.3E−04 | 0.776 | 7.4E−02 |
| M24 | 0.957 | 7.4E−01 | 0.871 | 3.6E−01 | 1.040 | 8.1E−01 |
| M25 | 1.176 | 4.8E−02 | 1.381 | 1.7E−03 | 1.581 | 2.4E−07 |
| M26 | 1.003 | 9.6E−01 | 1.021 | 7.9E−01 | 1.159 | 1.2E−01 |

TABLE 24

Effect of Dementia State on Serum Ethanolamine Phospholipid Levels in Females

| Metabolite Code | Cognitive Normal, Female Mean | SEM | SDAT_all, Female Mean | SEM | SDAT, ADAS 5-19, Female Mean | SEM | SDAT, ADAS 20-39, Female Mean | SEM | SDAT, ADAS 40-70, Female Mean | SEM |
|---|---|---|---|---|---|---|---|---|---|---|
| M01 | 0.118 | 0.005 | 0.113 | 0.003 | 0.109 | 0.004 | 0.112 | 0.005 | 0.118 | 0.006 |
| M02 | 0.062 | 0.005 | 0.053 | 0.002 | 0.050 | 0.003 | 0.057 | 0.004 | 0.052 | 0.004 |
| M03 | 0.099 | 0.005 | 0.076 | 0.002 | 0.080 | 0.004 | 0.076 | 0.004 | 0.073 | 0.004 |
| M04 | 0.026 | 0.002 | 0.025 | 0.001 | 0.024 | 0.002 | 0.027 | 0.002 | 0.024 | 0.003 |
| M05 | 0.011 | 0.001 | 0.009 | 0.000 | 0.010 | 0.001 | 0.009 | 0.001 | 0.009 | 0.001 |
| M06 | 0.027 | 0.001 | 0.022 | 0.001 | 0.024 | 0.001 | 0.023 | 0.001 | 0.020 | 0.001 |

TABLE 24-continued

Effect of Dementia State on Serum Ethanolamine Phospholipid Levels in Females

| Metabolite Code | Cognitive Normal, Female | | SDAT_all, Female | | SDAT, ADAS 5-19, Female | | SDAT, ADAS 20-39, Female | | SDAT, ADAS 40-70, Female | |
|---|---|---|---|---|---|---|---|---|---|---|
| | Mean | SEM | Mean | SEM | Mean | SEM | Mean | SEM | Mean | SEM |
| M07 | 0.056 | 0.005 | 0.041 | 0.002 | 0.044 | 0.004 | 0.042 | 0.004 | 0.036 | 0.003 |
| M08 | 0.006 | 0.001 | 0.005 | 0.000 | 0.005 | 0.000 | 0.006 | 0.001 | 0.005 | 0.000 |
| M09 | 0.019 | 0.002 | 0.013 | 0.001 | 0.015 | 0.001 | 0.014 | 0.001 | 0.012 | 0.001 |
| M10 | 0.054 | 0.003 | 0.048 | 0.001 | 0.049 | 0.002 | 0.047 | 0.002 | 0.048 | 0.003 |
| M11 | 0.105 | 0.004 | 0.088 | 0.003 | 0.094 | 0.004 | 0.090 | 0.005 | 0.080 | 0.004 |
| M12 | 0.196 | 0.012 | 0.153 | 0.005 | 0.166 | 0.009 | 0.152 | 0.010 | 0.142 | 0.010 |
| M13 | 0.013 | 0.001 | 0.010 | 0.000 | 0.011 | 0.000 | 0.010 | 0.001 | 0.010 | 0.001 |
| M14 | 0.046 | 0.003 | 0.035 | 0.002 | 0.040 | 0.003 | 0.034 | 0.002 | 0.033 | 0.003 |
| M15 | 0.073 | 0.004 | 0.059 | 0.002 | 0.061 | 0.003 | 0.061 | 0.003 | 0.056 | 0.003 |
| M16 | 0.250 | 0.013 | 0.192 | 0.007 | 0.214 | 0.013 | 0.201 | 0.012 | 0.164 | 0.008 |
| M17 | 0.408 | 0.033 | 0.288 | 0.015 | 0.317 | 0.026 | 0.304 | 0.026 | 0.247 | 0.021 |
| M18 | 0.024 | 0.002 | 0.018 | 0.001 | 0.019 | 0.001 | 0.019 | 0.002 | 0.016 | 0.001 |
| M19 | 0.103 | 0.008 | 0.071 | 0.004 | 0.079 | 0.007 | 0.072 | 0.006 | 0.063 | 0.006 |
| M20 | 0.077 | 0.004 | 0.059 | 0.002 | 0.064 | 0.004 | 0.060 | 0.004 | 0.054 | 0.003 |
| M21 | 0.265 | 0.015 | 0.195 | 0.008 | 0.219 | 0.015 | 0.205 | 0.015 | 0.165 | 0.011 |
| M22 | 0.933 | 0.077 | 0.702 | 0.036 | 0.753 | 0.061 | 0.738 | 0.066 | 0.620 | 0.057 |
| M23 | 0.018 | 0.001 | 0.014 | 0.001 | 0.015 | 0.001 | 0.014 | 0.001 | 0.013 | 0.001 |
| M24 | 0.103 | 0.009 | 0.073 | 0.004 | 0.079 | 0.008 | 0.073 | 0.007 | 0.067 | 0.008 |
| M25 | 0.241 | 0.013 | 0.211 | 0.007 | 0.218 | 0.013 | 0.212 | 0.014 | 0.204 | 0.011 |
| M26 | 0.069 | 0.003 | 0.073 | 0.002 | 0.076 | 0.003 | 0.072 | 0.004 | 0.072 | 0.003 |

TABLE 25

Ratio and T-test values between females of various levels of dementia

| Metabolite Code | AD, All to CN, Female | | ADAS 5-19 to CN, Female | | ADAS 20-39 to CN, Female | | ADAS 40-70 to CN, Female | |
|---|---|---|---|---|---|---|---|---|
| | Ratio | ttest | Ratio | ttest | Ratio | ttest | Ratio | ttest |
| M01 | 0.963 | 5.2E−01 | 0.929 | 2.1E−01 | 0.951 | 4.4E−01 | 1.004 | 9.6E−01 |
| M02 | 0.856 | 9.0E−02 | 0.806 | 4.5E−02 | 0.912 | 3.9E−01 | 0.833 | 1.2E−01 |
| M03 | 0.772 | 5.2E−05 | 0.814 | 6.0E−03 | 0.775 | 8.0E−04 | 0.737 | 1.8E−04 |
| M04 | 0.963 | 7.5E−01 | 0.912 | 3.8E−01 | 1.027 | 8.3E−01 | 0.932 | 6.2E−01 |
| M05 | 0.893 | 1.1E−01 | 0.925 | 3.4E−01 | 0.895 | 2.1E−01 | 0.867 | 8.4E−02 |
| M06 | 0.843 | 1.4E−02 | 0.910 | 2.2E−01 | 0.869 | 9.8E−02 | 0.761 | 5.1E−04 |
| M07 | 0.732 | 1.8E−03 | 0.798 | 5.9E−02 | 0.753 | 2.0E−02 | 0.656 | 1.1E−03 |
| M08 | 0.821 | 5.0E−02 | 0.849 | 1.4E−01 | 0.889 | 3.7E−01 | 0.722 | 4.7E−03 |
| M09 | 0.696 | 2.6E−04 | 0.777 | 3.9E−02 | 0.702 | 2.9E−03 | 0.624 | 4.3E−04 |
| M10 | 0.877 | 3.1E−02 | 0.895 | 8.6E−02 | 0.860 | 4.1E−02 | 0.883 | 9.8E−02 |
| M11 | 0.832 | 2.5E−03 | 0.894 | 7.5E−02 | 0.850 | 2.7E−02 | 0.762 | 1.4E−04 |
| M12 | 0.778 | 5.3E−04 | 0.847 | 4.2E−02 | 0.776 | 4.7E−03 | 0.726 | 5.8E−04 |
| M13 | 0.800 | 8.5E−04 | 0.834 | 2.5E−02 | 0.794 | 8.6E−03 | 0.780 | 3.2E−03 |
| M14 | 0.772 | 4.8E−03 | 0.869 | 1.9E−01 | 0.746 | 3.0E−03 | 0.724 | 5.6E−03 |
| M15 | 0.811 | 8.5E−04 | 0.835 | 1.5E−02 | 0.831 | 2.3E−02 | 0.770 | 4.4E−04 |
| M16 | 0.765 | 7.5E−05 | 0.853 | 4.3E−02 | 0.801 | 6.9E−03 | 0.656 | 6.4E−08 |
| M17 | 0.705 | 3.5E−04 | 0.776 | 3.2E−02 | 0.745 | 1.4E−02 | 0.605 | 4.3E−05 |
| M18 | 0.754 | 3.4E−03 | 0.804 | 5.9E−02 | 0.792 | 6.8E−02 | 0.673 | 7.9E−04 |
| M19 | 0.688 | 1.8E−04 | 0.768 | 2.5E−02 | 0.699 | 2.9E−03 | 0.612 | 7.0E−05 |
| M20 | 0.768 | 4.9E−04 | 0.828 | 3.0E−02 | 0.782 | 1.1E−02 | 0.703 | 4.8E−05 |
| M21 | 0.737 | 1.9E−04 | 0.826 | 3.7E−02 | 0.776 | 1.1E−02 | 0.624 | 6.8E−07 |
| M22 | 0.752 | 5.2E−03 | 0.807 | 7.0E−02 | 0.790 | 6.1E−02 | 0.665 | 1.3E−03 |
| M23 | 0.764 | 2.5E−03 | 0.809 | 3.2E−02 | 0.789 | 4.1E−02 | 0.699 | 7.8E−04 |
| M24 | 0.708 | 2.5E−03 | 0.768 | 4.5E−02 | 0.713 | 9.3E−03 | 0.654 | 4.2E−03 |
| M25 | 0.876 | 6.6E−02 | 0.907 | 2.3E−01 | 0.880 | 1.5E−01 | 0.847 | 3.5E−02 |
| M26 | 1.056 | 3.8E−01 | 1.092 | 1.8E−01 | 1.043 | 5.8E−01 | 1.041 | 5.5E−01 |

TABLE 26

Ratio and T-test values between females of various levels of dementia

| Metabolite Code | ADAS 20-39 to 5-19, Female Ratio | ttest | ADAS 40-70 to 5-19, Female Ratio | ttest | ADAS 40-70 to 20-39, Female Ratio | ttest |
|---|---|---|---|---|---|---|
| M01 | 1.023 | 7.2E-01 | 1.080 | 2.8E-01 | 1.056 | 4.4E-01 |
| M02 | 1.132 | 2.3E-01 | 1.034 | 7.6E-01 | 0.914 | 4.1E-01 |
| M03 | 0.951 | 5.1E-01 | 0.906 | 2.2E-01 | 0.952 | 5.3E-01 |
| M04 | 1.126 | 3.6E-01 | 1.022 | 8.8E-01 | 0.907 | 5.0E-01 |
| M05 | 0.967 | 7.0E-01 | 0.936 | 4.2E-01 | 0.968 | 7.1E-01 |
| M06 | 0.955 | 5.9E-01 | 0.837 | 2.5E-02 | 0.876 | 1.2E-01 |
| M07 | 0.944 | 6.4E-01 | 0.822 | 1.2E-01 | 0.871 | 2.8E-01 |
| M08 | 1.046 | 7.2E-01 | 0.850 | 1.1E-01 | 0.812 | 1.1E-01 |
| M09 | 0.903 | 3.9E-01 | 0.802 | 9.5E-02 | 0.889 | 3.5E-01 |
| M10 | 0.961 | 5.8E-01 | 0.987 | 8.6E-01 | 1.027 | 7.2E-01 |
| M11 | 0.951 | 5.1E-01 | 0.853 | 2.8E-02 | 0.896 | 1.6E-01 |
| M12 | 0.917 | 3.1E-01 | 0.858 | 7.7E-02 | 0.935 | 4.7E-01 |
| M13 | 0.953 | 5.4E-01 | 0.936 | 3.6E-01 | 0.982 | 8.2E-01 |
| M14 | 0.858 | 1.6E-01 | 0.833 | 1.5E-01 | 0.971 | 8.0E-01 |
| M15 | 0.996 | 9.6E-01 | 0.922 | 2.3E-01 | 0.926 | 3.1E-01 |
| M16 | 0.940 | 4.7E-01 | 0.769 | 9.7E-04 | 0.819 | 1.6E-02 |
| M17 | 0.960 | 7.4E-01 | 0.779 | 4.0E-02 | 0.812 | 9.8E-02 |
| M18 | 0.985 | 9.0E-01 | 0.837 | 7.6E-02 | 0.850 | 1.8E-01 |
| M19 | 0.911 | 4.7E-01 | 0.798 | 8.5E-02 | 0.875 | 3.1E-01 |
| M20 | 0.945 | 5.7E-01 | 0.849 | 5.8E-02 | 0.898 | 2.7E-01 |
| M21 | 0.939 | 5.5E-01 | 0.755 | 4.6E-03 | 0.804 | 4.1E-02 |
| M22 | 0.979 | 8.7E-01 | 0.824 | 1.2E-01 | 0.841 | 1.9E-01 |
| M23 | 0.975 | 8.3E-01 | 0.864 | 1.4E-01 | 0.886 | 3.0E-01 |
| M24 | 0.928 | 6.0E-01 | 0.852 | 3.2E-01 | 0.918 | 5.8E-01 |
| M25 | 0.971 | 7.5E-01 | 0.934 | 4.0E-01 | 0.962 | 6.6E-01 |
| M26 | 0.955 | 5.2E-01 | 0.954 | 4.5E-01 | 0.998 | 9.8E-01 |

TABLE 27

Average Serum Ethanolamine Phospholipid Levels in Males of Different Levels of Dementia Severity

| Metabolite Code | Cognitive Normal, Male Mean | SEM | SDAT_all, Male Mean | SEM | SDAT, ADAS 5-19, Male Mean | SEM | SDAT, ADAS 20-39, Male Mean | SEM | SDAT, ADAS 40-70, Male Mean | SEM |
|---|---|---|---|---|---|---|---|---|---|---|
| M01 | 0.116 | 0.006 | 0.119 | 0.004 | 0.117 | 0.006 | 0.117 | 0.006 | 0.117 | 0.011 |
| M02 | 0.066 | 0.006 | 0.056 | 0.004 | 0.060 | 0.009 | 0.054 | 0.004 | 0.046 | 0.006 |
| M03 | 0.109 | 0.007 | 0.084 | 0.004 | 0.091 | 0.006 | 0.080 | 0.005 | 0.072 | 0.007 |
| M04 | 0.030 | 0.002 | 0.026 | 0.002 | 0.025 | 0.004 | 0.027 | 0.002 | 0.022 | 0.003 |
| M05 | 0.012 | 0.001 | 0.010 | 0.000 | 0.011 | 0.001 | 0.010 | 0.001 | 0.010 | 0.001 |
| M06 | 0.028 | 0.002 | 0.025 | 0.001 | 0.024 | 0.002 | 0.025 | 0.002 | 0.024 | 0.002 |
| M07 | 0.062 | 0.005 | 0.044 | 0.002 | 0.047 | 0.004 | 0.044 | 0.003 | 0.036 | 0.004 |
| M08 | 0.007 | 0.001 | 0.005 | 0.000 | 0.006 | 0.001 | 0.005 | 0.000 | 0.004 | 0.001 |
| M09 | 0.022 | 0.002 | 0.015 | 0.001 | 0.016 | 0.002 | 0.015 | 0.001 | 0.011 | 0.001 |
| M10 | 0.054 | 0.002 | 0.052 | 0.002 | 0.053 | 0.003 | 0.051 | 0.002 | 0.047 | 0.005 |
| M11 | 0.110 | 0.005 | 0.095 | 0.004 | 0.095 | 0.007 | 0.095 | 0.006 | 0.088 | 0.009 |
| M12 | 0.205 | 0.011 | 0.162 | 0.006 | 0.170 | 0.011 | 0.160 | 0.008 | 0.141 | 0.013 |
| M13 | 0.013 | 0.001 | 0.011 | 0.000 | 0.011 | 0.001 | 0.010 | 0.001 | 0.010 | 0.001 |
| M14 | 0.051 | 0.004 | 0.036 | 0.002 | 0.041 | 0.004 | 0.034 | 0.002 | 0.028 | 0.003 |
| M15 | 0.076 | 0.004 | 0.064 | 0.002 | 0.067 | 0.005 | 0.062 | 0.003 | 0.060 | 0.006 |
| M16 | 0.266 | 0.015 | 0.207 | 0.009 | 0.213 | 0.015 | 0.202 | 0.012 | 0.191 | 0.018 |
| M17 | 0.470 | 0.038 | 0.302 | 0.015 | 0.338 | 0.031 | 0.292 | 0.020 | 0.242 | 0.026 |
| M18 | 0.026 | 0.003 | 0.019 | 0.001 | 0.020 | 0.002 | 0.018 | 0.001 | 0.016 | 0.002 |
| M19 | 0.127 | 0.013 | 0.078 | 0.004 | 0.088 | 0.009 | 0.076 | 0.006 | 0.056 | 0.006 |
| M20 | 0.078 | 0.005 | 0.064 | 0.003 | 0.069 | 0.005 | 0.061 | 0.003 | 0.059 | 0.007 |
| M21 | 0.265 | 0.017 | 0.217 | 0.010 | 0.226 | 0.019 | 0.211 | 0.014 | 0.201 | 0.023 |
| M22 | 1.040 | 0.087 | 0.736 | 0.037 | 0.789 | 0.071 | 0.723 | 0.052 | 0.624 | 0.067 |
| M23 | 0.018 | 0.001 | 0.015 | 0.001 | 0.016 | 0.001 | 0.014 | 0.001 | 0.013 | 0.001 |
| M24 | 0.116 | 0.012 | 0.079 | 0.005 | 0.090 | 0.010 | 0.075 | 0.006 | 0.061 | 0.008 |
| M25 | 0.240 | 0.017 | 0.218 | 0.009 | 0.249 | 0.018 | 0.208 | 0.010 | 0.183 | 0.017 |
| M26 | 0.072 | 0.003 | 0.070 | 0.002 | 0.074 | 0.004 | 0.070 | 0.003 | 0.065 | 0.006 |

TABLE 28

Ratio and T-test Values Between Males of Various Levels of Dementia

| Metabolite Code | AD, All to CN, Male Ratio | ttest | ADAS 5-19 to CN, Male Ratio | ttest | ADAS 20-39 to CN, Male Ratio | ttest | ADAS 40-70 to CN, Male Ratio | ttest |
|---|---|---|---|---|---|---|---|---|
| M01 | 1.028 | 7.1E-01 | 1.011 | 8.9E-01 | 1.016 | 8.3E-01 | 1.014 | 8.9E-01 |
| M02 | 0.845 | 2.1E-01 | 0.898 | 5.5E-01 | 0.816 | 7.5E-02 | 0.690 | 2.4E-02 |
| M03 | 0.769 | 1.6E-03 | 0.836 | 6.9E-02 | 0.735 | 6.4E-04 | 0.655 | 1.4E-03 |
| M04 | 0.882 | 3.9E-01 | 0.836 | 2.9E-01 | 0.896 | 4.1E-01 | 0.726 | 2.7E-02 |
| M05 | 0.882 | 1.3E-01 | 0.896 | 2.7E-01 | 0.865 | 9.1E-02 | 0.836 | 1.5E-01 |
| M06 | 0.877 | 1.3E-01 | 0.855 | 9.1E-02 | 0.876 | 1.6E-01 | 0.856 | 1.4E-01 |
| M07 | 0.709 | 3.9E-04 | 0.753 | 1.8E-02 | 0.704 | 1.6E-03 | 0.589 | 1.1E-03 |

TABLE 28-continued

Ratio and T-test Values Between Males of Various Levels of Dementia

| Metabolite Code | AD, All to CN, Male | | ADAS 5-19 to CN, Male | | ADAS 20-39 to CN, Male | | ADAS 40-70 to CN, Male | |
|---|---|---|---|---|---|---|---|---|
| | Ratio | ttest | Ratio | ttest | Ratio | ttest | Ratio | ttest |
| M08 | 0.759 | 1.9E−02 | 0.806 | 1.8E−01 | 0.755 | 2.1E−02 | 0.629 | 1.5E−02 |
| M09 | 0.658 | 2.7E−04 | 0.731 | 2.7E−02 | 0.654 | 1.4E−03 | 0.472 | 2.2E−04 |
| M10 | 0.960 | 6.0E−01 | 0.978 | 7.9E−01 | 0.942 | 4.0E−01 | 0.877 | 1.7E−01 |
| M11 | 0.866 | 9.3E−02 | 0.861 | 1.1E−01 | 0.861 | 8.1E−02 | 0.798 | 2.6E−02 |
| M12 | 0.793 | 1.8E−03 | 0.831 | 3.9E−02 | 0.783 | 2.2E−03 | 0.686 | 8.3E−04 |
| M13 | 0.850 | 2.7E−02 | 0.890 | 1.8E−01 | 0.827 | 1.3E−02 | 0.786 | 1.8E−02 |
| M14 | 0.704 | 3.7E−04 | 0.800 | 6.9E−02 | 0.666 | 1.1E−04 | 0.553 | 2.3E−04 |
| M15 | 0.842 | 2.2E−02 | 0.883 | 1.8E−01 | 0.810 | 3.0E−03 | 0.784 | 1.9E−02 |
| M16 | 0.778 | 1.6E−03 | 0.802 | 1.7E−02 | 0.759 | 1.2E−03 | 0.718 | 3.2E−03 |
| M17 | 0.644 | 4.5E−06 | 0.718 | 7.5E−03 | 0.621 | 1.3E−05 | 0.515 | 1.0E−04 |
| M18 | 0.708 | 1.6E−03 | 0.758 | 6.0E−02 | 0.689 | 2.0E−03 | 0.613 | 7.7E−03 |
| M19 | 0.611 | 1.0E−05 | 0.688 | 1.1E−02 | 0.596 | 6.1E−05 | 0.442 | 2.0E−04 |
| M20 | 0.826 | 2.3E−02 | 0.892 | 2.7E−01 | 0.786 | 6.1E−03 | 0.762 | 3.9E−02 |
| M21 | 0.818 | 2.7E−02 | 0.852 | 1.3E−01 | 0.796 | 2.0E−02 | 0.757 | 2.9E−02 |
| M22 | 0.708 | 4.4E−04 | 0.758 | 2.7E−02 | 0.695 | 1.3E−03 | 0.600 | 1.9E−03 |
| M23 | 0.801 | 1.1E−02 | 0.857 | 1.6E−01 | 0.776 | 4.0E−03 | 0.723 | 8.6E−03 |
| M24 | 0.680 | 1.1E−03 | 0.777 | 9.8E−02 | 0.647 | 1.3E−03 | 0.524 | 2.8E−03 |
| M25 | 0.909 | 2.4E−01 | 1.035 | 7.4E−01 | 0.865 | 8.0E−02 | 0.760 | 3.0E−02 |
| M26 | 0.978 | 7.4E−01 | 1.023 | 7.5E−01 | 0.968 | 6.5E−01 | 0.907 | 2.9E−01 |

TABLE 29

Ratio and T-test Values Between Males of Various Levels of Dementia

| Metabolite Code | ADAS 20-39 to 5-19, Male | | ADAS 40-70 to 5-19, Male | | ADAS 40-70 to 20-39, Male | |
|---|---|---|---|---|---|---|
| | Ratio | ttest | Ratio | ttest | Ratio | ttest |
| M01 | 1.005 | 9.4E−01 | 1.003 | 9.8E−01 | 0.998 | 9.8E−01 |
| M02 | 0.908 | 5.3E−01 | 0.768 | 3.2E−01 | 0.846 | 2.8E−01 |
| M03 | 0.880 | 1.5E−01 | 0.784 | 7.0E−02 | 0.891 | 3.4E−01 |
| M04 | 1.072 | 6.8E−01 | 0.868 | 5.8E−01 | 0.810 | 2.8E−01 |
| M05 | 0.966 | 7.0E−01 | 0.933 | 6.1E−01 | 0.966 | 7.7E−01 |
| M06 | 1.024 | 8.1E−01 | 1.001 | 9.9E−01 | 0.978 | 8.6E−01 |
| M07 | 0.935 | 5.5E−01 | 0.783 | 1.3E−01 | 0.837 | 2.5E−01 |
| M08 | 0.936 | 6.3E−01 | 0.780 | 2.7E−01 | 0.833 | 2.4E−01 |
| M09 | 0.895 | 4.2E−01 | 0.646 | 3.3E−02 | 0.721 | 1.0E−01 |
| M10 | 0.963 | 6.3E−01 | 0.897 | 3.7E−01 | 0.932 | 5.0E−01 |
| M11 | 1.000 | 1.0E+00 | 0.927 | 5.7E−01 | 0.927 | 5.4E−01 |
| M12 | 0.942 | 4.8E−01 | 0.826 | 1.3E−01 | 0.877 | 2.4E−01 |
| M13 | 0.930 | 3.8E−01 | 0.883 | 3.2E−01 | 0.950 | 6.3E−01 |
| M14 | 0.832 | 1.1E−01 | 0.691 | 4.5E−02 | 0.830 | 2.0E−01 |
| M15 | 0.917 | 3.0E−01 | 0.888 | 3.7E−01 | 0.968 | 7.4E−01 |
| M16 | 0.947 | 5.4E−01 | 0.895 | 3.9E−01 | 0.946 | 6.4E−01 |
| M17 | 0.865 | 1.9E−01 | 0.716 | 5.6E−02 | 0.828 | 1.9E−01 |
| M18 | 0.909 | 4.5E−01 | 0.809 | 2.8E−01 | 0.890 | 4.4E−01 |
| M19 | 0.866 | 2.5E−01 | 0.642 | 3.1E−02 | 0.741 | 7.4E−02 |
| M20 | 0.880 | 1.6E−01 | 0.854 | 2.7E−01 | 0.970 | 8.0E−01 |
| M21 | 0.934 | 5.2E−01 | 0.889 | 4.4E−01 | 0.952 | 7.2E−01 |
| M22 | 0.917 | 4.5E−01 | 0.791 | 1.6E−01 | 0.863 | 3.3E−01 |
| M23 | 0.906 | 3.3E−01 | 0.844 | 2.8E−01 | 0.931 | 5.6E−01 |
| M24 | 0.833 | 1.7E−01 | 0.674 | 5.9E−02 | 0.810 | 2.3E−01 |
| M25 | 0.836 | 3.7E−02 | 0.735 | 2.8E−02 | 0.879 | 2.1E−01 |
| M26 | 0.946 | 4.3E−01 | 0.887 | 2.3E−01 | 0.937 | 5.2E−01 |

TABLE 30

Effect of Pathology State on Serum Ethanolamine Phospholipid Levels in Males

| Metabolite Code | Post Mortem Ctl, Male | | Post Mortem SDAT Male | | SDAT vs Control | |
|---|---|---|---|---|---|---|
| | Mean | SEM | Mean | SEM | Ratio | ttest |
| M01 | 0.127 | 0.017 | 0.089 | 0.013 | 0.702 | 0.091 |
| M02 | 0.046 | 0.006 | 0.026 | 0.005 | 0.568 | 0.022 |
| M03 | 0.059 | 0.006 | 0.036 | 0.006 | 0.610 | 0.014 |
| M04 | 0.017 | 0.004 | 0.007 | 0.002 | 0.420 | 0.024 |
| M05 | 0.006 | 0.001 | 0.004 | 0.000 | 0.479 | 0.019 |
| M06 | 0.009 | 0.001 | 0.006 | 0.001 | 0.475 | 0.005 |
| M07 | 0.012 | 0.003 | 0.009 | 0.001 | 0.451 | 0.033 |
| M08 | 0.003 | 0.001 | 0.002 | 0.000 | 0.410 | 0.015 |
| M09 | 0.006 | 0.002 | 0.003 | 0.001 | 0.269 | 0.048 |
| M10 | 0.041 | 0.005 | 0.036 | 0.006 | 0.608 | 0.019 |
| M11 | 0.052 | 0.006 | 0.041 | 0.006 | 0.474 | 0.001 |
| M12 | 0.094 | 0.013 | 0.084 | 0.012 | 0.587 | 0.024 |
| M13 | 0.009 | 0.001 | 0.008 | 0.001 | 0.576 | 0.008 |
| M14 | 0.025 | 0.005 | 0.021 | 0.007 | 0.429 | 0.009 |
| M15 | 0.045 | 0.005 | 0.029 | 0.004 | 0.648 | 0.026 |
| M16 | 0.092 | 0.012 | 0.053 | 0.007 | 0.570 | 0.012 |
| M17 | 0.097 | 0.021 | 0.047 | 0.007 | 0.489 | 0.036 |
| M18 | 0.010 | 0.001 | 0.005 | 0.001 | 0.521 | 0.004 |
| M19 | 0.032 | 0.006 | 0.014 | 0.002 | 0.452 | 0.011 |
| M20 | 0.031 | 0.004 | 0.017 | 0.002 | 0.542 | 0.006 |
| M21 | 0.072 | 0.011 | 0.033 | 0.006 | 0.464 | 0.006 |
| M22 | 0.217 | 0.040 | 0.106 | 0.017 | 0.486 | 0.020 |
| M23 | 0.009 | 0.001 | 0.005 | 0.001 | 0.565 | 0.005 |
| M24 | 0.029 | 0.004 | 0.013 | 0.003 | 0.448 | 0.007 |
| M25 | 0.238 | 0.023 | 0.180 | 0.026 | 0.757 | 0.114 |
| M26 | 0.073 | 0.008 | 0.050 | 0.006 | 0.684 | 0.034 |

TABLE 31

Effect of Pathology State on Serum Ethanolamine Phospholipid Levels in Females

| Metabolite Code | Post Mortem Ctl, Female | | Post Mortem SDAT Female | | Autopsy AD vs. Control, Female | |
|---|---|---|---|---|---|---|
| | Mean | SEM | Mean | SEM | Ratio | ttest |
| M01 | 0.179 | 0.050 | 0.124 | 0.016 | 0.697 | 0.300 |
| M02 | 0.062 | 0.022 | 0.048 | 0.011 | 0.773 | 0.557 |

TABLE 31-continued

Effect of Pathology State on Serum Ethanolamine Phospholipid Levels in Females

| Metabolite Code | Post Mortem Ctl, Female Mean | SEM | Post Mortem SDAT Female Mean | SEM | Autopsy AD vs. Control, Female Ratio | ttest |
|---|---|---|---|---|---|---|
| M03 | 0.070 | 0.019 | 0.043 | 0.005 | 0.619 | 0.178 |
| M04 | 0.016 | 0.005 | 0.012 | 0.004 | 0.775 | 0.563 |
| M05 | 0.007 | 0.002 | 0.003 | 0.001 | 0.508 | 0.095 |
| M06 | 0.011 | 0.003 | 0.004 | 0.001 | 0.531 | 0.060 |
| M07 | 0.016 | 0.003 | 0.005 | 0.001 | 0.530 | 0.037 |
| M08 | 0.003 | 0.001 | 0.001 | 0.000 | 0.684 | 0.258 |
| M09 | 0.005 | 0.001 | 0.002 | 0.000 | 0.566 | 0.047 |
| M10 | 0.053 | 0.015 | 0.025 | 0.004 | 0.672 | 0.293 |
| M11 | 0.064 | 0.013 | 0.025 | 0.004 | 0.650 | 0.132 |
| M12 | 0.114 | 0.021 | 0.055 | 0.008 | 0.742 | 0.241 |
| M13 | 0.010 | 0.002 | 0.005 | 0.001 | 0.865 | 0.537 |
| M14 | 0.023 | 0.004 | 0.011 | 0.002 | 0.904 | 0.792 |
| M15 | 0.060 | 0.017 | 0.034 | 0.004 | 0.577 | 0.151 |
| M16 | 0.107 | 0.021 | 0.064 | 0.008 | 0.594 | 0.061 |
| M17 | 0.113 | 0.024 | 0.067 | 0.009 | 0.592 | 0.079 |
| M18 | 0.014 | 0.004 | 0.008 | 0.001 | 0.579 | 0.186 |
| M19 | 0.035 | 0.007 | 0.022 | 0.004 | 0.635 | 0.132 |
| M20 | 0.050 | 0.014 | 0.021 | 0.002 | 0.410 | 0.042 |
| M21 | 0.100 | 0.020 | 0.041 | 0.007 | 0.414 | 0.010 |
| M22 | 0.283 | 0.058 | 0.168 | 0.024 | 0.593 | 0.071 |
| M23 | 0.012 | 0.003 | 0.007 | 0.001 | 0.560 | 0.112 |
| M24 | 0.035 | 0.007 | 0.018 | 0.002 | 0.496 | 0.025 |
| M25 | 0.189 | 0.015 | 0.198 | 0.022 | 1.051 | 0.727 |
| M26 | 0.054 | 0.008 | 0.061 | 0.006 | 1.123 | 0.496 |

TABLE 32

Effect of Age on Ethanolamine Phospholipid Ratios to M01 in Males

| Metabolite Code | Age Ctl, 30-39, Male Mean | SEM | Age Ctl, 40-49, Male Mean | SEM | Age Ctl, 50-59, Male Mean | SEM | Age Ctl, 60-69, Male Mean | SEM | Age Ctl, 70+ Male Mean | SEM |
|---|---|---|---|---|---|---|---|---|---|---|
| M01 | 1.000 | 0.000 | 1.000 | 0.000 | 1.000 | 0.000 | 1.000 | 0.000 | 1.000 | 0.000 |
| M02 | 0.476 | 0.042 | 0.477 | 0.034 | 0.517 | 0.027 | 0.431 | 0.031 | 0.420 | 0.028 |
| M03 | 0.863 | 0.063 | 0.751 | 0.049 | 0.864 | 0.030 | 0.792 | 0.051 | 0.848 | 0.071 |
| M04 | 0.224 | 0.025 | 0.229 | 0.026 | 0.235 | 0.013 | 0.203 | 0.019 | 0.204 | 0.017 |
| M05 | 0.113 | 0.008 | 0.102 | 0.007 | 0.101 | 0.004 | 0.091 | 0.005 | 0.088 | 0.005 |
| M06 | 0.263 | 0.029 | 0.234 | 0.021 | 0.243 | 0.012 | 0.199 | 0.016 | 0.210 | 0.012 |
| M07 | 0.683 | 0.136 | 0.493 | 0.070 | 0.581 | 0.041 | 0.479 | 0.052 | 0.457 | 0.039 |
| M08 | 0.079 | 0.010 | 0.064 | 0.007 | 0.067 | 0.004 | 0.054 | 0.005 | 0.049 | 0.004 |
| M09 | 0.161 | 0.025 | 0.124 | 0.017 | 0.173 | 0.013 | 0.154 | 0.018 | 0.172 | 0.024 |
| M10 | 0.464 | 0.025 | 0.454 | 0.022 | 0.445 | 0.012 | 0.419 | 0.018 | 0.407 | 0.016 |
| M11 | 1.063 | 0.111 | 0.899 | 0.069 | 0.908 | 0.037 | 0.789 | 0.052 | 0.811 | 0.038 |
| M12 | 2.068 | 0.251 | 1.728 | 0.168 | 1.942 | 0.099 | 1.664 | 0.111 | 1.552 | 0.087 |
| M13 | 0.126 | 0.009 | 0.117 | 0.009 | 0.121 | 0.005 | 0.102 | 0.006 | 0.092 | 0.005 |
| M14 | 0.294 | 0.033 | 0.242 | 0.029 | 0.332 | 0.020 | 0.316 | 0.029 | 0.363 | 0.041 |
| M15 | 0.699 | 0.034 | 0.658 | 0.041 | 0.675 | 0.023 | 0.567 | 0.031 | 0.590 | 0.029 |
| M16 | 2.429 | 0.285 | 2.020 | 0.175 | 2.284 | 0.118 | 1.778 | 0.145 | 1.922 | 0.112 |
| M17 | 4.127 | 0.757 | 3.164 | 0.418 | 3.980 | 0.257 | 3.167 | 0.320 | 3.178 | 0.294 |
| M18 | 0.258 | 0.025 | 0.229 | 0.025 | 0.244 | 0.014 | 0.195 | 0.021 | 0.174 | 0.014 |
| M19 | 0.725 | 0.101 | 0.607 | 0.094 | 0.865 | 0.063 | 0.769 | 0.085 | 0.881 | 0.131 |
| M20 | 0.691 | 0.049 | 0.616 | 0.043 | 0.619 | 0.030 | 0.529 | 0.034 | 0.553 | 0.034 |
| M21 | 2.395 | 0.215 | 2.163 | 0.189 | 2.287 | 0.122 | 1.773 | 0.148 | 1.840 | 0.108 |
| M22 | 8.811 | 1.529 | 7.346 | 0.883 | 8.537 | 0.549 | 7.124 | 0.644 | 6.920 | 0.635 |
| M23 | 0.189 | 0.019 | 0.175 | 0.016 | 0.178 | 0.009 | 0.150 | 0.016 | 0.133 | 0.008 |
| M24 | 0.649 | 0.086 | 0.606 | 0.098 | 0.787 | 0.057 | 0.700 | 0.072 | 0.799 | 0.122 |
| M25 | 2.182 | 0.444 | 1.975 | 0.265 | 2.747 | 0.211 | 2.608 | 0.251 | 3.066 | 0.284 |

TABLE 33

Ratio and T-test values of Ethanolamine Phospholipid Ratios to M01 between males of different ages

| Metabolite Code | 50-59 vs. 40-49, Male Ratio | ttest | 60-69 vs. 40-49, Male Ratio | ttest | 70+ vs. 40-49, Male Ratio | ttest |
|---|---|---|---|---|---|---|
| M01 | 1.000 | #DIV/0! | 1.000 | #DIV/0! | 1.000 | #DIV/0! |
| M02 | 1.082 | 3.9E-01 | 0.903 | 3.2E-01 | 0.879 | 1.9E-01 |
| M03 | 1.149 | 4.5E-02 | 1.054 | 5.8E-01 | 1.128 | 3.0E-01 |
| M04 | 1.023 | 8.4E-01 | 0.883 | 4.0E-01 | 0.889 | 3.9E-01 |
| M05 | 0.984 | 8.3E-01 | 0.884 | 1.6E-01 | 0.863 | 8.5E-02 |
| M06 | 1.041 | 6.8E-01 | 0.851 | 1.9E-01 | 0.898 | 3.1E-01 |
| M07 | 1.177 | 2.6E-01 | 0.970 | 8.6E-01 | 0.927 | 6.4E-01 |
| M08 | 1.053 | 6.7E-01 | 0.847 | 2.6E-01 | 0.765 | 5.4E-02 |
| M09 | 1.404 | 2.5E-02 | 1.243 | 2.4E-01 | 1.391 | 1.3E-01 |
| M10 | 0.981 | 7.1E-01 | 0.924 | 2.3E-01 | 0.896 | 7.6E-02 |
| M11 | 1.010 | 9.0E-01 | 0.878 | 2.0E-01 | 0.903 | 2.5E-01 |
| M12 | 1.124 | 2.5E-01 | 0.963 | 7.4E-01 | 0.898 | 3.3E-01 |
| M13 | 1.035 | 6.7E-01 | 0.873 | 1.7E-01 | 0.787 | 1.3E-02 |
| M14 | 1.372 | 1.2E-02 | 1.306 | 7.7E-02 | 1.500 | 2.7E-02 |
| M15 | 1.026 | 7.0E-01 | 0.862 | 7.8E-02 | 0.896 | 1.7E-01 |
| M16 | 1.131 | 2.1E-01 | 0.880 | 2.9E-01 | 0.951 | 6.2E-01 |
| M17 | 1.258 | 8.8E-02 | 1.001 | 1.0E+00 | 1.004 | 9.8E-01 |
| M18 | 1.067 | 5.6E-01 | 0.851 | 3.0E-01 | 0.761 | 4.9E-02 |
| M19 | 1.426 | 2.4E-02 | 1.266 | 2.1E-01 | 1.451 | 1.1E-01 |
| M20 | 1.004 | 9.6E-01 | 0.858 | 1.1E-01 | 0.898 | 2.5E-01 |
| M21 | 1.057 | 5.8E-01 | 0.820 | 1.0E-01 | 0.851 | 1.2E-01 |
| M22 | 1.162 | 2.4E-01 | 0.970 | 8.4E-01 | 0.942 | 6.9E-01 |
| M23 | 1.016 | 8.7E-01 | 0.858 | 2.8E-01 | 0.759 | 1.5E-02 |
| M24 | 1.300 | 9.4E-02 | 1.156 | 4.3E-01 | 1.319 | 2.4E-01 |
| M25 | 1.391 | 3.5E-02 | 1.321 | 9.0E-02 | 1.553 | 8.2E-03 |

TABLE 34

Effect of Age on Ethanolamine Phospholipid Ratios to M01 in Females

| Metabolite Code | Age Ctl, 30-39, Female Mean | SEM | Age Ctl, 40-49, Female Mean | SEM | Age Ctl, 50-59, Female Mean | SEM | Age Ctl, 60-69, Female Mean | SEM | Age Ctl, 70+ Female Mean | SEM |
|---|---|---|---|---|---|---|---|---|---|---|
| M01 | 1.000 | 0.000 | 1.000 | 0.000 | 1.000 | 0.000 | 1.000 | 0.000 | 1.000 | 0.000 |
| M02 | 0.474 | 0.037 | 0.597 | 0.028 | 0.551 | 0.020 | 0.460 | 0.018 | 0.455 | 0.023 |
| M03 | 0.931 | 0.089 | 0.911 | 0.043 | 0.926 | 0.030 | 0.750 | 0.034 | 0.838 | 0.048 |
| M04 | 0.279 | 0.036 | 0.283 | 0.017 | 0.241 | 0.011 | 0.184 | 0.010 | 0.221 | 0.020 |
| M05 | 0.112 | 0.009 | 0.118 | 0.006 | 0.105 | 0.003 | 0.085 | 0.005 | 0.089 | 0.006 |
| M06 | 0.311 | 0.044 | 0.291 | 0.019 | 0.261 | 0.010 | 0.193 | 0.012 | 0.213 | 0.017 |
| M07 | 0.618 | 0.090 | 0.667 | 0.056 | 0.582 | 0.030 | 0.435 | 0.039 | 0.430 | 0.041 |
| M08 | 0.079 | 0.008 | 0.089 | 0.007 | 0.070 | 0.003 | 0.047 | 0.004 | 0.052 | 0.007 |
| M09 | 0.204 | 0.036 | 0.194 | 0.017 | 0.197 | 0.011 | 0.139 | 0.012 | 0.163 | 0.015 |
| M10 | 0.491 | 0.027 | 0.535 | 0.024 | 0.490 | 0.010 | 0.424 | 0.015 | 0.422 | 0.022 |
| M11 | 1.220 | 0.159 | 1.092 | 0.060 | 1.021 | 0.031 | 0.823 | 0.037 | 0.840 | 0.058 |
| M12 | 1.979 | 0.150 | 2.044 | 0.117 | 1.952 | 0.063 | 1.534 | 0.086 | 1.564 | 0.100 |
| M13 | 0.129 | 0.008 | 0.136 | 0.007 | 0.122 | 0.004 | 0.092 | 0.005 | 0.104 | 0.010 |
| M14 | 0.379 | 0.047 | 0.381 | 0.024 | 0.414 | 0.018 | 0.333 | 0.021 | 0.412 | 0.033 |
| M15 | 0.706 | 0.044 | 0.720 | 0.034 | 0.699 | 0.019 | 0.560 | 0.024 | 0.578 | 0.033 |
| M16 | 2.739 | 0.333 | 2.483 | 0.161 | 2.345 | 0.091 | 1.783 | 0.096 | 1.964 | 0.136 |
| M17 | 4.055 | 0.499 | 4.149 | 0.401 | 3.987 | 0.209 | 2.963 | 0.275 | 3.010 | 0.268 |
| M18 | 0.282 | 0.022 | 0.289 | 0.022 | 0.245 | 0.010 | 0.160 | 0.012 | 0.191 | 0.024 |
| M19 | 1.009 | 0.175 | 0.902 | 0.085 | 0.974 | 0.056 | 0.716 | 0.061 | 0.877 | 0.077 |
| M20 | 0.708 | 0.059 | 0.682 | 0.045 | 0.637 | 0.021 | 0.524 | 0.029 | 0.565 | 0.039 |
| M21 | 2.885 | 0.411 | 2.537 | 0.187 | 2.331 | 0.092 | 1.757 | 0.105 | 1.935 | 0.158 |
| M22 | 8.971 | 0.932 | 9.244 | 0.790 | 8.625 | 0.450 | 6.263 | 0.484 | 6.923 | 0.683 |
| M23 | 0.198 | 0.011 | 0.202 | 0.014 | 0.177 | 0.006 | 0.124 | 0.008 | 0.140 | 0.014 |
| M24 | 0.955 | 0.174 | 0.834 | 0.078 | 0.882 | 0.049 | 0.661 | 0.054 | 0.814 | 0.071 |
| M25 | 2.505 | 0.217 | 2.286 | 0.164 | 3.219 | 0.181 | 2.995 | 0.239 | 3.280 | 0.248 |

TABLE 35

Ratio and T-test values of Ethanolamine Phospholipid Ratios to M01 between females of different ages

| Metabolite Code | 50-59 vs. 40-49, Female Ratio | ttest | 60-69 vs. 40-49, Female Ratio | ttest | 70+ vs. 40-49, Female Ratio | ttest |
|---|---|---|---|---|---|---|
| M01 | 1.000 | #DIV/0! | 1.000 | #DIV/0! | 1.000 | #DIV/0! |
| M02 | 0.923 | 2.1E-01 | 0.771 | 5.7E-05 | 0.763 | 8.4E-04 |
| M03 | 1.017 | 7.8E-01 | 0.823 | 3.7E-03 | 0.920 | 2.8E-01 |
| M04 | 0.850 | 3.5E-02 | 0.652 | 1.1E-06 | 0.782 | 2.3E-02 |
| M05 | 0.892 | 4.7E-02 | 0.721 | 5.0E-05 | 0.758 | 3.7E-03 |
| M06 | 0.896 | 1.3E-01 | 0.662 | 1.3E-05 | 0.733 | 6.5E-03 |
| M07 | 0.873 | 1.5E-01 | 0.652 | 7.2E-04 | 0.644 | 3.5E-03 |
| M08 | 0.783 | 4.7E-03 | 0.533 | 6.9E-07 | 0.583 | 9.9E-04 |
| M09 | 1.016 | 8.8E-01 | 0.717 | 7.8E-03 | 0.841 | 2.2E-01 |
| M10 | 0.917 | 4.8E-02 | 0.792 | 7.9E-05 | 0.789 | 2.0E-03 |
| M11 | 0.935 | 2.5E-01 | 0.754 | 1.3E-04 | 0.770 | 5.9E-03 |
| M12 | 0.955 | 4.6E-01 | 0.751 | 5.1E-04 | 0.765 | 5.8E-03 |
| M13 | 0.900 | 7.0E-02 | 0.680 | 4.8E-06 | 0.764 | 9.1E-03 |
| M14 | 1.088 | 3.1E-01 | 0.876 | 1.4E-01 | 1.083 | 4.3E-01 |
| M15 | 0.970 | 5.6E-01 | 0.778 | 1.8E-04 | 0.802 | 6.7E-03 |
| M16 | 0.944 | 4.3E-01 | 0.718 | 1.8E-04 | 0.791 | 2.8E-02 |
| M17 | 0.961 | 7.0E-01 | 0.714 | 1.4E-02 | 0.726 | 4.4E-02 |
| M18 | 0.847 | 4.1E-02 | 0.552 | 6.0E-07 | 0.660 | 5.6E-03 |
| M19 | 1.079 | 4.9E-01 | 0.794 | 7.2E-02 | 0.972 | 8.4E-01 |
| M20 | 0.935 | 3.1E-01 | 0.769 | 2.9E-03 | 0.828 | 7.5E-02 |
| M21 | 0.919 | 2.7E-01 | 0.693 | 2.4E-04 | 0.763 | 2.9E-02 |
| M22 | 0.933 | 4.8E-01 | 0.678 | 1.2E-03 | 0.749 | 4.6E-02 |
| M23 | 0.876 | 5.5E-02 | 0.614 | 1.3E-06 | 0.696 | 3.9E-03 |
| M24 | 1.058 | 6.0E-01 | 0.793 | 6.5E-02 | 0.976 | 8.6E-01 |
| M25 | 1.408 | 2.4E-03 | 1.310 | 2.2E-02 | 1.435 | 8.6E-04 |

TABLE 36

Average Serum Ethanolamine Phospholipid Ratios to M01 in Males of Different Levels of Dementia Severity

| Metabolite Code | Cognitive Normal, Male Mean | SEM | SDAT_all, Male Mean | SEM | SDAT, ADAS 5-19, Male Mean | SEM | SDAT, ADAS 20-39, Male Mean | SEM | SDAT, ADAS 40-70, Male Mean | SEM |
|---|---|---|---|---|---|---|---|---|---|---|
| M01 | 1.000 | 0.000 | 1.000 | 0.000 | 1.000 | 0.000 | 1.000 | 0.000 | 1.000 | 0.000 |
| M02 | 0.564 | 0.031 | 0.453 | 0.015 | 0.475 | 0.032 | 0.455 | 0.017 | 0.383 | 0.022 |
| M03 | 0.960 | 0.050 | 0.712 | 0.018 | 0.779 | 0.037 | 0.694 | 0.024 | 0.617 | 0.027 |
| M04 | 0.262 | 0.015 | 0.210 | 0.009 | 0.203 | 0.017 | 0.219 | 0.013 | 0.183 | 0.014 |
| M05 | 0.106 | 0.006 | 0.089 | 0.002 | 0.091 | 0.004 | 0.089 | 0.003 | 0.085 | 0.004 |
| M06 | 0.255 | 0.014 | 0.213 | 0.007 | 0.211 | 0.012 | 0.214 | 0.010 | 0.211 | 0.012 |
| M07 | 0.554 | 0.041 | 0.373 | 0.014 | 0.396 | 0.025 | 0.375 | 0.020 | 0.321 | 0.028 |
| M08 | 0.062 | 0.005 | 0.044 | 0.002 | 0.047 | 0.004 | 0.045 | 0.003 | 0.038 | 0.003 |

TABLE 36-continued

Average Serum Ethanolamine Phospholipid Ratios to M01 in Males of Different Levels of Dementia Severity

| Metabolite Code | Cognitive Normal, Male | | SDAT_all, Male | | SDAT, ADAS 5-19, Male | | SDAT, ADAS 20-39, Male | | SDAT, ADAS 40-70, Male | |
|---|---|---|---|---|---|---|---|---|---|---|
| | Mean | SEM | Mean | SEM | Mean | SEM | Mean | SEM | Mean | SEM |
| M09 | 0.195 | 0.015 | 0.126 | 0.006 | 0.139 | 0.012 | 0.127 | 0.009 | 0.093 | 0.008 |
| M10 | 0.483 | 0.021 | 0.440 | 0.009 | 0.450 | 0.016 | 0.441 | 0.013 | 0.408 | 0.016 |
| M11 | 0.985 | 0.043 | 0.817 | 0.025 | 0.828 | 0.051 | 0.824 | 0.035 | 0.761 | 0.036 |
| M12 | 1.843 | 0.088 | 1.399 | 0.036 | 1.460 | 0.059 | 1.406 | 0.053 | 1.252 | 0.090 |
| M13 | 0.114 | 0.006 | 0.092 | 0.002 | 0.096 | 0.004 | 0.091 | 0.003 | 0.088 | 0.006 |
| M14 | 0.442 | 0.023 | 0.310 | 0.013 | 0.348 | 0.028 | 0.301 | 0.015 | 0.255 | 0.025 |
| M15 | 0.682 | 0.031 | 0.548 | 0.012 | 0.571 | 0.022 | 0.541 | 0.016 | 0.520 | 0.024 |
| M16 | 2.398 | 0.128 | 1.790 | 0.057 | 1.856 | 0.105 | 1.777 | 0.082 | 1.687 | 0.115 |
| M17 | 4.203 | 0.304 | 2.569 | 0.105 | 2.853 | 0.205 | 2.501 | 0.135 | 2.187 | 0.243 |
| M18 | 0.232 | 0.017 | 0.156 | 0.006 | 0.166 | 0.012 | 0.155 | 0.009 | 0.140 | 0.010 |
| M19 | 1.103 | 0.092 | 0.663 | 0.032 | 0.740 | 0.066 | 0.660 | 0.041 | 0.503 | 0.045 |
| M20 | 0.692 | 0.037 | 0.548 | 0.016 | 0.593 | 0.030 | 0.532 | 0.021 | 0.509 | 0.034 |
| M21 | 2.377 | 0.126 | 1.857 | 0.066 | 1.951 | 0.128 | 1.829 | 0.090 | 1.754 | 0.143 |
| M22 | 9.309 | 0.674 | 6.230 | 0.231 | 6.651 | 0.434 | 6.157 | 0.305 | 5.616 | 0.592 |
| M23 | 0.164 | 0.009 | 0.125 | 0.004 | 0.133 | 0.008 | 0.124 | 0.006 | 0.114 | 0.008 |
| M24 | 1.010 | 0.088 | 0.672 | 0.034 | 0.770 | 0.076 | 0.647 | 0.039 | 0.539 | 0.053 |
| M25 | 2.160 | 0.133 | 2.085 | 0.115 | 2.215 | 0.145 | 2.102 | 0.197 | 1.811 | 0.222 |

TABLE 37

Ratio and T-test Values of Ethanolamine Phospholipid Ratios to M01 between Males of Various Levels of Dementia

| Metabolite Code | AD, All to CN, Male | | ADAS 5-19 to CN, Male | | ADAS 20-39 to CN, Male | | ADAS 40-70 to CN, Male | |
|---|---|---|---|---|---|---|---|---|
| | Ratio | ttest | Ratio | ttest | Ratio | ttest | Ratio | ttest |
| M01 | 1.000 | #DIV/0! | 1.000 | #DIV/0! | 1.000 | #DIV/0! | 1.000 | #DIV/0! |
| M02 | 0.803 | 7.2E−04 | 0.842 | 5.2E−02 | 0.807 | 1.2E−03 | 0.680 | 1.8E−04 |
| M03 | 0.742 | 6.4E−08 | 0.812 | 3.8E−03 | 0.724 | 4.5E−07 | 0.643 | 9.8E−06 |
| M04 | 0.802 | 8.4E−03 | 0.774 | 1.6E−02 | 0.836 | 4.1E−02 | 0.700 | 1.3E−03 |
| M05 | 0.840 | 9.2E−04 | 0.858 | 2.9E−02 | 0.841 | 5.5E−03 | 0.798 | 1.2E−02 |
| M06 | 0.833 | 5.0E−03 | 0.827 | 2.0E−02 | 0.840 | 2.2E−02 | 0.828 | 4.7E−02 |
| M07 | 0.673 | 4.7E−07 | 0.715 | 1.1E−03 | 0.676 | 3.1E−05 | 0.580 | 2.4E−04 |
| M08 | 0.713 | 1.1E−04 | 0.747 | 1.3E−02 | 0.727 | 1.5E−03 | 0.602 | 8.4E−04 |
| M09 | 0.645 | 2.8E−06 | 0.713 | 4.4E−03 | 0.654 | 7.5E−05 | 0.476 | 1.6E−05 |
| M10 | 0.910 | 3.4E−02 | 0.932 | 2.1E−01 | 0.913 | 8.0E−02 | 0.843 | 1.8E−02 |
| M11 | 0.830 | 1.9E−03 | 0.841 | 2.5E−02 | 0.837 | 5.8E−03 | 0.773 | 9.3E−04 |
| M12 | 0.759 | 3.4E−07 | 0.792 | 3.9E−04 | 0.763 | 1.9E−05 | 0.679 | 7.0E−05 |
| M13 | 0.811 | 1.0E−04 | 0.846 | 1.2E−02 | 0.802 | 4.0E−04 | 0.772 | 4.7E−03 |
| M14 | 0.701 | 4.1E−06 | 0.787 | 1.4E−02 | 0.680 | 1.1E−06 | 0.576 | 4.9E−06 |
| M15 | 0.803 | 2.7E−06 | 0.837 | 3.8E−03 | 0.792 | 2.4E−05 | 0.762 | 8.6E−04 |
| M16 | 0.747 | 4.3E−06 | 0.774 | 1.5E−03 | 0.741 | 4.8E−05 | 0.704 | 5.4E−04 |
| M17 | 0.611 | 2.1E−09 | 0.679 | 3.1E−04 | 0.595 | 7.2E−08 | 0.520 | 4.0E−05 |
| M18 | 0.672 | 9.8E−07 | 0.714 | 1.7E−03 | 0.666 | 2.3E−05 | 0.603 | 3.3E−04 |
| M19 | 0.601 | 6.5E−08 | 0.672 | 1.7E−03 | 0.599 | 2.1E−06 | 0.456 | 2.2E−05 |
| M20 | 0.793 | 9.1E−05 | 0.858 | 3.8E−02 | 0.769 | 1.0E−04 | 0.736 | 1.8E−03 |
| M21 | 0.782 | 3.7E−04 | 0.821 | 2.2E−02 | 0.770 | 5.6E−04 | 0.738 | 3.0E−03 |
| M22 | 0.669 | 2.0E−07 | 0.714 | 9.9E−04 | 0.661 | 4.8E−06 | 0.603 | 6.0E−04 |
| M23 | 0.763 | 1.2E−04 | 0.810 | 1.5E−02 | 0.754 | 4.8E−04 | 0.696 | 6.5E−04 |
| M24 | 0.665 | 3.5E−05 | 0.763 | 4.2E−02 | 0.641 | 3.5E−05 | 0.533 | 4.0E−04 |
| M25 | 0.965 | 7.5E−01 | 1.025 | 7.9E−01 | 0.973 | 8.4E−01 | 0.838 | 1.6E−01 |

TABLE 38

Ratio and T-test Values of Ethanolamine Phospholipid Ratios to M01 Between Males of Various Levels of Dementia

| Metabolite Code | ADAS 20-39 to 5-19, Male | | ADAS 40-70 to 5-19, Male | | ADAS 40-70 to 20-39, Male | |
|---|---|---|---|---|---|---|
| | Ratio | ttest | Ratio | ttest | Ratio | ttest |
| M01 | 1.000 | #DIV/0! | 1.000 | #DIV/0! | 1.000 | #DIV/0! |
| M02 | 0.958 | 5.5E−01 | 0.807 | 7.1E−02 | 0.843 | 3.5E−02 |
| M03 | 0.891 | 4.6E−02 | 0.792 | 6.9E−03 | 0.888 | 9.3E−02 |
| M04 | 1.080 | 4.5E−01 | 0.903 | 4.8E−01 | 0.837 | 1.4E−01 |
| M05 | 0.980 | 7.2E−01 | 0.930 | 3.2E−01 | 0.948 | 4.4E−01 |
| M06 | 1.016 | 8.4E−01 | 1.002 | 9.8E−01 | 0.987 | 8.9E−01 |

TABLE 38-continued

Ratio and T-test Values of Ethanolamine Phospholipid Ratios to M01 Between Males of Various Levels of Dementia

| Metabolite Code | ADAS 20-39 to 5-19, Male | | ADAS 40-70 to 5-19, Male | | ADAS 40-70 to 20-39, Male | |
|---|---|---|---|---|---|---|
| | Ratio | ttest | Ratio | ttest | Ratio | ttest |
| M07 | 0.946 | 5.1E−01 | 0.811 | 8.4E−02 | 0.857 | 1.8E−01 |
| M08 | 0.973 | 7.8E−01 | 0.806 | 1.3E−01 | 0.828 | 1.3E−01 |
| M09 | 0.917 | 4.2E−01 | 0.668 | 1.5E−02 | 0.728 | 3.5E−02 |
| M10 | 0.980 | 6.6E−01 | 0.905 | 1.1E−01 | 0.923 | 1.9E−01 |
| M11 | 0.995 | 9.4E−01 | 0.919 | 4.0E−01 | 0.924 | 3.5E−01 |
| M12 | 0.964 | 5.1E−01 | 0.858 | 5.8E−02 | 0.890 | 1.6E−01 |
| M13 | 0.948 | 3.5E−01 | 0.913 | 2.6E−01 | 0.963 | 6.3E−01 |
| M14 | 0.864 | 1.1E−01 | 0.732 | 4.1E−02 | 0.847 | 1.4E−01 |
| M15 | 0.947 | 2.6E−01 | 0.911 | 1.7E−01 | 0.962 | 5.2E−01 |
| M16 | 0.957 | 5.5E−01 | 0.909 | 3.4E−01 | 0.950 | 5.8E−01 |
| M17 | 0.877 | 1.4E−01 | 0.767 | 6.0E−02 | 0.875 | 2.6E−01 |
| M18 | 0.932 | 4.5E−01 | 0.844 | 1.9E−01 | 0.905 | 3.9E−01 |
| M19 | 0.891 | 2.8E−01 | 0.679 | 2.6E−02 | 0.762 | 4.5E−02 |
| M20 | 0.896 | 8.6E−02 | 0.858 | 9.6E−02 | 0.957 | 5.9E−01 |
| M21 | 0.937 | 4.2E−01 | 0.899 | 3.6E−01 | 0.959 | 6.8E−01 |
| M22 | 0.926 | 3.4E−01 | 0.844 | 1.8E−01 | 0.912 | 4.0E−01 |
| M23 | 0.931 | 3.9E−01 | 0.860 | 1.8E−01 | 0.923 | 4.5E−01 |
| M24 | 0.840 | 1.2E−01 | 0.699 | 5.7E−02 | 0.832 | 1.5E−01 |
| M25 | 0.949 | 6.7E−01 | 0.818 | 1.3E−01 | 0.862 | 4.4E−01 |

TABLE 39

Effect of Dementia State on Ethanolamine Phospholipid Ratios to M01 in Females

| Metabolite Code | Cognitive Normal, Female | | SDAT_all, Female | | SDAT, ADAS 5-19, Female | | SDAT, ADAS 20-39, Female | | SDAT, ADAS 40-70, Female | |
|---|---|---|---|---|---|---|---|---|---|---|
| | Mean | SEM | Mean | SEM | Mean | SEM | Mean | SEM | Mean | SEM |
| M01 | 1.000 | 0.000 | 1.000 | 0.000 | 1.000 | 0.000 | 1.000 | 0.000 | 1.000 | 0.000 |
| M02 | 0.520 | 0.029 | 0.463 | 0.012 | 0.454 | 0.021 | 0.499 | 0.023 | 0.431 | 0.018 |
| M03 | 0.852 | 0.034 | 0.687 | 0.017 | 0.742 | 0.030 | 0.704 | 0.031 | 0.624 | 0.022 |
| M04 | 0.222 | 0.013 | 0.219 | 0.010 | 0.215 | 0.013 | 0.241 | 0.021 | 0.197 | 0.015 |
| M05 | 0.092 | 0.004 | 0.086 | 0.003 | 0.091 | 0.004 | 0.088 | 0.005 | 0.081 | 0.004 |
| M06 | 0.234 | 0.012 | 0.207 | 0.007 | 0.226 | 0.011 | 0.217 | 0.013 | 0.180 | 0.009 |
| M07 | 0.474 | 0.034 | 0.368 | 0.018 | 0.422 | 0.039 | 0.377 | 0.028 | 0.314 | 0.025 |
| M08 | 0.054 | 0.004 | 0.047 | 0.002 | 0.050 | 0.003 | 0.051 | 0.004 | 0.039 | 0.002 |
| M09 | 0.167 | 0.013 | 0.121 | 0.005 | 0.140 | 0.010 | 0.123 | 0.009 | 0.103 | 0.008 |
| M10 | 0.469 | 0.016 | 0.431 | 0.010 | 0.451 | 0.016 | 0.428 | 0.018 | 0.418 | 0.016 |
| M11 | 0.929 | 0.039 | 0.807 | 0.023 | 0.886 | 0.041 | 0.839 | 0.044 | 0.708 | 0.030 |
| M12 | 1.682 | 0.078 | 1.384 | 0.042 | 1.568 | 0.090 | 1.384 | 0.067 | 1.239 | 0.062 |
| M13 | 0.111 | 0.005 | 0.095 | 0.003 | 0.101 | 0.005 | 0.095 | 0.005 | 0.089 | 0.004 |
| M14 | 0.392 | 0.023 | 0.315 | 0.013 | 0.367 | 0.029 | 0.309 | 0.019 | 0.279 | 0.019 |
| M15 | 0.627 | 0.024 | 0.539 | 0.014 | 0.564 | 0.021 | 0.563 | 0.030 | 0.493 | 0.016 |
| M16 | 2.214 | 0.114 | 1.780 | 0.064 | 1.994 | 0.107 | 1.906 | 0.127 | 1.470 | 0.069 |
| M17 | 3.497 | 0.247 | 2.593 | 0.127 | 2.976 | 0.266 | 2.750 | 0.226 | 2.115 | 0.146 |
| M18 | 0.202 | 0.014 | 0.161 | 0.007 | 0.178 | 0.011 | 0.170 | 0.014 | 0.138 | 0.008 |
| M19 | 0.895 | 0.061 | 0.634 | 0.030 | 0.728 | 0.057 | 0.656 | 0.055 | 0.537 | 0.041 |
| M20 | 0.669 | 0.035 | 0.535 | 0.018 | 0.587 | 0.032 | 0.553 | 0.036 | 0.474 | 0.022 |
| M21 | 2.318 | 0.118 | 1.798 | 0.076 | 2.039 | 0.132 | 1.922 | 0.147 | 1.467 | 0.086 |
| M22 | 8.068 | 0.596 | 6.310 | 0.304 | 7.041 | 0.600 | 6.681 | 0.568 | 5.313 | 0.360 |
| M23 | 0.158 | 0.009 | 0.127 | 0.005 | 0.139 | 0.009 | 0.131 | 0.010 | 0.112 | 0.006 |
| M24 | 0.893 | 0.068 | 0.651 | 0.034 | 0.724 | 0.063 | 0.669 | 0.059 | 0.573 | 0.053 |
| M25 | 2.145 | 0.127 | 2.031 | 0.086 | 2.072 | 0.129 | 2.109 | 0.162 | 1.910 | 0.139 |

TABLE 40

Ratio and T-test values of Ethanolamine Phospholipid Ratios to M01 between females of various levels of dementia

| Metabolite Code | AD, All to CN, Female | | ADAS 5-19 to CN, Female | | ADAS 20-39 to CN, Female | | ADAS 40-70 to CN, Female | |
|---|---|---|---|---|---|---|---|---|
| | Ratio | ttest | Ratio | ttest | Ratio | ttest | Ratio | ttest |
| M01 | 1.000 | #DIV/0! | 1.000 | #DIV/0! | 1.000 | #DIV/0! | 1.000 | #DIV/0! |
| M02 | 0.891 | 4.7E−02 | 0.872 | 6.4E−02 | 0.960 | 5.7E−01 | 0.828 | 7.0E−03 |
| M03 | 0.806 | 1.3E−05 | 0.871 | 1.6E−02 | 0.826 | 2.1E−03 | 0.732 | 6.8E−08 |
| M04 | 0.986 | 8.8E−01 | 0.968 | 7.0E−01 | 1.086 | 4.9E−01 | 0.887 | 2.3E−01 |
| M05 | 0.941 | 3.5E−01 | 0.989 | 8.7E−01 | 0.962 | 6.4E−01 | 0.879 | 5.5E−02 |
| M06 | 0.885 | 6.6E−02 | 0.966 | 6.3E−01 | 0.928 | 3.7E−01 | 0.771 | 2.8E−04 |
| M07 | 0.776 | 6.7E−03 | 0.890 | 3.2E−01 | 0.796 | 3.2E−02 | 0.663 | 2.3E−04 |
| M08 | 0.869 | 1.3E−01 | 0.934 | 4.9E−01 | 0.943 | 6.2E−01 | 0.735 | 1.5E−03 |
| M09 | 0.724 | 3.1E−04 | 0.837 | 1.0E−01 | 0.740 | 5.4E−03 | 0.618 | 4.2E−05 |
| M10 | 0.919 | 7.3E−02 | 0.963 | 4.4E−01 | 0.913 | 1.1E−01 | 0.892 | 3.1E−02 |
| M11 | 0.868 | 1.6E−02 | 0.953 | 4.4E−01 | 0.902 | 1.5E−01 | 0.762 | 2.0E−05 |
| M12 | 0.823 | 1.5E−03 | 0.932 | 3.4E−01 | 0.823 | 5.0E−03 | 0.736 | 2.0E−05 |

TABLE 40-continued

Ratio and T-test values of Ethanolamine Phospholipid Ratios to M01 between females of various levels of dementia

| Metabolite Code | AD, All to CN, Female Ratio | ttest | ADAS 5-19 to CN, Female Ratio | ttest | ADAS 20-39 to CN, Female Ratio | ttest | ADAS 40-70 to CN, Female Ratio | ttest |
|---|---|---|---|---|---|---|---|---|
| M13 | 0.854 | 6.6E−03 | 0.914 | 1.8E−01 | 0.854 | 3.1E−02 | 0.806 | 9.4E−04 |
| M14 | 0.802 | 5.5E−03 | 0.935 | 4.9E−01 | 0.789 | 6.6E−03 | 0.711 | 2.4E−04 |
| M15 | 0.860 | 4.8E−03 | 0.900 | 5.1E−02 | 0.897 | 1.3E−01 | 0.786 | 9.1E−06 |
| M16 | 0.804 | 2.1E−03 | 0.901 | 1.6E−01 | 0.861 | 9.3E−02 | 0.664 | 8.8E−08 |
| M17 | 0.742 | 1.5E−03 | 0.851 | 1.6E−01 | 0.786 | 3.2E−02 | 0.605 | 2.3E−06 |
| M18 | 0.798 | 9.5E−03 | 0.879 | 1.8E−01 | 0.844 | 1.4E−01 | 0.683 | 6.3E−05 |
| M19 | 0.709 | 1.6E−04 | 0.813 | 5.1E−02 | 0.733 | 5.3E−03 | 0.600 | 3.2E−06 |
| M20 | 0.800 | 1.0E−03 | 0.878 | 8.7E−02 | 0.826 | 2.8E−02 | 0.709 | 3.4E−06 |
| M21 | 0.776 | 1.4E−03 | 0.879 | 1.2E−01 | 0.829 | 5.6E−02 | 0.633 | 5.4E−08 |
| M22 | 0.782 | 9.6E−03 | 0.873 | 2.3E−01 | 0.828 | 1.1E−01 | 0.659 | 7.8E−05 |
| M23 | 0.801 | 5.3E−03 | 0.877 | 1.3E−01 | 0.831 | 6.8E−02 | 0.707 | 4.5E−05 |
| M24 | 0.729 | 1.6E−03 | 0.811 | 7.2E−02 | 0.750 | 1.7E−02 | 0.642 | 3.3E−04 |
| M25 | 0.947 | 5.3E−01 | 0.966 | 6.9E−01 | 0.983 | 8.7E−01 | 0.890 | 2.3E−01 |

TABLE 41

Ratio and T-test values of Ethanolamine Phospholipid Ratios to M01 between females of various levels of dementia

| Metabolite Code | ADAS 20-39 to 5-19, Female Ratio | ttest | ADAS 40-70 to 5-19, Female Ratio | ttest | ADAS 40-70 to 20-39, Female Ratio | ttest |
|---|---|---|---|---|---|---|
| M01 | 1.000 | #DIV/0! | 1.000 | #DIV/0! | 1.000 | #DIV/0! |
| M02 | 1.101 | 1.6E−01 | 0.949 | 4.1E−01 | 0.862 | 2.2E−02 |
| M03 | 0.949 | 4.0E−01 | 0.841 | 1.5E−03 | 0.887 | 4.2E−02 |
| M04 | 1.122 | 3.3E−01 | 0.917 | 3.8E−01 | 0.817 | 9.2E−02 |
| M05 | 0.972 | 7.3E−01 | 0.889 | 7.6E−02 | 0.914 | 2.6E−01 |
| M06 | 0.961 | 6.3E−01 | 0.797 | 1.3E−03 | 0.830 | 2.4E−02 |
| M07 | 0.895 | 3.4E−01 | 0.745 | 1.7E−02 | 0.833 | 9.8E−02 |
| M08 | 1.010 | 9.4E−01 | 0.787 | 1.1E−02 | 0.780 | 3.5E−02 |
| M09 | 0.884 | 2.4E−01 | 0.738 | 6.7E−03 | 0.835 | 1.0E−01 |
| M10 | 0.948 | 3.5E−01 | 0.926 | 1.5E−01 | 0.977 | 6.8E−01 |
| M11 | 0.947 | 4.6E−01 | 0.799 | 6.4E−04 | 0.844 | 1.9E−02 |
| M12 | 0.883 | 9.7E−02 | 0.790 | 2.5E−03 | 0.895 | 1.2E−01 |
| M13 | 0.934 | 3.6E−01 | 0.882 | 5.3E−02 | 0.944 | 4.1E−01 |
| M14 | 0.844 | 8.6E−02 | 0.761 | 9.9E−03 | 0.902 | 2.6E−01 |
| M15 | 0.998 | 9.7E−01 | 0.874 | 7.7E−03 | 0.876 | 5.3E−02 |
| M16 | 0.956 | 6.2E−01 | 0.737 | 5.0E−05 | 0.771 | 4.2E−03 |
| M17 | 0.924 | 5.2E−01 | 0.711 | 3.6E−03 | 0.769 | 2.4E−02 |
| M18 | 0.960 | 7.2E−01 | 0.777 | 4.1E−03 | 0.809 | 5.7E−02 |
| M19 | 0.901 | 3.8E−01 | 0.738 | 7.1E−03 | 0.819 | 9.2E−02 |
| M20 | 0.941 | 4.9E−01 | 0.808 | 3.7E−03 | 0.858 | 7.3E−02 |
| M21 | 0.943 | 5.8E−01 | 0.720 | 3.1E−04 | 0.763 | 1.1E−02 |
| M22 | 0.949 | 6.7E−01 | 0.755 | 1.2E−02 | 0.795 | 5.1E−02 |
| M23 | 0.948 | 6.1E−01 | 0.806 | 1.4E−02 | 0.851 | 1.1E−01 |
| M24 | 0.925 | 5.4E−01 | 0.791 | 6.9E−02 | 0.856 | 2.3E−01 |
| M25 | 1.018 | 8.7E−01 | 0.922 | 4.0E−01 | 0.906 | 3.6E−01 |

TABLE 42

Effect of Pathology State on Ethanolamine Phospholipid Ratios to M01 in Males

| Metabolite Code | Post Mortem Ctl, Male Mean | SEM | Post Mortem SDAT Male Mean | SEM | SDAT vs Control Ratio | ttest |
|---|---|---|---|---|---|---|
| M01 | 1.000 | 0.000 | 1.000 | 0.000 | 1.000 | #DIV/0! |
| M02 | 0.367 | 0.029 | 0.290 | 0.029 | 0.791 | 0.076 |
| M03 | 0.482 | 0.042 | 0.391 | 0.013 | 0.811 | 0.054 |
| M04 | 0.143 | 0.031 | 0.076 | 0.009 | 0.529 | 0.052 |
| M05 | 0.048 | 0.009 | 0.029 | 0.002 | 0.607 | 0.052 |
| M06 | 0.080 | 0.014 | 0.046 | 0.003 | 0.581 | 0.033 |
| M07 | 0.107 | 0.025 | 0.059 | 0.005 | 0.549 | 0.074 |
| M08 | 0.024 | 0.005 | 0.012 | 0.001 | 0.511 | 0.037 |
| M09 | 0.052 | 0.018 | 0.018 | 0.002 | 0.341 | 0.074 |
| M10 | 0.337 | 0.038 | 0.269 | 0.013 | 0.798 | 0.107 |
| M11 | 0.452 | 0.066 | 0.272 | 0.017 | 0.602 | 0.016 |
| M12 | 0.819 | 0.130 | 0.616 | 0.024 | 0.753 | 0.143 |
| M13 | 0.079 | 0.009 | 0.060 | 0.005 | 0.759 | 0.085 |
| M14 | 0.212 | 0.039 | 0.115 | 0.010 | 0.542 | 0.026 |
| M15 | 0.375 | 0.035 | 0.344 | 0.025 | 0.918 | 0.483 |
| M16 | 0.792 | 0.128 | 0.627 | 0.047 | 0.791 | 0.240 |
| M17 | 0.849 | 0.191 | 0.561 | 0.040 | 0.660 | 0.156 |
| M18 | 0.085 | 0.011 | 0.056 | 0.004 | 0.656 | 0.018 |
| M19 | 0.273 | 0.051 | 0.164 | 0.015 | 0.601 | 0.056 |
| M20 | 0.254 | 0.027 | 0.187 | 0.009 | 0.737 | 0.028 |
| M21 | 0.613 | 0.109 | 0.371 | 0.021 | 0.605 | 0.042 |
| M22 | 1.890 | 0.379 | 1.199 | 0.083 | 0.634 | 0.092 |
| M23 | 0.074 | 0.008 | 0.055 | 0.004 | 0.750 | 0.061 |
| M24 | 0.241 | 0.039 | 0.142 | 0.011 | 0.588 | 0.025 |
| M25 | 2.066 | 0.225 | 2.384 | 0.388 | 1.154 | 0.487 |

TABLE 43

Effect of Pathology State on Ethanolamine Phospholipid Ratios to M01 in Females

| Metabolite Code | Post Mortem Ctl, Female Mean | SEM | Post Mortem DAT Female Mean | SEM | Autopsy AD vs. Control, Female Ratio | ttest |
|---|---|---|---|---|---|---|
| M01 | 1.000 | 0.000 | 1.000 | 0.000 | 1.000 | #DIV/0! |
| M02 | 0.322 | 0.028 | 0.367 | 0.047 | 1.140 | 0.440 |
| M03 | 0.400 | 0.022 | 0.361 | 0.023 | 0.902 | 0.237 |
| M04 | 0.086 | 0.012 | 0.092 | 0.019 | 1.069 | 0.798 |
| M05 | 0.040 | 0.003 | 0.032 | 0.005 | 0.809 | 0.225 |
| M06 | 0.069 | 0.008 | 0.059 | 0.017 | 0.855 | 0.605 |
| M07 | 0.102 | 0.016 | 0.077 | 0.013 | 0.752 | 0.242 |
| M08 | 0.017 | 0.002 | 0.017 | 0.002 | 0.981 | 0.922 |
| M09 | 0.033 | 0.005 | 0.024 | 0.003 | 0.725 | 0.133 |
| M10 | 0.290 | 0.025 | 0.291 | 0.027 | 1.003 | 0.981 |
| M11 | 0.384 | 0.044 | 0.364 | 0.057 | 0.950 | 0.797 |
| M12 | 0.731 | 0.096 | 0.699 | 0.059 | 0.957 | 0.777 |
| M13 | 0.061 | 0.008 | 0.069 | 0.007 | 1.122 | 0.489 |
| M14 | 0.144 | 0.015 | 0.155 | 0.033 | 1.071 | 0.791 |

TABLE 43-continued

Effect of Pathology State on Ethanolamine Phospholipid Ratios to M01 in Females

| Metabolite Code | Post Mortem Ctl, Female Mean | SEM | Post Mortem DAT Female Mean | SEM | Autopsy AD vs. Control, Female Ratio | ttest |
|---|---|---|---|---|---|---|
| M15 | 0.339 | 0.021 | 0.301 | 0.027 | 0.889 | 0.297 |
| M16 | 0.670 | 0.066 | 0.599 | 0.112 | 0.895 | 0.605 |
| M17 | 0.697 | 0.063 | 0.591 | 0.082 | 0.848 | 0.329 |
| M18 | 0.081 | 0.014 | 0.069 | 0.008 | 0.854 | 0.462 |
| M19 | 0.211 | 0.017 | 0.180 | 0.018 | 0.853 | 0.230 |
| M20 | 0.283 | 0.025 | 0.193 | 0.032 | 0.680 | 0.042 |
| M21 | 0.624 | 0.079 | 0.421 | 0.127 | 0.674 | 0.203 |
| M22 | 1.782 | 0.251 | 1.480 | 0.225 | 0.831 | 0.382 |
| M23 | 0.073 | 0.011 | 0.060 | 0.006 | 0.816 | 0.275 |
| M24 | 0.214 | 0.018 | 0.149 | 0.016 | 0.697 | 0.016 |
| M25 | 1.382 | 0.214 | 1.767 | 0.221 | 1.279 | 0.229 |

TABLE 44

Effect of Dementia State on White and Gray Matter Scores in Males

| Cohort | White Matter Score Mean | SEM | Gray Matter Score Mean | SEM |
|---|---|---|---|---|
| Cognitive Normal, Male | −0.25 | 0.08 | −0.44 | 0.11 |
| SDAT_all, Male | −0.63 | 0.06 | −1.11 | 0.08 |
| SDAT, ADAS 5-19, Male | −0.56 | 0.09 | −1.00 | 0.13 |
| SDAT, ADAS 20-39, Male | −0.67 | 0.08 | −1.11 | 0.10 |
| SDAT, ADAS 40-70, Male | −0.71 | 0.14 | −1.45 | 0.16 |
| Post Mortem Ctl, Male | −0.44 | 0.13 | −0.41 | 0.21 |
| Post Mortem SDAT Male | −1.62 | 0.19 | −1.28 | 0.23 |

| Comparison | White Matter Score | | Gray Matter Score | |
|---|---|---|---|---|
| AD, All to CN, Male | Delta | −0.37 | Delta | −0.67 |
| | ttest | 1.9E−03 | ttest | 2.4E−05 |
| ADAS 5-19 to CN, Male | Delta | −0.31 | Delta | −0.56 |
| | ttest | 1.8E−02 | ttest | 2.5E−03 |
| ADAS 20-39 to CN, Male | Delta | −0.41 | Delta | −0.67 |
| | ttest | 1.5E−03 | ttest | 7.8E−05 |
| ADAS 40-70 to CN, Male | Delta | −0.46 | Delta | −1.01 |
| | ttest | 3.7E−03 | ttest | 1.8E−06 |
| ADAS 20-39 to 5-19, Male | Delta | −0.10 | Delta | −0.11 |
| | ttest | 4.2E−01 | ttest | 5.0E−01 |
| ADAS 40-70 to 5-19, Male | Delta | −0.15 | Delta | −0.45 |
| | ttest | 3.9E−01 | ttest | 5.2E−02 |
| ADAS 40-70 to 20-39, Male | Delta | −0.04 | Delta | −0.34 |
| | ttest | 8.0E−01 | ttest | 1.1E−01 |
| Autopsy AD vs. Control, Mal | Delta | −0.89 | Delta | −1.13 |
| | ttest | 8.9E−03 | ttest | 2.8E−03 |

TABLE 45

Effect of Dementia State on White and Gray Matter Scores in Females

| Cohort | White Matter Score Mean | SEM | Gray Matter Score Mean | SEM |
|---|---|---|---|---|
| Cognitive Normal, Female | −0.27 | 0.09 | −0.42 | 0.13 |
| SDAT_all, Female | −0.73 | 0.05 | −1.01 | 0.07 |
| SDAT, ADAS 5-19, Female | −0.55 | 0.08 | −0.85 | 0.11 |
| SDAT, ADAS 20-39, Female | −0.69 | 0.09 | −0.94 | 0.11 |
| SDAT, ADAS 40-70, Female | −0.91 | 0.08 | −1.21 | 0.12 |
| Post Mortem Ctl, Female | −0.50 | 0.29 | −0.53 | 0.26 |
| Post Mortem SDAT Female | −1.34 | 0.27 | −1.54 | 0.25 |

| Comparison | White Matter Score | | Gray Matter Score | |
|---|---|---|---|---|
| AD, All to CN, Female | Delta | −0.46 | Delta | −0.59 |
| | ttest | 4.6E−05 | ttest | 1.1E−04 |
| ADAS 5-19 to CN, Female | Delta | −0.29 | Delta | −0.43 |
| | ttest | 1.7E−02 | ttest | 1.3E−02 |
| ADAS 20-39 to CN, Female | Delta | −0.43 | Delta | −0.52 |
| | ttest | 1.9E−03 | ttest | 3.6E−03 |
| ADAS 40-70 to CN, Female | Delta | −0.64 | Delta | −0.79 |
| | ttest | 9.5E−07 | ttest | 2.2E−05 |
| ADAS 20-39 to 5-19, Female | Delta | −0.14 | Delta | −0.09 |
| | ttest | 2.7E−01 | ttest | 5.8E−01 |
| ADAS 40-70 to 5-19, Female | Delta | −0.36 | Delta | −0.37 |
| | ttest | 2.9E−03 | ttest | 3.1E−02 |
| ADAS 40-70 to 20-39, Female | Delta | −0.21 | Delta | −0.27 |
| | ttest | 9.4E−02 | ttest | 1.0E−01 |
| Autopsy AD vs. Control, Female | Delta | −1.17 | Delta | −0.81 |
| | ttest | 2.0E−03 | ttest | 2.5E−02 |

TABLE 46

Distribution of White and Gray Matter Scores in Males (Mean Normalized to CN Male)

| Bin | MMSE ≧ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| White Matter Distribution | | | | | | |
| −2 | 0 | 1 | 1 | 0 | 0 | 2 |
| −1.75 | 0 | 0 | 0 | 0 | 0 | 0 |
| −1.5 | 0 | 0 | 3 | 1 | 0 | 0 |
| −1.25 | 0 | 2 | 4 | 0 | 0 | 1 |
| −1 | 1 | 2 | 3 | 1 | 0 | 2 |
| −0.75 | 1 | 3 | 3 | 4 | 0 | 2 |
| −0.5 | 3 | 2 | 6 | 4 | 2 | 0 |
| −0.25 | 3 | 8 | 13 | 4 | 3 | 1 |
| 0 | 7 | 13 | 12 | 0 | 2 | 1 |
| 0.25 | 9 | 6 | 5 | 1 | 2 | 1 |
| 0.5 | 5 | 1 | 5 | 2 | 0 | 0 |
| 0.75 | 1 | 0 | 1 | 0 | 1 | 0 |
| 1 | 2 | 0 | 2 | 1 | 0 | 0 |
| More | 0 | 2 | 0 | 0 | 0 | 0 |
| Gray Matter distribution | | | | | | |
| −2 | 0 | 1 | 4 | 2 | 0 | 2 |
| −1.75 | 0 | 2 | 2 | 1 | 0 | 0 |
| −1.5 | 0 | 1 | 3 | 0 | 0 | 0 |

TABLE 46-continued

Distribution of White and Gray Matter Scores in Males (Mean Normalized to CN Male)

| Bin | MMSE ≥ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| −1.25 | 1 | 4 | 2 | 2 | 0 | 1 |
| −1 | 0 | 6 | 7 | 4 | 0 | 2 |
| −0.75 | 1 | 4 | 9 | 2 | 1 | 3 |
| −0.5 | 7 | 3 | 5 | 4 | 1 | 1 |
| −0.25 | 3 | 5 | 9 | 1 | 2 | 0 |
| 0 | 3 | 2 | 7 | 1 | 1 | 0 |
| 0.25 | 5 | 4 | 2 | 1 | 3 | 0 |
| 0.5 | 7 | 3 | 4 | 0 | 1 | 1 |
| 0.75 | 3 | 1 | 2 | 0 | 0 | 0 |
| 1 | 0 | 3 | 2 | 0 | 0 | 0 |
| More | 2 | 1 | 0 | 0 | 1 | 0 |

TABLE 47

Distribution of White and Gray Matter Scores in Females (Mean Normalized to CN Female)

| Bin | MMSE ≥ 28 Frequency | ADAS-cog 8-19 Frequency | ADAS-cog 20-39 Frequency | ADAS-cog 40-70 Frequency | Autopsy Control Frequency | Autopsy AD Frequency |
|---|---|---|---|---|---|---|
| White Matter Distribution | | | | | | |
| −2 | 0 | 0 | 0 | 1 | 0 | 1 |
| −1.75 | 0 | 0 | 0 | 0 | 0 | 1 |
| −1.5 | 0 | 0 | 3 | 4 | 1 | 3 |
| −1.25 | 1 | 0 | 2 | 1 | 0 | 0 |
| −1 | 1 | 2 | 8 | 4 | 0 | 3 |
| −0.75 | 1 | 5 | 6 | 11 | 1 | 0 |
| −0.5 | 2 | 6 | 6 | 10 | 1 | 1 |
| −0.25 | 4 | 8 | 6 | 3 | 2 | 1 |
| 0 | 9 | 5 | 8 | 9 | 1 | 0 |
| 0.25 | 8 | 6 | 5 | 3 | 2 | 0 |
| 0.5 | 3 | 3 | 6 | 1 | 0 | 0 |
| 0.75 | 4 | 3 | 1 | 1 | 0 | 0 |
| 1 | 3 | 0 | 2 | 0 | 0 | 0 |
| More | 0 | 0 | 1 | 0 | 1 | 0 |
| Gray Matter distribution | | | | | | |
| −2 | 0 | 0 | 1 | 4 | 0 | 1 |
| −1.75 | 0 | 1 | 2 | 1 | 0 | 1 |
| −1.5 | 1 | 1 | 3 | 6 | 0 | 0 |
| −1.25 | 2 | 2 | 4 | 6 | 0 | 0 |
| −1 | 2 | 3 | 8 | 4 | 1 | 2 |
| −0.75 | 1 | 5 | 6 | 5 | 0 | 1 |
| −0.5 | 1 | 6 | 4 | 6 | 1 | 2 |
| −0.25 | 5 | 6 | 7 | 3 | 2 | 0 |
| 0 | 4 | 5 | 4 | 3 | 2 | 2 |
| 0.25 | 6 | 3 | 6 | 6 | 2 | 1 |
| 0.5 | 5 | 2 | 2 | 1 | 0 | 0 |
| 0.75 | 3 | 1 | 2 | 2 | 0 | 0 |
| 1 | 3 | 2 | 2 | 0 | 0 | 0 |
| More | 3 | 1 | 3 | 1 | 1 | 0 |

TABLE 48

Effect of Age on White and Gray Matter Scores in Males

| Cohort | White Matter Score Mean | SEM | Gray Matter Score Mean | SEM |
|---|---|---|---|---|
| Age Ctl, 30-39, Male | −0.25 | 0.29 | −0.92 | 0.28 |
| Age Ctl, 40-49, Male | −0.48 | 0.10 | −1.28 | 0.14 |
| Age Ctl, 50-59, Male | −0.47 | 0.08 | −0.90 | 0.11 |
| Age Ctl, 60-69, Male | −0.53 | 0.10 | −0.84 | 0.14 |
| Age Ctl, 70+_Male | −0.43 | 0.09 | −0.78 | 0.14 |

TABLE 48-continued

Effect of Age on White and Gray Matter Scores in Males

| Comparison | White Matter Score | | Gray Matter Score | |
|---|---|---|---|---|
| 50-59 vs. 40-49, Male | Delta | 0.01 | Delta | 0.38 |
|  | ttest | 9.4E−01 | ttest | 4.2E−02 |
| 60-69 vs. 40-49, Male | Delta | −0.05 | Delta | 0.45 |
|  | ttest | 7.4E−01 | ttest | 3.2E−02 |
| 70+ vs. 40-49, Male | Delta | 0.05 | Delta | 0.50 |
|  | ttest | 7.2E−01 | ttest | 1.4E−02 |

TABLE 49

Effect of Age on White and Gray Matter Scores in Females

| Cohort | White Matter Score Mean | SEM | Gray Matter Score Mean | SEM |
|---|---|---|---|---|
| Age Ctl, 30-39, Female | −0.36 | 0.18 | −0.56 | 0.27 |
| Age Ctl, 40-49, Female | −0.33 | 0.10 | −0.61 | 0.13 |
| Age Ctl, 50-59, Female | −0.55 | 0.06 | −0.71 | 0.09 |
| Age Ctl, 60-69, Female | −0.62 | 0.09 | −0.90 | 0.12 |
| Age Ctl, 70+_Female | −0.47 | 0.11 | −0.58 | 0.14 |

TABLE 49-continued

Effect of Age on White and Gray Matter Scores in Females

| Comparison | White Matter Score | | Gray Matter Score | |
|---|---|---|---|---|
| 50-59 vs. 40-49, Female | Delta | −0.22 | Delta | −0.10 |
| | ttest | 6.9E−02 | ttest | 5.4E−01 |
| 60-69 vs. 40-49, Female | Delta | −0.29 | Delta | −0.30 |
| | ttest | 3.6E−02 | ttest | 1.1E−01 |
| 70+ vs. 40-49, Female | Delta | −0.14 | Delta | 0.03 |
| | ttest | 3.7E−01 | ttest | 8.8E−01 |

TABLE 50

Risk prediction in Males

| Stats | | CN White Matter Score Control Normalized | Low White Matter Score Control Normalized | Moderate White Matter Score Control Normalized | Severe White Matter Score Control Normalized | PM Ctl White Matter Score Control Normalized | PM SDAT White Matter Score Control Normalized |
|---|---|---|---|---|---|---|---|
| Total N | | 32 | 40 | 58 | 18 | 10 | 10 |
| Total L | | 27 | 30 | 38 | 8 | 8 | 3 |
| Total H | | 5 | 10 | 20 | 10 | 2 | 7 |
| L % | | 84.4 | 75.0 | 65.5 | 44.4 | 80.0 | 30.0 |

| | | Gray Matter Score Control Normalized | Gray Matter Score Control Normalized | Gray Matter Score Control Normalized | Gray Matter Score Control Normalized | Gray Matter Score Control Normalized | Gray Matter Score Control Normalized |
|---|---|---|---|---|---|---|---|
| | Total N | 32 | 40 | 58 | 18 | 10 | 10 |
| | Total L | 23 | 19 | 26 | 3 | 8 | 1 |
| | Total H | 9 | 21 | 32 | 15 | 2 | 9 |
| | L % | 71.9 | 47.5 | 44.8 | 16.7 | 80.0 | 10.0 |
| Low risk % | LL | 22 | 19 | 25 | 3 | 7 | 1 |
| | LL | 68.8 | 47.5 | 43.1 | 16.7 | 70.0 | 10.0 |
| Intermediate risk % | IM | 6 | 11 | 14 | 5 | 2 | 2 |
| | IM | 18.8 | 27.5 | 24.1 | 27.8 | 20.0 | 20.0 |
| High risk % | HH | 4 | 10 | 19 | 10 | 1 | 7 |
| | HH | 12.5 | 25.0 | 32.8 | 55.6 | 10.0 | 70.0 |

TABLE 51

Risk Prediction in Females

| Stats | | CN White Matter Score Control Normalized | Low White Matter Score Control Normalized | Moderate White Matter Score Control Normalized | Severe White Matter Score Control Normalized | PM Ctl White Matter Score Control Normalized | PM SDAT White Matter Score Control Normalized |
|---|---|---|---|---|---|---|---|
| Total N | | 36 | 38 | 54 | 48 | 9 | 10 |
| Total L | | 31 | 25 | 29 | 17 | 6 | 1 |
| Total H | | 5 | 13 | 25 | 31 | 3 | 9 |
| L % | | 86.1 | 65.8 | 53.7 | 35.4 | 66.7 | 10.0 |

| | | Gray Matter Score Control Normalized | Gray Matter Score Control Normalized | Gray Matter Score Control Normalized | Gray Matter Score Control Normalized | Gray Matter Score Control Normalized | Gray Matter Score Control Normalized |
|---|---|---|---|---|---|---|---|
| | Total N | 36 | 38 | 54 | 48 | 9 | 10 |
| | Total L | 29 | 20 | 26 | 16 | 7 | 3 |
| | Total H | 7 | 18 | 28 | 32 | 2 | 7 |
| | L % | 80.6 | 52.6 | 48.1 | 33.3 | 77.8 | 30.0 |
| Low risk % | LL | 29 | 17 | 24 | 11 | 5 | 0 |
| | LL | 80.6 | 44.7 | 44.4 | 22.9 | 55.6 | 0.0 |
| Intermediate risk % | IM | 2 | 11 | 7 | 11 | 3 | 4 |
| | IM | 5.6 | 28.9 | 13.0 | 22.9 | 33.3 | 40.0 |
| High risk % | HH | 5 | 10 | 23 | 26 | 1 | 6 |
| | HH | 13.9 | 26.3 | 42.6 | 54.2 | 11.1 | 60.0 |

TABLE 52

Summary of key ratio and p-value statistics
for EtnPls 16:0/22:6 (M19) to PtdEt

| Comparison | Ratio | T-test |
|---|---|---|
| 60-69 to 50-59 | 0.75 | 1.2E−02 |
| 70-95 to 50-59 | 0.95 | 6.4E−01 |
| CN to 50-59 | 1.07 | 4.8E−01 |
| SDAT to 50-59 | 0.70 | 4.7E−07 |
| 70-95 to 60-69 | 1.26 | 6.9E−02 |
| CN to 60-69 | 1.42 | 3.8E−04 |
| SDAT to 70-95 | 0.74 | 1.3E−04 |
| SDAT to CN | 0.65 | 7.6E−11 |
| ADAS 5-19 to CN | 0.74 | 3.0E−04 |
| ADAS 20-39 to CN | 0.66 | 1.3E−07 |
| ADAS 40-70 to CN | 0.53 | 3.9E−11 |
| ADAS 20-39 to ADAS 5-19 | 0.90 | 1.6E−01 |
| ADAS 40-70 to ADAS 5-19 | 0.72 | 3.4E−04 |
| ADAS 40-70 to ADAS 20-39 | 0.80 | 1.0E−02 |
| Post-Mortem SDAT to Control* | 0.55 | 4.7E−03 |

16:0/18:0 (M01) serum ratio for males and females combined.
*ratio and p-value of EtnPls 16:0/22:6 alone.

REFERENCES

1. American Psychiatric Association. Diagnostic and Statistical Manual of Mental Disorders—Fourth Edition. Washington D.C.: American Psychiatric Association; 1994.
2. Canadian Study of Health and Aging Working Group. Canadian Study of Health and Aging: study methods and prevalence of dementia. CMAJ, 1994. 150: p. 899-913.
3. Cummings, J. L., and Benson, D. F. Dementia: a clinical approach. Stoneham Mass.: Butterworth, 1992.
4. Duguè, M., et al. Review of Dementia. Mt Sinai J Med, 2003. 72: p. 45-53.
5. McKhann, G., et al. Clinical diagnosis of Alzheimer's disease: report of the NINCDS-ADRDA Work Group under the auspices of Department of Health and Human Services Task Force on Alzheimer's Disease. Neurology, 1984. 34: p. 939-44.
6. McKeith, I. G., et al. Consensus guidelines for the clinical and pathologic diagnosis of dementia with Lewy bodies (DLB): report of the consortium on DLB internal workshop. Neurology, 1996. 47: p. 1113-24.
7. Neary, D., et al. Frontotemporal lobar degeneration: a consensus on clinical diagnostic criteria. Neurology, 1998. 51: p. 1546-54.
8. Polvikoski, T., et al. Prevalence of Alzheimer's disease in very elderly people: a prospective neuropathological study. Neurology, 2001. 56: p. 1690-6.
9. Lee, V. M. Y., et al. Neurodengerative tauopathies. Annu Rev Neurosci, 2001. 24: p. 1121-59.
10. Morishima-Kawashima, M. and Ihara, Y. Alzheimer's disease: β-Amyloid protein and tau. J Neurosci Res, 2002. 70: p. 392-410
11. Morris, J. C., et al. Very mild Alzheimer's disease: informant-based clinical, psychometric, and pathological distinction from normal aging. Neurology, 1991. 41: p. 469-78.
12. Price, J. L. et al. The distribution of tangles, plaques and related immunohistochemical markers in healthy aging and Alzheimer's disease. Neurobiol Aging, 1991. 12: p. 295-312.
13. Price, J. L., and Morris, J. C. Tangles and plaques in nondemented aging and "preclinical" Alzheimer's disease. Ann Neurol, 1999. 45: p. 358-68.
14. Price, J. L., et al. Neuron number in the entorhinal cortex and CA1 in preclinical Alzheimer disease. Arch Neurol, 2001. 58: p. 1395-402.
15. Petersen, R. C., et al. Mild cognitive impairment: clinical characterization and outcome. Arch Neurol, 1999. 56: p. 303-8.
16. Bennett, D. A., et al. Natural history of mild cognitive impairment in older persons. Neurology, 2002. 59: p. 198-205.
17. Growdon, J. H., et al. Application of the National Institute on Aging (NIA)-Reagan Institute criteria for the neuropathological diagnosis of Alzheimer disease. Neuropathol Exp Neurol, 1999. 58: p. 1147-55.
18. Reo, N. V., NMR-based metabolomics. Drug Chem Toxicol, 2002. 2:5(4): p. 375-82.
19. Fiehn, O., et al. Metabolite profiling for plant functional genomics. Nat Biotechnol, 2000. 18(11): p. 1157-61.
20. Viani, P., et al., Effect of endothelin-1 induced ischemia on peroxidative damage and membrane properties in rat striatum synaptosomes. Neurochem Res, 1995. 20: p. 689-95.
21. Zhang, J.-P., Sun, G. Y. Free fatty acids, neutral glycerides, and phosphoglycerides in transient focal cerebral ischemia. J Neurochem, 1995. 64: p. 1688095.
22. Demediuk, P., et al. Membrane lipid changes in laminectomized and traumatized cat spinal cord. Proc Natl Acad Sci USA, 1985. 82: p. 7071-5.
23. Wells, K., et al., Neural membrane phospholipids in Alzheimer disease. Neurochem Res, 1995. 20: p. 1329-33.
24. Ginsberg, L., et al., Disease and anatomic specificity of ethanolamine plasmalogen deficiency in Alzheimer's disease brain. Brain Res, 1995. 698: 223-6.
25. Ginsberg, L., Xuereb, J. H. Gershfeld, N. L. Membrane instability, plasmalogen content, and Alzheimer's disease. J Neurochem, 1998. 70: p. 2533-8.
26. Guan, Z., et al. Decrease and structural modifications of phosphatidylethanolamine plasmalogen in the brain with Alzheimer disease. J Neuropathol Exp Neurol, 1999. 58: 740-7.
27. Pettegrew, J. W., et al., Brain membrane phospholipid alterations in Alzheimer's disease. Neurochem Res, 2001. 26: p. 771-82.
28. Graham, D. P., et al. The alzheimer's disease assessment scale-cognitive subscale: normative date for older adult controls. Alzheimer Dis Assoc Disord, 2004. 18: p. 236-40.
29. Emre, M., Dementia associated with Parkinson's disease. Lancet Neurol, 2003. 2(4): p. 229-37.
30. Hager, J. W., et al., High-performance liquid chromatography-tandem mass spectrometry with a new quadrupole/linear ion trap instrument. J Chromatogr A, 2003. 1020(1): p. 3-9.
31. Hopfgartner, G., et al., Triple quadrupole linear ion trap mass spectrometer for the analysis of small molecules and macromolecules. J Mass Spectrom, 2004. 39(8): p. 845-55.
32. Xia, Y. Q., et al., Use of a quadrupole linear ion trap mass spectrometer in metabolite identification and bioanalysis. Rapid Commun Mass Spectrom, 2003. 17(11): p. 1137-45.
33. Zhang, M. Y., et al., Hybrid triple quadrupole-linear ion trap mass spectrometry in fragmentation mechanism studies: application to structure elucidation of buspirone and one of its metabolites. J Mass Spectrom, 2005. 40(8): p. 1017-1029.
34. Cummings, J. L., Kaufer, D. Neuropsychiatric aspects of Alzheimer's disease: the cholinergic hypothesis revisited. Neurology, 1996. 47(4): p. 876-83.

What is claimed is:

1. A method for diagnosing a patient's Alzheimer's disease health state or change in health state, or for diagnosing Alzheimer's disease, dementia, the risk of Alzheimer's disease, or the risk of dementia in a living patient, the method comprising the steps of:
- a) analyzing a blood sample from said patient by mass spectrometry to obtain quantifying data for one or more than one metabolite marker;
- b) comparing the quantifying data for said one or more than one metabolite marker to corresponding data obtained for one or more than one reference sample to identify an increase or decrease in a level of said one or more than one metabolite marker in said blood sample; and
- c) using said increase or decrease in the level of said one or more than one metabolite marker in said blood sample for diagnosing said patient's Alzheimer's disease health state or change in Alzheimer's disease health state, or for diagnosing Alzheimer's disease, dementia, the risk of Alzheimer's disease, or the risk of dementia in said patient, wherein the one or more than one metabolite marker comprises one or more molecule selected from the group consisting of: plasmenylethanolamine, plasmanylethanolamine, and combinations thereof.

2. The method of claim 1, wherein the plasmanylethanolamine is selected from the group of plasmanylethanolamines consisting of: plasmanyl 16:0/18:1, plasmanyl 16:0/18:2, plasmanyl 16:0/20:4, plasmanyl 16:0/22:4, plasmanyl 16:0/22:6, plasmanyl 18:0/18:1, plasmanyl 18:0/18:2, plasmanyl 18:0/20:4, plasmanyl 18:0/22:4, plasmanyl 18:0/22:6, and combinations thereof, and the plasmenylethanolamine is selected from the group of plasmenylethanolamines consisting of: plasmenyl 16:0/18:1, plasmenyl 16:0/18:2, plasmenyl 16:0/20:4, plasmenyl 16:0/22:4, plasmenyl 16:0/22:6, plasmenyl 18:0/18:1, plasmenyl 18:0/18:2, plasmenyl 18:0/20:4, plasmenyl 18:0/22:4, plasmenyl 18:0/22:6, and combinations thereof.

3. The method of claim 2, wherein an extracted sample is obtained from said blood sample and the extracted sample is analyzed by MS/MS transitions for the plasmanylethanolamines and for the plasmenylethanolamines, and
- the MS/MS transitions for the plasmanylethanolamines are 702.0/281.0, 700.0/279.0, 724.0/303.0, 752.0/331.0, 748.0/327.0, 730.0/281.0, 728.0/279.0, 752.0/303.0, 780.0/331.0 and 776.0/327.0, respectively; and
- the MS/MS transitions for the plasmenylethanolamines are 700.0/281.0, 698.0/279.0, 722.0/303.0, 750.0/331.0, 746.0/327.0, 728.0/281.0, 726.0/279.0, 750.6/303.2, 778.0/331.0 and 774.0/327.0, respectively.

4. The method of claim 1, wherein the quantifying data is obtained using a Fourier transform ion cyclotron resonance, time of flight, orbitrap, quadrupole or triple quadrupole mass spectrometer.

5. The method of claim 4, wherein the mass spectrometer is equipped with a chromatographic system.

6. The method of claim 1, wherein the blood sample is a blood serum sample.

7. The method of claim 1, wherein a liquid/liquid extraction is performed on the blood sample whereby non-polar metabolites are dissolved in an organic solvent and polar metabolites are dissolved in an aqueous solvent.

8. The method of claim 7, wherein an extracted sample obtained from the blood sample is analyzed by positive or negative electrospray ionization or positive or negative atmospheric pressure chemical ionization.

9. The method of claim 7, wherein an extracted sample obtained from the blood sample is analyzed by MS/MS transition.

10. The method of claim 7, wherein an extracted sample obtained from the blood sample is analyzed by extracted ion current (EIC) chromatography and MS/MS transition.

11. The method of claim 1, wherein said one or more than one reference sample is
- a) one or more than one reference sample obtained from a non-demented control individual;
- b) one or more than one reference sample obtained from a demented subject;
- c) one or more than one reference sample obtained from a subject pathologically diagnosed as having Alzheimer's Disease;
- d) one or more than one reference sample obtained from a subject clinically diagnosed as having Alzheimer's Disease;
- e) one or more than one reference sample obtained from a patient with cognitive impairment as measured by Alzheimer's Disease Assessment Scale-cognitive subset (ADAS-cog);
- f) one or more than one reference sample obtained from a patient with cognitive impairment as measured by Folstein's Mini-Mental State Exam (MMSE); or
- g) any combination of a) to f) above.

12. The method of claim 1, further comprising:
- analyzing a blood sample from said patient by mass spectrometry to obtain quantifying data for one or more than one internal control metabolite; and
- obtaining a ratio of the level of said one or more than one metabolite marker to a level obtained for the one or more than one internal control metabolite;
- wherein the comparing step (b) comprises comparing the ratio to one or more corresponding ratios obtained for the one or more than one reference sample.

13. The method of claim 12, wherein the one or more than one internal control metabolite is a phosphatidylethanolamine (PtdEt).

14. The method of claim 13, wherein the phosphatidylethanolamine is selected from the group consisting of PtdEt 16:0/18:0, PtdEt 16:0/18:1, PtdEt 18:0/18:0, PtdEt 18:0/18:1, and combinations thereof.

15. The method of claim 1, wherein a decrease in the level of said one or more than one metabolite marker in said blood sample is identified in the comparing step (b).

16. A method for evaluating the efficacy of a therapy for treating Alzheimer's disease or dementia in a living patient, comprising the steps of:
- a) analyzing a blood sample from said patient by mass spectrometry to obtain quantifying data for one or more than one metabolite marker;
- b) comparing the quantifying data for said one or more than one metabolite marker to corresponding data obtained for one or more than one reference sample to identify an increase or decrease in a level of said one or more than one metabolite marker in said blood sample; and
- c) using said increase or decrease in the level of said one or more than one metabolite marker in said blood sample to determine whether the therapy is improving a biochemical state of the patient, wherein the one or more than one metabolite marker comprises one or more molecule selected from the group consisting of: plasmenylethanolamine, plasmanylethanolamine, and combinations thereof.

17. The method of claim 16, wherein the plasmanylethanolamine is selected from the group of plasmanylethanolamines consisting of: plasmanyl 16:0/18:1, plasmanyl 16:0/18:2, plasmanyl 16:0/20:4, plasmanyl 16:0/22:4, plasmanyl 16:0/22:6, plasmanyl 18:0/18:1, plasmanyl 18:0/18:2, plasmanyl 18:0/20:4, plasmanyl 18:0/22:4, plasmanyl 18:0/22:6, and combinations thereof; and, the plasmenylethanolamine is selected from the group of plasmenylethanolamines consisting of: plasmenyl 16:0/18:1, plasmenyl 16:0/18:2, plasmenyl 16:0/20:4, plasmenyl 16:0/22:4, plasmenyl 16:0/22:6, plasmenyl 18:0/18:1, plasmenyl 18:0/18:2, plasmenyl 18:0/20:4, plasmenyl 18:0/22:4, plasmenyl 18:0/22:6, and combinations thereof.

18. The method of claim 16, wherein the quantifying data is obtained using a Fourier transform ion cyclotron resonance, time of flight, orbitrap, quadrupole or triple quadrupole mass spectrometer.

19. The method of claim 18, wherein the mass spectrometer is equipped with a chromatographic system.

20. The method of claim 16, wherein the blood sample is a blood serum sample.

21. The method of claim 16, wherein a liquid/liquid extraction is performed on the blood sample whereby non-polar metabolites are dissolved in an organic solvent and polar metabolites are dissolved in an aqueous solvent.

22. The method of claim 21, wherein an extracted sample obtained from the blood sample is analyzed by positive or negative electrospray ionization or positive or negative atmospheric pressure chemical ionization.

23. The method of claim 21, wherein an extracted sample obtained from the blood sample is analyzed by MS/MS transition.

24. The method of claim 21, wherein an extracted sample obtained from the blood sample is analyzed by extracted ion current (EIC) chromatography and MS/MS transition.

25. The method of claim 16, wherein said one or more than one reference sample is
  a) one or more than one reference sample obtained from a non-demented control individual;
  b) one or more than one reference sample obtained from a demented subject;
  c) one or more than one reference sample obtained from a subject pathologically diagnosed as having Alzheimer's Disease;
  d) one or more than one reference sample obtained from a subject clinically diagnosed as having Alzheimer's Disease;
  e) one or more than one reference sample obtained from a patient with cognitive impairment as measured by Alzheimer's Disease Assessment Scale-cognitive subset (ADAS-cog);
  f) one or more than one reference sample obtained from a patient with cognitive impairment as measured by Folstein's Mini-Mental State Exam (MMSE); or
  g) any combination of a) to f) above.

26. The method according to claim 16, further comprising:
  analyzing a blood sample from said patient to obtain quantifying data for one or more than one internal control metabolite; and
  obtaining a ratio of the level of said one or more than one metabolite marker to a level obtained for the one or more than one internal control metabolite;
  wherein the comparing step (b) comprises comparing the ratio to one or more corresponding ratios obtained for the one or more than one reference sample.

27. The method of claim 26, wherein the one or more than one internal control metabolite is a phosphatidylethanolamine (PtdEt).

28. The method of claim 27, wherein the phosphatidylethanolamine is selected from the group consisting of PtdEt 16:0/18:0, PtdEt 16:0/18:1, PtdEt 18:0/18:0, PtdEt 18:0/18:1, and combinations thereof.

29. The method of claim 16, wherein an increase in the level of said one or more than one metabolite marker in said blood sample is identified in the comparing step (b).

30. The method of claim 17, wherein an extracted sample is obtained from said blood sample and the extracted sample is analyzed by MS/MS transitions for the plasmanylethanolamines and for the plasmenylethanolamines, and
  the MS/MS transitions for the plasmanylethanolamines are 702.0/281.0, 700.0/279.0, 724.0/303.0, 752.0/331.0, 748.0/327.0, 730.0/281.0, 728.0/279.0, 752.0/303.0, 780.0/331.0 and 776.0/327.0, respectively; and
  the MS/MS transitions for the plasmenylethanolamines are 700.0/281.0, 698.0/279.0, 722.0/303.0, 750.0/331.0, 746.0/327.0, 728.0/281.0, 726.0/279.0, 750.6/303.2, 778.0/331.0 and 774.0/327.0, respectively.

* * * * *

UNITED STATES PATENT AND TRADEMARK OFFICE
CERTIFICATE OF CORRECTION

| | |
|---|---|
| PATENT NO. | : 8,304,246 B2 |
| APPLICATION NO. | : 12/280920 |
| DATED | : November 6, 2012 |
| INVENTOR(S) | : Lisa Cook et al. |

Page 1 of 1

It is certified that error appears in the above-identified patent and that said Letters Patent is hereby corrected as shown below:

On the Title page, under the Assignee field: delete "Phenomenome Discoveries, Inc." and insert --Phenomenome Discoveries Inc.--.

In claim 26, at col. 132, line 14, delete "the" appearing before "level".

Signed and Sealed this
Fifth Day of February, 2013

Teresa Stanek Rea
*Acting Director of the United States Patent and Trademark Office*